United States Patent
Xia et al.

(10) Patent No.: US 11,316,113 B2
(45) Date of Patent: *Apr. 26, 2022

(54) ORGANIC ELECTROLUMINESCENT MATERIALS AND DEVICES

(71) Applicant: UNIVERSAL DISPLAY CORPORATION, Ewing, NJ (US)

(72) Inventors: Chuanjun Xia, Lawrenceville, NJ (US); Raymond Kwong, Plainsboro, NJ (US); Ken-Tsung Wong, Tapei County (TW); Ming-Cheng Kuo, Taichung County (TW)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 125 days.

This patent is subject to a terminal disclaimer.

(21) Appl. No.: 15/915,199

(22) Filed: Mar. 8, 2018

(65) Prior Publication Data

US 2019/0081246 A1    Mar. 14, 2019

Related U.S. Application Data

(63) Continuation of application No. 13/816,407, filed as application No. PCT/US2010/046218 on Aug. 20, 2010, now Pat. No. 9,954,180.

(51) Int. Cl.
| | | |
|---|---|---|
| C07D 401/14 | (2006.01) | |
| C07D 403/14 | (2006.01) | |
| C07D 405/14 | (2006.01) | |
| C07D 409/14 | (2006.01) | |
| H01L 51/54 | (2006.01) | |
| H01L 51/00 | (2006.01) | |
| H01L 51/50 | (2006.01) | |

(52) U.S. Cl.
CPC ........ *H01L 51/0067* (2013.01); *C07D 401/14* (2013.01); *C07D 403/14* (2013.01); *C07D 405/14* (2013.01); *C07D 409/14* (2013.01); *H01L 51/0072* (2013.01); *H01L 51/0085* (2013.01); *H01L 51/5016* (2013.01)

(58) Field of Classification Search
CPC ............... H01L 51/005; H01L 51/0051; H01L 51/0062; H01L 51/0067; H01L 51/0071; H01L 51/0072; H01L 51/0052; H01L 51/0054; H01L 51/0055; H01L 51/0058; H01L 51/0085; H01L 51/50; H01L 51/5012; H01L 51/5016; H01L 51/5056; H01L 51/5072; H01L 51/5092; C09K 11/06; C09K 2211/1018; C09K 2211/1029; C09K 2211/1059; C09K 2211/1007; C09K 2211/1011; C09K 2211/1044; C09K 2211/185; C09K 11/025; C07D 251/00; C07D 251/02; C07D 251/14; C07D 251/24; C07D 209/00; C07D 209/82; C07D 209/86; C07D 401/14; C07D 403/04; C07D 403/14; C07D 405/14; C07D 209/60; C07D 209/80; C07D 209/88
USPC ................ 544/180, 194, 211, 212; 548/440; 257/40, E51.024, E51.025, E51.047, 257/E51.048, E51.049, E51.05, 88–104, 257/E51.001–E51.052; 428/690, 917, 428/691; 313/500–512; 427/58, 66; 252/301.16–301.35

See application file for complete search history.

(56) References Cited

U.S. PATENT DOCUMENTS

| | | |
|---|---|---|
| 4,769,292 A | 9/1988 | Tang et al. |
| 5,061,569 A | 10/1991 | VanSlyke et al. |
| 5,247,190 A | 9/1993 | Friend et al. |
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A * | 8/2000 | Baldo ................. H01L 51/5096 313/498 |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |
| 6,528,187 B1 | 3/2003 | Okada |
| 6,687,266 B1 | 2/2004 | Ma et al. |
| 6,835,469 B2 | 12/2004 | Kwong et al. |
| 6,921,915 B2 | 7/2005 | Takiguchi et al. |
| 7,087,321 B2 | 8/2006 | Kwong et al. |

(Continued)

FOREIGN PATENT DOCUMENTS

| | | |
|---|---|---|
| EP | 0650955 | 5/1995 |
| EP | 1725079 | 11/2006 |

(Continued)

OTHER PUBLICATIONS

Tominaga, Takeshi et al., Machine translation of JP-2008135498-A, pp. 1-23. (Year: 2008).*

(Continued)

*Primary Examiner* — Dylan C Kershner

(74) *Attorney, Agent, or Firm* — Duane Morris LLP

(57) ABSTRACT

Novel organic compounds comprising a bicarbazole core are provided. In particular, the compounds has a 3,3'-bicarbazole core substituted at the 9-position with a triazine or pyrimidine. The compounds may be used in organic light emitting devices to provide devices having improved efficiency and improved lifetime.

19 Claims, 3 Drawing Sheets

(56) References Cited

U.S. PATENT DOCUMENTS

| | | | |
|---|---|---|---|
| 7,090,928 B2 | 8/2006 | Thompson et al. | |
| 7,154,114 B2 | 12/2006 | Brooks et al. | |
| 7,250,226 B2 | 7/2007 | Tokito et al. | |
| 7,279,704 B2 | 10/2007 | Walters et al. | |
| 7,332,232 B2 | 2/2008 | Ma et al. | |
| 7,338,722 B2 | 3/2008 | Thompson et al. | |
| 7,393,599 B2 | 7/2008 | Thompson et al. | |
| 7,396,598 B2 | 7/2008 | Takeuchi et al. | |
| 7,431,968 B1 | 10/2008 | Shtein et al. | |
| 7,445,855 B2 | 11/2008 | Mackenzie et al. | |
| 7,534,505 B2 | 5/2009 | Lin et al. | |
| 9,954,180 B2 * | 4/2018 | Xia | C07D 401/14 |
| 2002/0034656 A1 | 3/2002 | Thompson et al. | |
| 2002/0134984 A1 | 9/2002 | Igarashi | |
| 2002/0158242 A1 | 10/2002 | Son et al. | |
| 2003/0138657 A1 | 7/2003 | Li et al. | |
| 2003/0152802 A1 | 8/2003 | Tsuboyama et al. | |
| 2003/0162053 A1 | 8/2003 | Marks et al. | |
| 2003/0175553 A1 | 9/2003 | Thompson et al. | |
| 2003/0230980 A1 | 12/2003 | Forrest et al. | |
| 2004/0036077 A1 | 2/2004 | Ise | |
| 2004/0110031 A1 * | 6/2004 | Fukuda | C09K 11/06 428/690 |
| 2004/0137267 A1 | 7/2004 | Igarashi et al. | |
| 2004/0137268 A1 | 7/2004 | Igarashi et al. | |
| 2004/0174116 A1 | 9/2004 | Lu et al. | |
| 2005/0025993 A1 | 2/2005 | Thompson et al. | |
| 2005/0112407 A1 | 5/2005 | Ogasawara et al. | |
| 2005/0238919 A1 | 10/2005 | Ogasawara | |
| 2005/0244673 A1 | 11/2005 | Satoh et al. | |
| 2005/0260441 A1 | 11/2005 | Thompson et al. | |
| 2005/0260449 A1 | 11/2005 | Walters et al. | |
| 2006/0008670 A1 | 1/2006 | Lin et al. | |
| 2006/0202194 A1 | 9/2006 | Jeong et al. | |
| 2006/0240279 A1 | 10/2006 | Adamovich et al. | |
| 2006/0251923 A1 | 11/2006 | Lin et al. | |
| 2006/0263635 A1 | 11/2006 | Ise | |
| 2006/0280965 A1 | 12/2006 | Kwong et al. | |
| 2007/0190359 A1 | 8/2007 | Knowles et al. | |
| 2007/0278938 A1 | 12/2007 | Yabunouchi et al. | |
| 2008/0015355 A1 | 1/2008 | Schafer et al. | |
| 2008/0018221 A1 | 1/2008 | Egen et al. | |
| 2008/0106190 A1 | 5/2008 | Yabunouchi et al. | |
| 2008/0124572 A1 | 5/2008 | Mizuki et al. | |
| 2008/0220265 A1 | 9/2008 | Xia et al. | |
| 2008/0297033 A1 | 12/2008 | Knowles et al. | |
| 2009/0008605 A1 | 1/2009 | Kawamura et al. | |
| 2009/0009065 A1 | 1/2009 | Nishimura et al. | |
| 2009/0017330 A1 | 1/2009 | Iwakuma et al. | |
| 2009/0030202 A1 | 1/2009 | Iwakuma et al. | |
| 2009/0039776 A1 | 2/2009 | Yamada et al. | |
| 2009/0045730 A1 | 2/2009 | Nishimura et al. | |
| 2009/0045731 A1 | 2/2009 | Nishimura et al. | |
| 2009/0066235 A1 * | 3/2009 | Yabunouchi | C07D 209/86 313/504 |
| 2009/0101870 A1 | 4/2009 | Pakash et al. | |
| 2009/0108737 A1 | 4/2009 | Kwong et al. | |
| 2009/0115316 A1 | 5/2009 | Zheng et al. | |
| 2009/0165846 A1 | 7/2009 | Johannes et al. | |
| 2009/0167162 A1 | 7/2009 | Lin et al. | |
| 2009/0179554 A1 | 7/2009 | Kuma et al. | |
| 2009/0242876 A1 | 10/2009 | Brunner et al. | |
| 2009/0302745 A1 * | 12/2009 | Otsu | C07D 403/14 313/504 |
| 2010/0044695 A1 * | 2/2010 | Kai | C07D 251/18 257/40 |
| 2010/0237339 A1 * | 9/2010 | Nomura | C07D 403/12 257/40 |
| 2011/0279020 A1 * | 11/2011 | Inoue | C07D 209/82 313/504 |
| 2012/0235123 A1 * | 9/2012 | Lee | H01L 51/0072 257/40 |
| 2014/0131665 A1 | 5/2014 | Xia et al. | |
| 2014/0231783 A1 | 8/2014 | Bae et al. | |

FOREIGN PATENT DOCUMENTS

| | | | | |
|---|---|---|---|---|
| EP | 2034538 | | 3/2009 | |
| EP | 2568030 | | 3/2013 | |
| JP | 2003133075 | | 5/2003 | |
| JP | 2003133075 A | * | 5/2003 | |
| JP | 200511610 | | 1/2005 | |
| JP | 2007123392 | | 5/2007 | |
| JP | 2007254297 | | 10/2007 | |
| JP | 2008074939 | | 4/2008 | |
| JP | 2008135498 | | 6/2008 | |
| JP | 2008135498 A | * | 6/2008 | |
| KR | 20120013173 | | 2/2012 | |
| TW | 201120186 | | 6/2011 | |
| TW | 201130805 | | 9/2011 | |
| WO | 01/39234 | | 5/2001 | |
| WO | 02/02714 | | 1/2002 | |
| WO | 02015654 | | 2/2002 | |
| WO | 03040257 | | 5/2003 | |
| WO | 03060956 | | 7/2003 | |
| WO | 2004093207 | | 10/2004 | |
| WO | 04107822 | | 12/2004 | |
| WO | 2005014551 | | 2/2005 | |
| WO | 2005019373 | | 3/2005 | |
| WO | 2005030900 | | 4/2005 | |
| WO | 2005089025 | | 9/2005 | |
| WO | 2005123873 | | 12/2005 | |
| WO | 2006009024 | | 1/2006 | |
| WO | 2006056418 | | 6/2006 | |
| WO | 2006072002 | | 7/2006 | |
| WO | 2006082742 | | 8/2006 | |
| WO | 2006098120 | | 9/2006 | |
| WO | 2006100298 | | 9/2006 | |
| WO | 2006103874 | | 10/2006 | |
| WO | 2006114966 | | 11/2006 | |
| WO | 2006132173 | | 12/2006 | |
| WO | 2007002683 | | 1/2007 | |
| WO | 2007004380 | | 1/2007 | |
| WO | 2007063754 | | 6/2007 | |
| WO | 2007063796 | | 6/2007 | |
| WO | 2007119816 | | 10/2007 | |
| WO | WO-2007119816 A1 | * | 10/2007 | C07D 403/14 |
| WO | 2008056746 | | 5/2008 | |
| WO | 2008101842 | | 8/2008 | |
| WO | 2008123189 | | 10/2008 | |
| WO | WO-2008123189 A1 | * | 10/2008 | C07D 251/18 |
| WO | 2008132085 | | 11/2008 | |
| WO | 2009000673 | | 12/2008 | |
| WO | 2009003898 | | 1/2009 | |
| WO | 2009008311 | | 1/2009 | |
| WO | 2009018009 | | 2/2009 | |
| WO | 2009021126 | | 2/2009 | |
| WO | 2009050290 | | 4/2009 | |
| WO | 2009062578 | | 5/2009 | |
| WO | 2009063833 | | 5/2009 | |
| WO | 2009066778 | | 5/2009 | |
| WO | 2009066779 | | 5/2009 | |
| WO | 2009086028 | | 7/2009 | |
| WO | 2009100991 | | 8/2009 | |
| WO | 2011055934 | | 5/2011 | |
| WO | 2011071255 | | 6/2011 | |
| WO | 2011132683 | | 10/2011 | |
| WO | 2011139055 | | 11/2011 | |
| WO | 2011162162 | | 12/2011 | |

OTHER PUBLICATIONS

Tominaga, Takeshi et al., Machine translation of JP-2003133075-A, pp. 1-15. (Year: 2003).*

Adachi, Chihaya et al., "Organic Electroluminescent Device Having a Hole Conductor as an Emitting Layer," Appl. Phys. Lett., 55(15): 1489-1491 (1989).

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

(56) References Cited

OTHER PUBLICATIONS

Aonuma, Masaki et al., "Material Design of Hole Transport Materials Capable of Thick-Film Formation in Organic Light Emitting Diodes," Appl. Phys. Lett., 90, Apr. 30, 2007, 183503-1-183503-3.
Baldo et al., Highly Efficient Phosphorescent Emission from Organic Electroluminescent Devices, Nature, vol. 395, 151-154, (1998).
Baldo et al., Very high-efficiency green organic light-emitting devices based on electrophosphorescence, Appl. Phys. Lett., vol. 75, No. 1, 4-6 (1999).
Gao, Zhiqiang et al., "Bright-Blue Electroluminescence From a Silyl-Substituted ter-(phenylene-vinylene) derivative," Appl. Phys. Lett., 74(6): 865-867 (1999).
Guo, Tzung-Fang et al., "Highly Efficient Electrophosphorescent Polymer Light-Emitting Devices," Organic Electronics, 1: 15-20 (2000).
Hamada, Yuji et al., "High Luminance in Organic Electroluminescent Devices with Bis(10-hydroxybenzo[h]quinolinato) beryllium as an Emitter," Chem. Lett., 905-906 (1993).
Holmes, R.J. et al., "Blue Organic Electrophosphorescence Using Exothermic Host-Guest Energy Transfer," Appl. Phys. Lett., 82(15):2422-2424 (2003).
Hu, Nan-Xing et al., "Novel High Tg Hole-Transport Molecules Based on Indolo[3,2-b]carbazoles for Organic Light-Emitting Devices," Synthetic Metals, 111-112:421-424 (2000).
Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
Hung, L.S. et al., "Anode Modification in Organic Light-Emitting Diodes by Low-Frequency Plasma Polymerization of CHF3," Appl. Phys. Lett., 78(5):673-675 (2001).
Ikai, Masamichi et al., "Highly Efficient Phosphorescence From Organic Light-Emitting Devices with an Exciton-Block Layer," Appl. Phys. Lett., 79(2):156-158 (2001).
Ikeda, Hisao et al., "P-185 Low-Drive-Voltage OLEDs with a Buffer Layer Having Molybdenum Oxide," SID Symposium Digest, 37:923-926 (2006).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials," Adv. Mater., 6(9):677-679 (1994).
Kwong, Raymond C. et al., "High Operational Stability of Electrophosphorescent Devices," Appl. Phys. Lett., 81(1) 162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Lo, Shih-Chun et al., "Blue Phosphorescence from Iridium(III) Complexes at Room Temperature," Chem. Mater., 18(21)5119-5129 (2006).

Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota,Yasuhiko, "5,5'-Bis(dimesitylboryl)-2,2'-bithiophene and 5,5"-Bis(dimesitylboryl)-2,2'5',2"-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based On Silole Derivatives And Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91: 209-215 (1997).
Shirota, Yasuhiko et al., "Starburst Molecules Based on pi-Electron Systems as Materials for Organic Electroluminescent Devices," Journal of Luminescence, 72-74:985-991 (1997).
Sotoyama, Wataru et al., "Efficient Organic LIght-Emitting Diodes with Phosphorescent Platinum Complexes Containing $N^{\wedge}C^{\wedge}N$-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergård et al., "Langmuir-Blodgett Light-Emitting Diodes Of Poly(3-Hexylthiophene) Electro-Optical Characteristics Related to Structure," Synthetic Metals, 88:171-177 (1997).
Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett., 69(15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).
Montalti et al., Handbook of Photochemistry, Marco Montalti, Alberto Credi, Luca Prodi, and M. Teresa Gandolfi, 3rd edition.
Vaitkeviciene et al., "Well-defined [3,3] bicarbazolyl-based electroactive compounds for optoelectronics" Synthetic Metals, 2008, vol. 158, pp. 383-390.

(56) References Cited

OTHER PUBLICATIONS

Tominaga et al., Machine Translation of JP 2003-133075, Date of Japanese Language publication: 2003, pp. 1-15.

* cited by examiner

ORGANIC ELECTROLUMINESCENT MATERIALS AND DEVICES

CROSS REFERENCE TO RELATED APPLICATIONS

This application is a continuation of U.S. application Ser. No. 13/816,407, filed Feb. 11, 2013, which is a U.S. national phase application filed under 35 U.S.C. § 371 of International Application No.: PCT/US2010/046218, filed Aug. 20, 2010, the entireties of which are included herein.

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to organic light emitting devices (OLEDs). More specifically, the present invention pertains to phosphorescent organic materials comprising a bicarbazole having a nitrogen-containing heterocycle at the 9 position.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the structure:

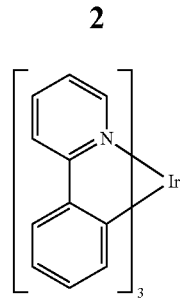

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher"

HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

Compounds comprising a bicarbazole are provided. The compounds have the formula:

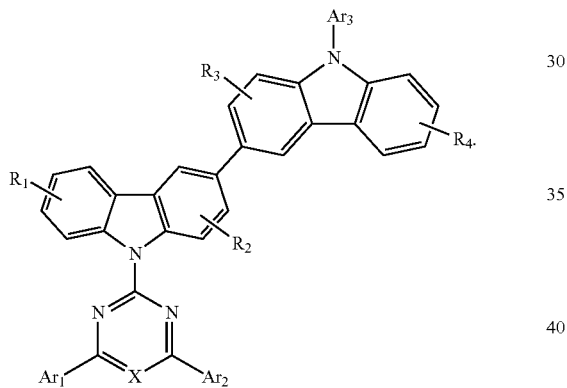

Formula I $R_1$, $R_2$, $R_3$, and $R_4$ may represent mono, di, tri, or tetra substitutions. $R_1$, $R_2$, $R_3$, and $R_4$ are independently selected from the group consisting of hydrogen, alkyl, alkoxy, amino, alkenyl, alkynyl, aryl and heteroaryl. $Ar_1$, $Ar_2$, and $Ar_3$ are independently selected from aryl or heteroaryl. $Ar_1$, $Ar_2$, and $Ar_3$ may be further substituted. X is C or N.

In one aspect, $Ar_1$, $Ar_2$, and $Ar_3$ are independently selected from the group consisting of phenyl, pyridine, naphthalene, biphenyl, terphenyl, fluorene, dibenzofuran, dibenzothiophene, phenanthrene, and triphenylene. $Ar_1$, $Ar_2$, and $Ar_3$ are independently further substituted with a substituent selected from the group consisting of hydrogen, alkyl, alkoxy, amino, alkenyl, alkynyl, aryl and heteroaryl, but the substituent is not an aryl or heteroaryl fused directly to $Ar_1$, $Ar_2$, and $Ar_3$. Preferably, $Ar_1$ and $Ar_2$ are independently selected from the group consisting of phenyl, pyridine, and naphthalene. Preferably, $Ar_3$ is selected from the group consisting of phenyl, biphenyl, dibenzofuran, and dibenzothiophene.

In another aspect, $R_1$, $R_2$, $R_3$, and $R_4$ are hydrogen.

Specific examples of compounds comprising bicarbazole are also provided. In particular, the compound is selected from the group consisting of:

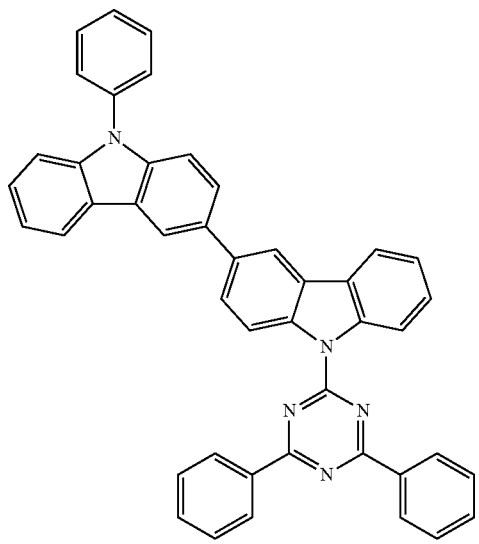

Compound 1

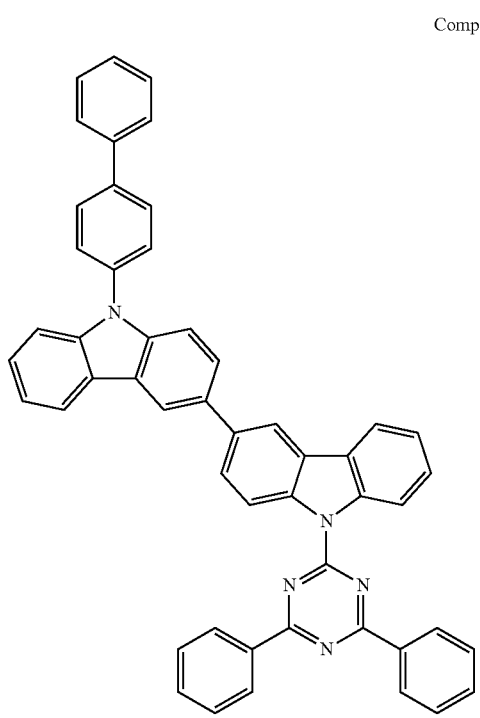

Compound 2

Compound 3
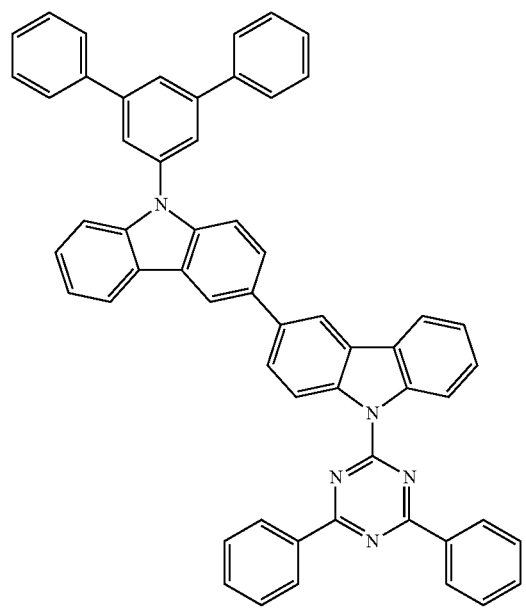
Compound 4
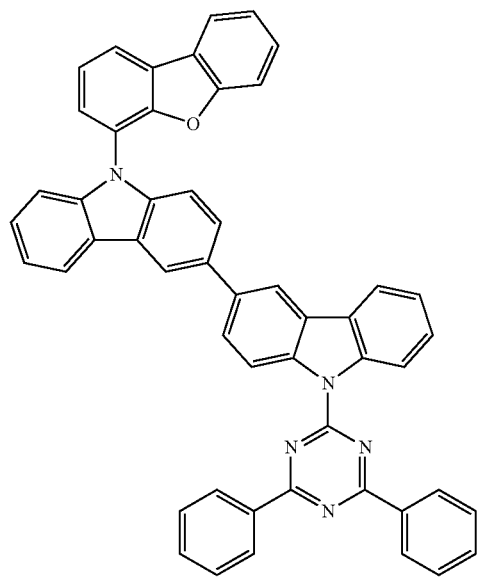
Compound 5
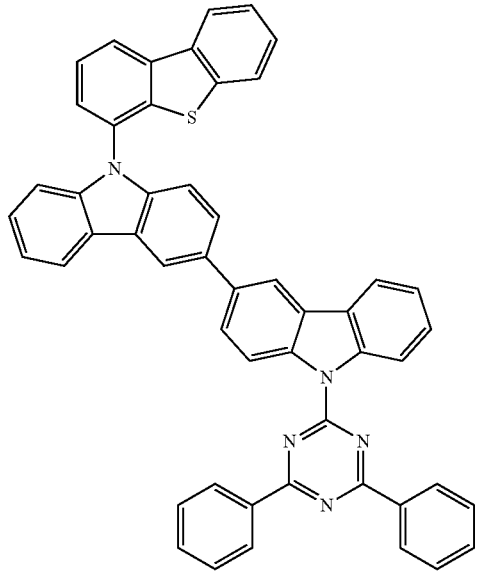
Compound 6
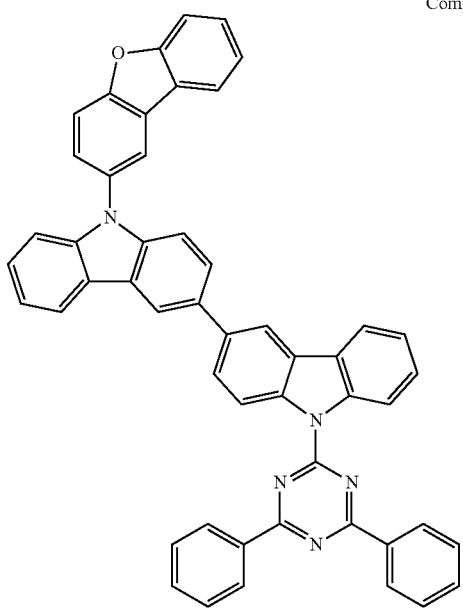

Compound 7
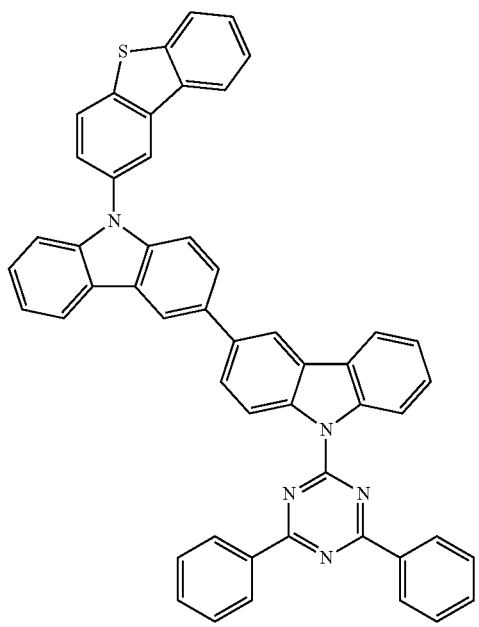
Compound 8
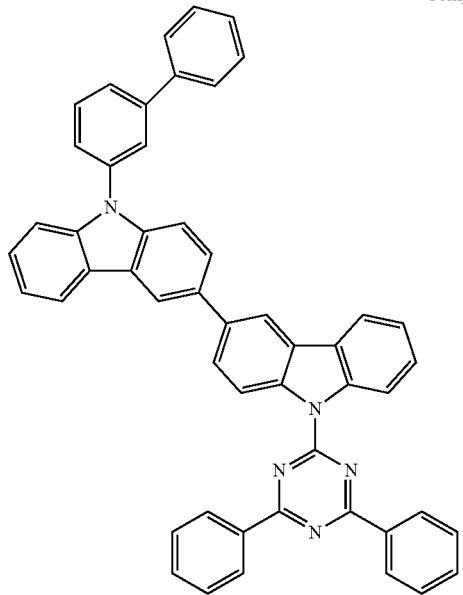
Compound 9
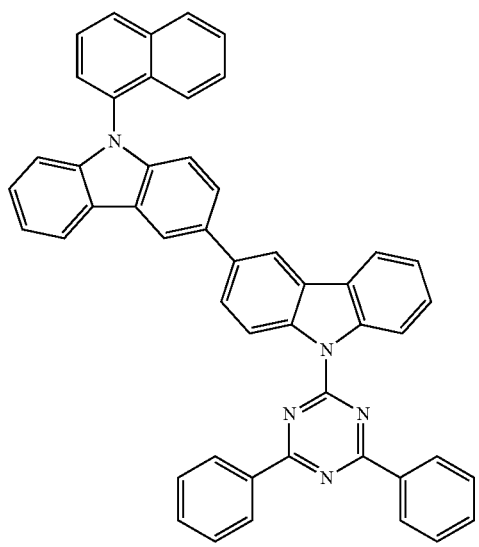
Compound 10
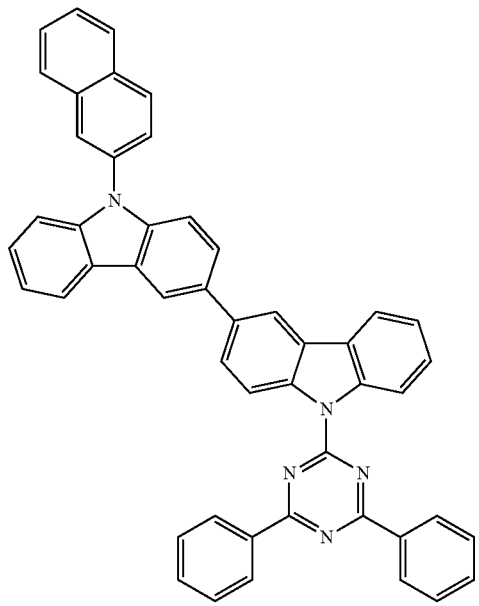

Compound 11
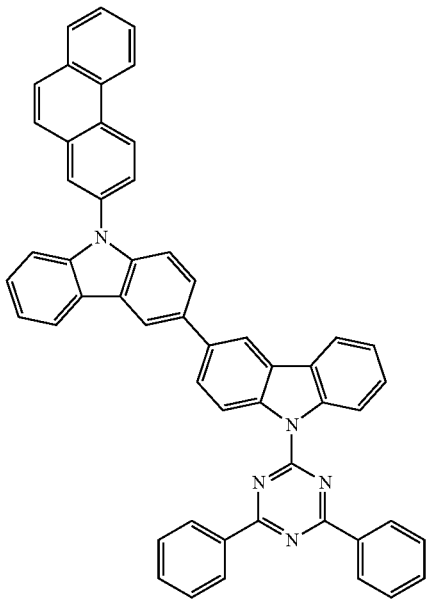
Compound 12
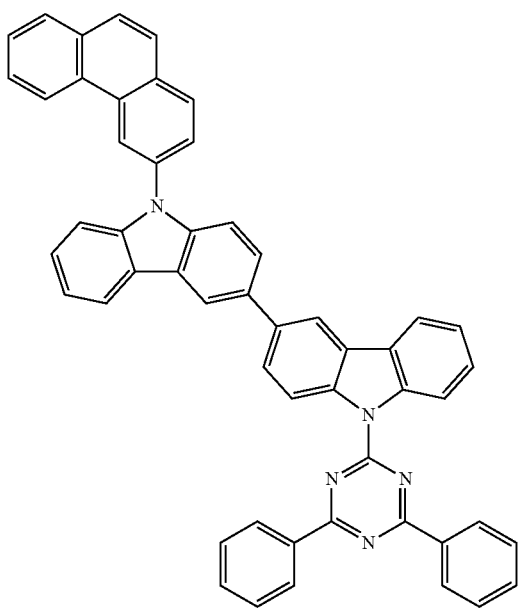
Compound 13
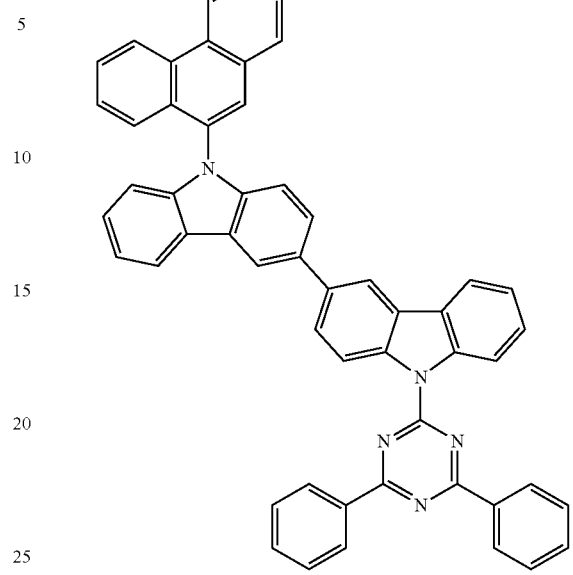
Compound 14
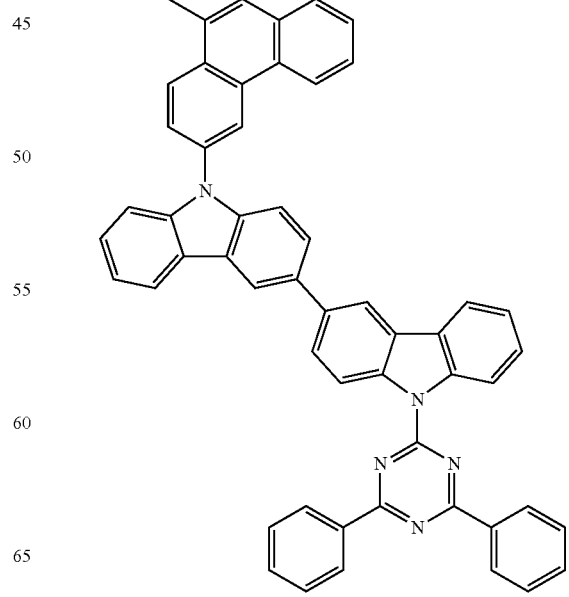

Compound 15
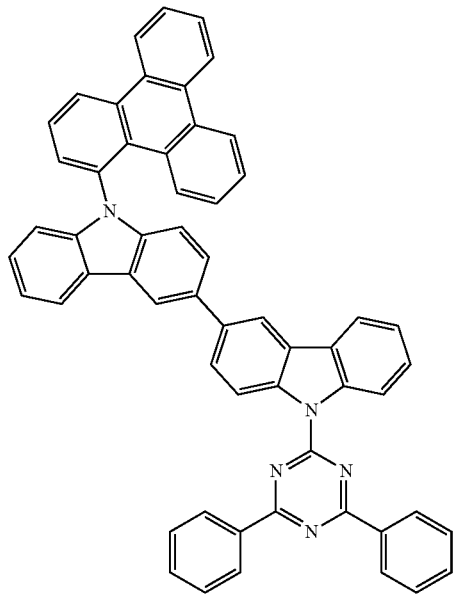
Compound 16
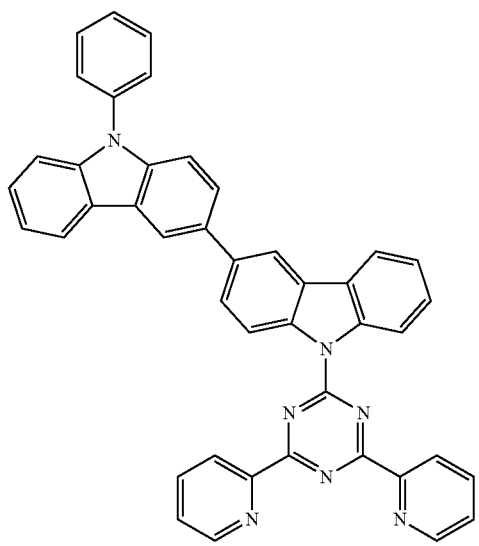
Compound 17
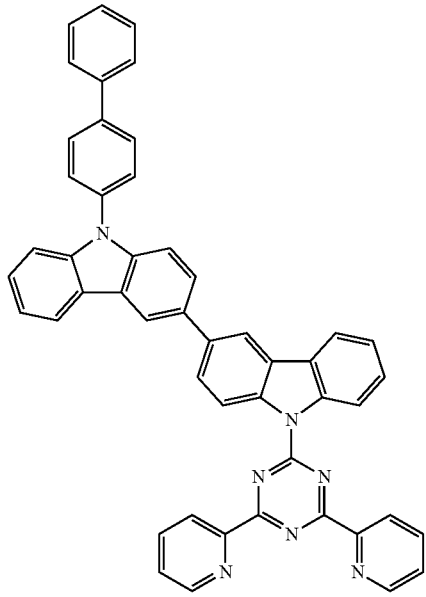
Compound 18
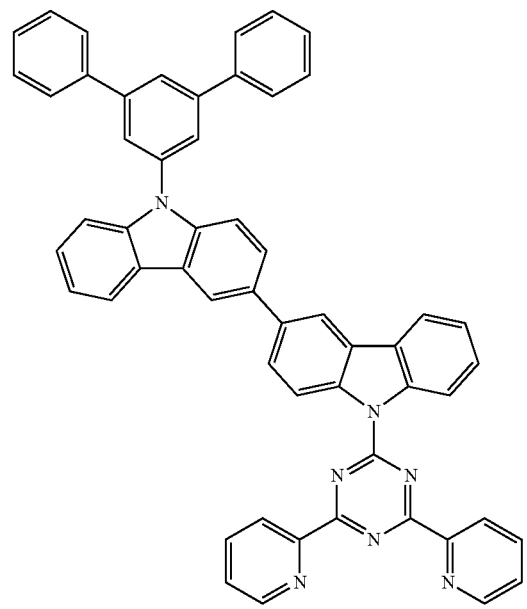

Compound 19
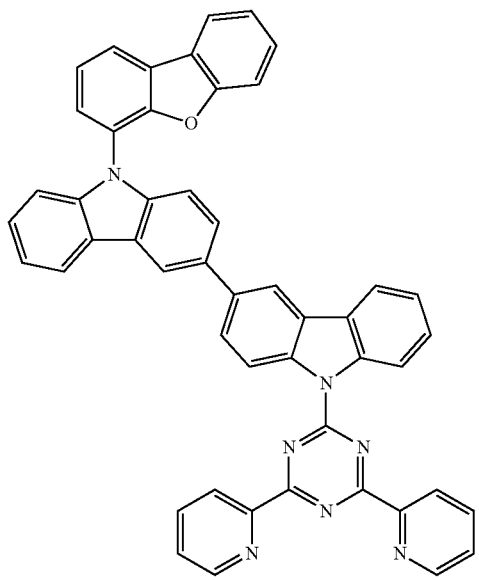
Compound 20
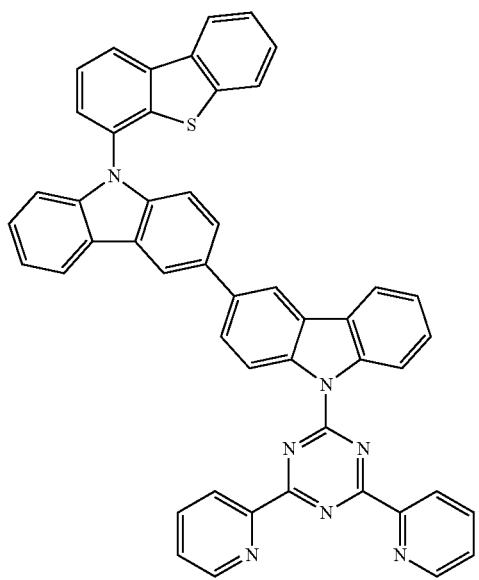
Compound 21
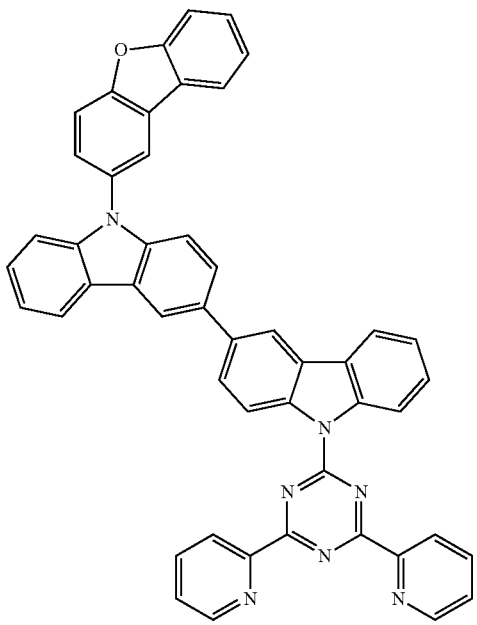
Compound 22
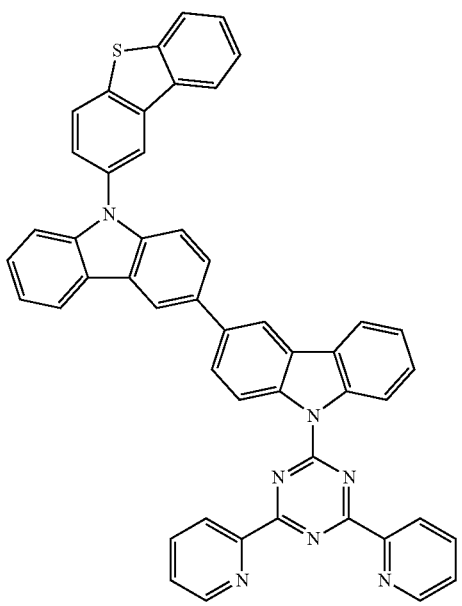

Compound 23
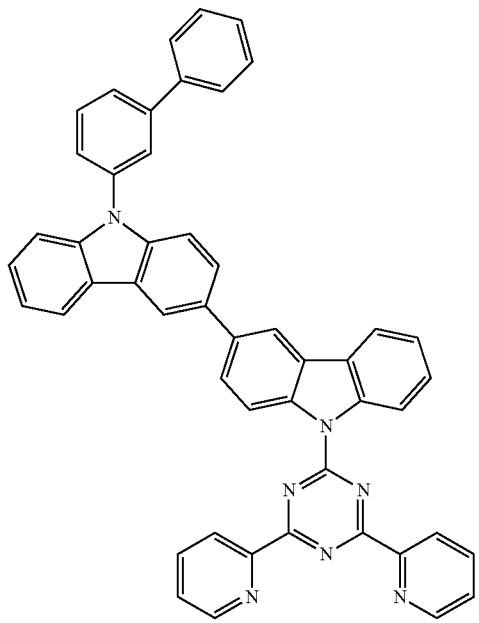
Compound 24
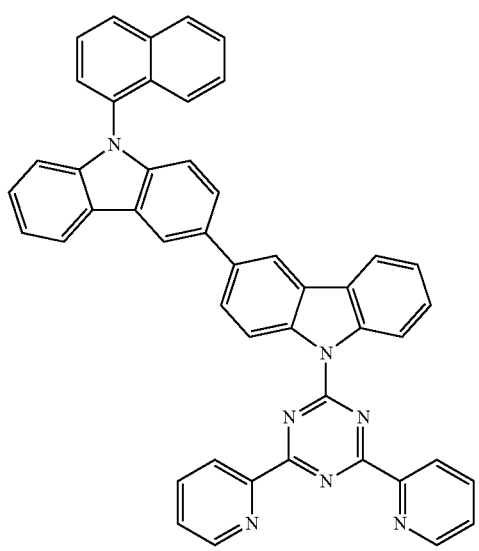
Compound 25
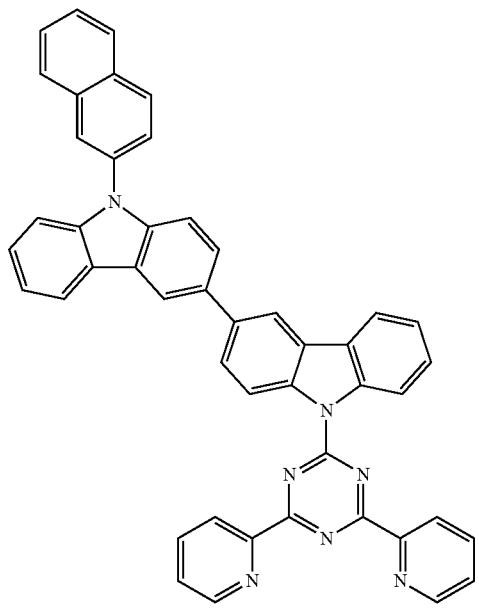
Compound 26
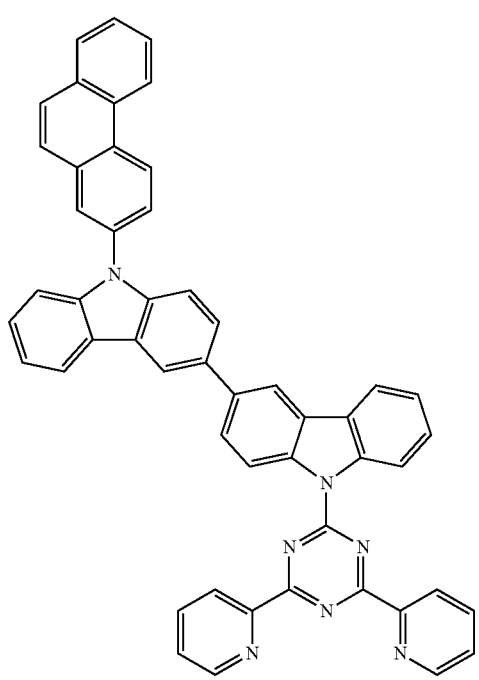

Compound 27
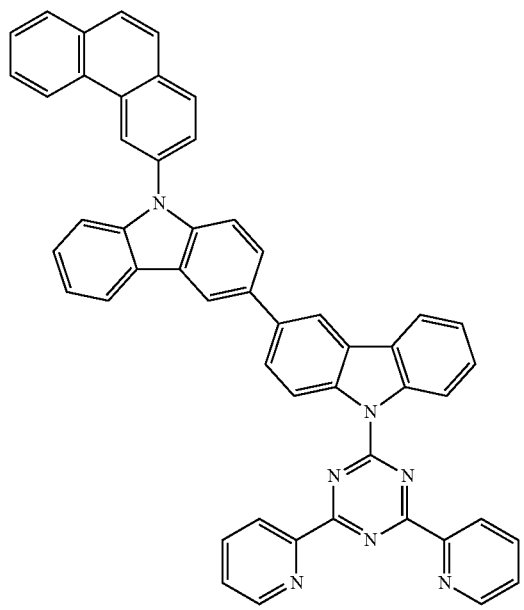
Compound 28
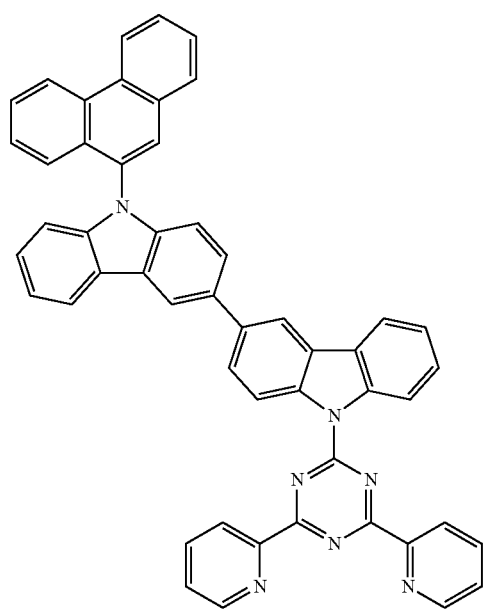
Compound 29
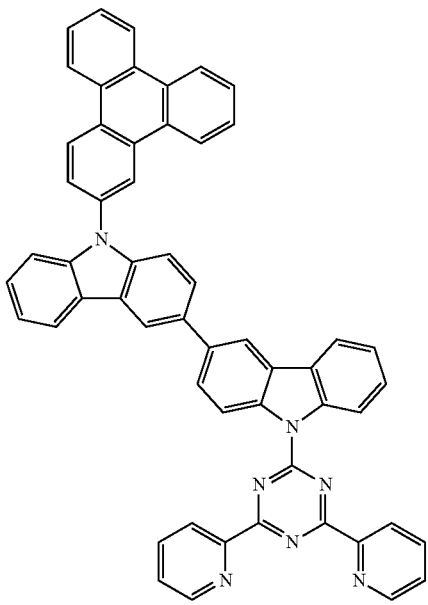
Compound 30
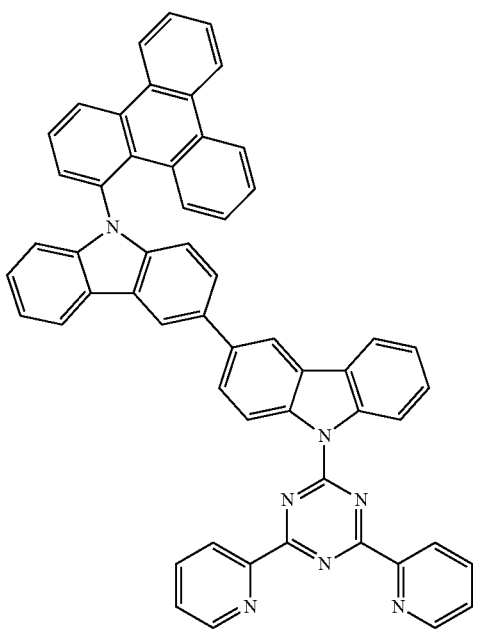

Compound 31
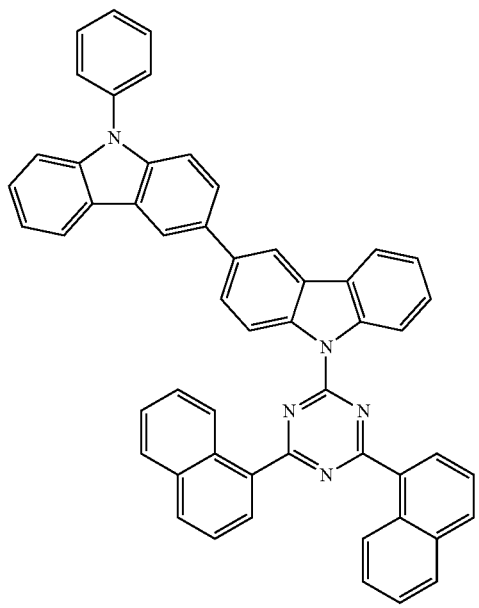
Compound 32
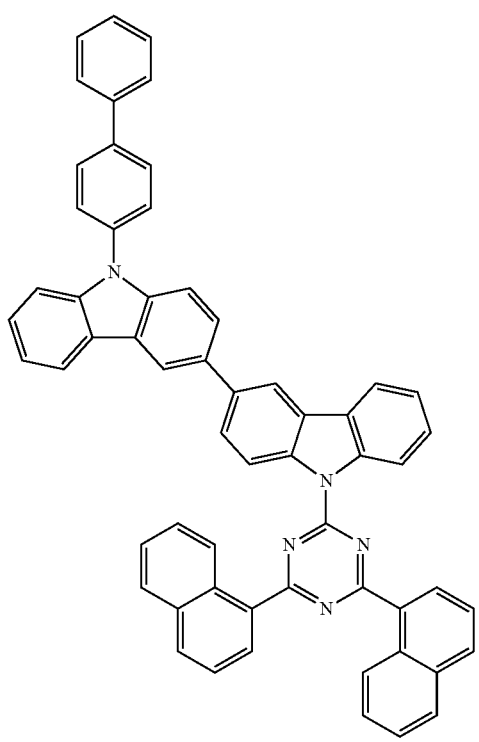
Compound 33
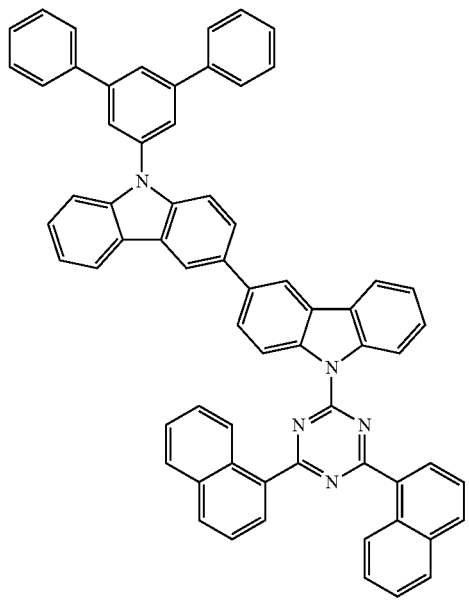
Compound 34
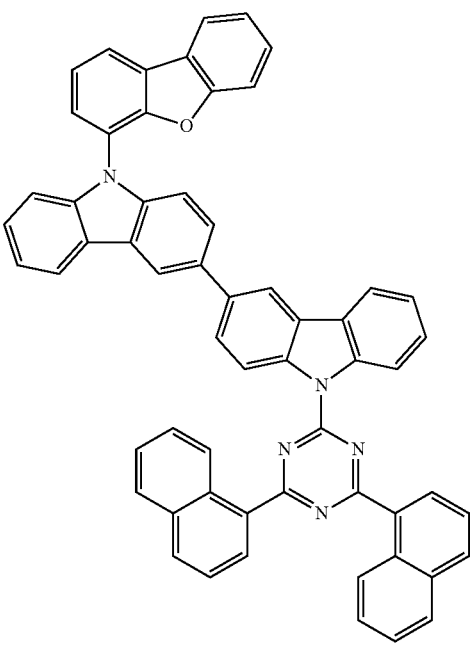

Compound 35
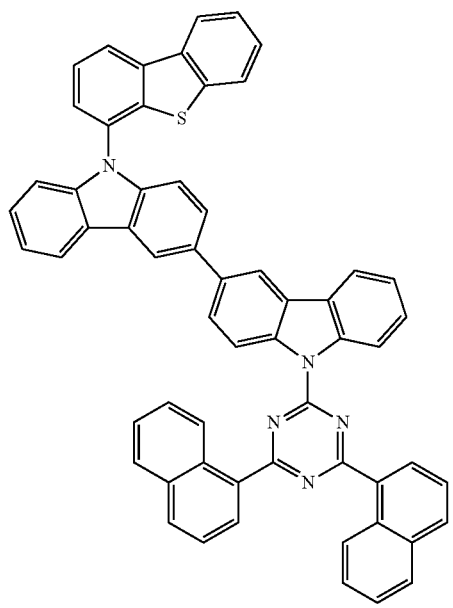
Compound 37
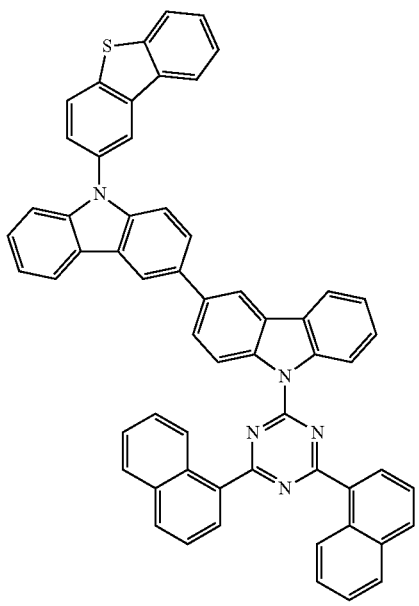
Compound 36
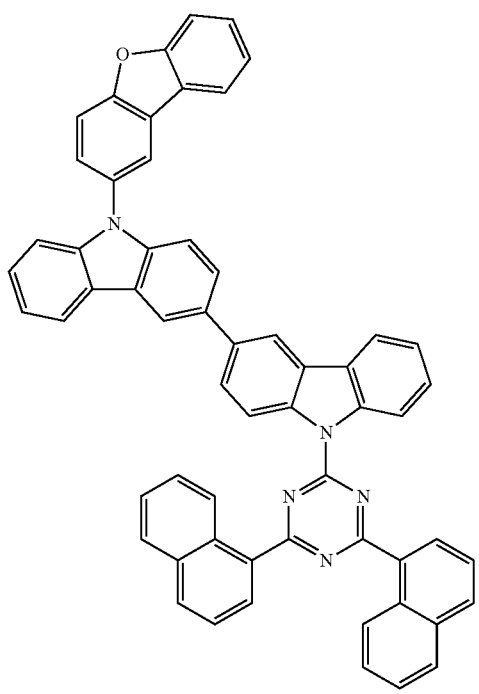
Compound 38
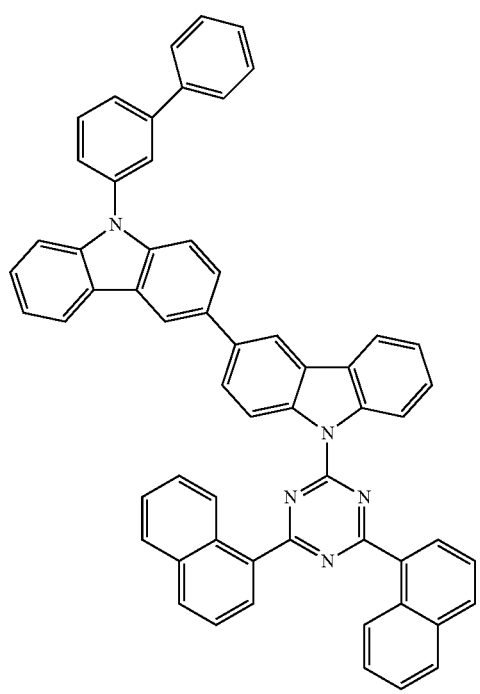

Compound 39
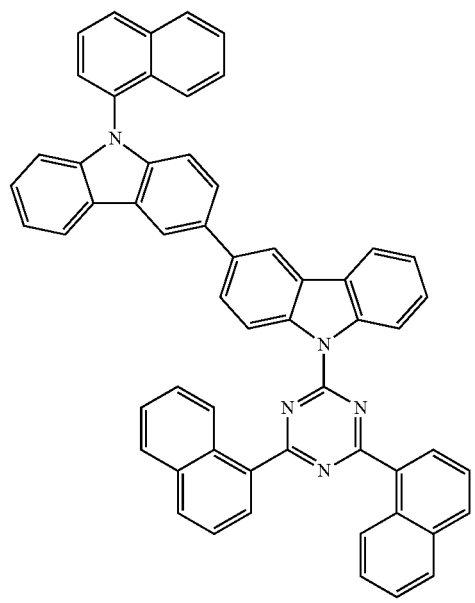
Compound 40
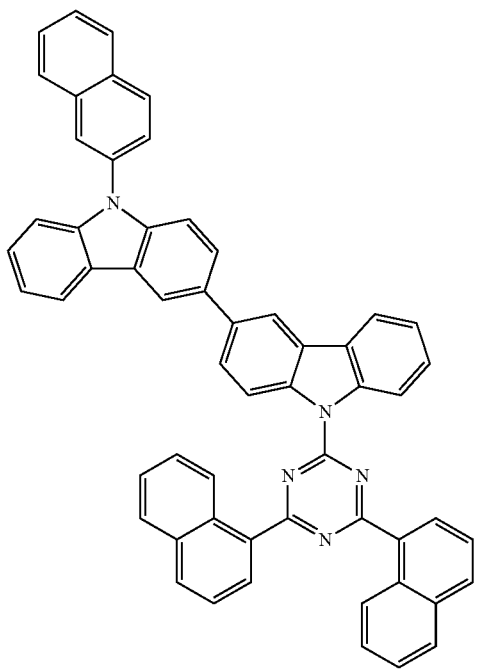
Compound 41
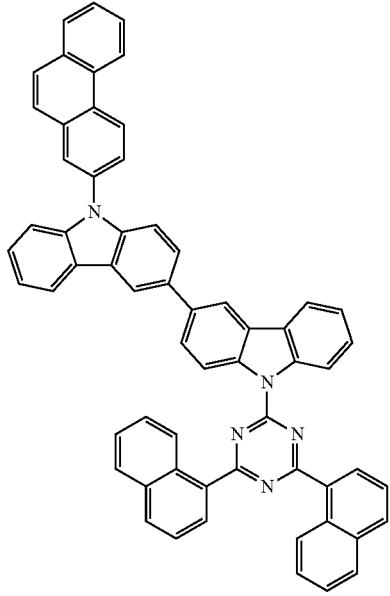
Compound 42
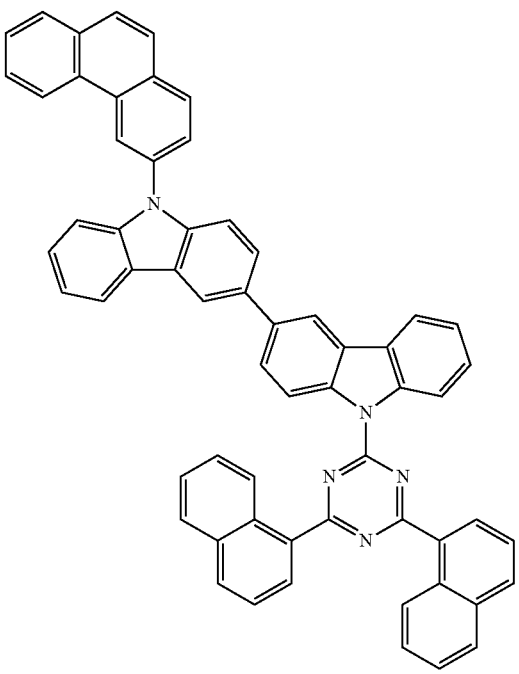

Compound 43
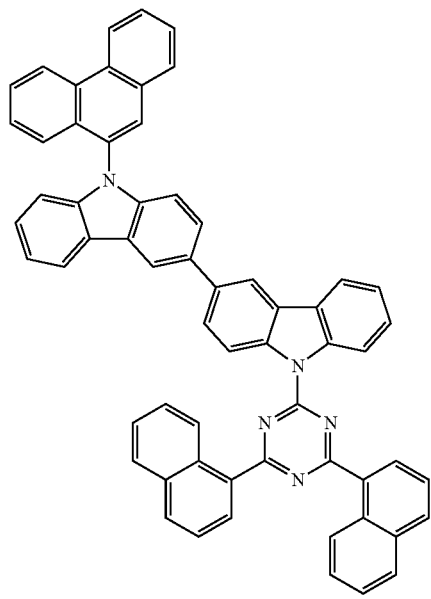
Compound 44
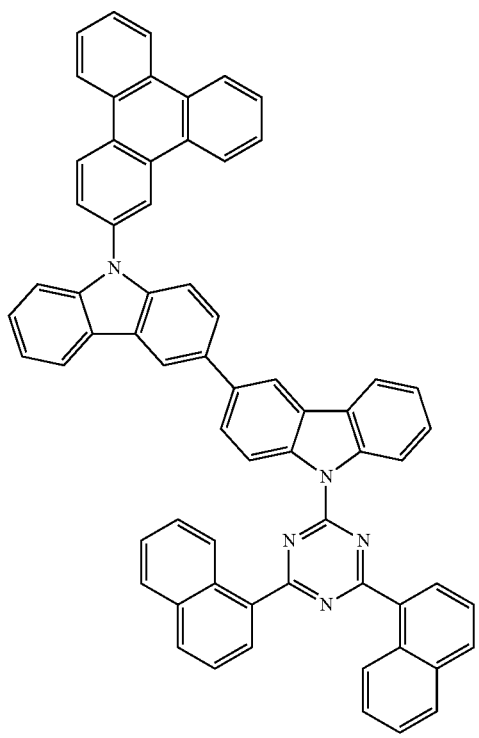
Compound 45
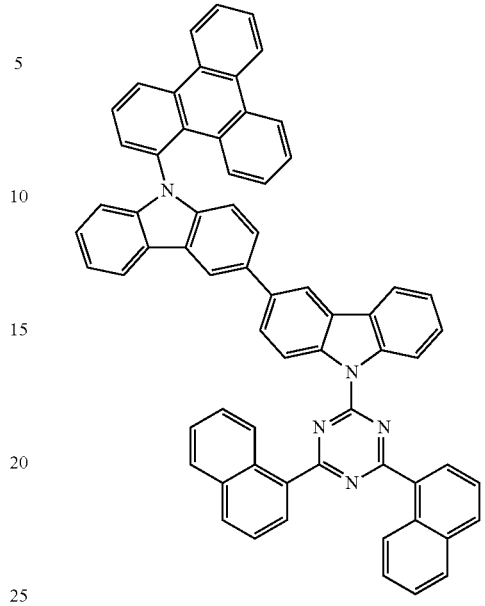
Compound 46
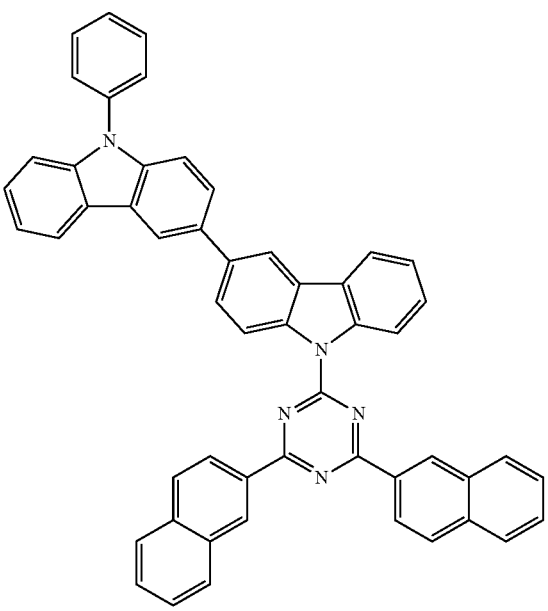

Compound 47
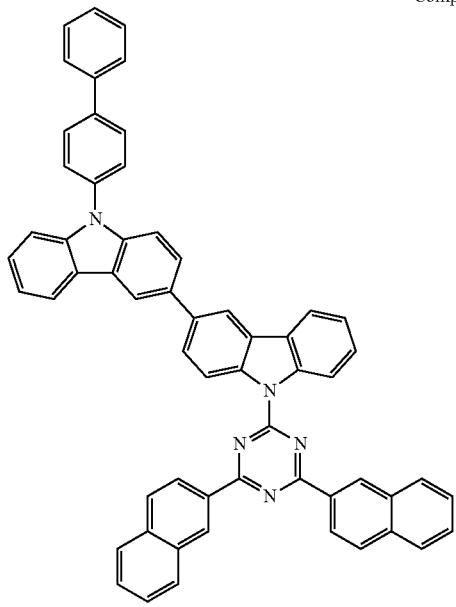
Compound 49
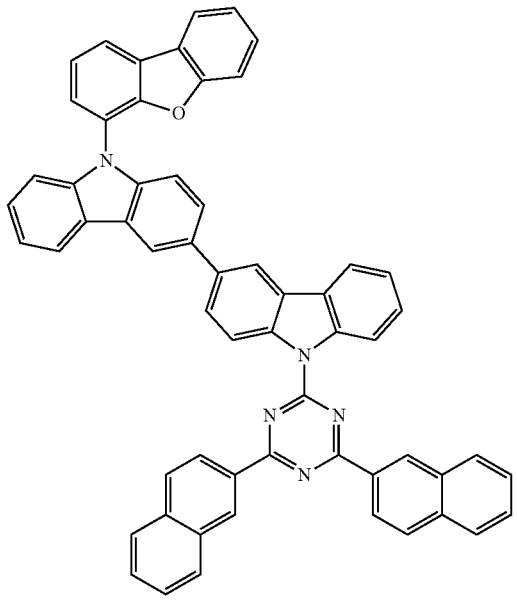
Compound 48
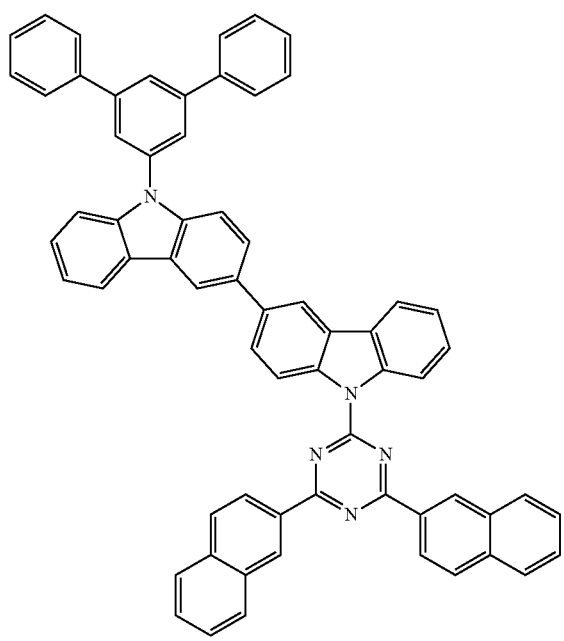
Compound 50
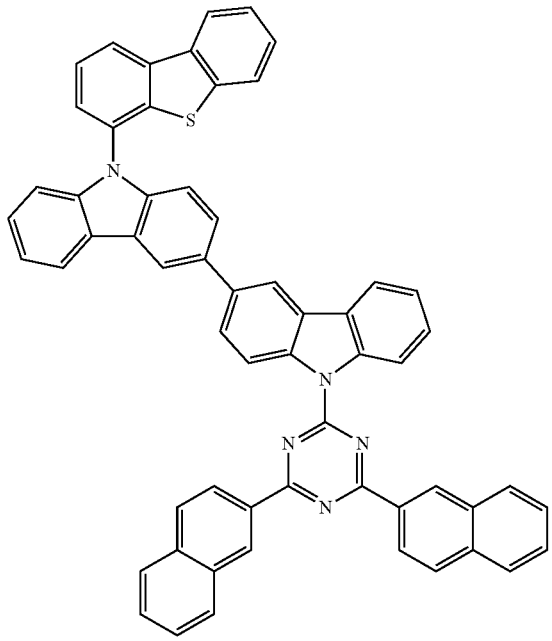

Compound 51
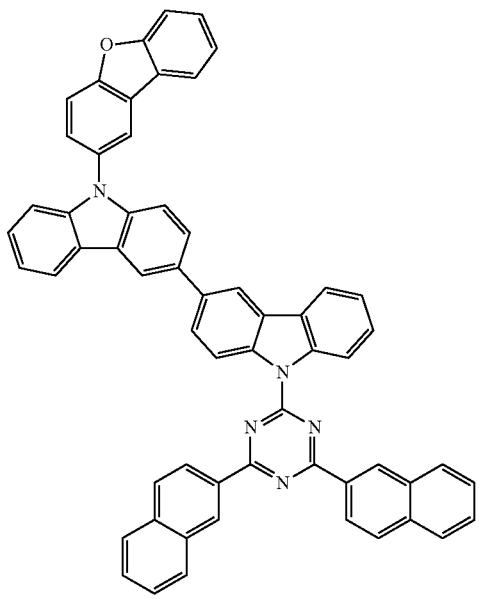
Compound 52
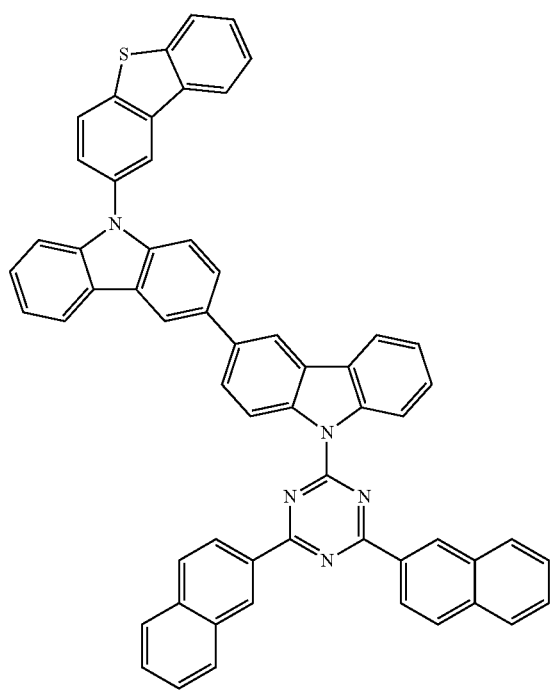
Compound 53
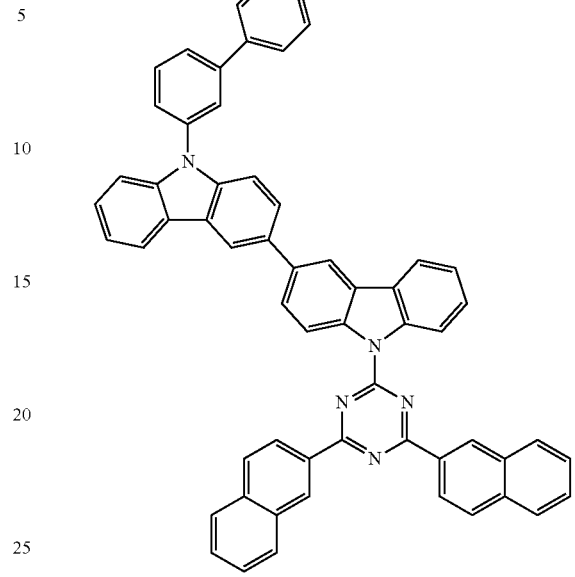
Compound 54
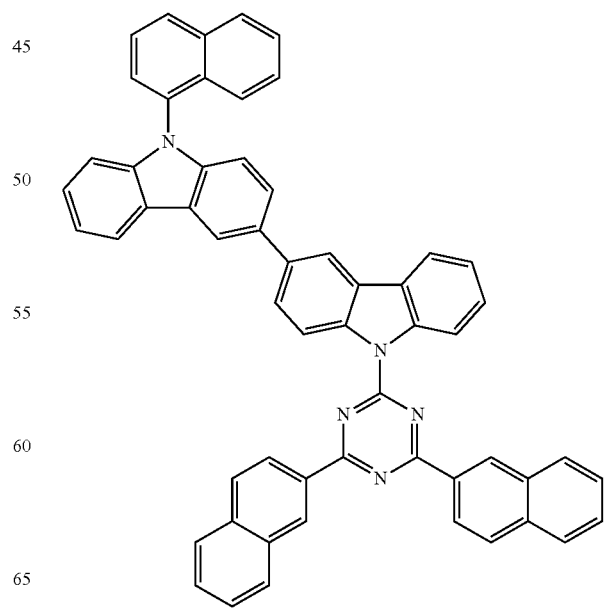

Compound 55
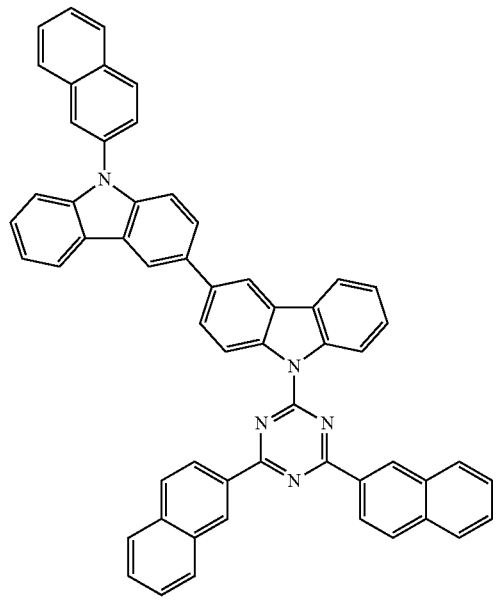
Compound 56
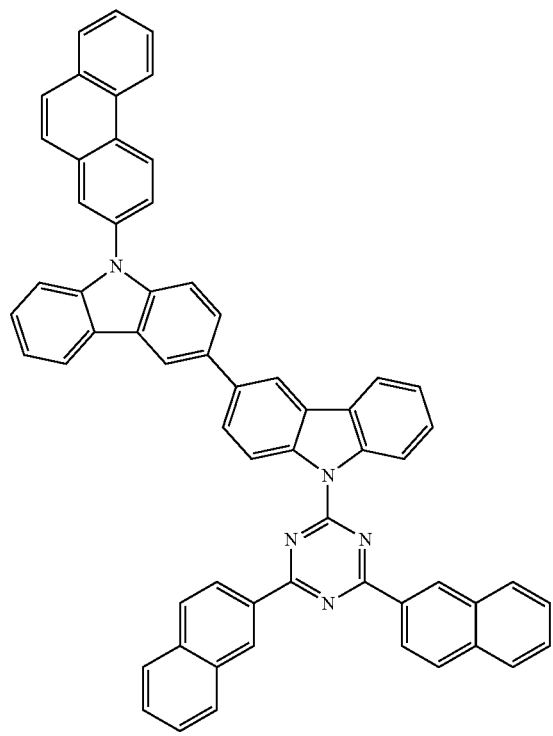
Compound 57
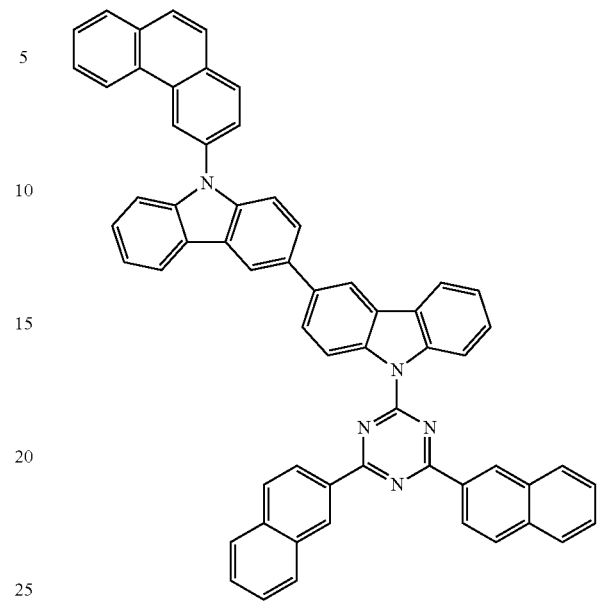
Compound 58
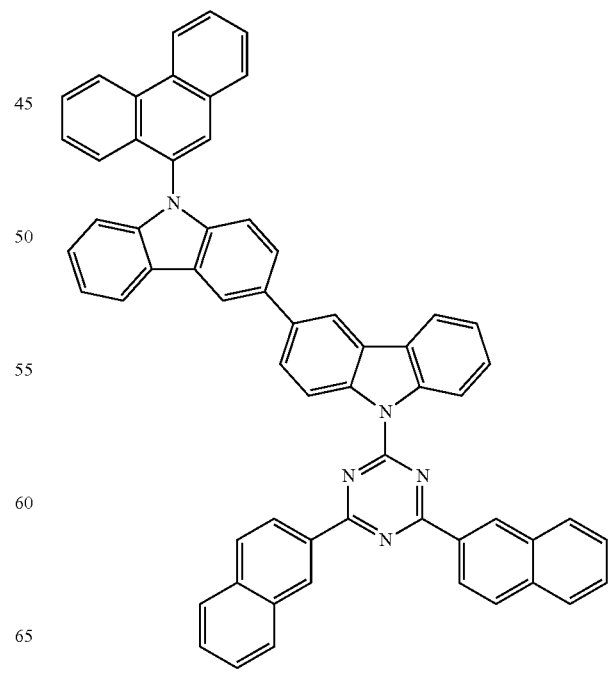

Compound 59
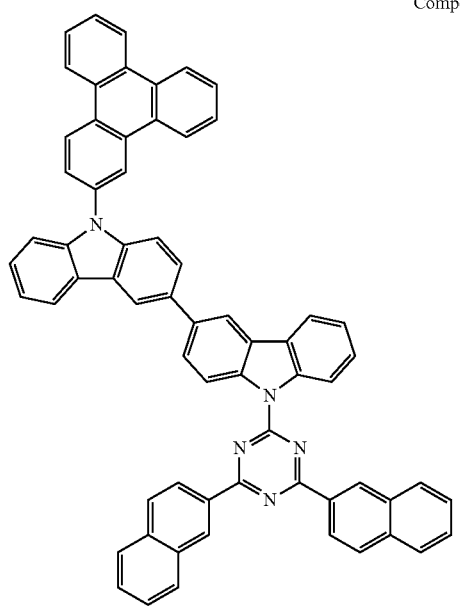
Compound 60
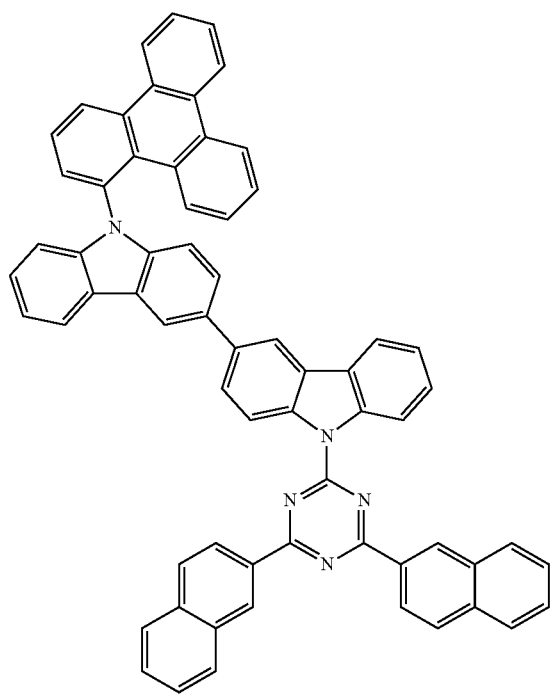
Compound 61
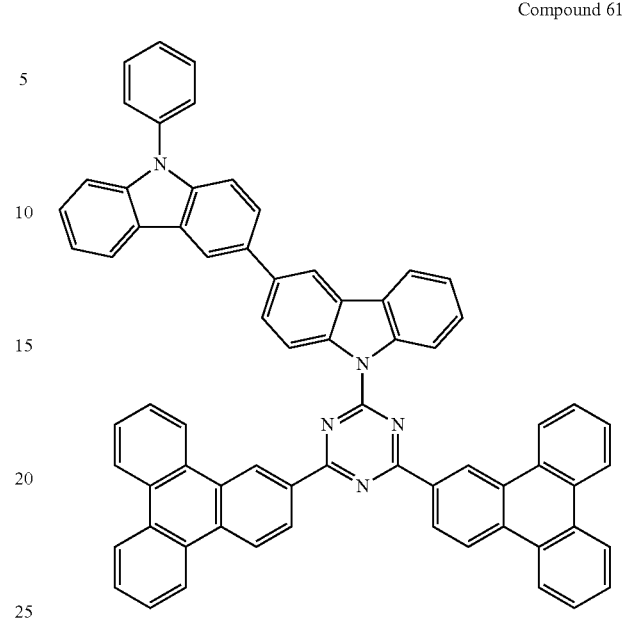
Compound 62
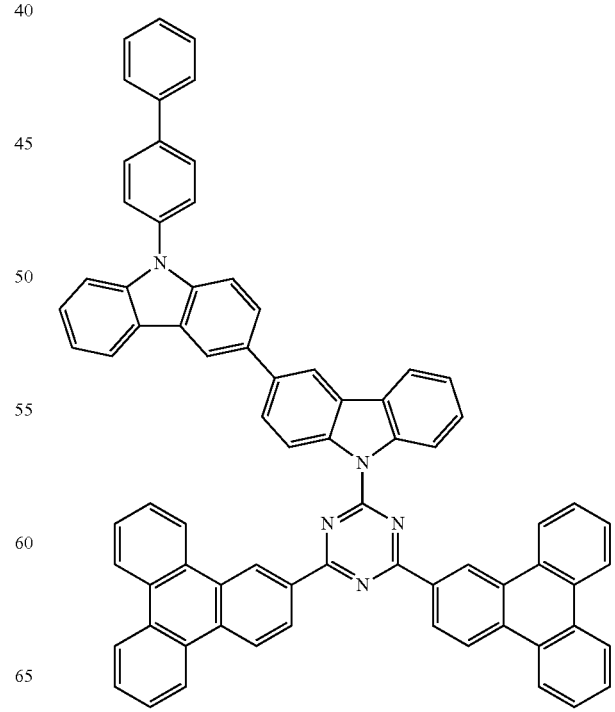

Compound 63
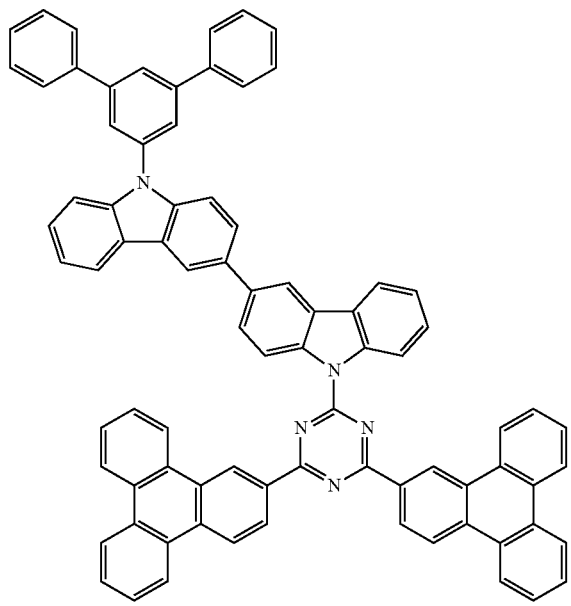
Compound 64
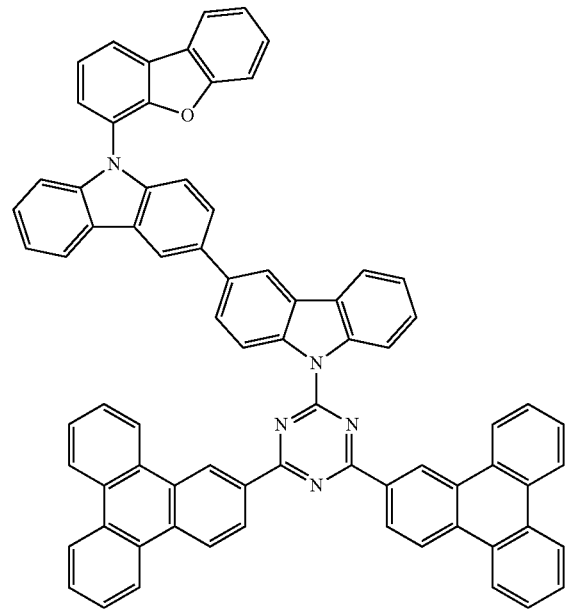
Compound 65
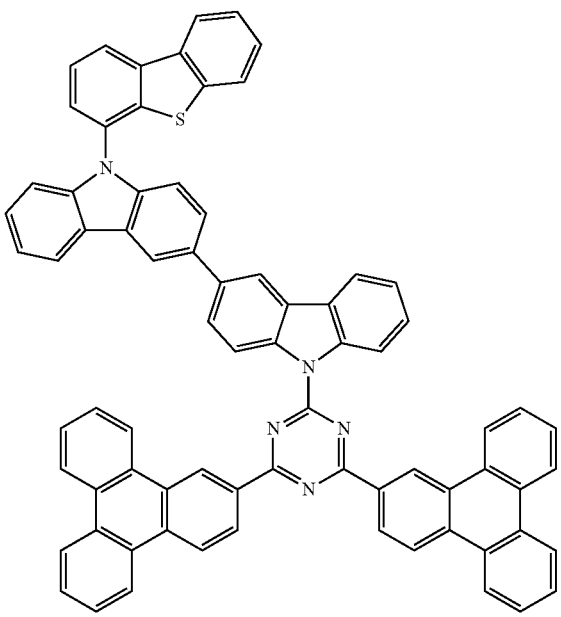
Compound 66
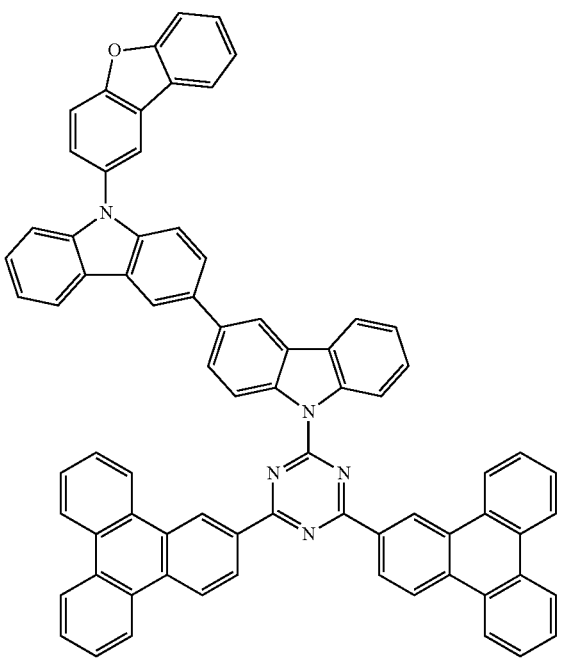

Compound 67
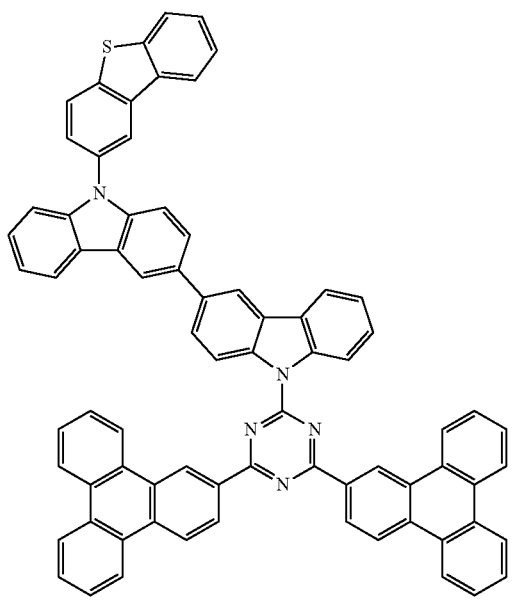
Compound 68
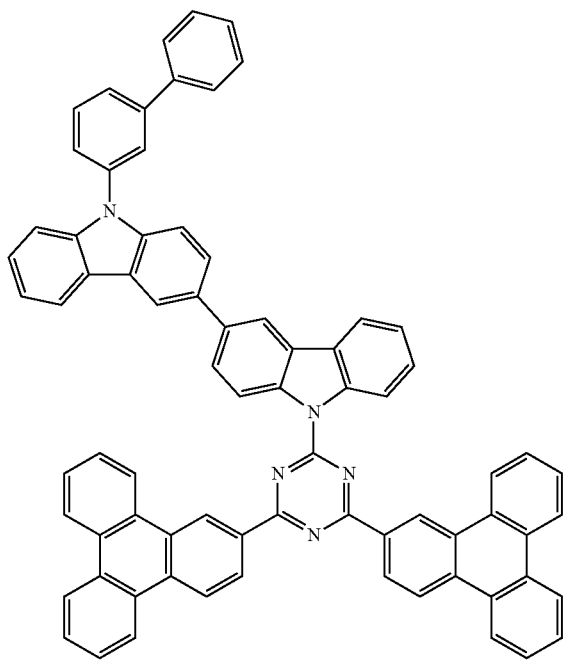
Compound 69
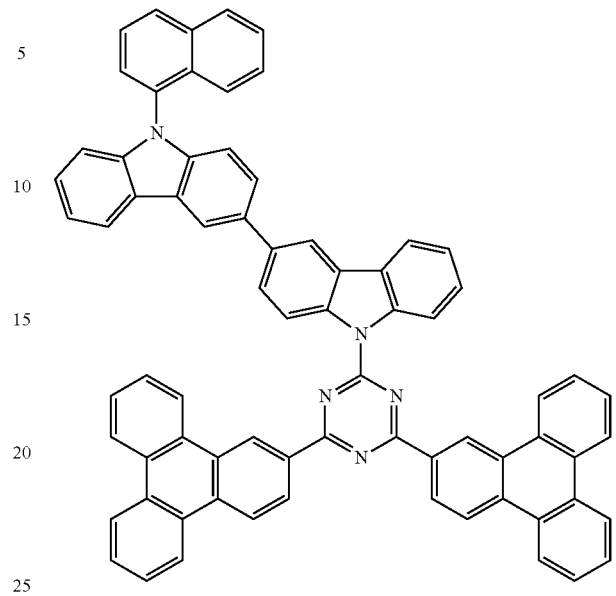
Compound 70

Compound 71
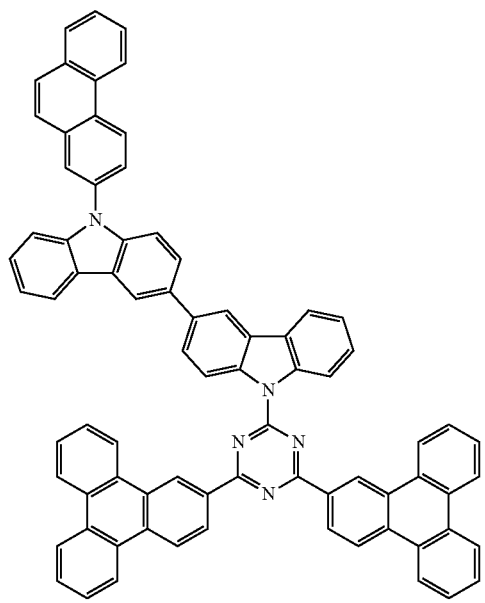
Compound 72
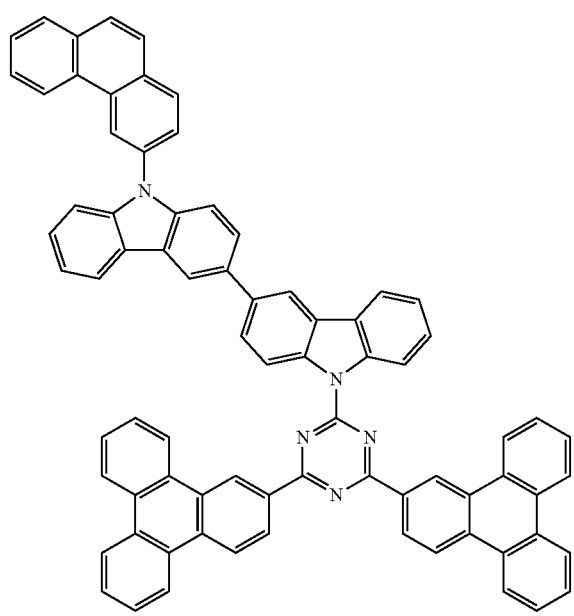
Compound 73
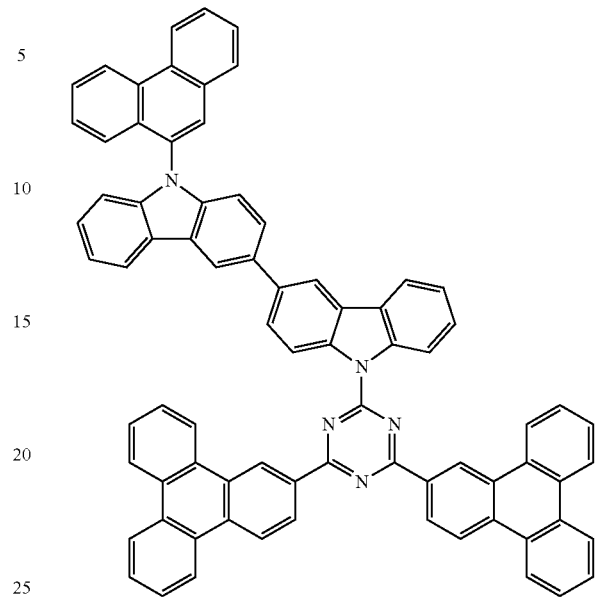
Compound 74

Compound 75
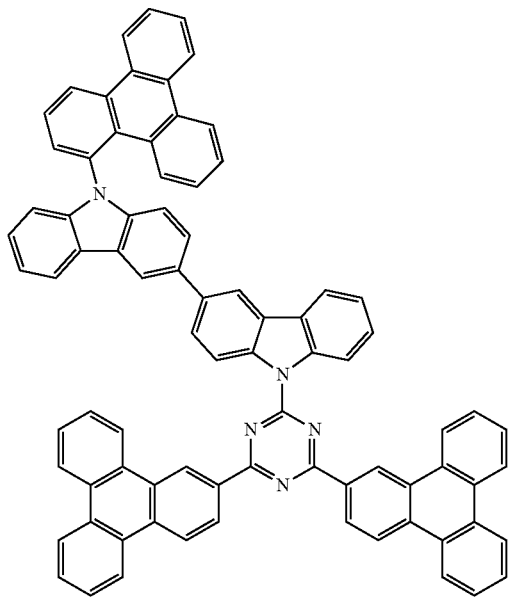
Compound 77
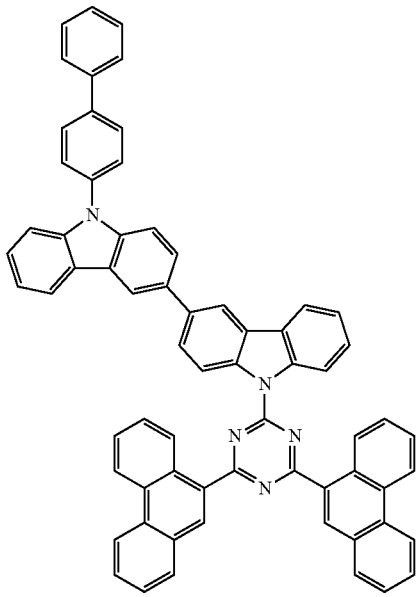
Compound 76
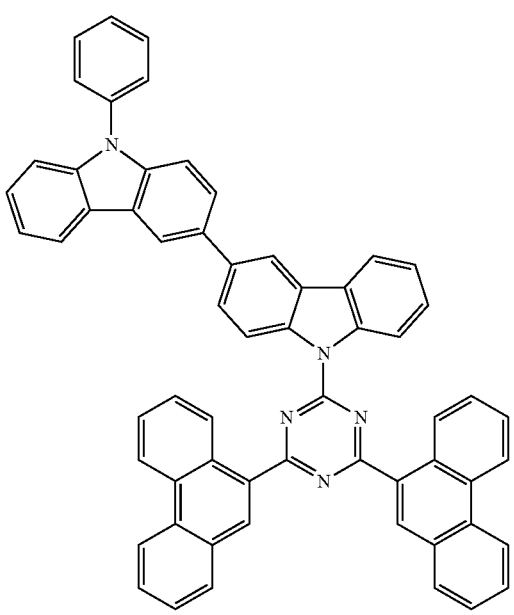
Compound 78
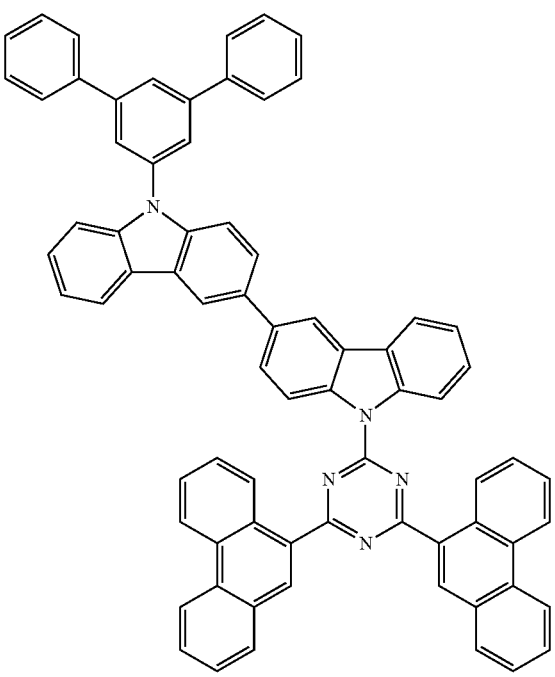

Compound 79
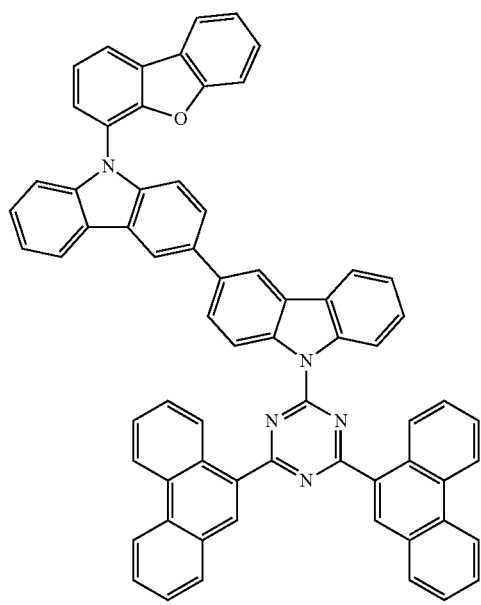
Compound 81
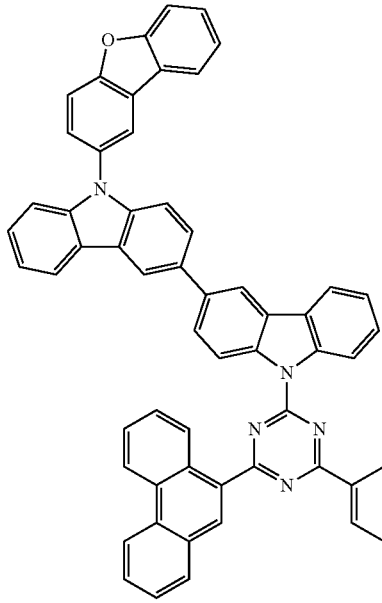
Compound 80
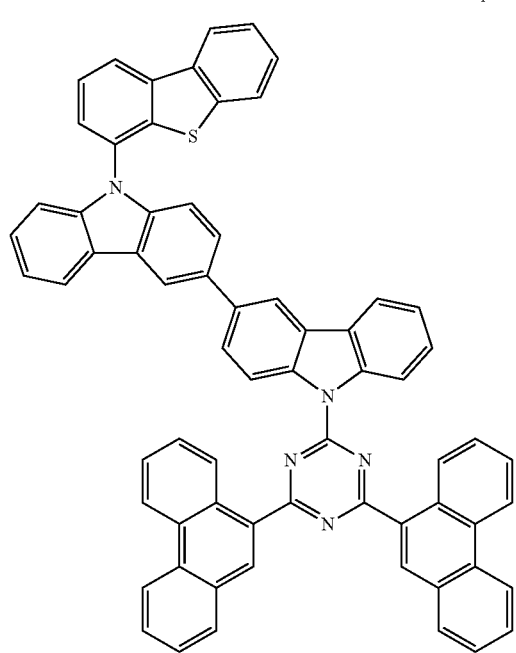
Compound 82
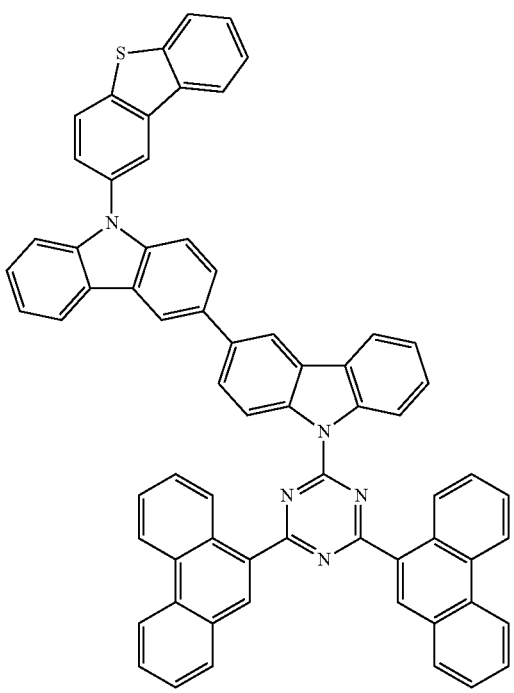

Compound 83
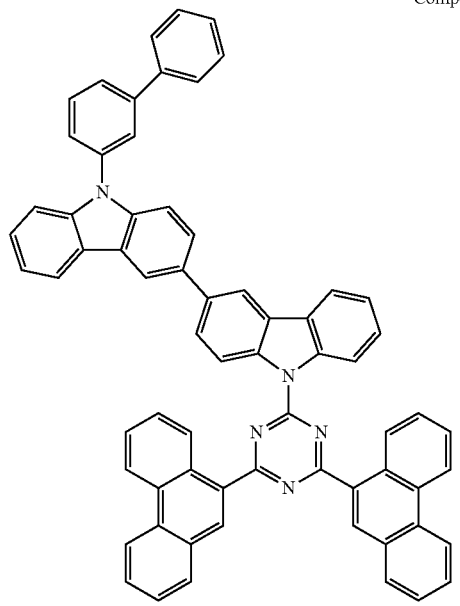
Compound 85
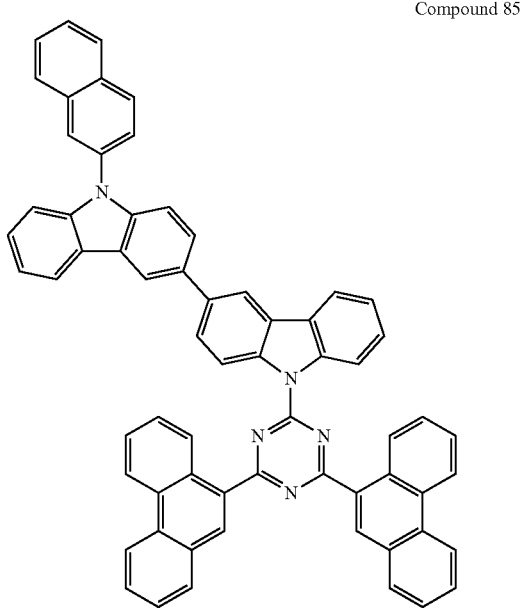
Compound 84
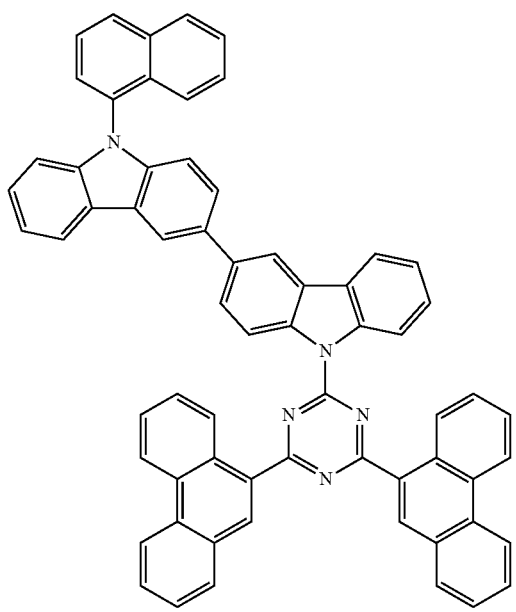
Compound 86
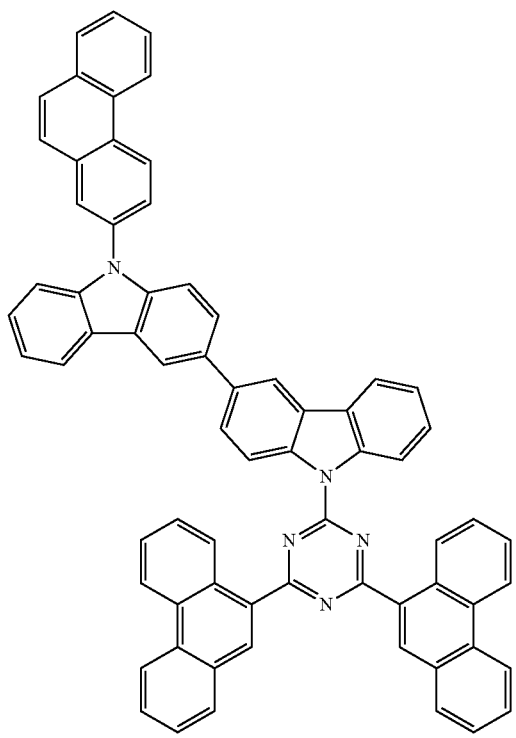

Compound 87
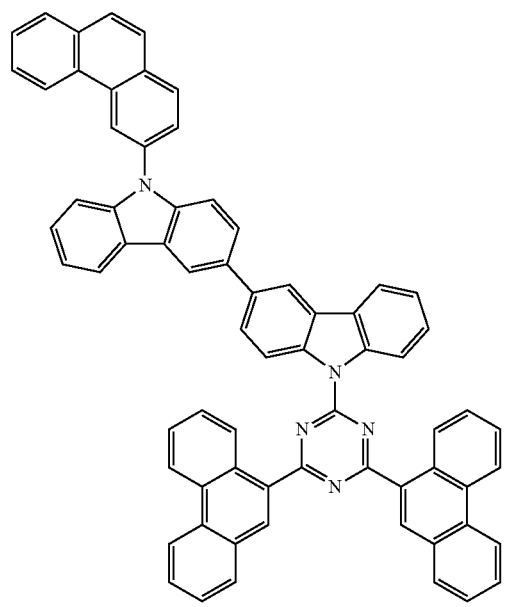
Compound 89
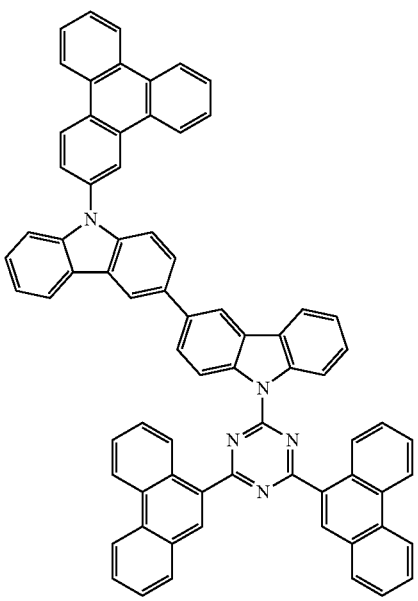
Compound 88
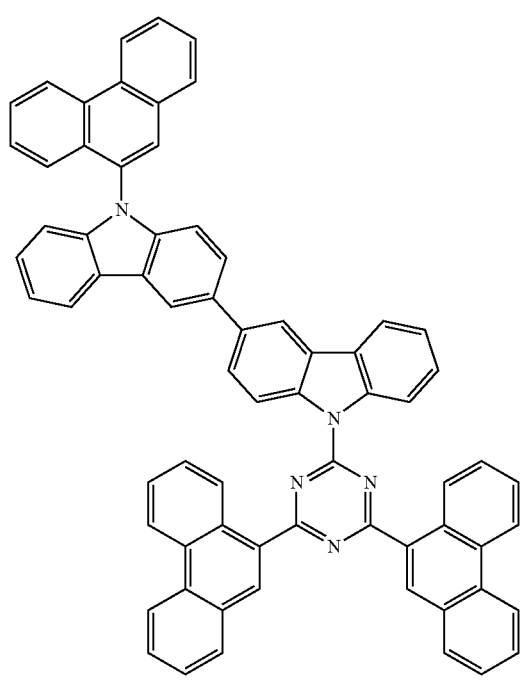
Compound 90
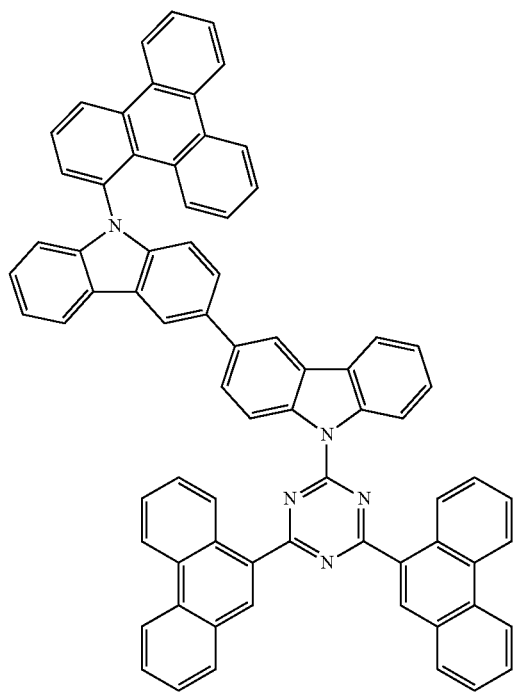

Compound 91
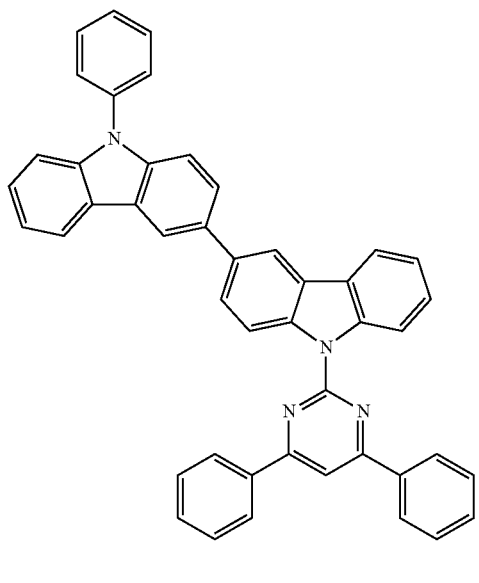
Compound 93
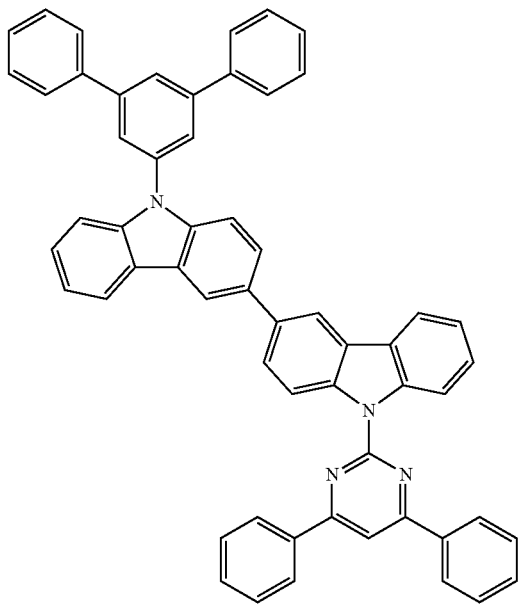
Compound 92
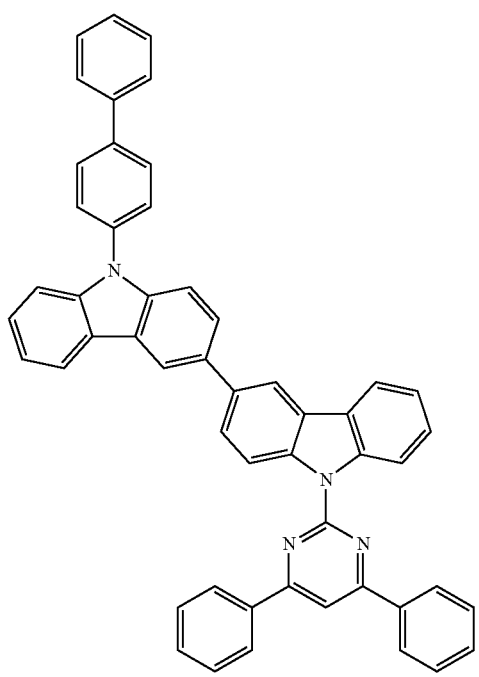
Compound 94
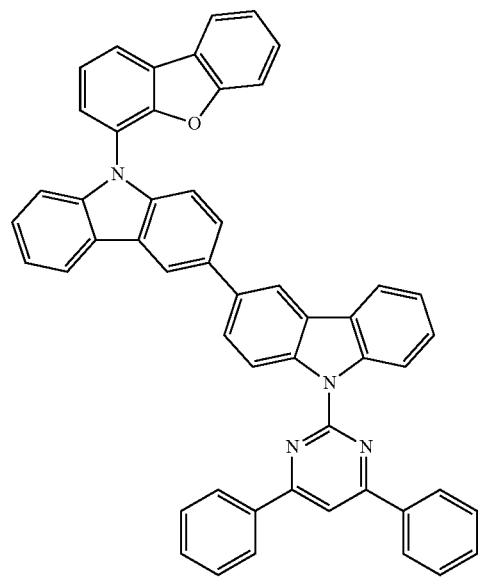

Compound 95
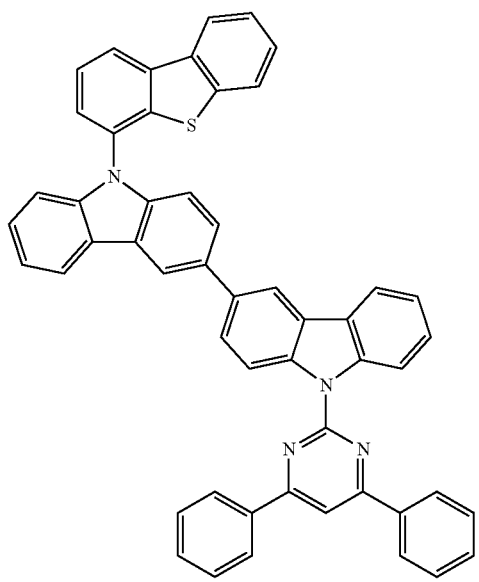
Compound 97
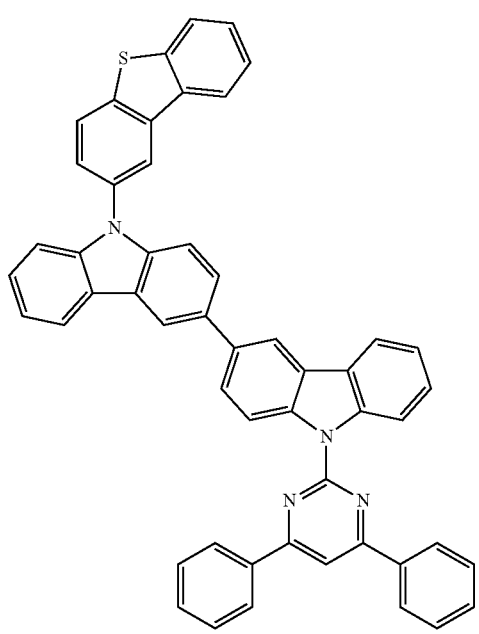
Compound 96
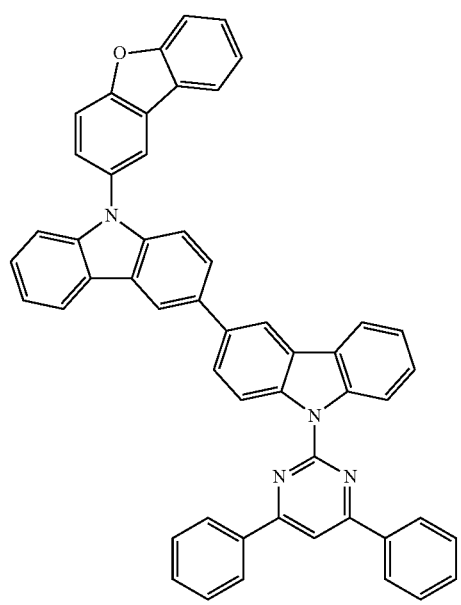
Compound 98
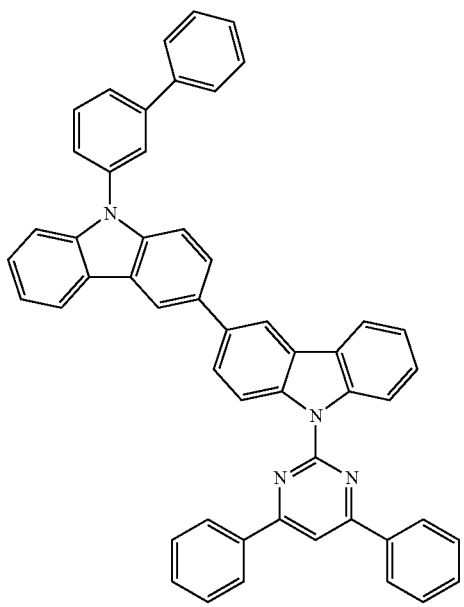

Compound 99
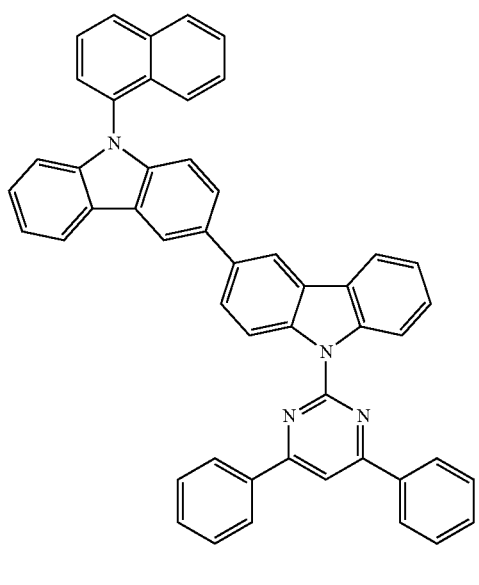
Compound 100
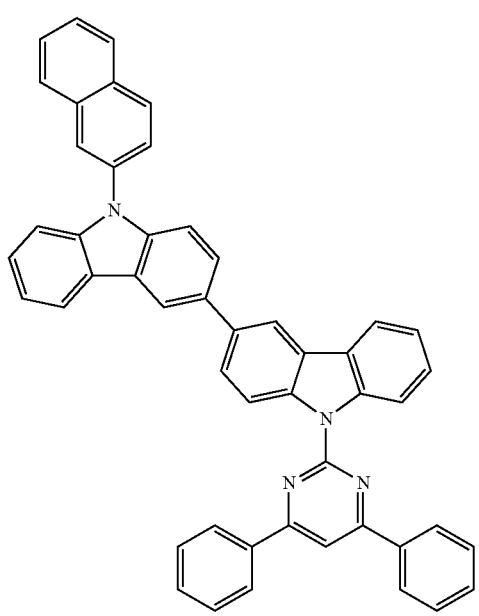
Compound 101
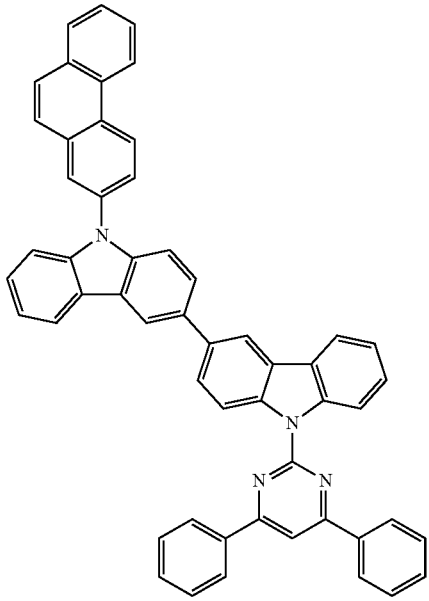
Compound 102

Compound 103
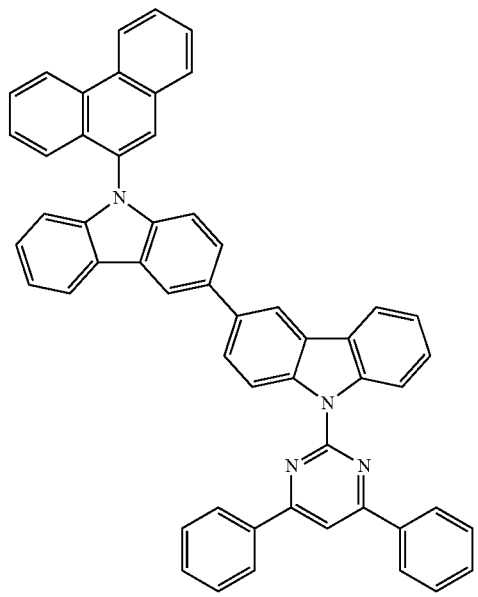
Compound 104
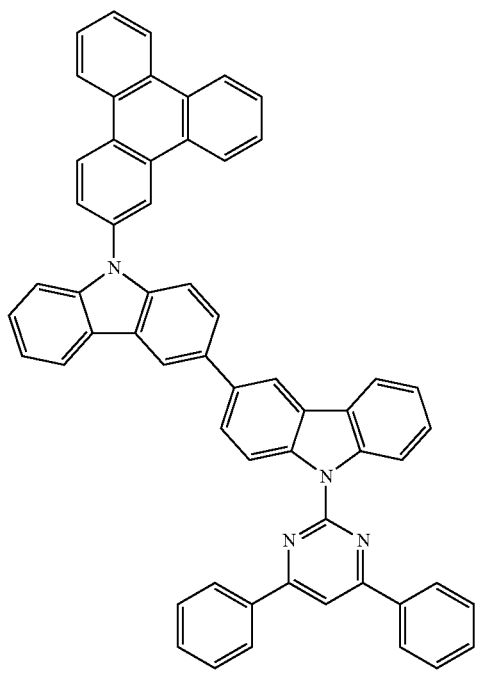
Compound 105
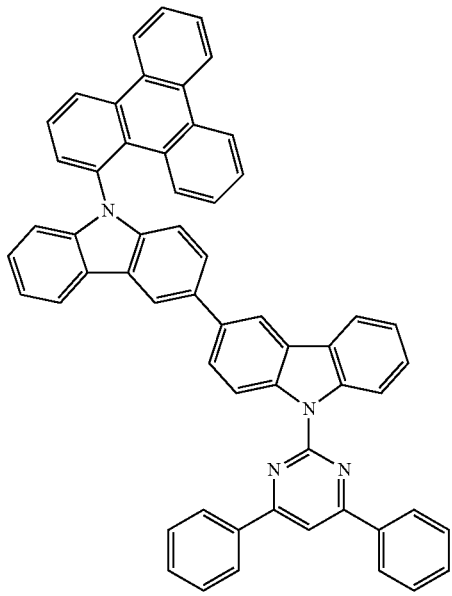
Compound 106
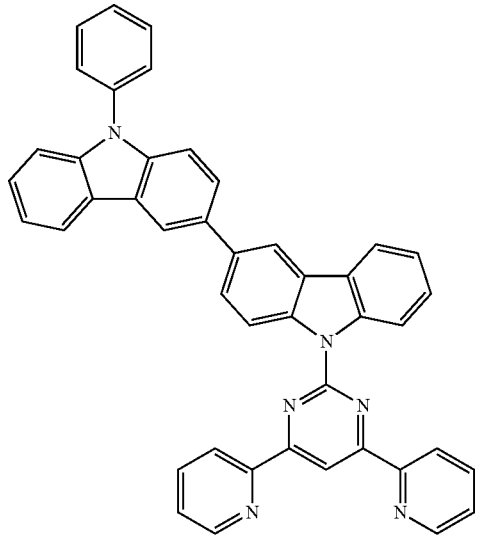

Compound 107
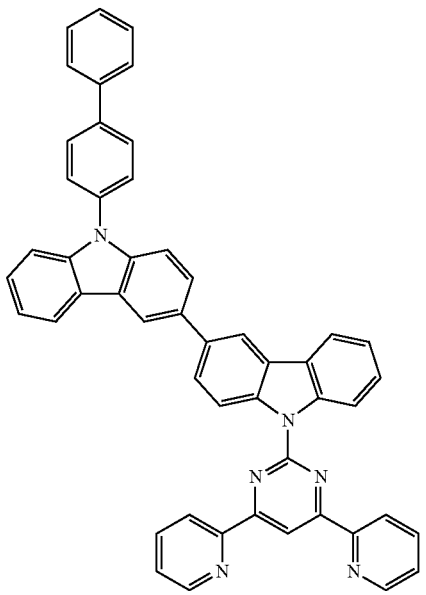
Compound 108
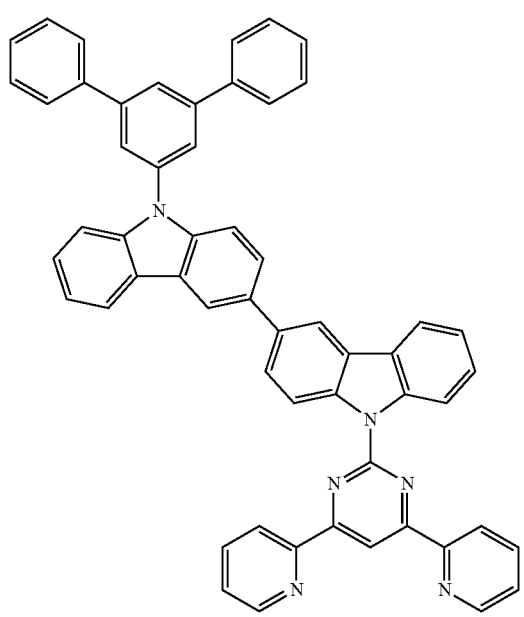
Compound 109
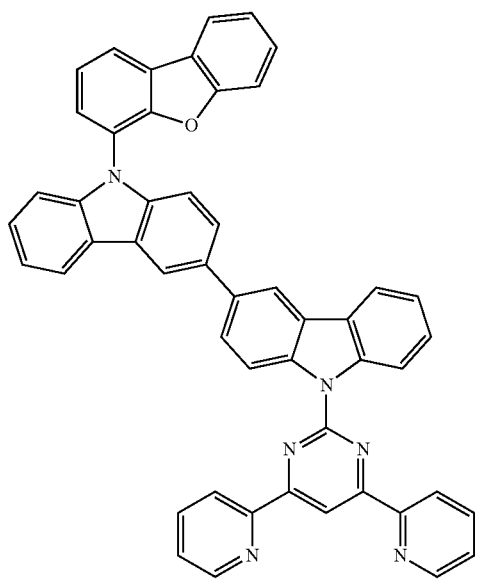
Compound 110
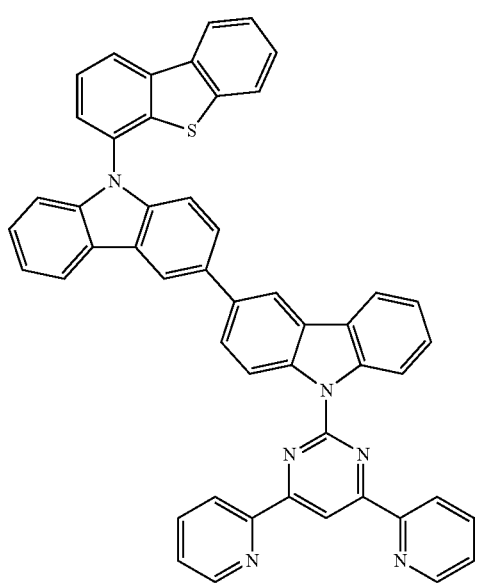

Compound 111
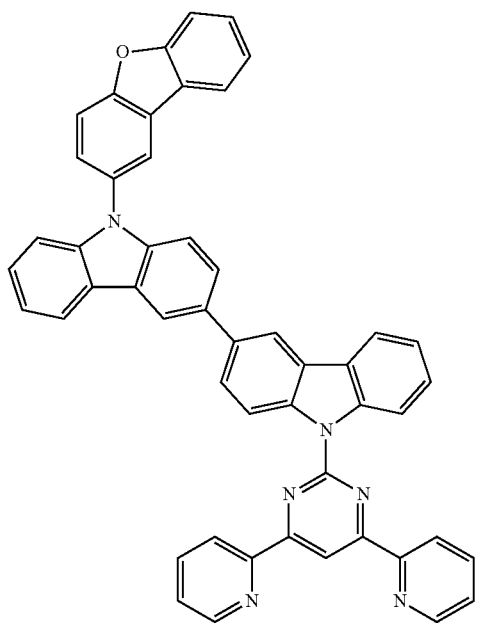
Compound 113
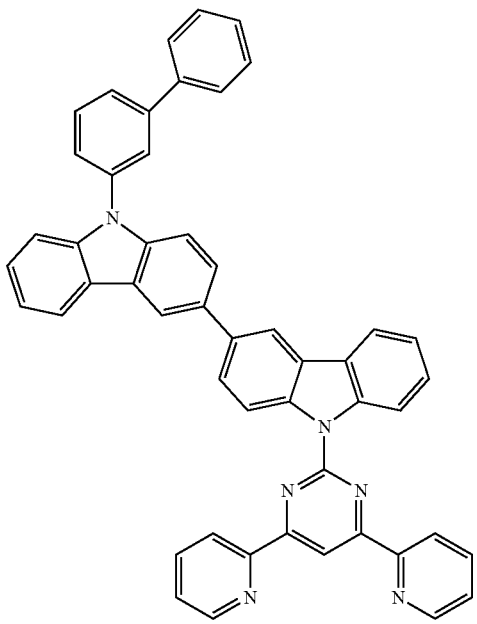
Compound 112
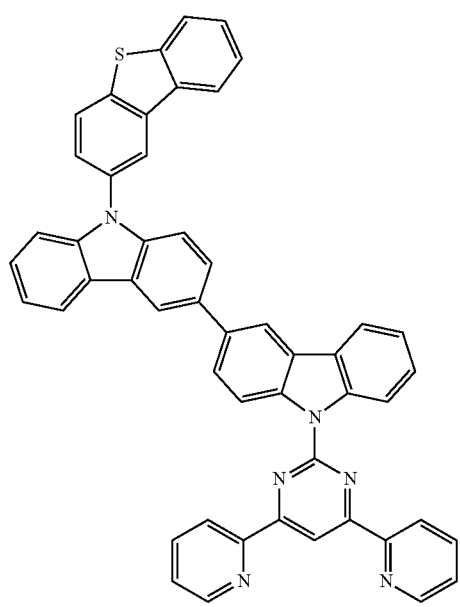
Compound 114
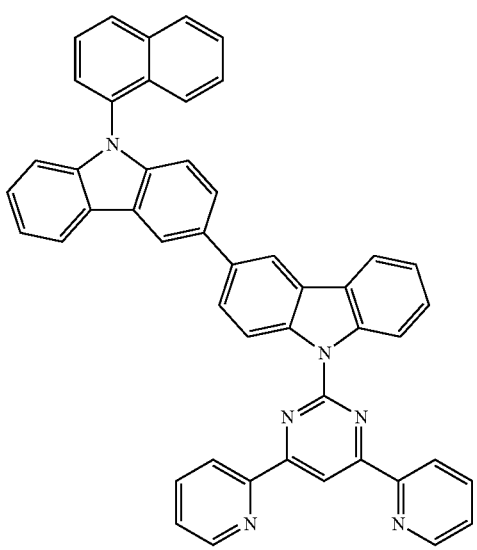

Compound 115
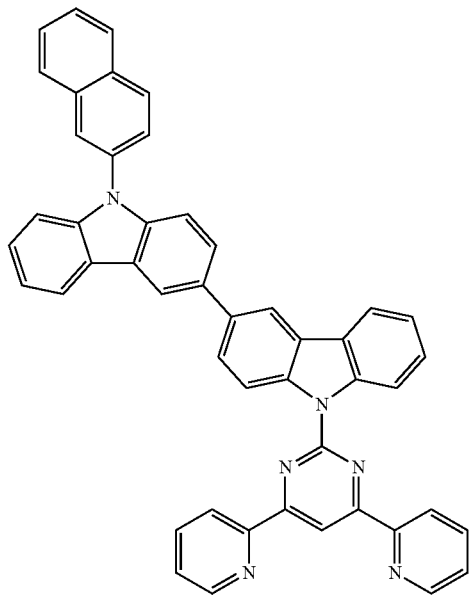
Compound 116
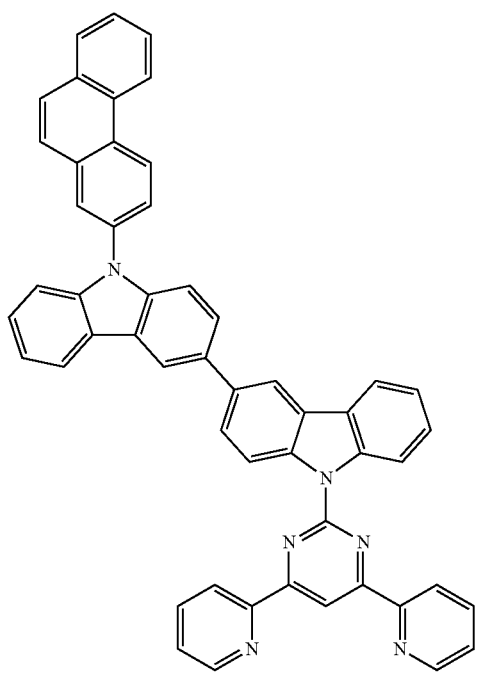
Compound 117
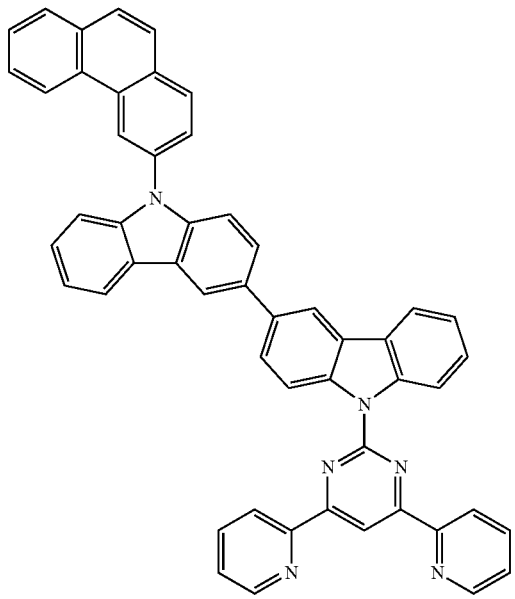
Compound 118
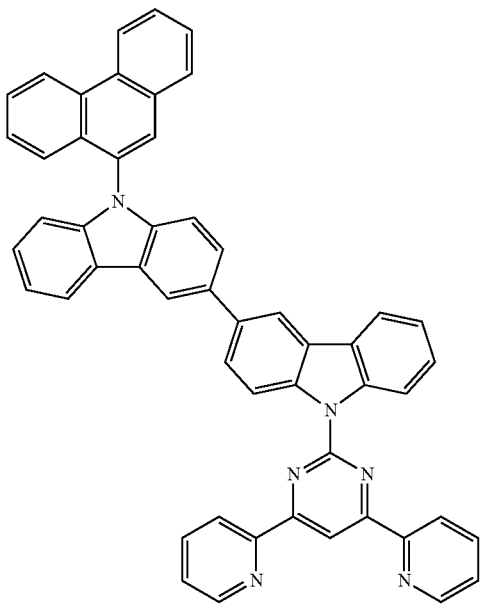

Compound 119
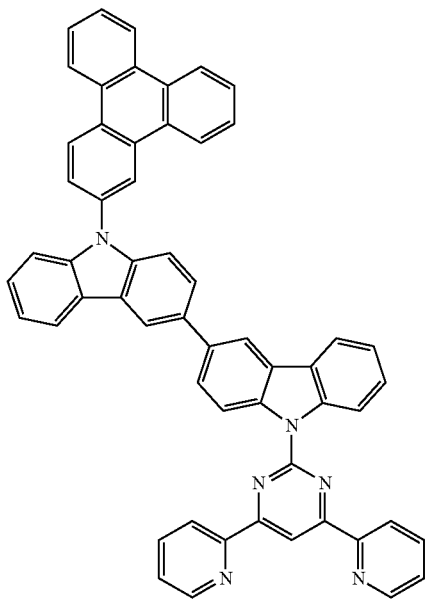
Compound 120
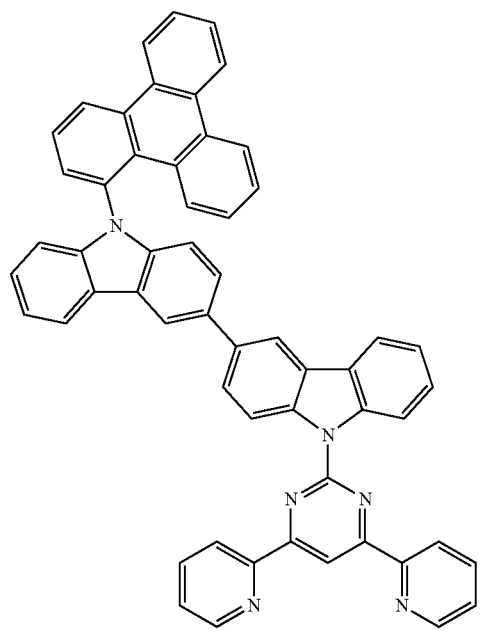
Compound 121
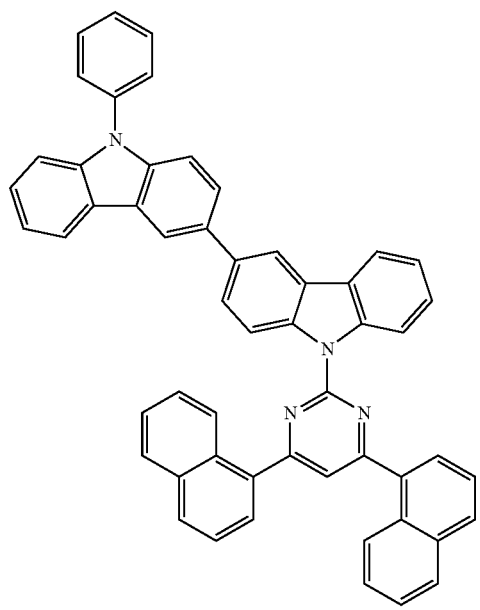
Compound 122
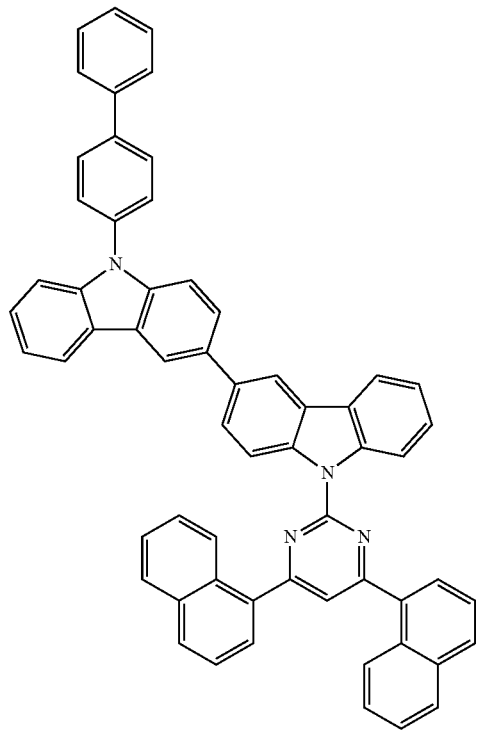

Compound 123
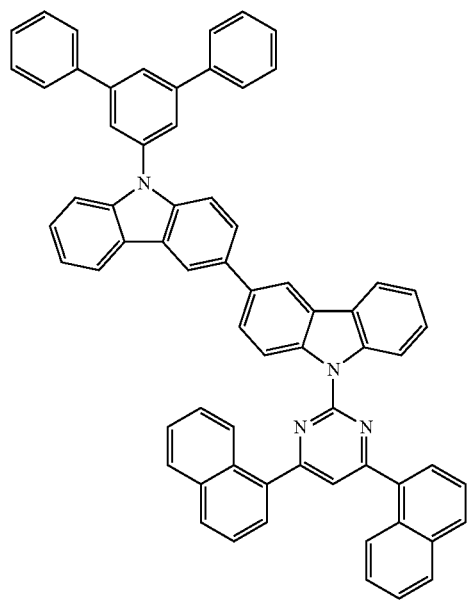
Compound 124
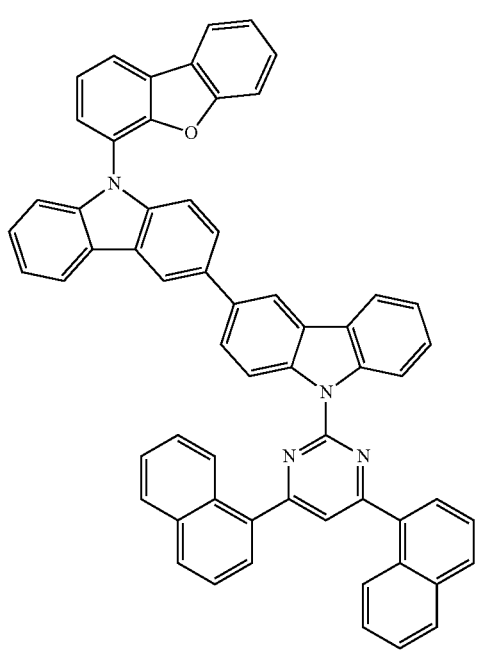
Compound 125
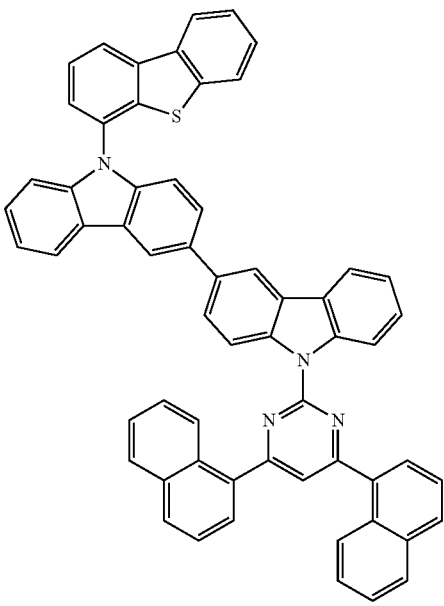
Compound 126
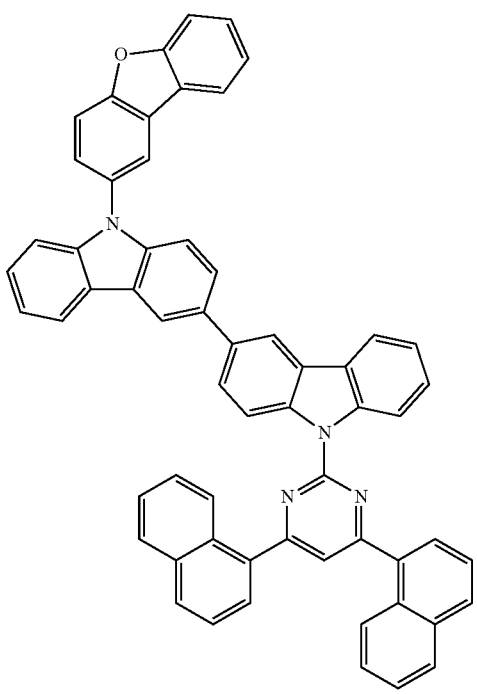

Compound 127
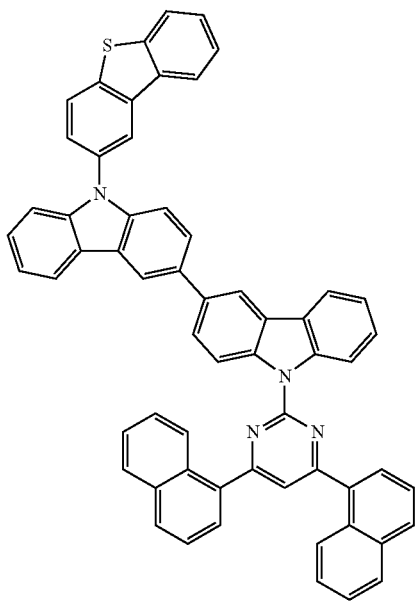
Compound 128
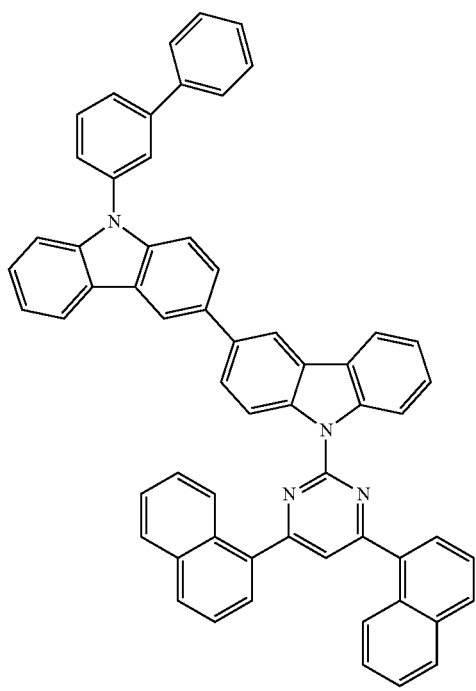
Compound 129
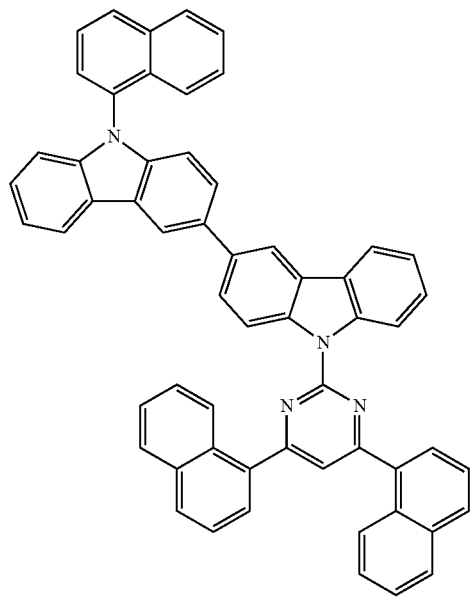
Compound 130
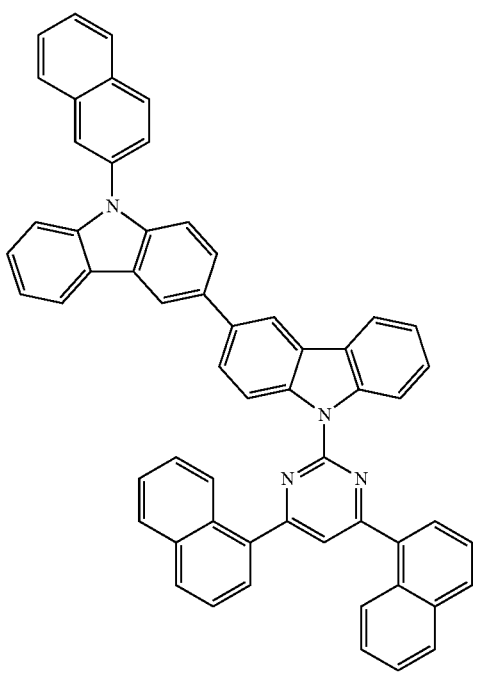

Compound 131
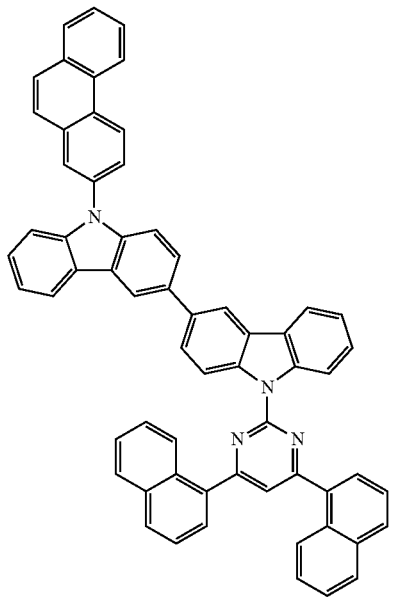
Compound 132
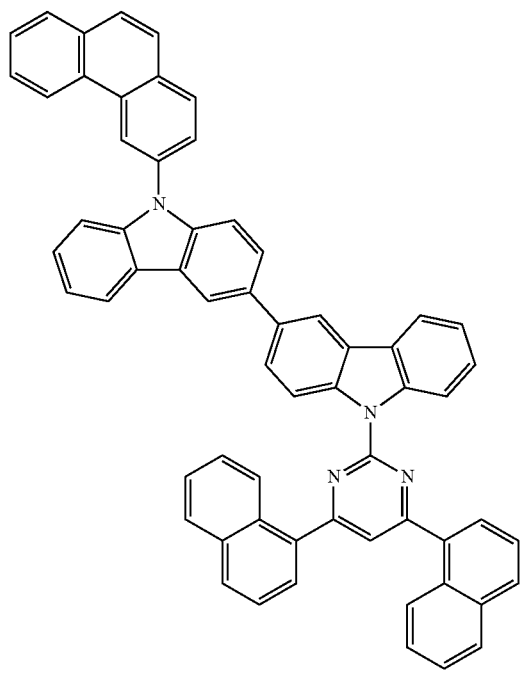
Compound 133
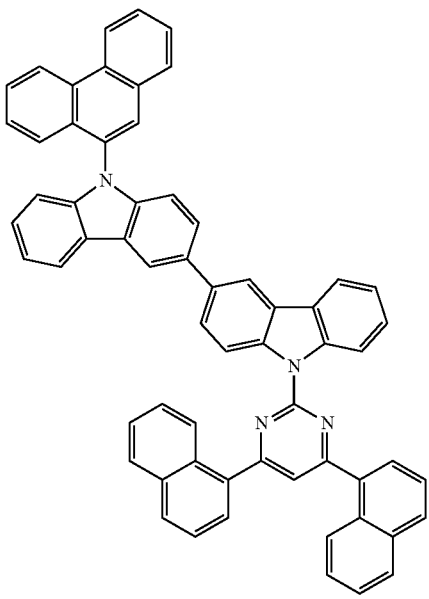
Compound 134
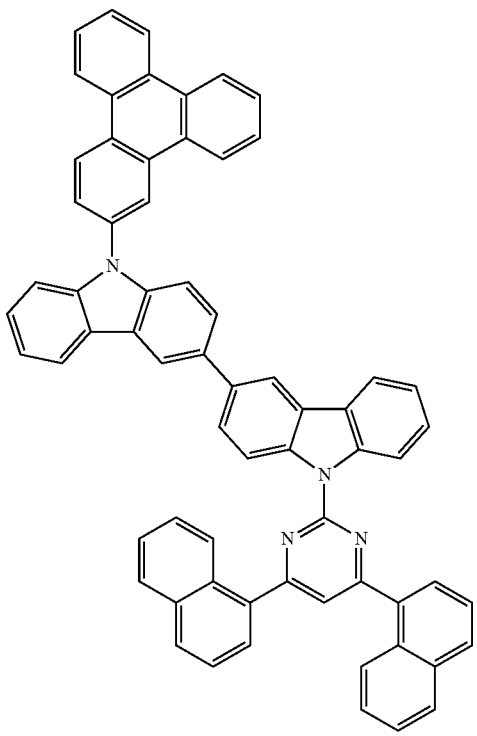

Compound 135
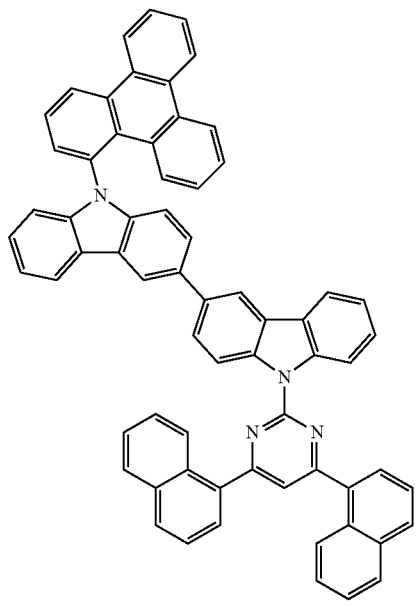
Compound 136
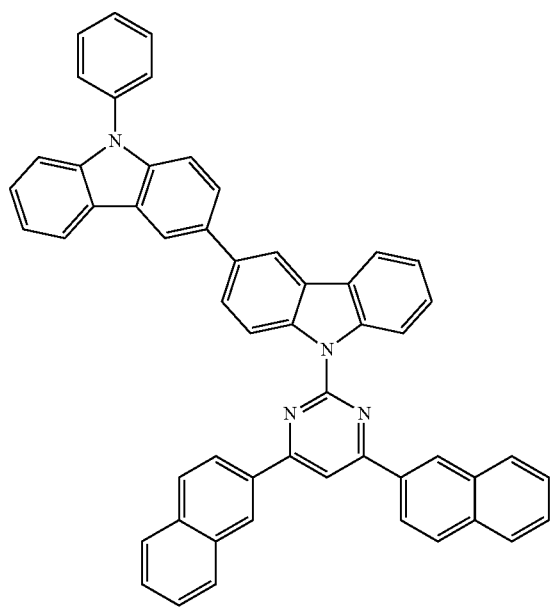
Compound 137
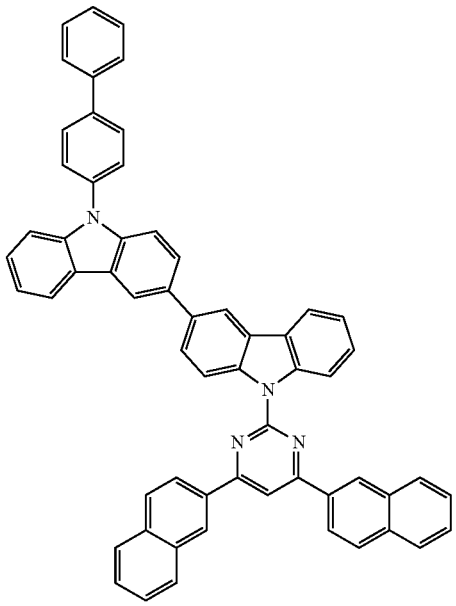
Compound 138
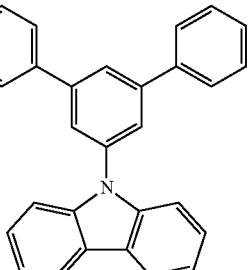
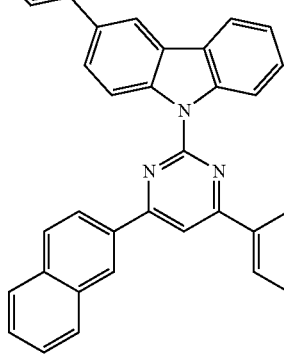

Compound 139
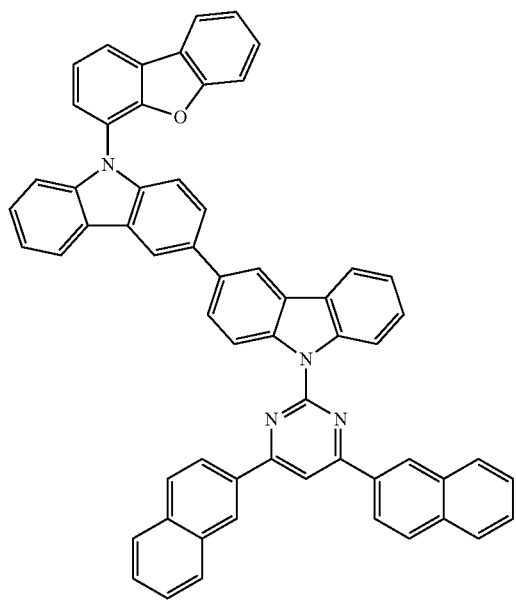
Compound 141
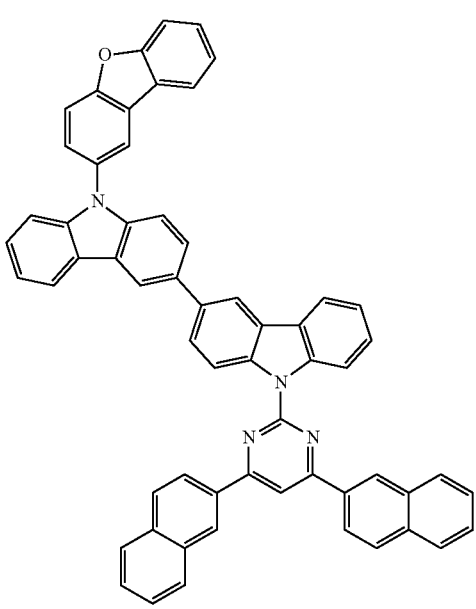
Compound 140
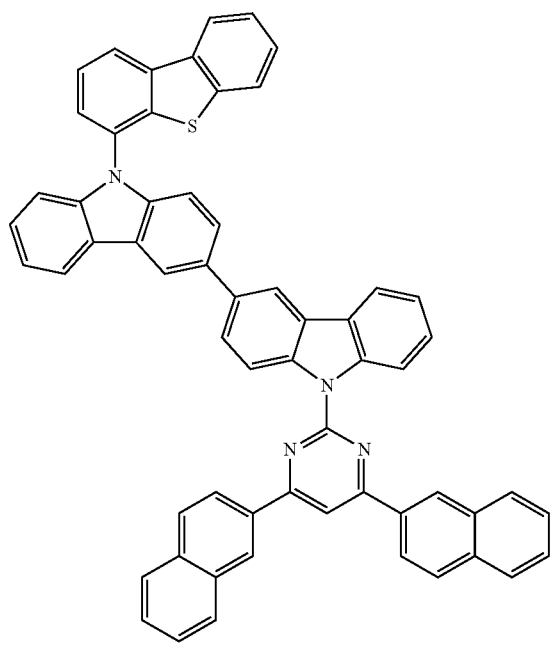
Compound 142
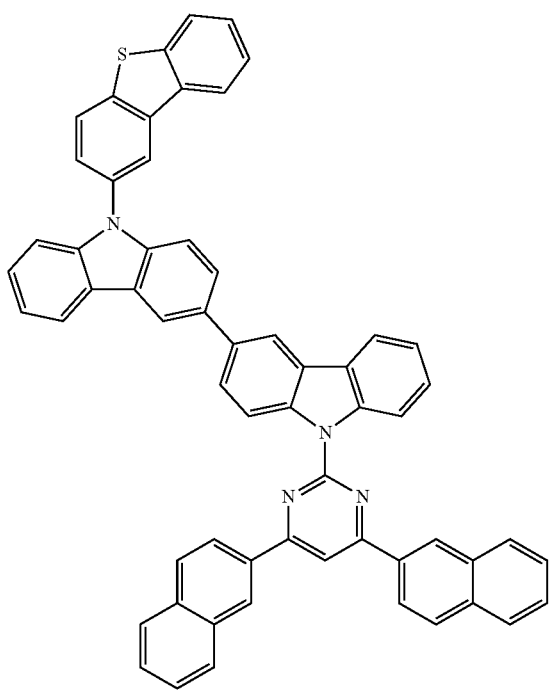

Compound 143
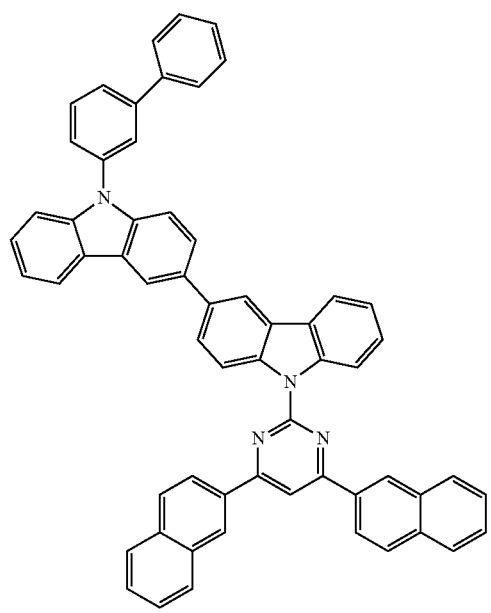
Compound 144
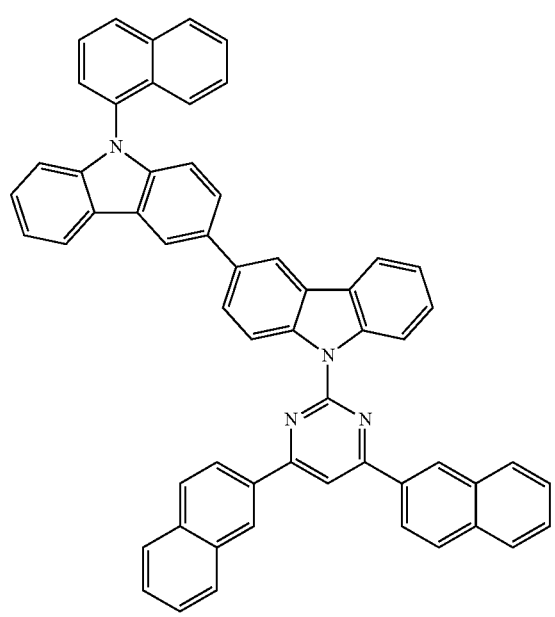
Compound 145
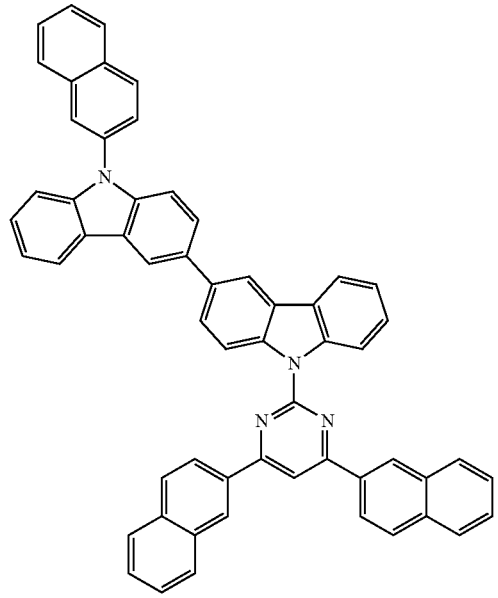
Compound 146
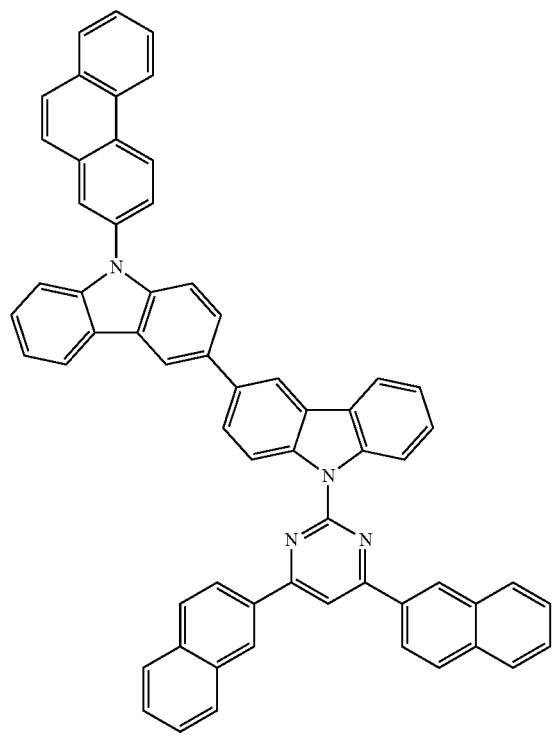

Compound 147
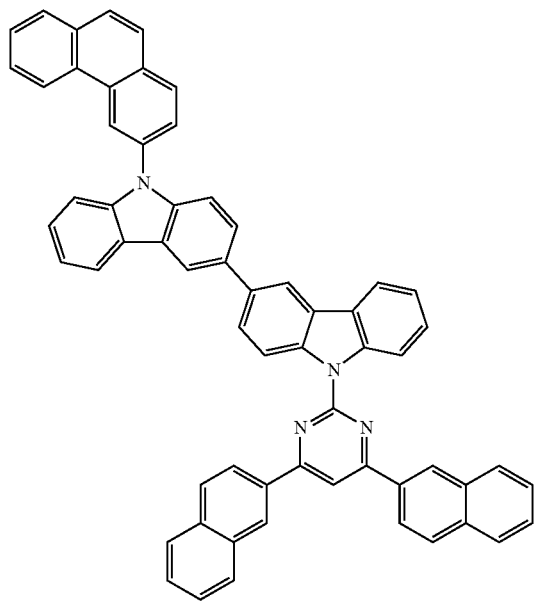
Compound 148
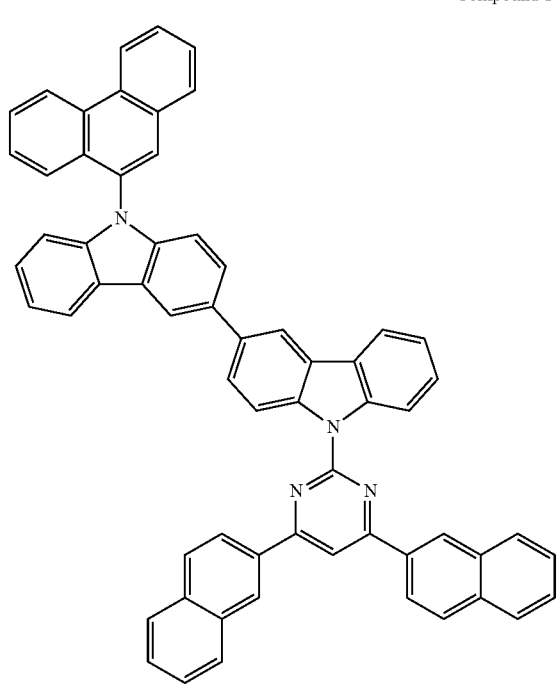
Compound 149
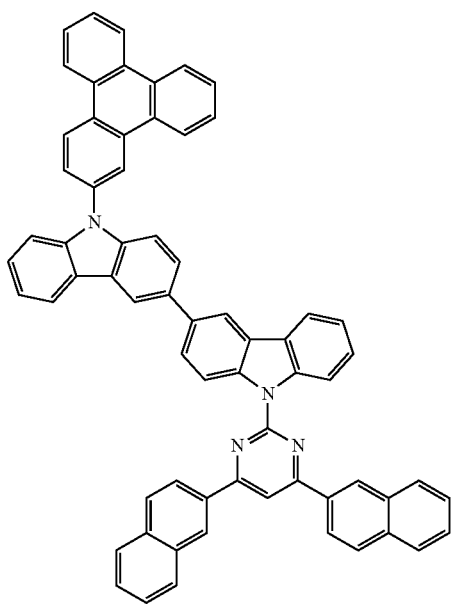
Compound 150
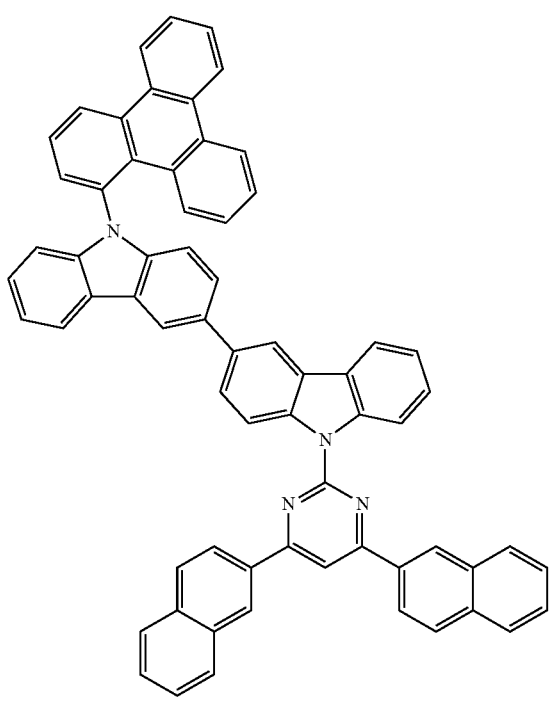

Compound 151
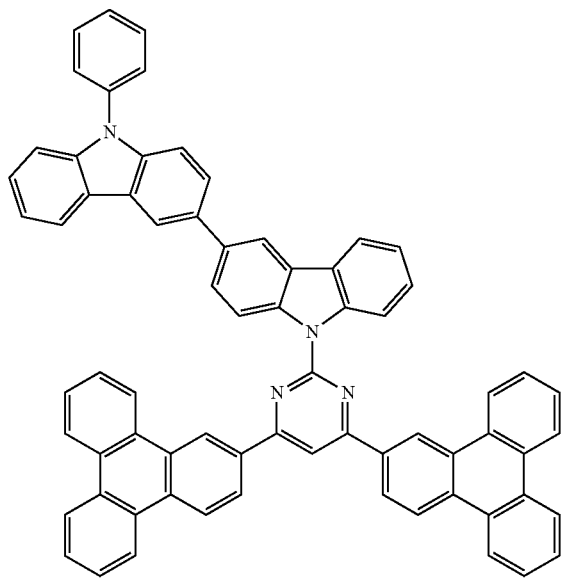
Compound 153
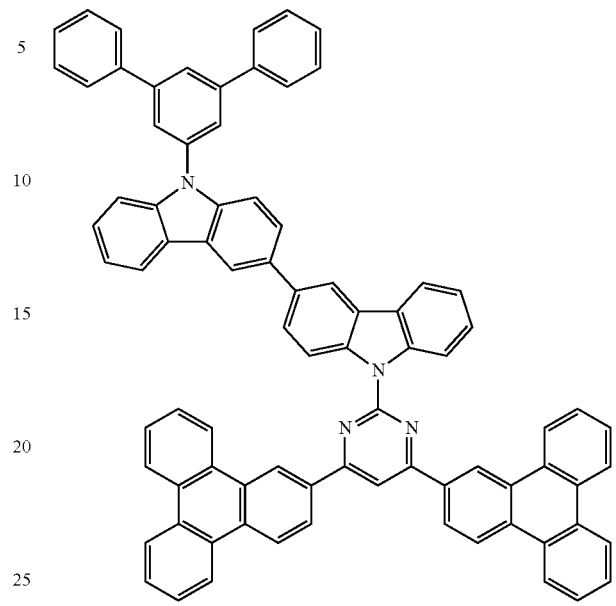
Compound 152
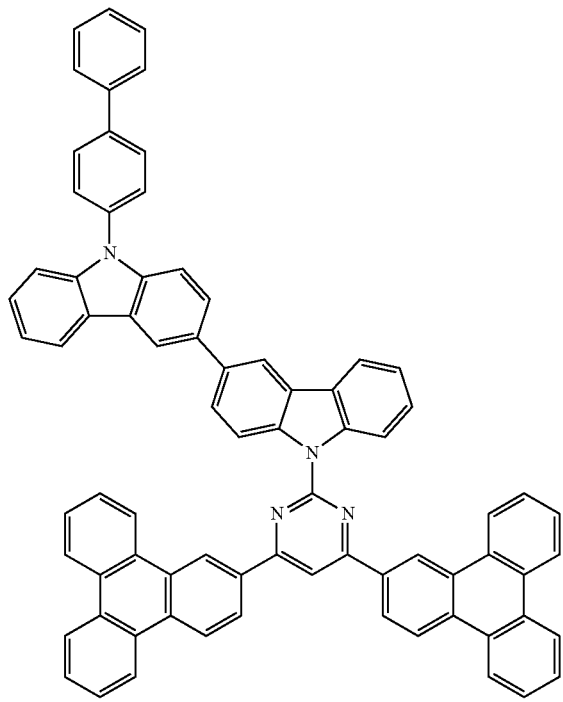
Compound 154

Compound 155
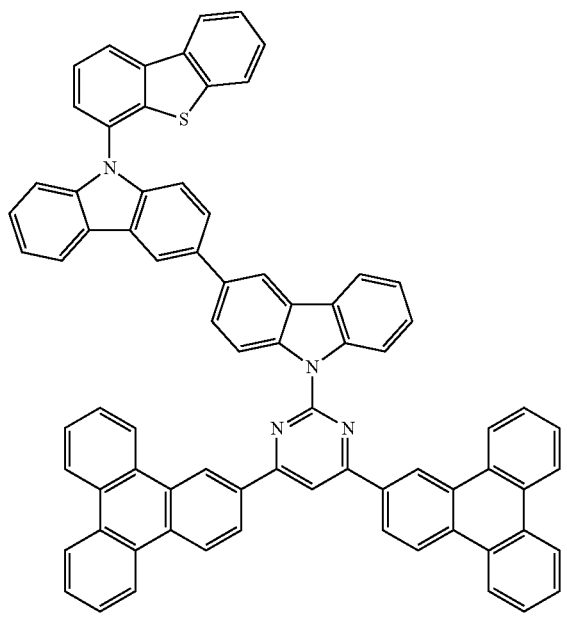
Compound 157
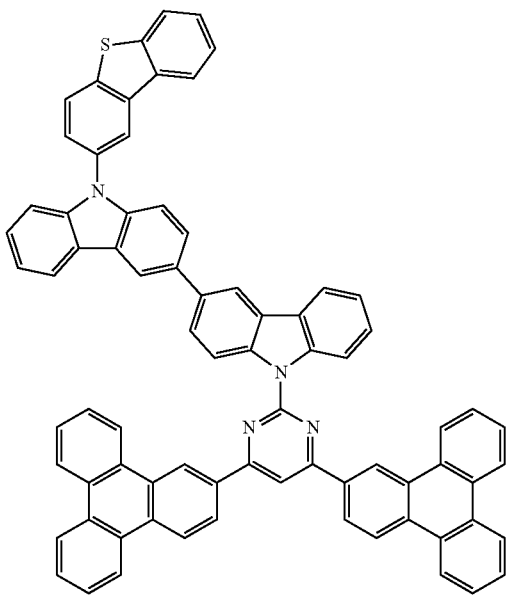
Compound 156
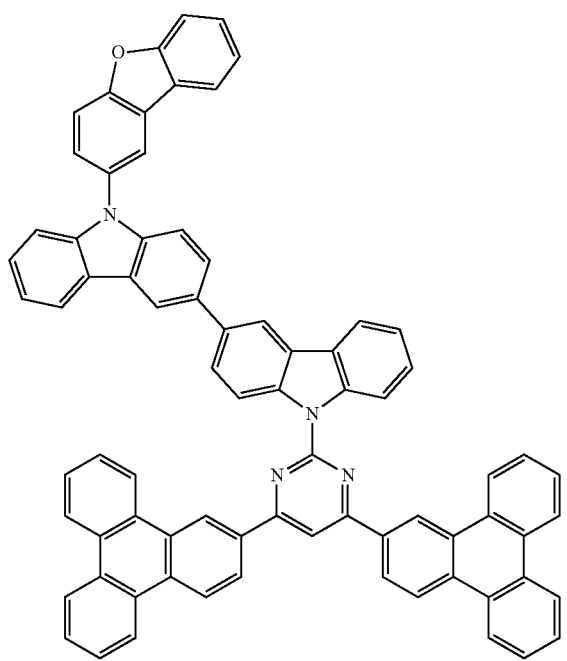
Compound 158
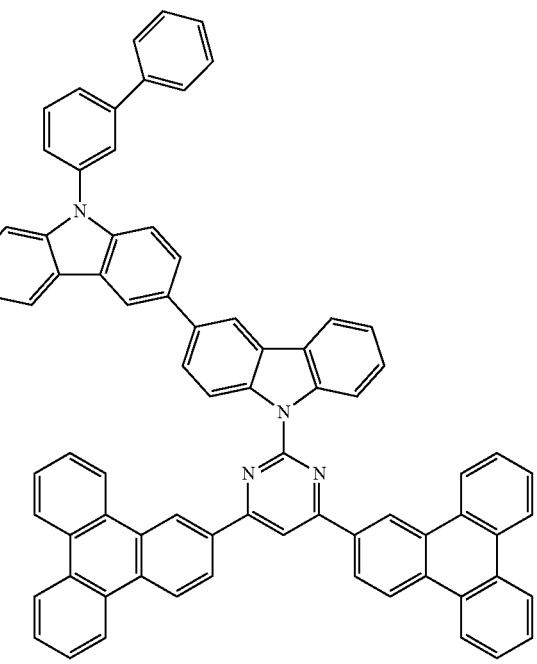

Compound 159
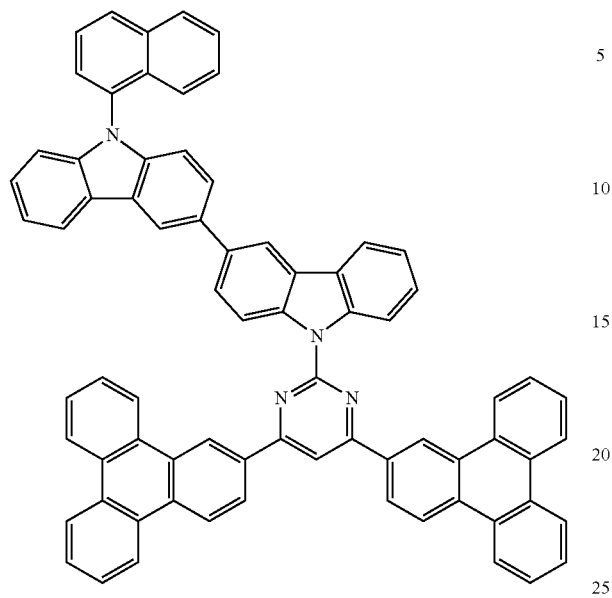
Compound 161
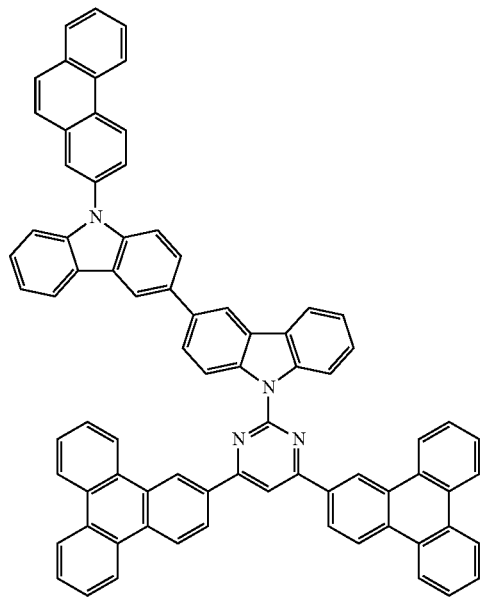
Compound 160
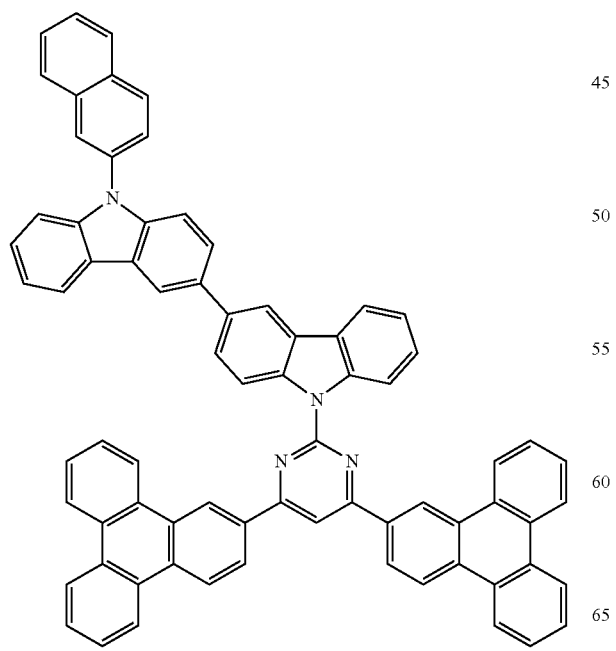
Compound 162
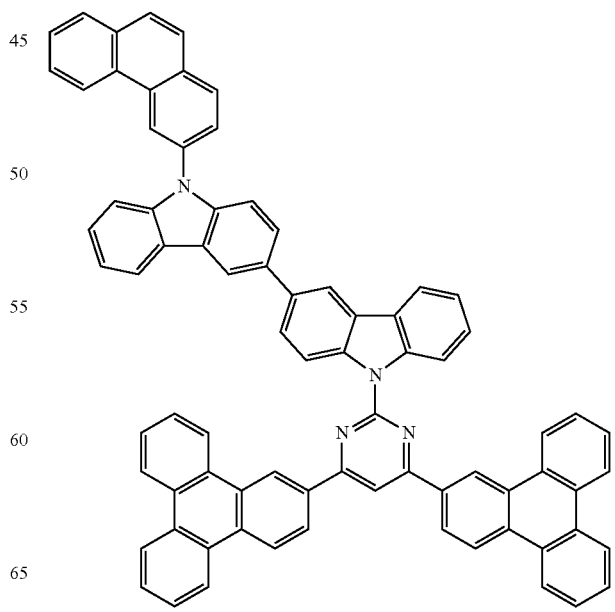

Compound 163
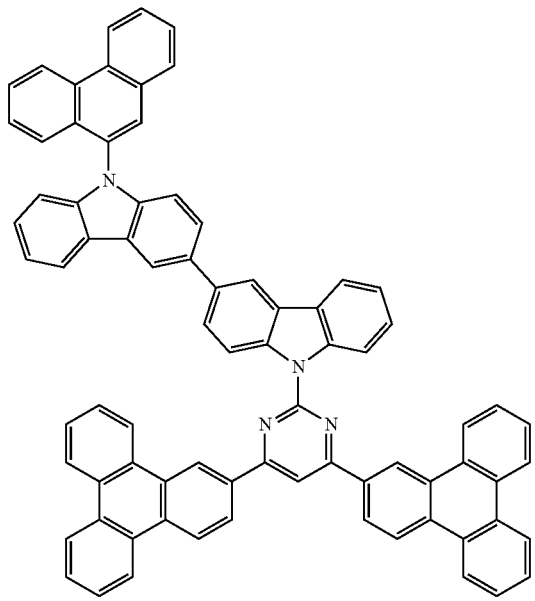
Compound 164
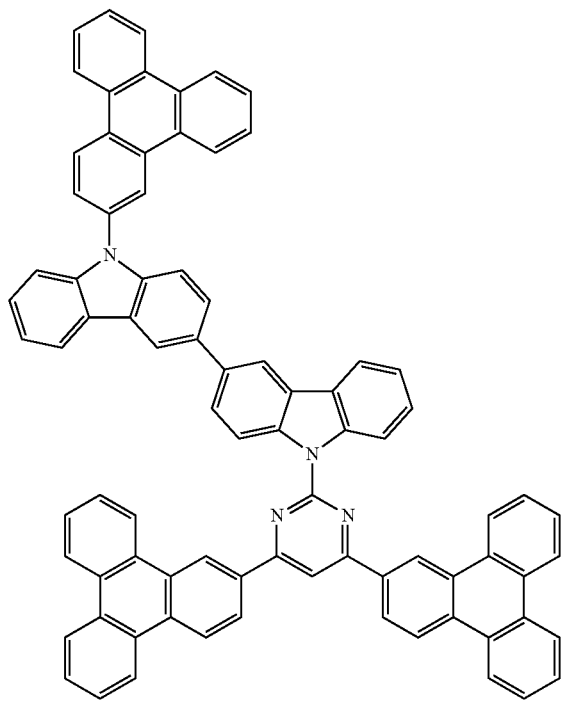
Compound 165
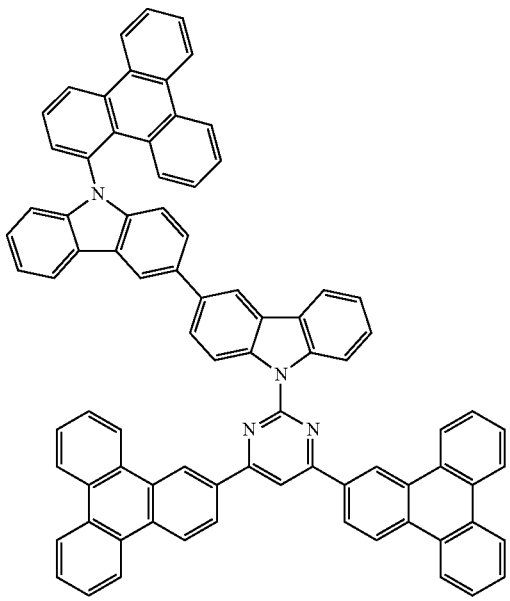
Compound 166
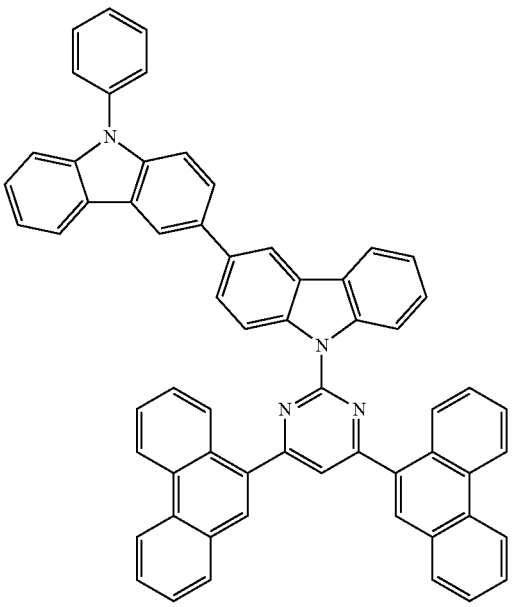

Compound 167
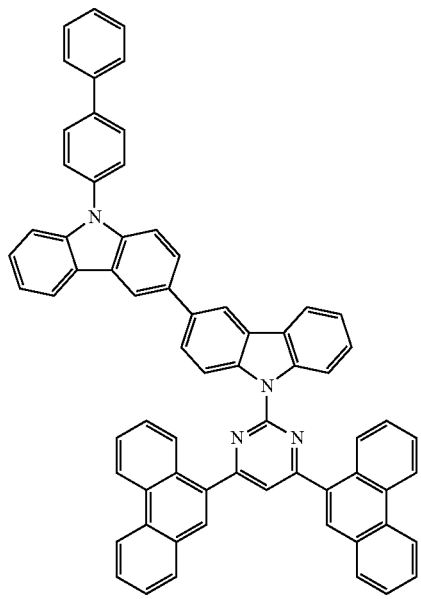
Compound 168
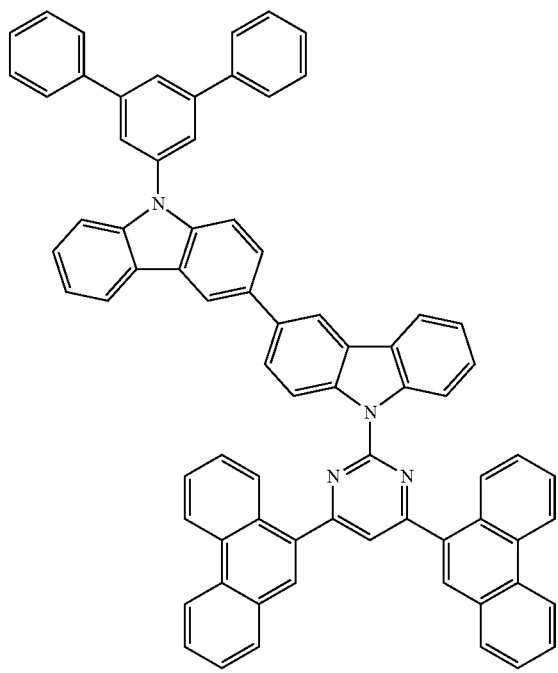
Compound 169
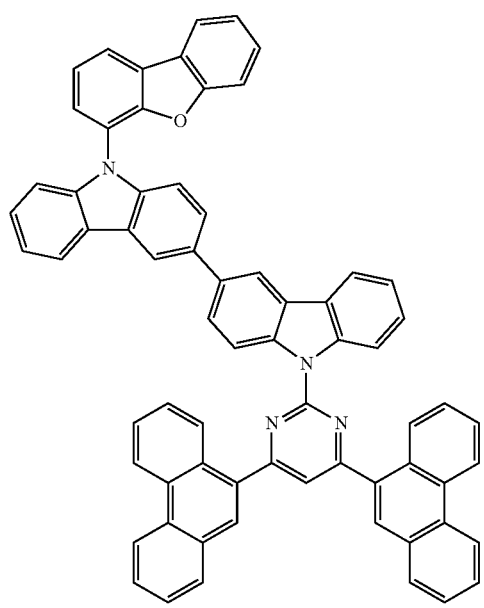
Compound 170
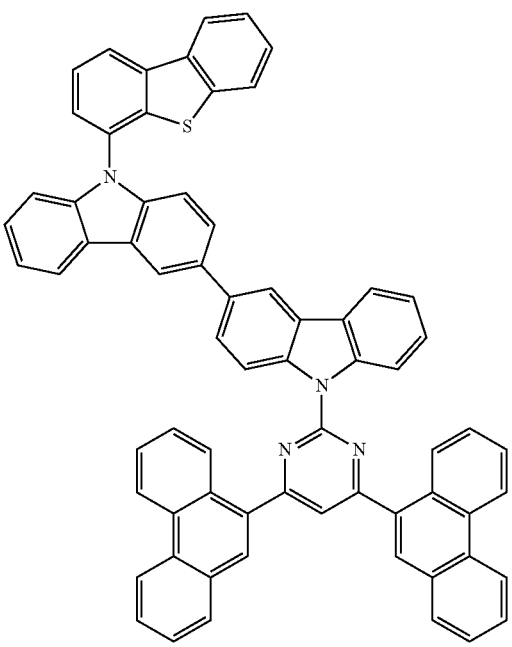

Compound 171
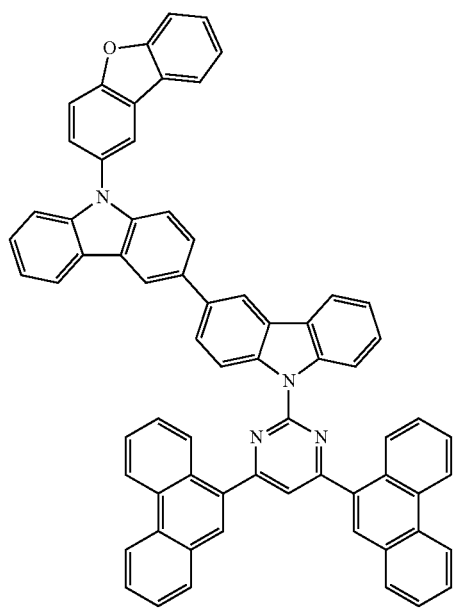
Compound 172
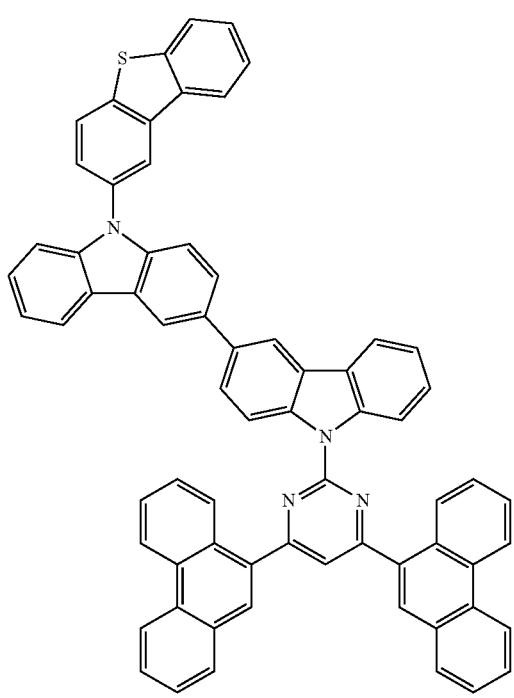
Compound 173
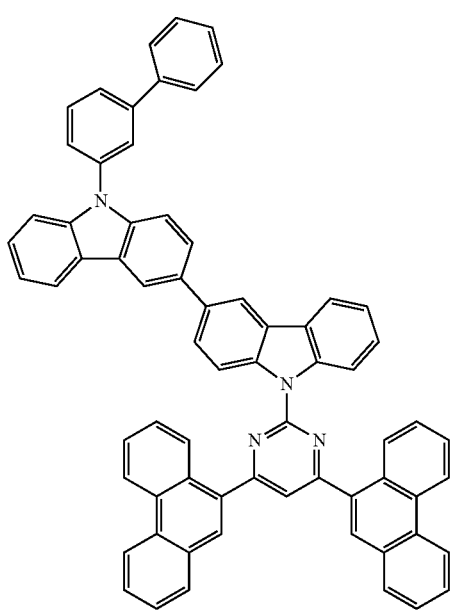
Compound 174
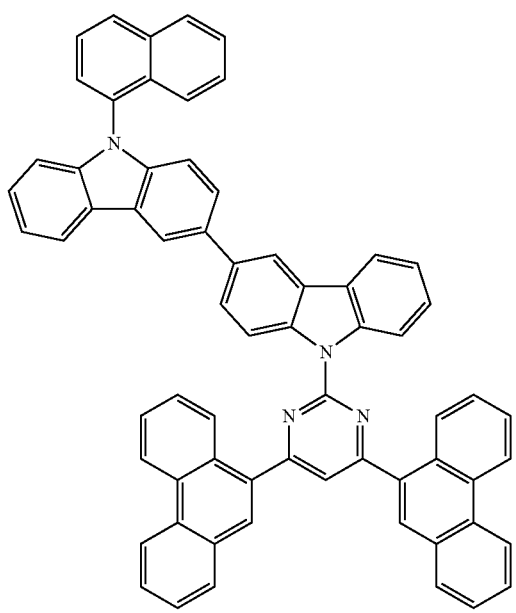

Compound 175
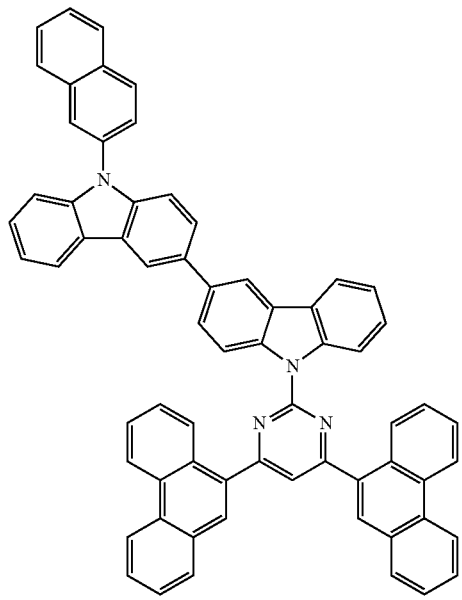
Compound 176
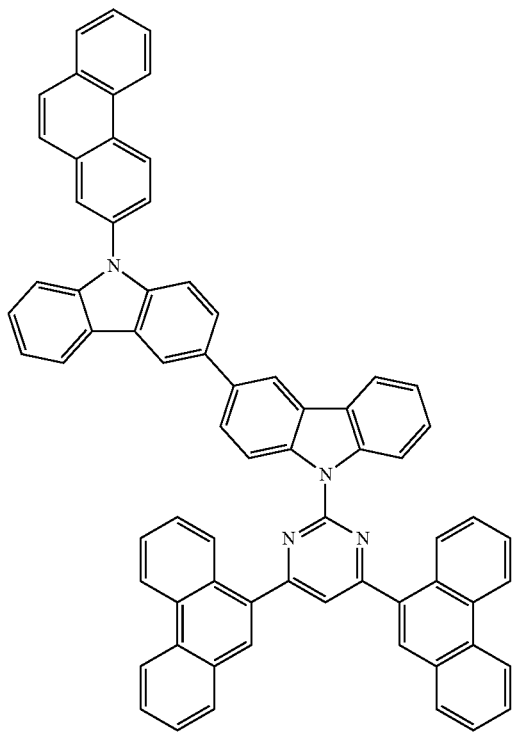
Compound 177
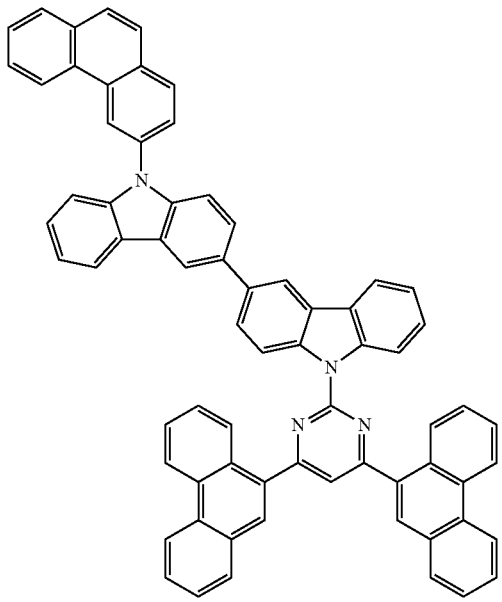
Compound 178
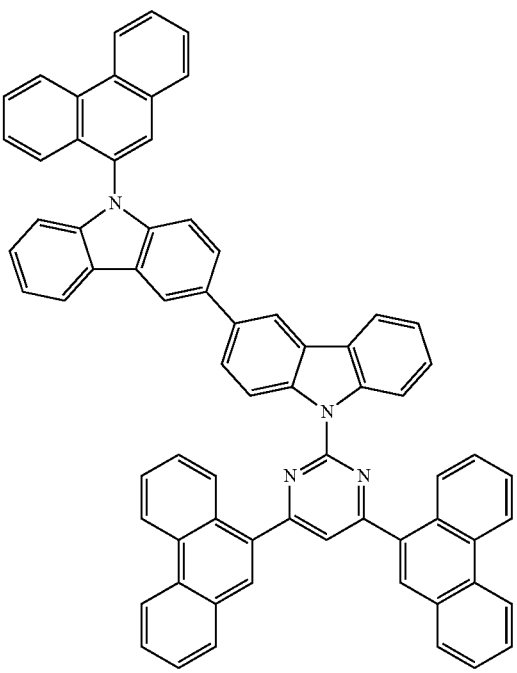

Compound 179
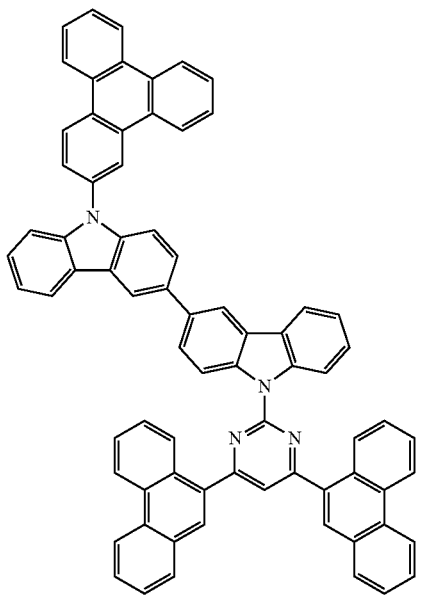
Compound 180
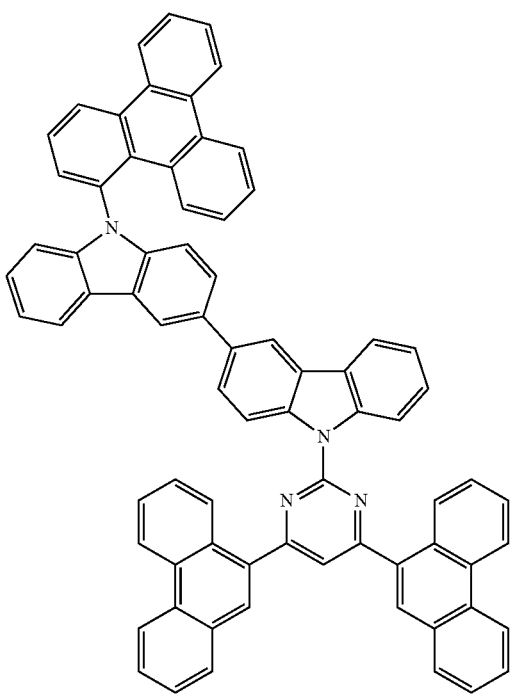
Compound 181
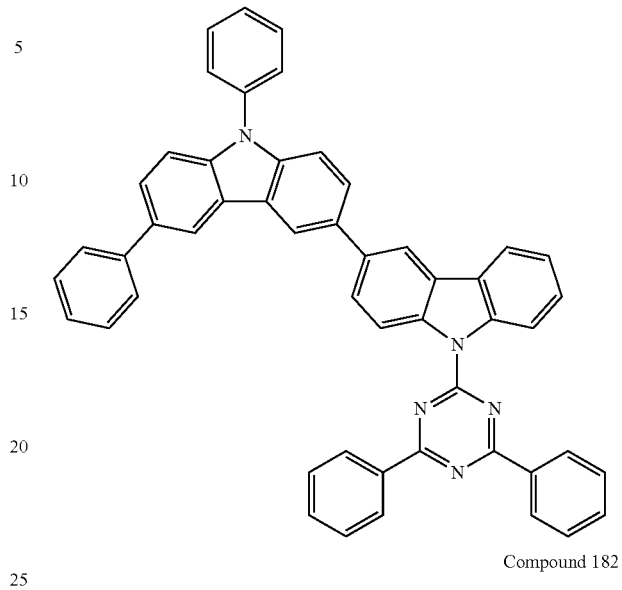
Compound 182
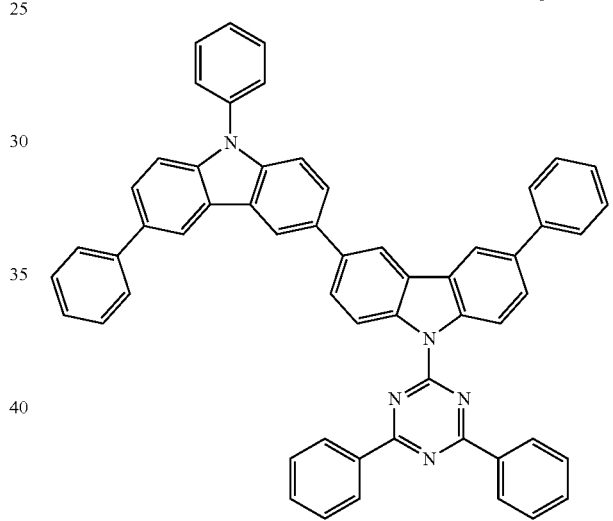
Compound 183

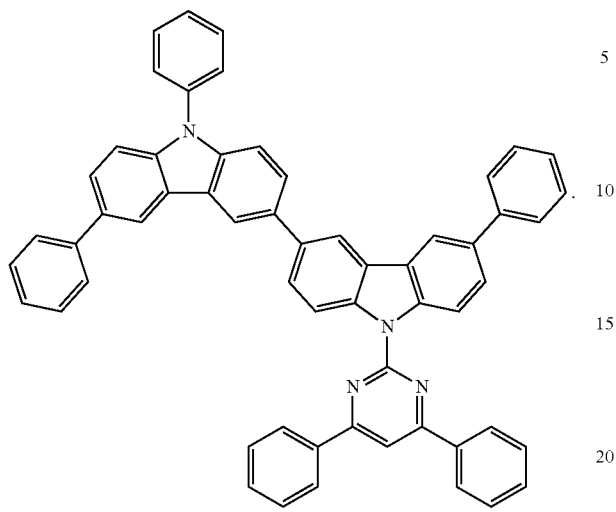

184

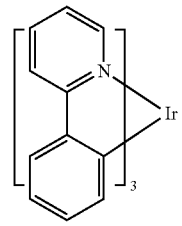

D1

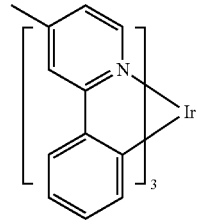

D2

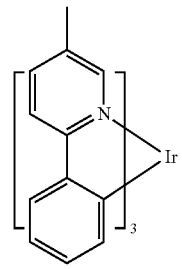

D3

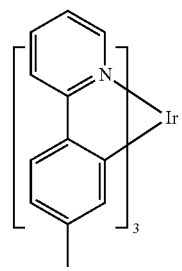

D4

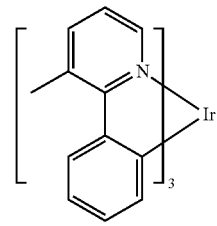

D5

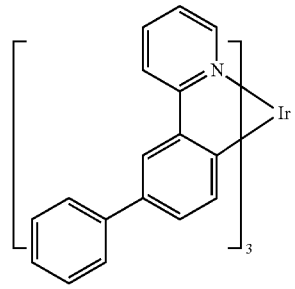

D6

A first device comprising an organic light emitting device is also provided. The device further comprises an anode, a cathode, and an organic layer, disposed between the anode and the cathode. The organic layer comprises a compound having Formula I, as described above.

$R_1$, $R_2$, $R_3$, and $R_4$ may represent mono, di, tri, or tetra substitutions. $R_1$, $R_2$, $R_3$, and $R_4$ are independently selected from the group consisting of hydrogen, alkyl, alkoxy, amino, alkenyl, alkynyl, aryl and heteroaryl. $Ar_1$, $Ar_2$, and $Ar_3$ are independently selected from aryl or heteroaryl. $Ar_1$, $Ar_2$, and $Ar_3$ may be further substituted. X is C or N.

In one aspect, $Ar_1$, $Ar_2$, and $Ar_3$ are independently selected from the group consisting of phenyl, pyridine, naphthalene, biphenyl, terphenyl, fluorene, dibenzofuran, dibenzothiophene, phenanthrene, and triphenylene. $Ar_1$, $Ar_2$, and $Ar_3$ are independently further substituted with a substituent selected from the group consisting of hydrogen, alkyl, alkoxy, amino, alkenyl, alkynyl, aryl and heteroaryl, but the substituent is not an aryl or heteroaryl fused directly to $Ar_1$, $Ar_2$, and $Ar_3$. Preferably, $Ar_1$ and $Ar_2$ are independently selected from the group consisting of phenyl, pyridine, and naphthalene. Preferably, $Ar_3$ is selected from the group consisting of phenyl, biphenyl, dibenzofuran, and dibenzothiophene.

In another aspect, $R_1$, $R_2$, $R_3$, and $R_4$ are hydrogen.

Specific examples of devices containing compounds comprising bicarbazole are also provided. In particular, the compound is selected from the group consisting of Compound 1-Compound 184.

In one aspect, the organic layer is deposited using solution processing.

In one aspect, the organic layer is an emissive layer and the compound having Formula I is a host.

In another aspect, the organic layer further comprises an emissive dopant having the formula:

-continued
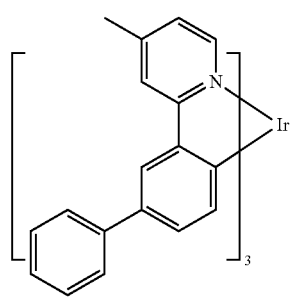 D7
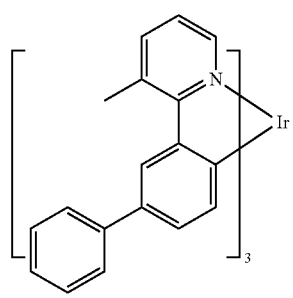 D8
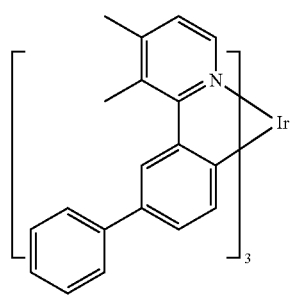 D9
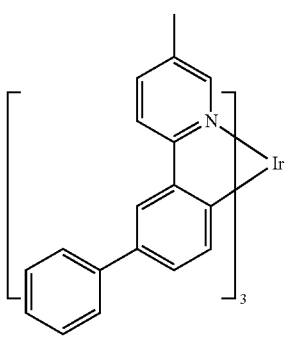 D10
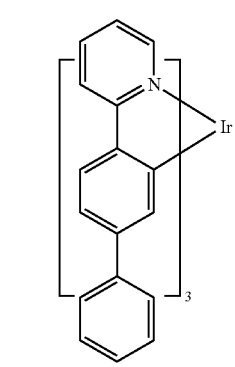 D11
-continued
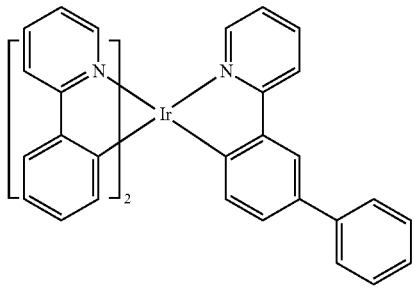 D12
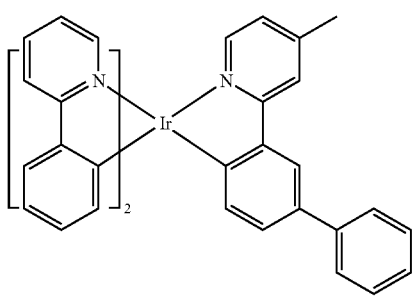 D13
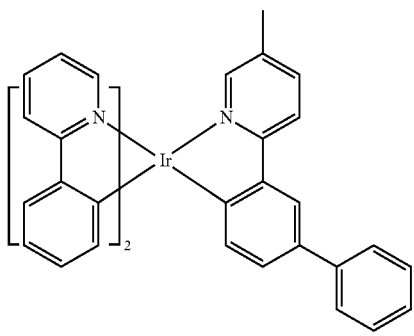 D14
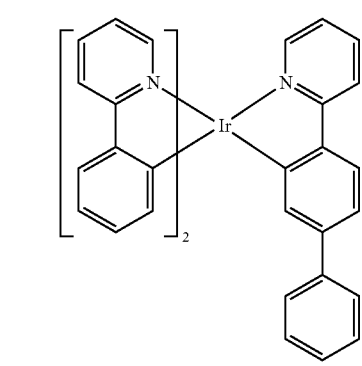 D15

D16
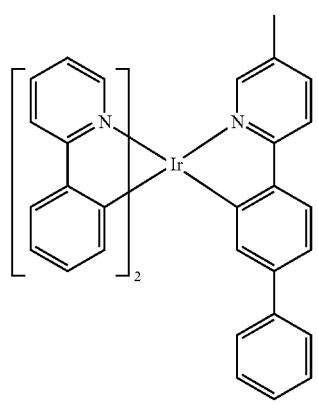
D17
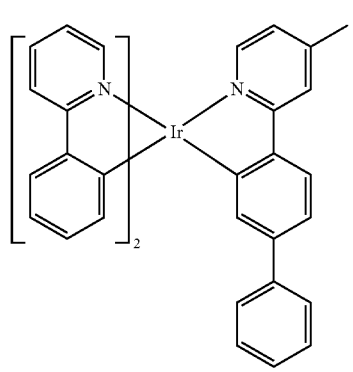
D18
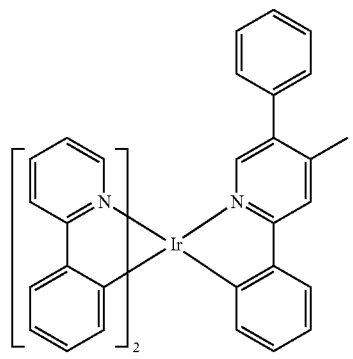
D19
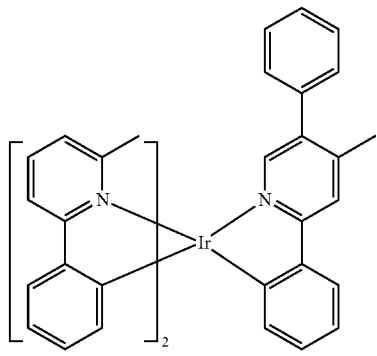
D20
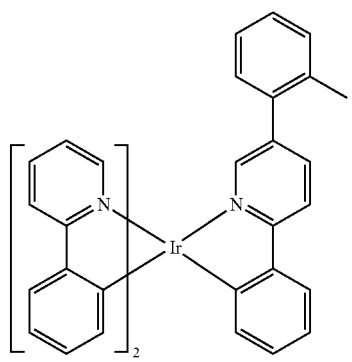
D21
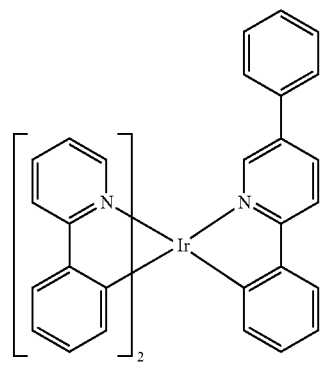
D22
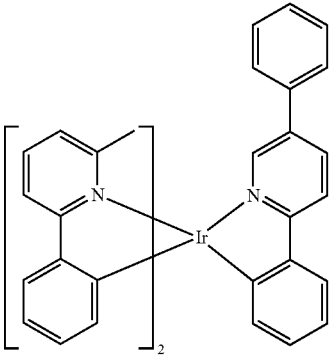
D23
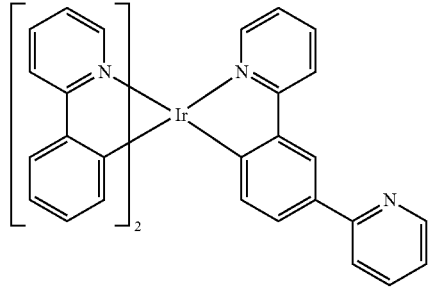

D24
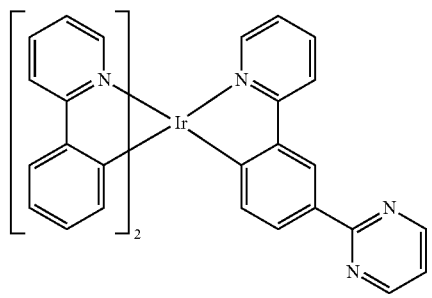
D25
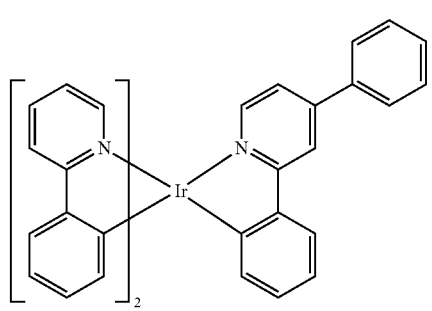
D26
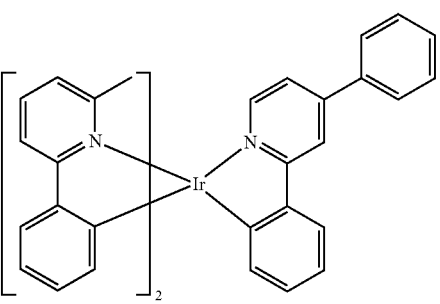
D27
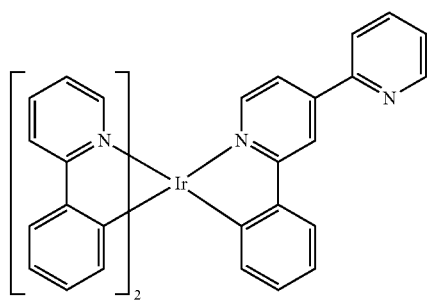
D28
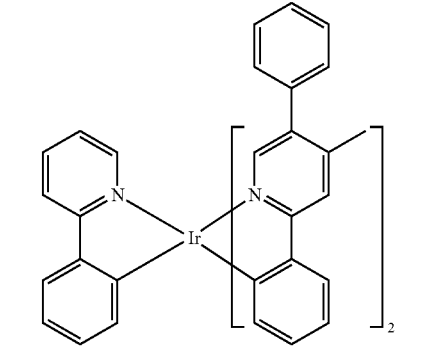
D29
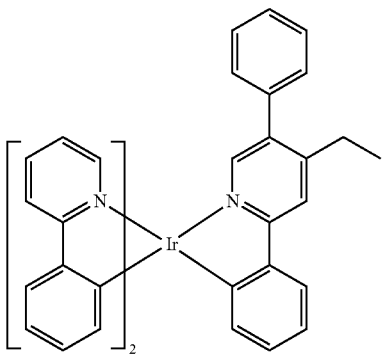
D30
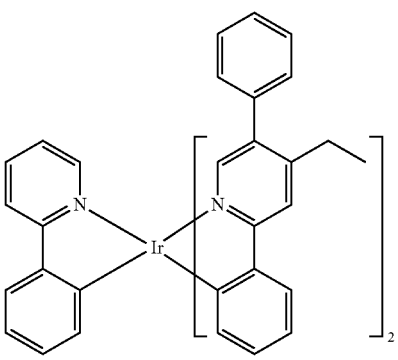
D31
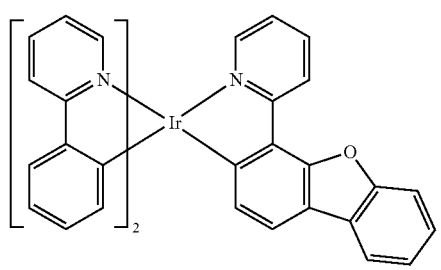
D32
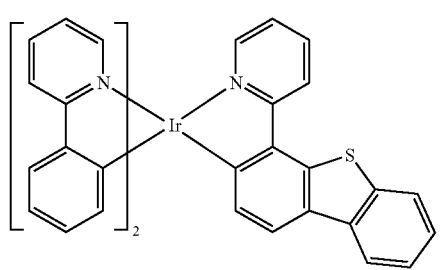
D33
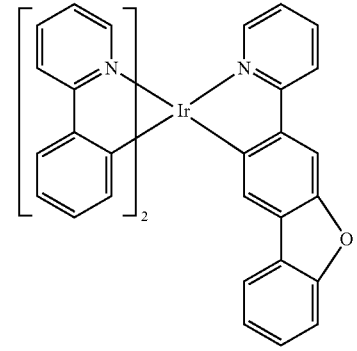

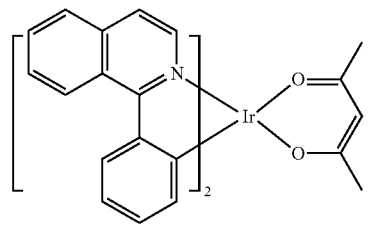
D34
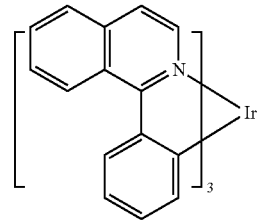
D35
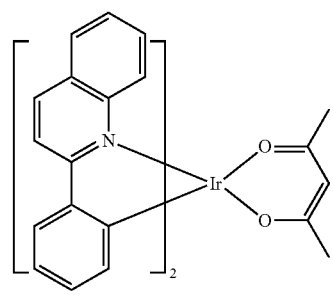
D36
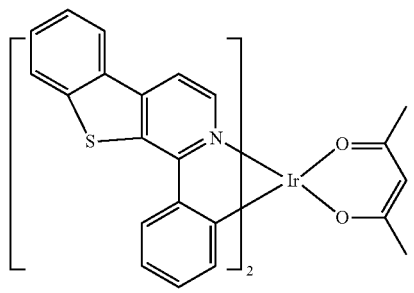
D37
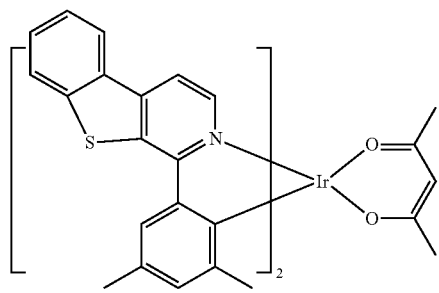
D38
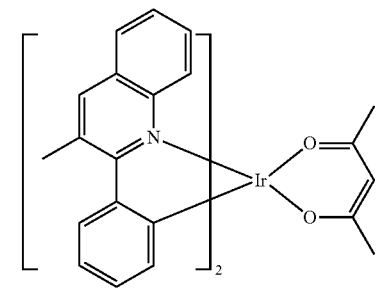
D39
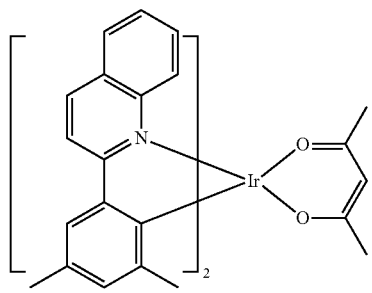
D40
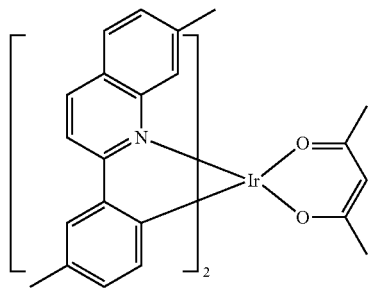
D41
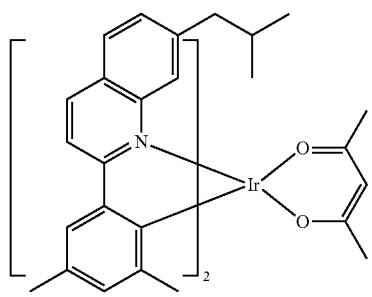
D42
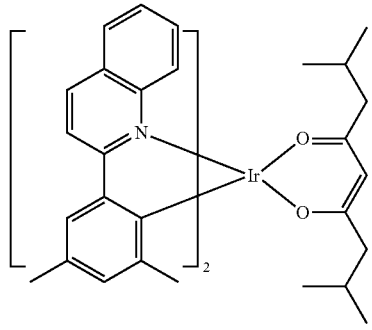
D43
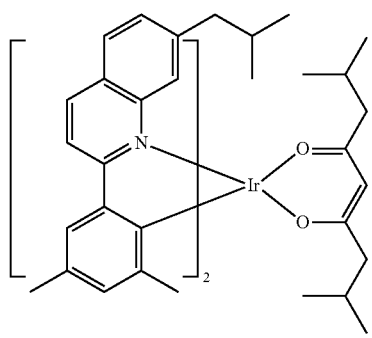
D44

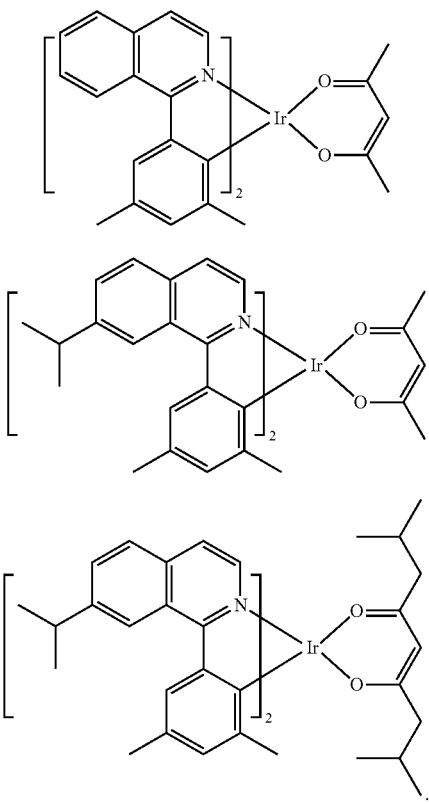

In one aspect, the first device is a consumer product. In another aspect, the first device is an organic light emitting device.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
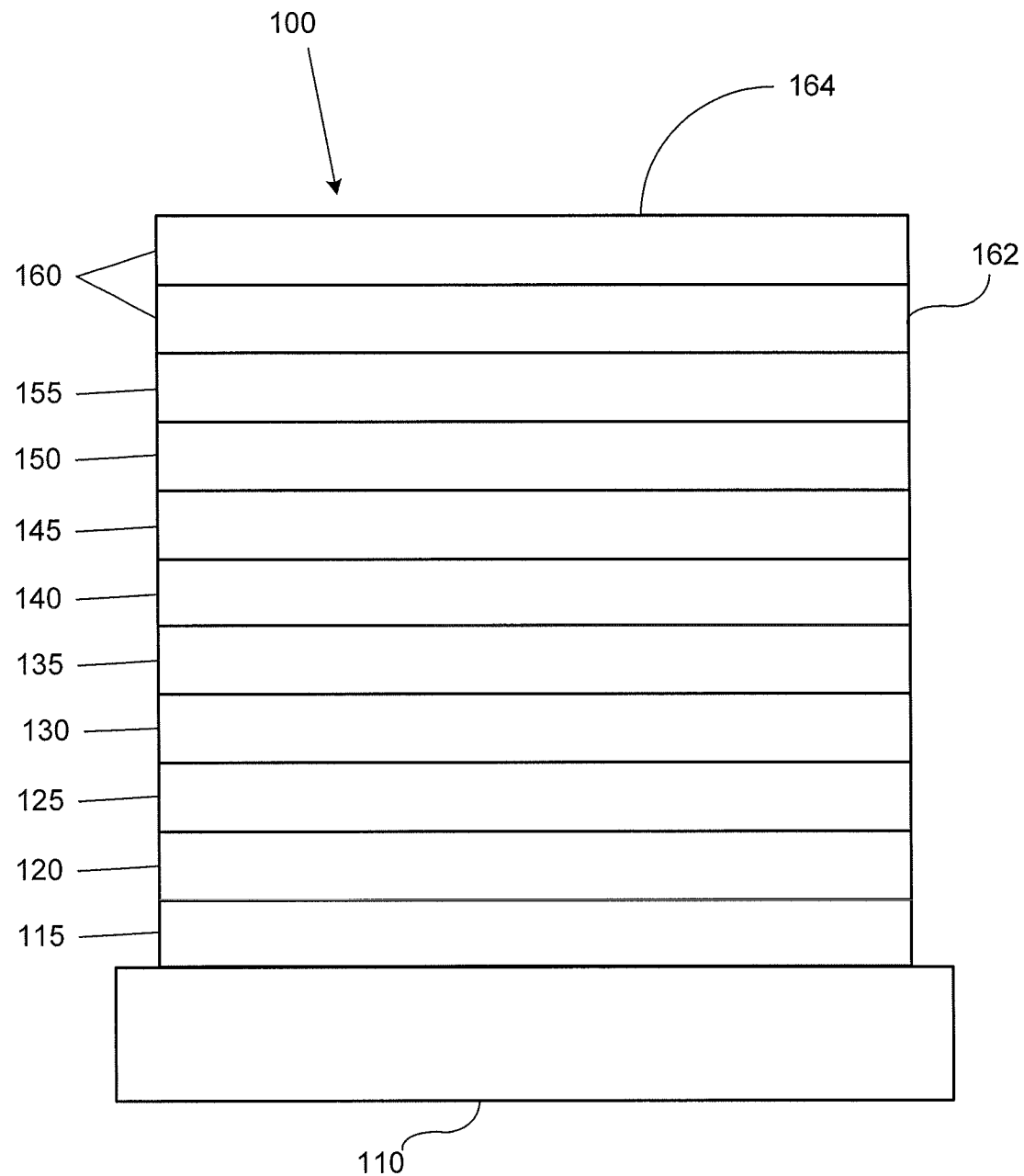
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F.sub.4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
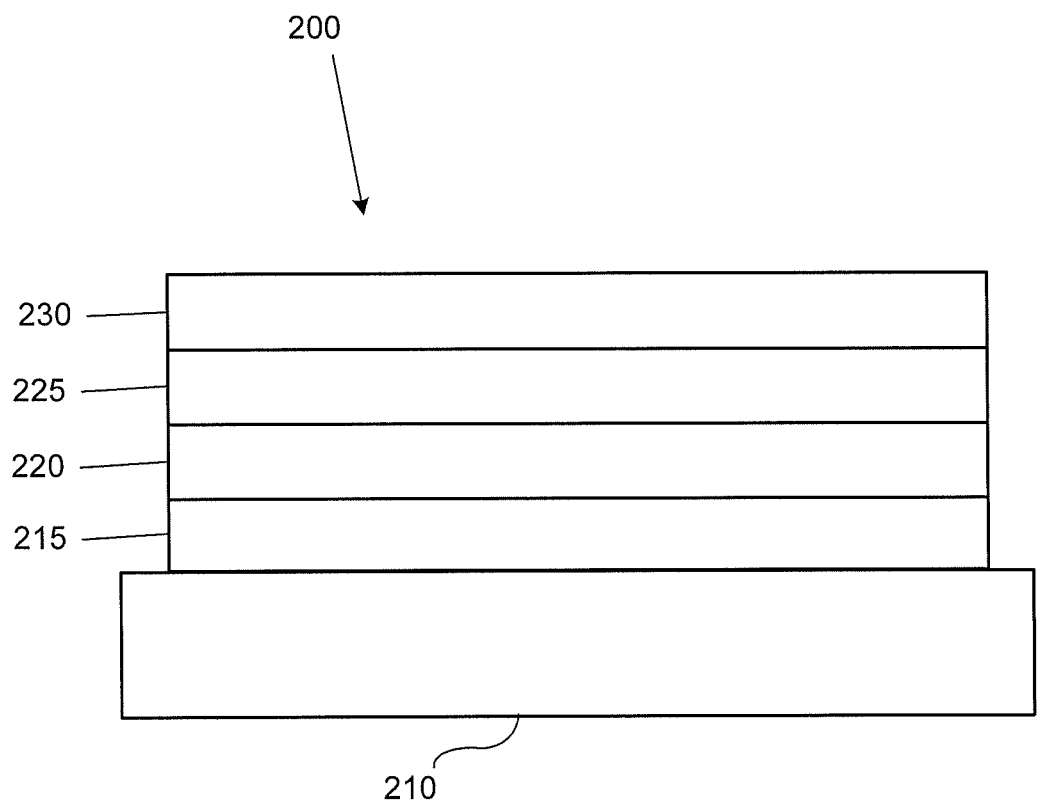
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

Figure 3:
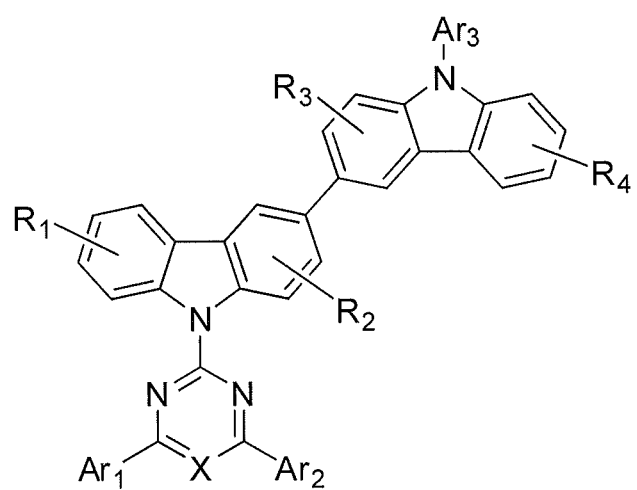
FIG. 3 shows a bicarbazole compound with a nitrogen-containing heterocycle substitution at the 9-position.

Novel bicarbazole containing compounds are provided (illustrated in FIG. 3). More specifically, these compounds contain a 3,3'-bicarbazole core and triazine or pyrimidine substitution at the 9-position. These compounds may be used as hosts for phosphorescent OLEDs.

Carbazole containing compounds for use as OLED materials have been previously described. In particular, 3,3'-bicarbazole compounds have good hole transporting properties, but have poor stability toward electrons. Alkyl and aryl substituted 3,3'-bicarbazole compounds have been used as hole transporting materials and hosts in OLEDs; however, these compounds also have imbalanced charge transporting properties and poor electron stability and may provide devices with low efficiency and limited lifetime. For example, a diaryl substituted 3,3'-bicarbazole, i.e. H1, has a HOMO around 5.6 eV, very good for hole transporting but poor for electron transporting and stability. Therefore, the 3,3'-bicarbazole compounds reported in the literature may have limited use.

In the present invention, nitrogen containing electron deficient heterocycles were introduced to 3,3'-bicarbazole compounds. In particular, the compounds contain a 3,3'-bicarbazole core and triazine or pyrimidine substitution at the 9 position. The nitrogen containing heterocycle tunes the HOMO/LUMO levels as well as increases the compound's stability toward electrons. In addition, these compounds contain a donor part, i.e. bicarbazole, and an acceptor part, i.e. electron deficient nitrogen heterocycle. Without being bound by theory, it is believed that these donor-acceptor type molecules can shrink singlet and triplet gap and improve stability to both hole and electrons. Therefore, these 3,3'-bicarbazole compounds containing a nitrogen heterocycle may provide devices having better stability and lower operating voltage.

Compounds comprising a bicarbazole are provided. The compounds have the formula:

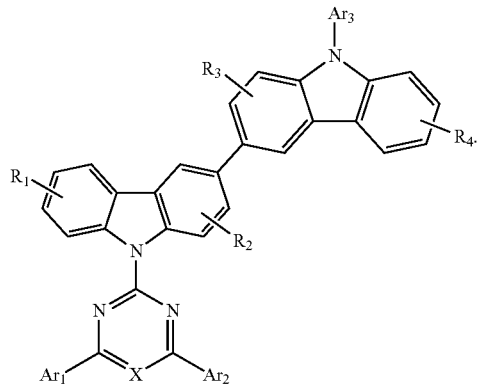

Formula I $R_1$, $R_2$, $R_3$, and $R_4$ may represent mono, di, tri, or tetra substitutions. $R_1$, $R_2$, $R_3$, and $R_4$ are independently selected from the group consisting of hydrogen, alkyl, alkoxy, amino, alkenyl, alkynyl, aryl and heteroaryl. $Ar_1$, $Ar_2$, and $Ar_3$ are independently selected from aryl or heteroaryl. $Ar_1$, $Ar_2$, and $Ar_3$ may be further substituted. X is C or N.

In one aspect, $Ar_1$, $Ar_2$, and $Ar_3$ are independently selected from the group consisting of phenyl, pyridine, naphthalene, biphenyl, terphenyl, fluorene, dibenzofuran, dibenzothiophene, phenanthrene, and triphenylene, and $Ar_1$, $Ar_2$, and $Ar_3$ are independently further substituted with a substituent selected from the group consisting of hydrogen, alkyl, alkoxy, amino, alkenyl, alkynyl, aryl and heteroaryl, but the substituent is not an aryl or heteroaryl fused directly to $Ar_1$, $Ar_2$, and $Ar_3$. Preferably, $Ar_1$ and $Ar_2$ are independently selected from the group consisting of phenyl, pyridine, and naphthalene. Preferably, $Ar_3$ is selected from the group consisting of phenyl, biphenyl, dibenzofuran, and dibenzothiophene.

In another aspect, $R_1$, $R_2$, $R_3$, and $R_4$ are hydrogen.

Specific examples of compounds comprising bicarbazole are also provided. In particular, the compound is selected from the group consisting of:

Compound 1

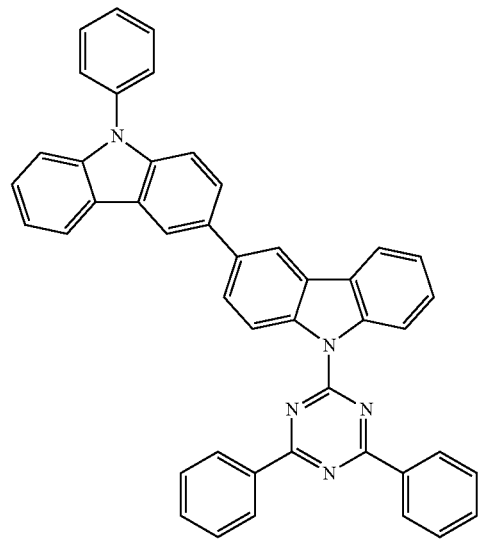

Compound 2

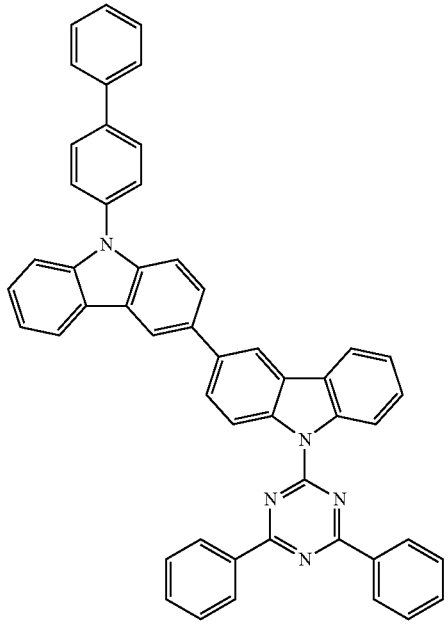

Compound 3

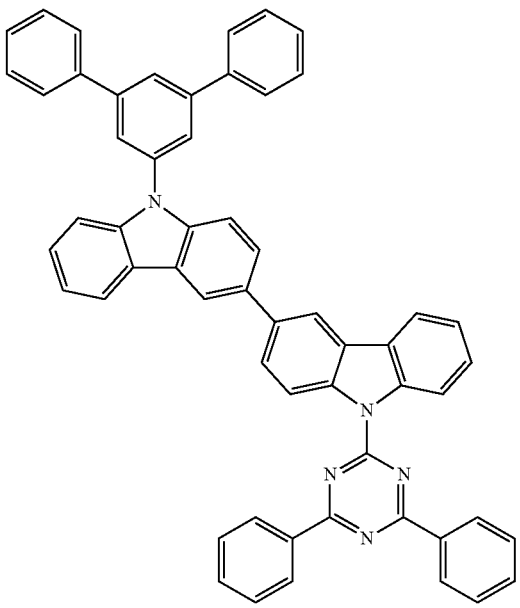

Compound 4
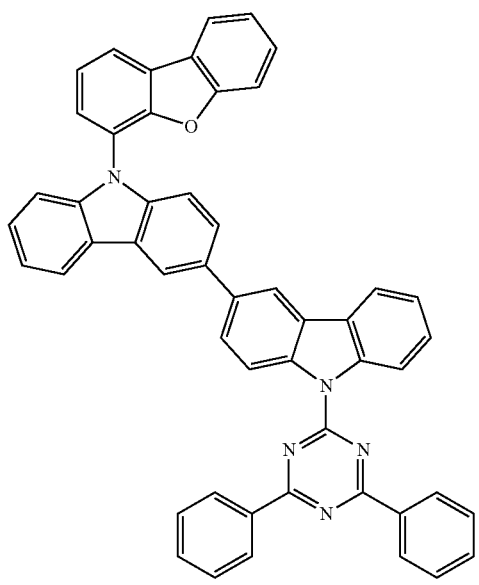
Compound 5
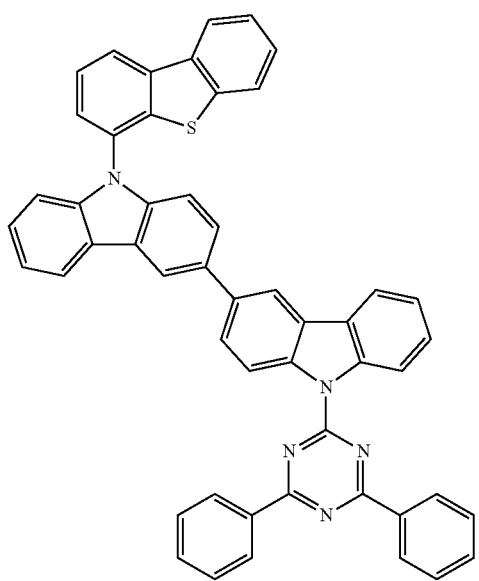
Compound 6
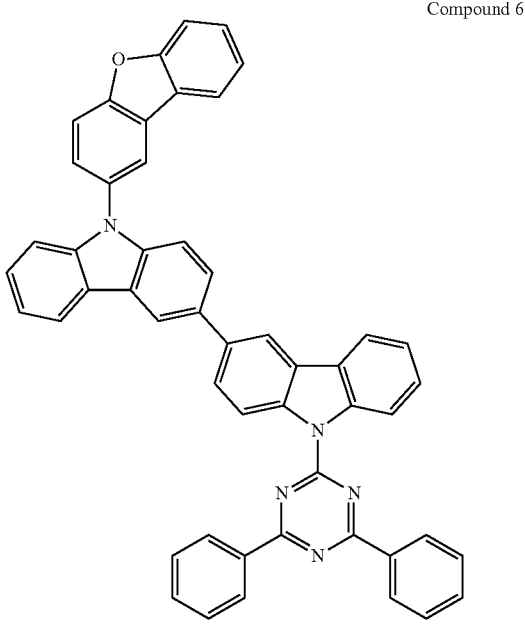
Compound 7
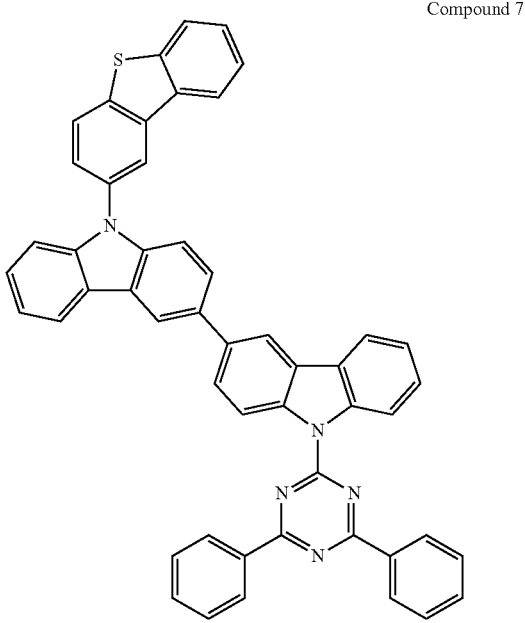

Compound 8
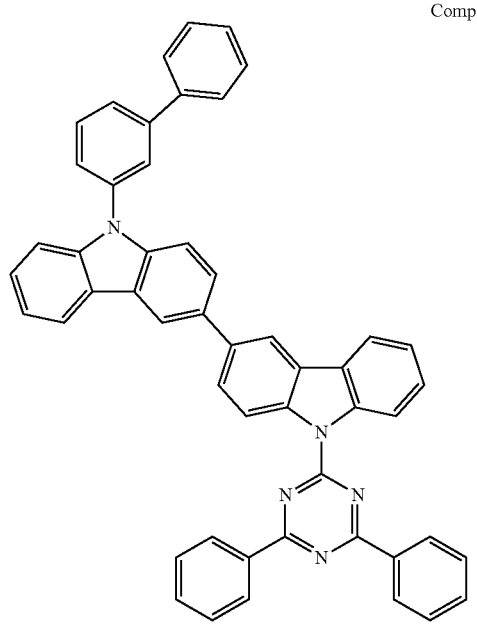
Compound 10
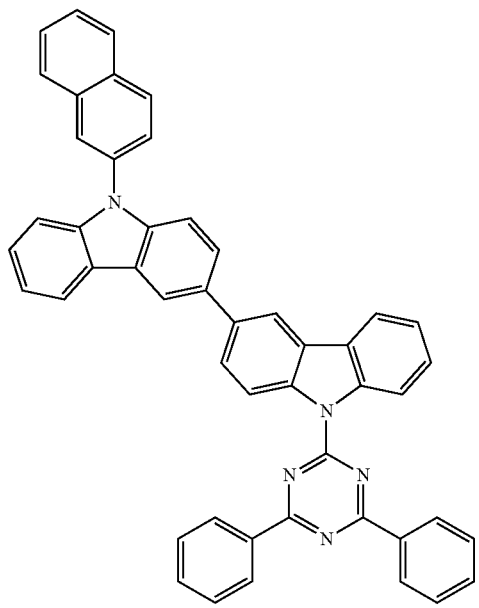
Compound 9
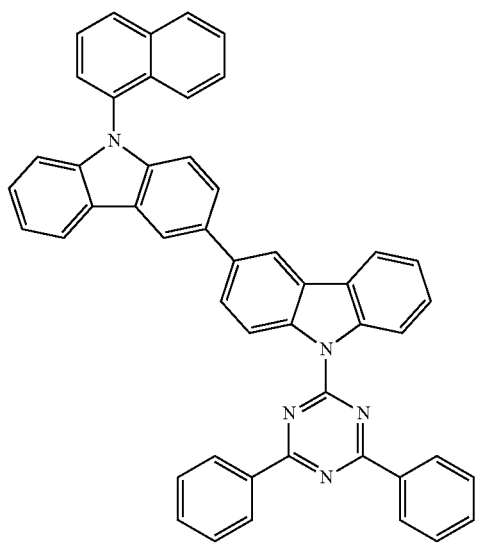
Compound 11
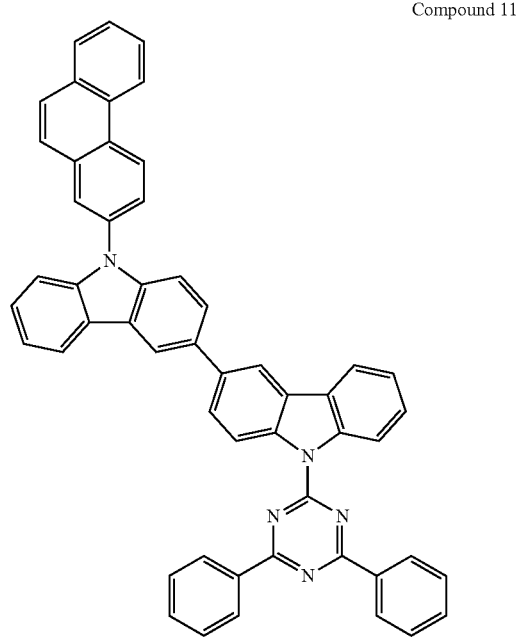

Compound 12
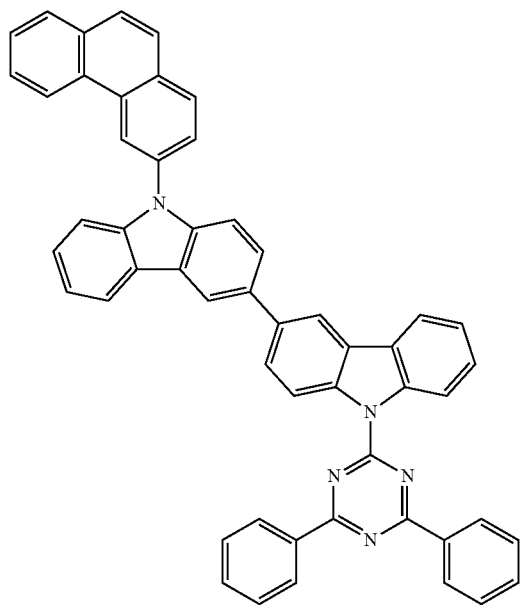
Compound 13
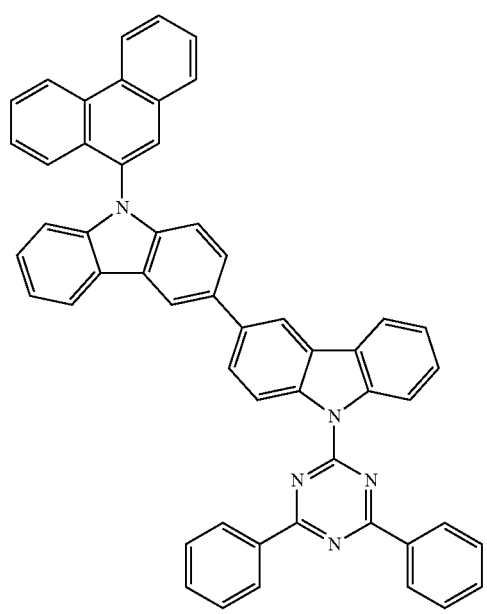
Compound 14
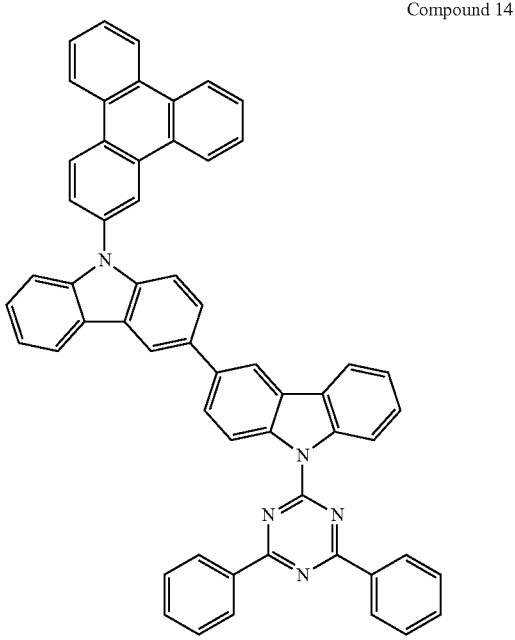
Compound 15
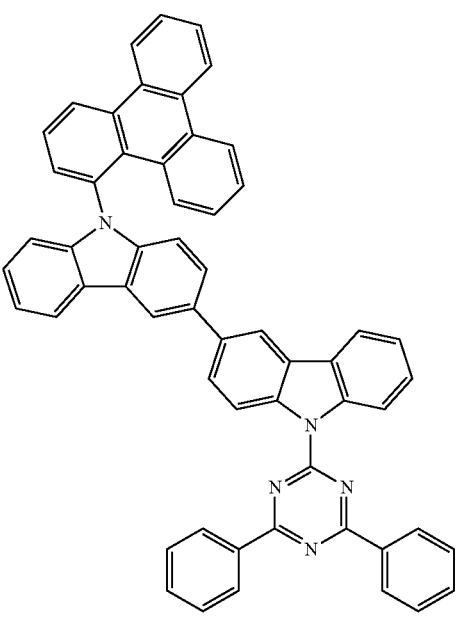

Compound 16
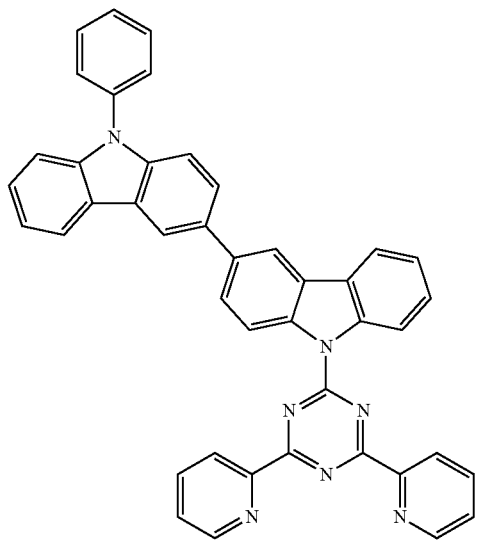
Compound 17
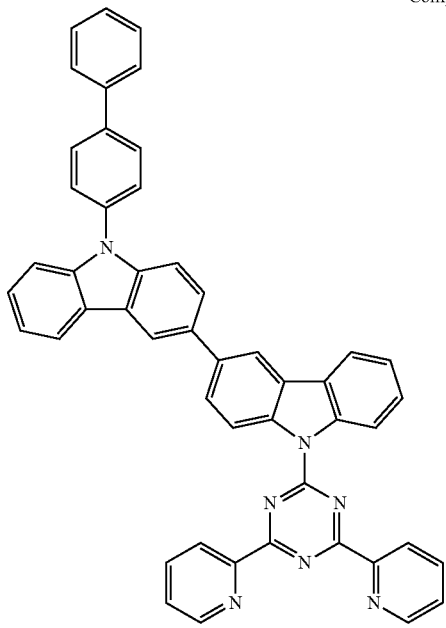
Compound 18
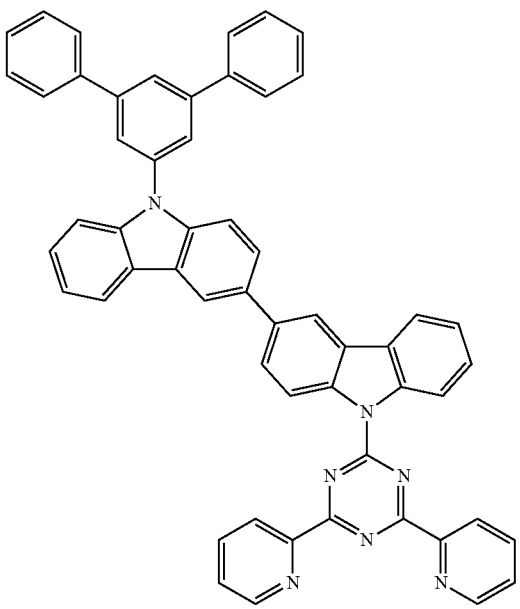
Compound 19
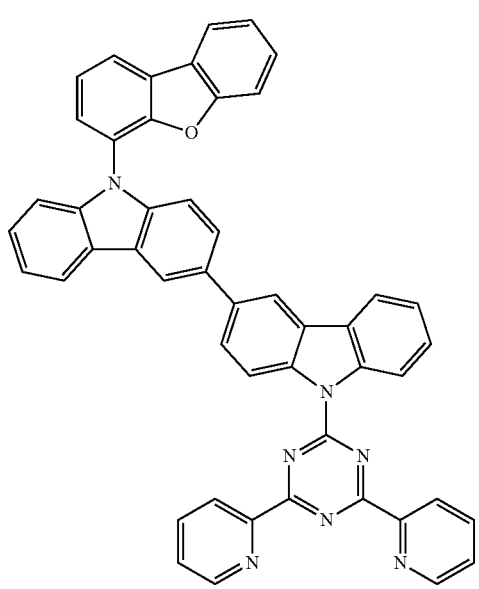

Compound 20
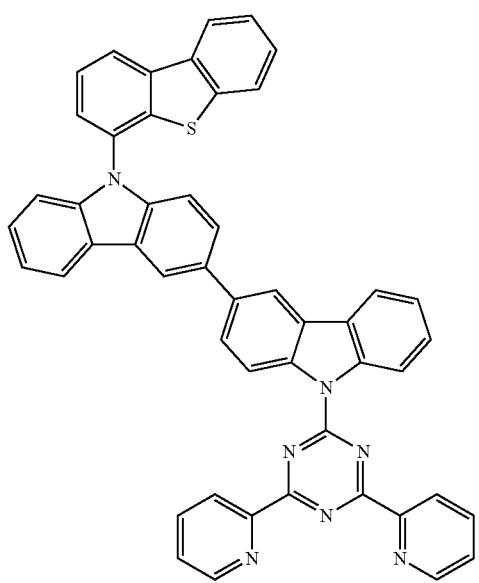
Compound 22
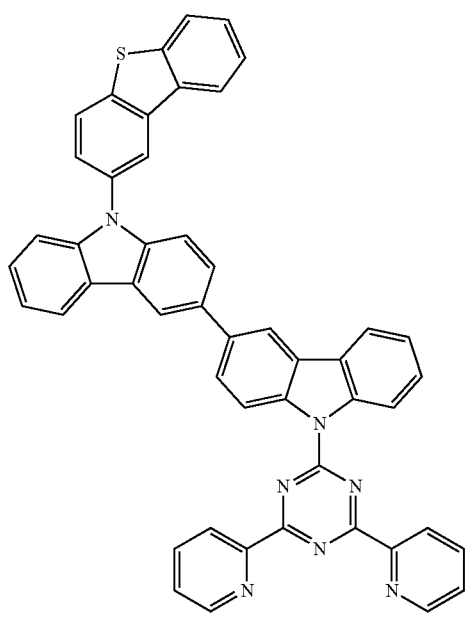
Compound 21
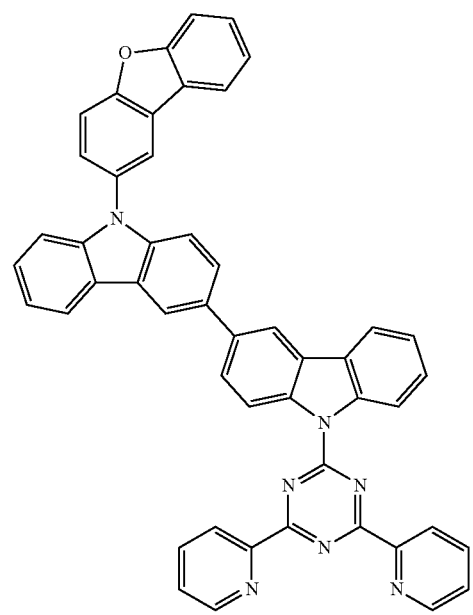
Compound 23
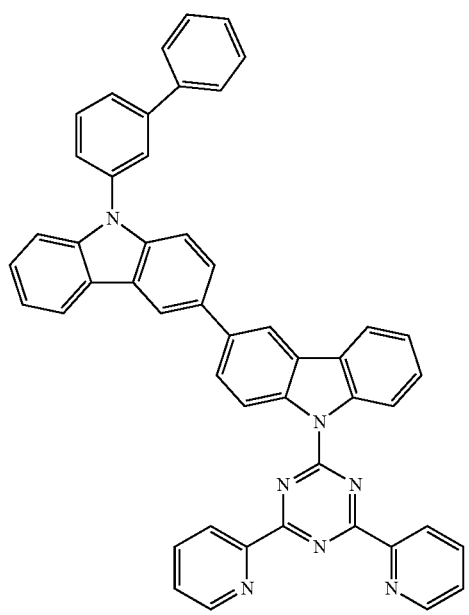

Compound 24
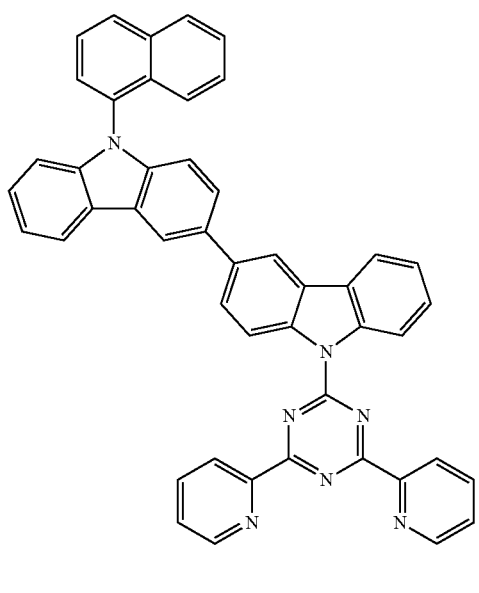
Compound 25
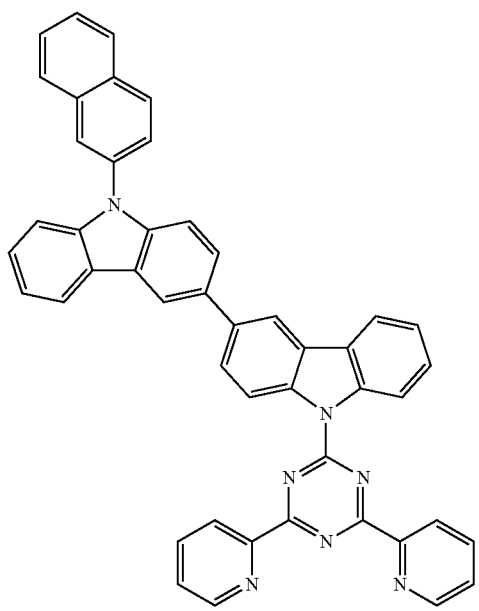
Compound 26
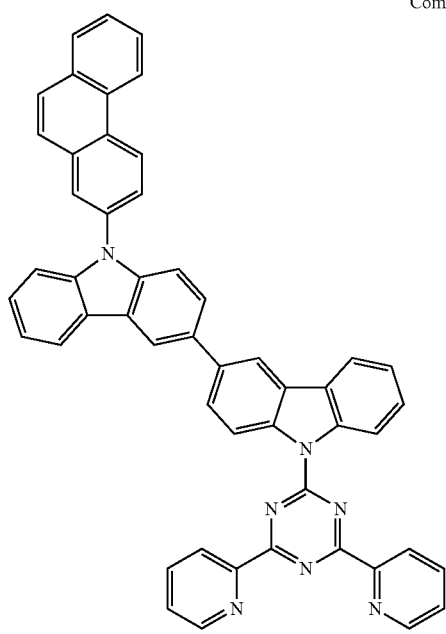
Compound 27
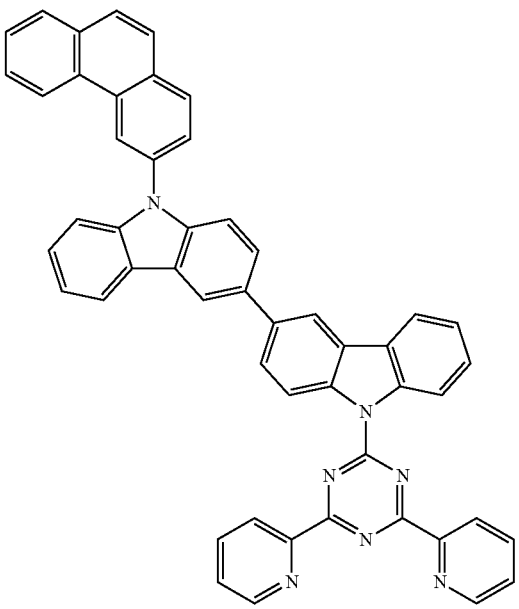

Compound 28
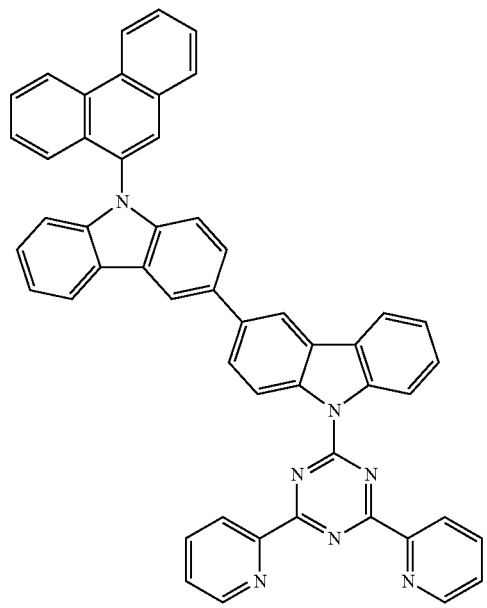
Compound 29
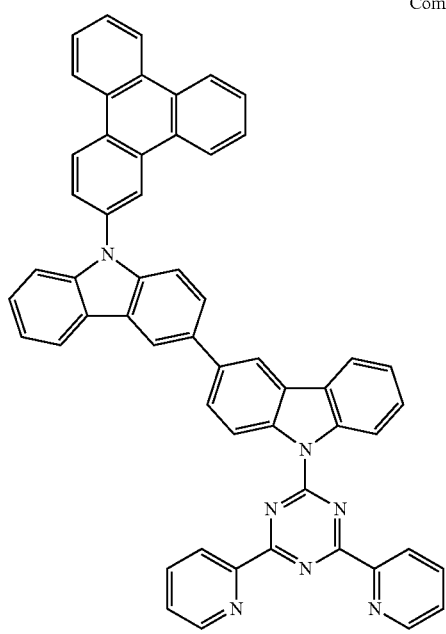
Compound 30
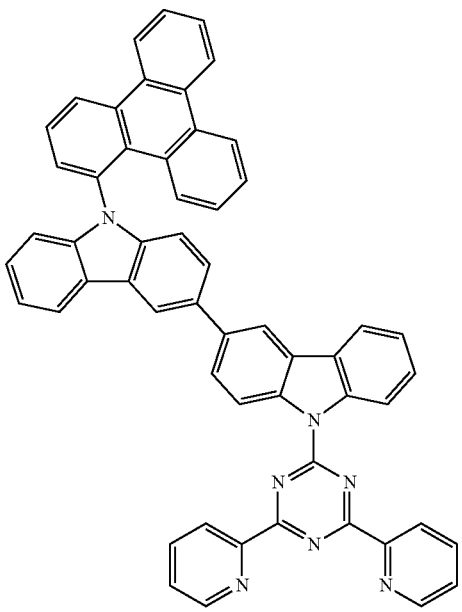
Compound 31
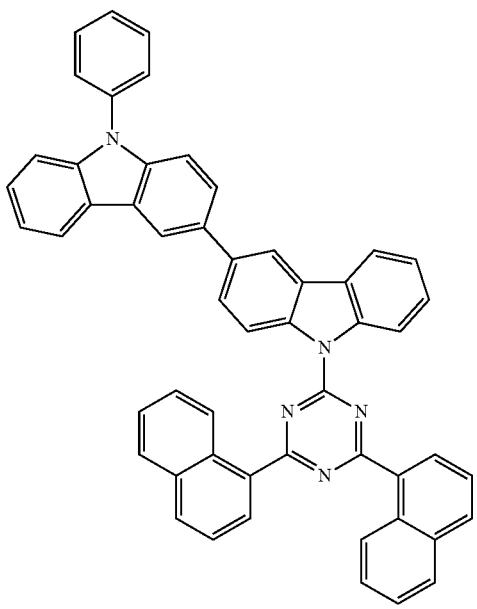

Compound 32
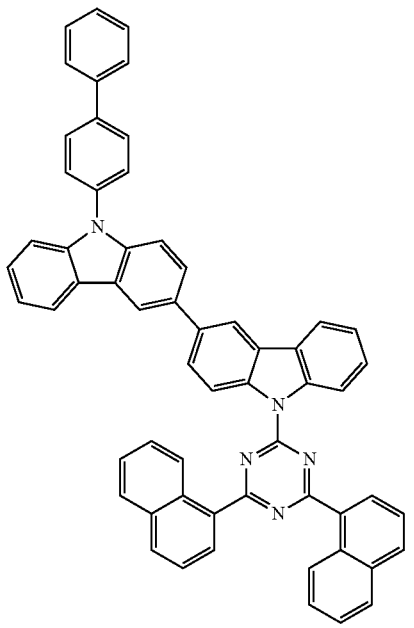
Compound 33
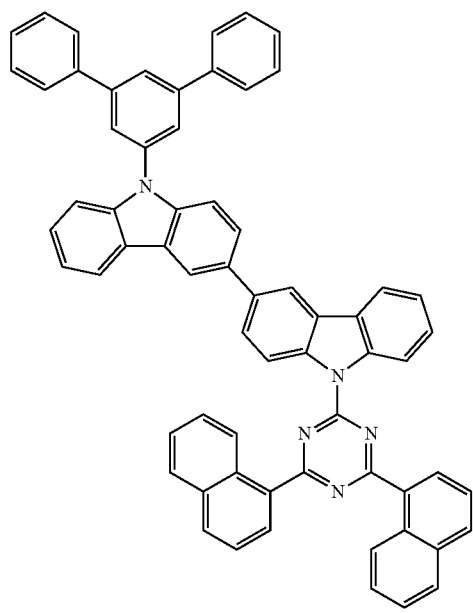
Compound 34
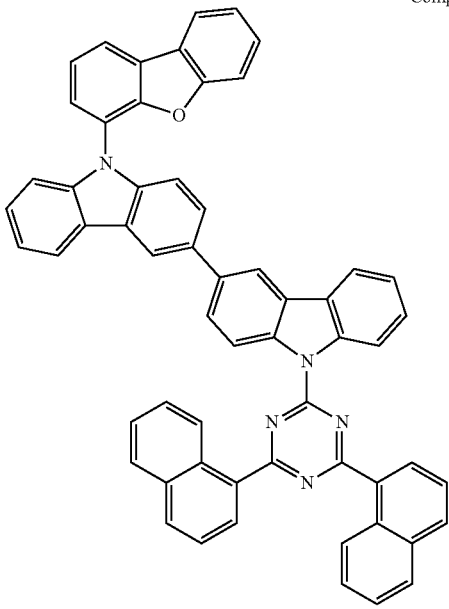
Compound 35
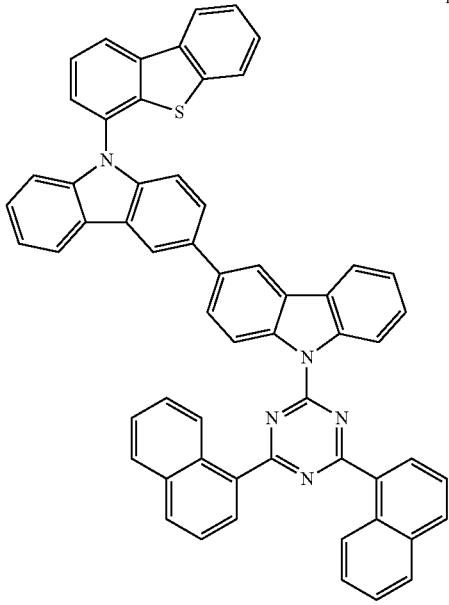

Compound 36
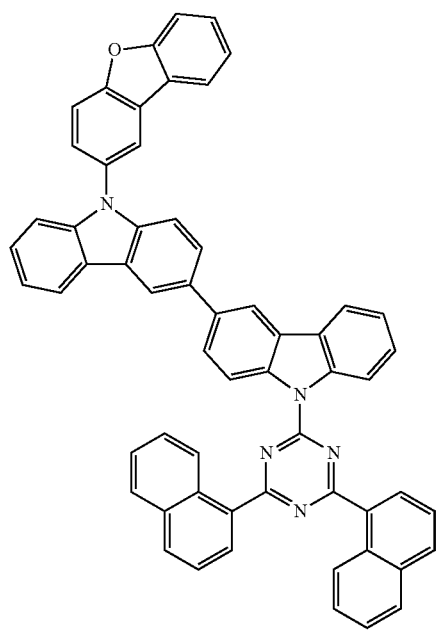
Compound 37
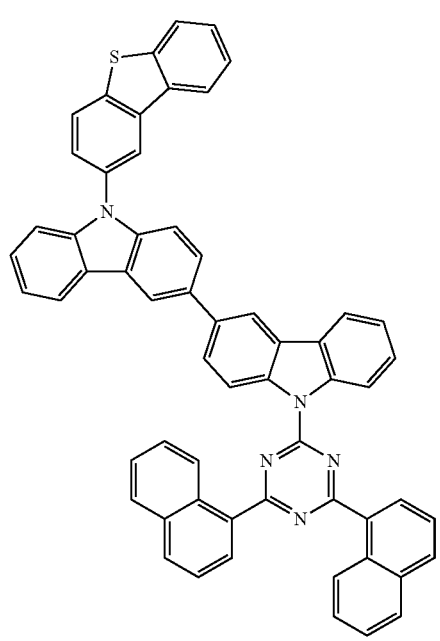
Compound 38
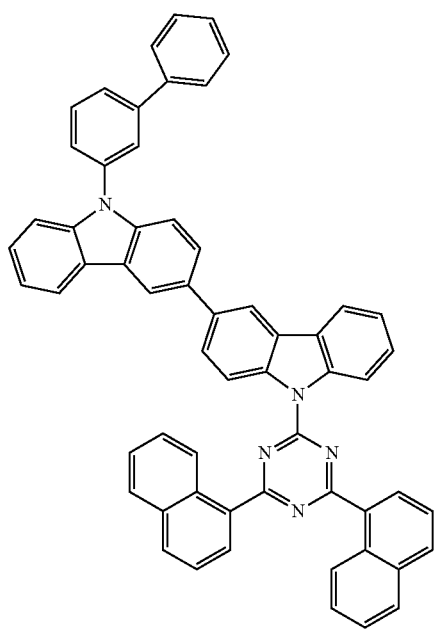
Compound 39
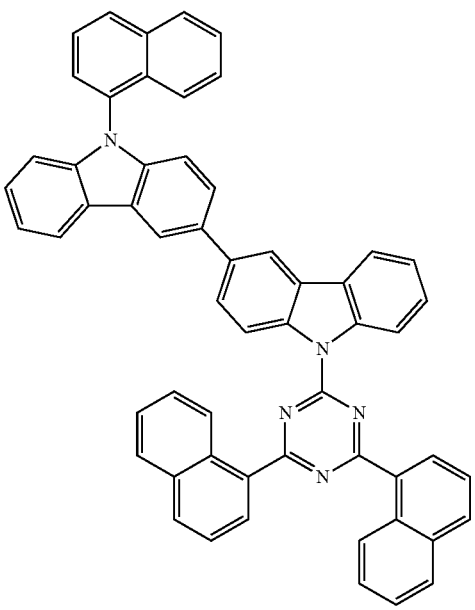

Compound 40
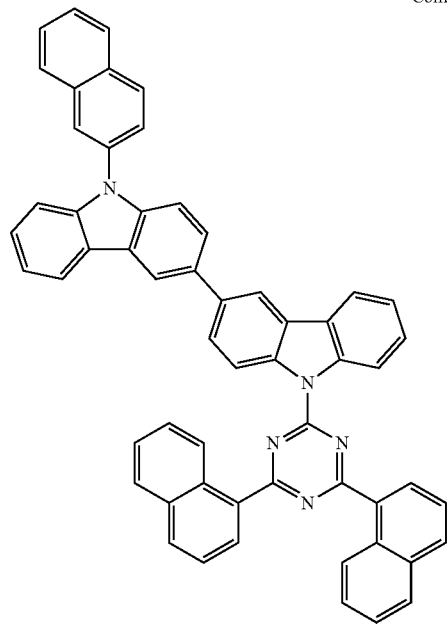
Compound 41
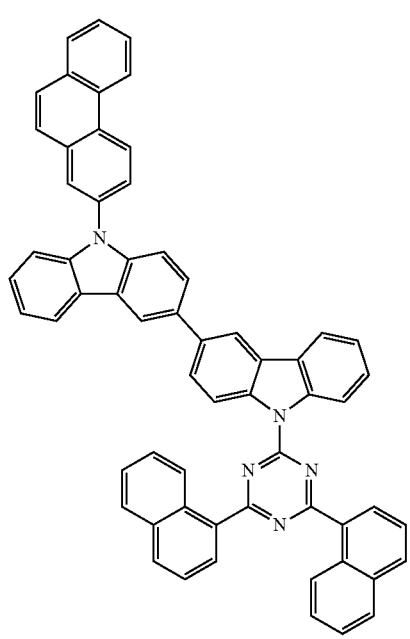
Compound 42
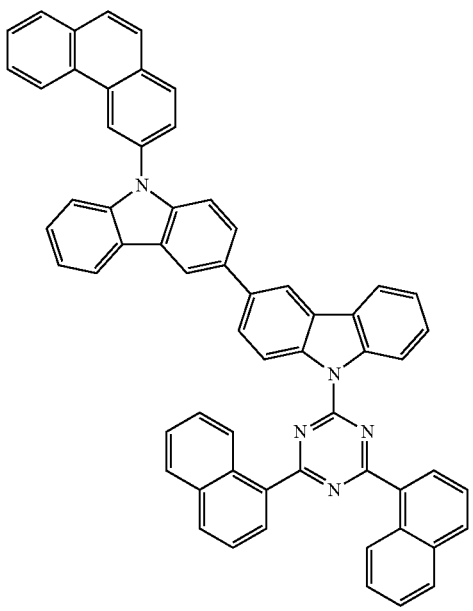
Compound 43
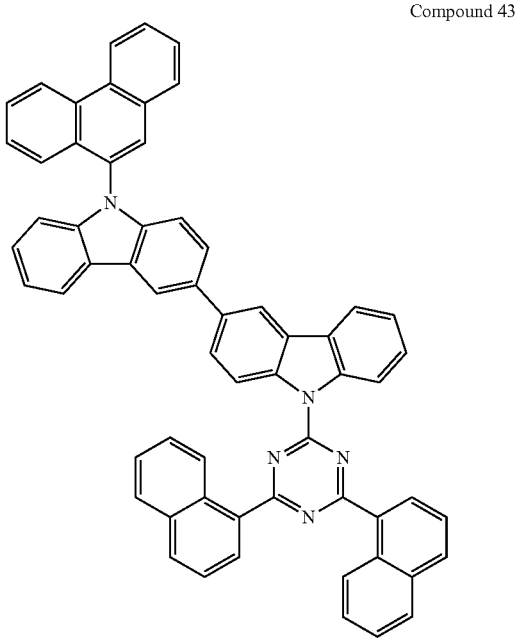

Compound 44
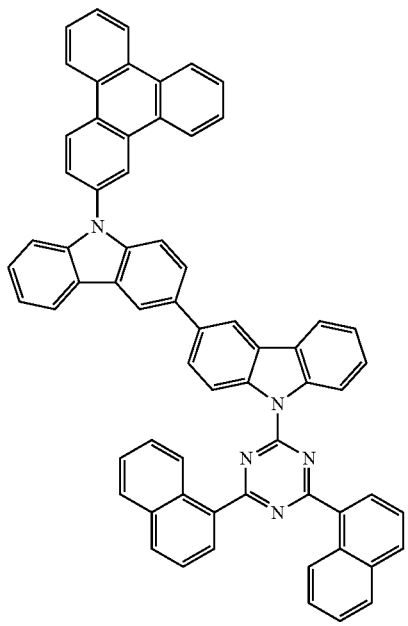
Compound 45
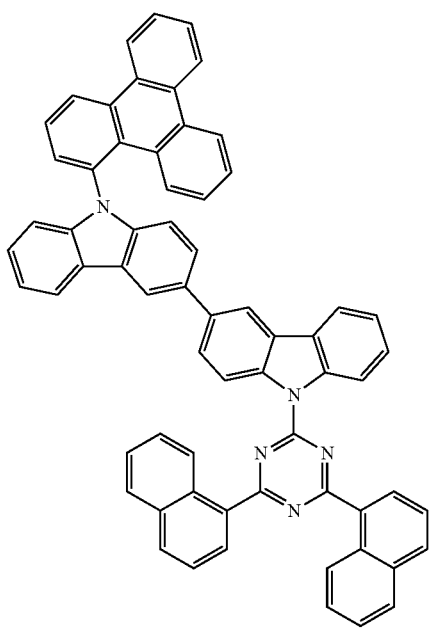
Compound 46
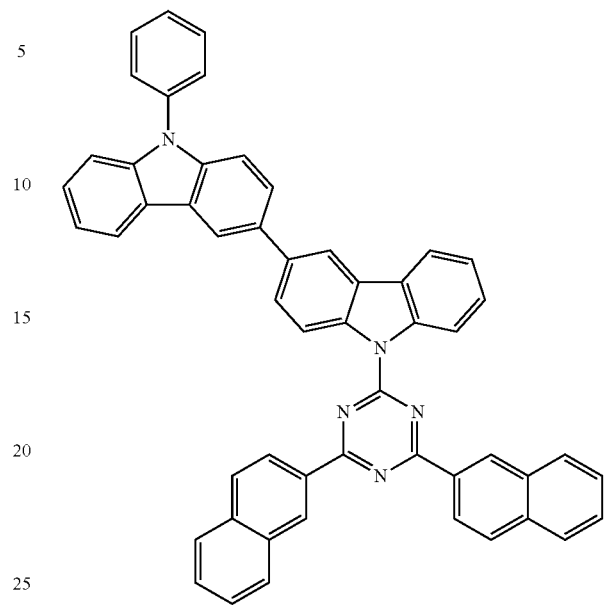
Compound 47
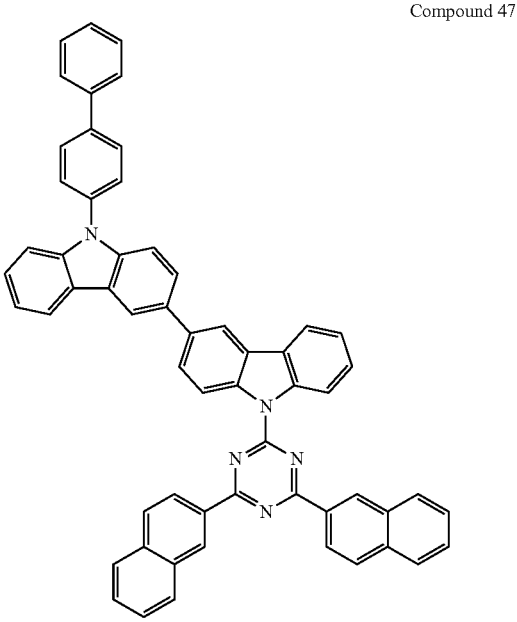

Compound 48
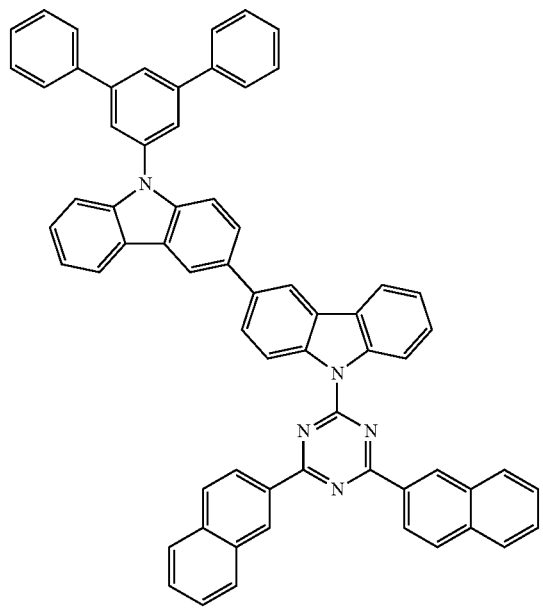
Compound 49
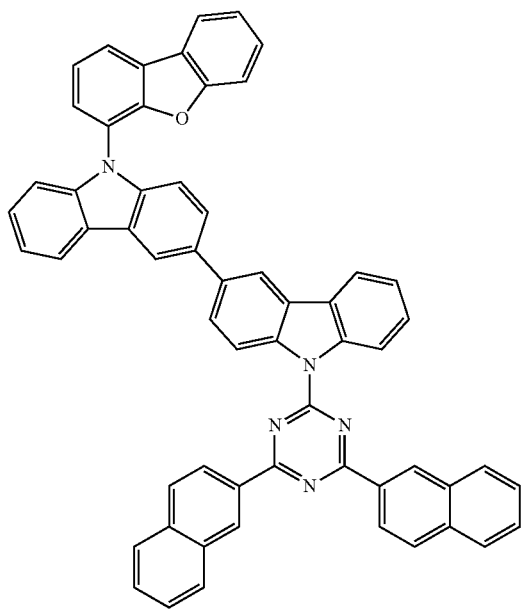
Compound 50
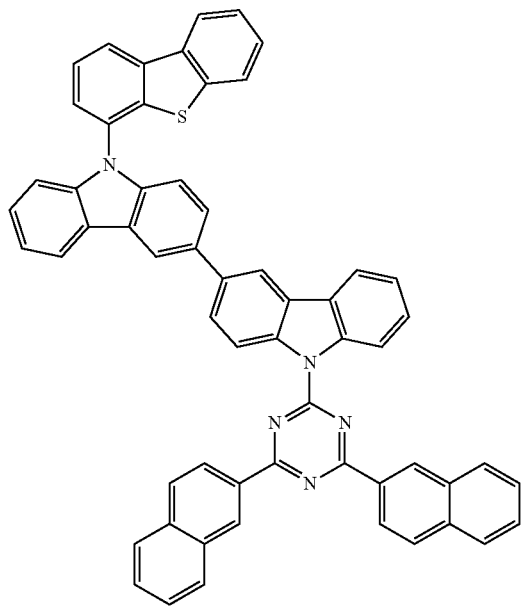
Compound 51
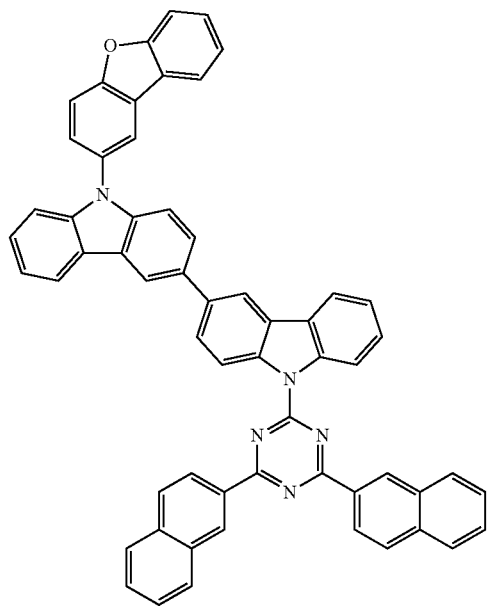

Compound 52
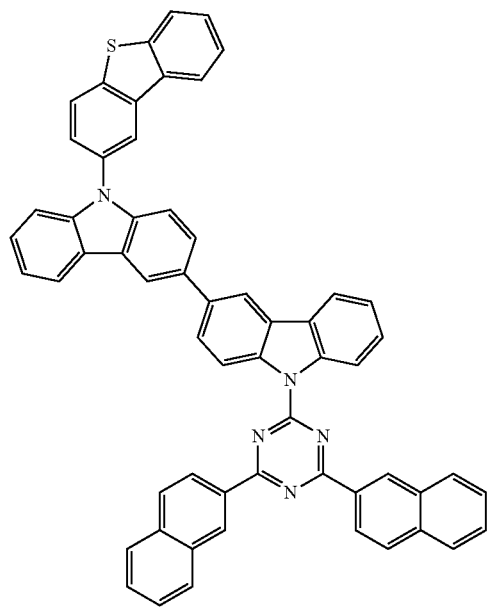
Compound 53
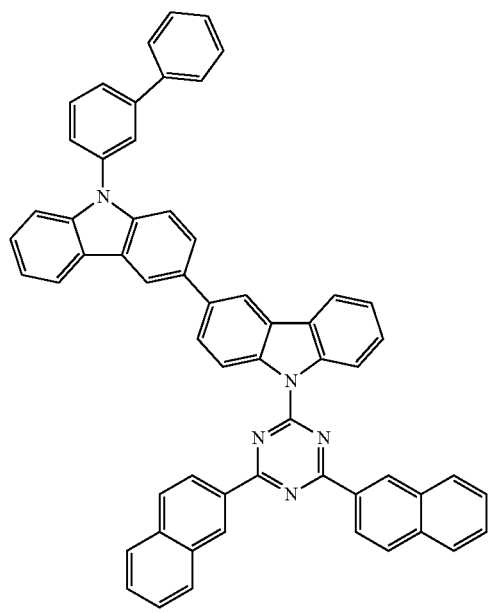
Compound 54
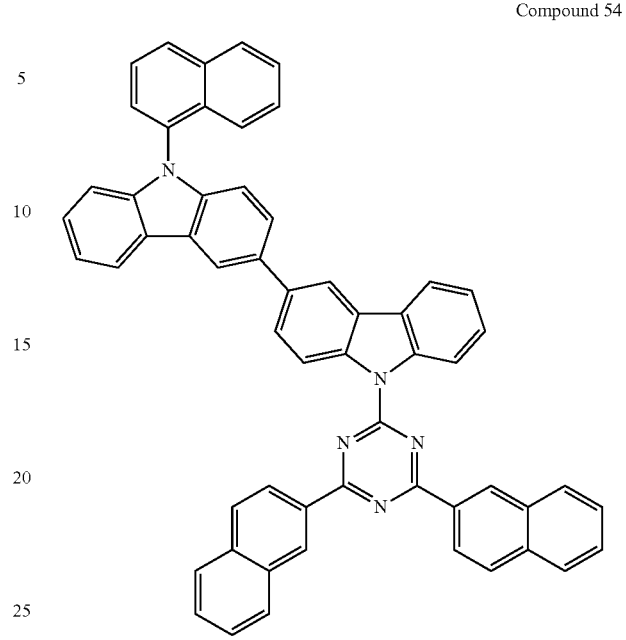
Compound 55
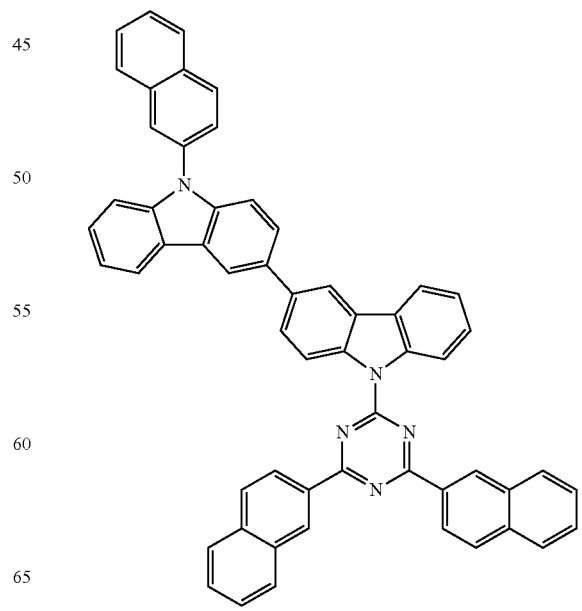

Compound 56
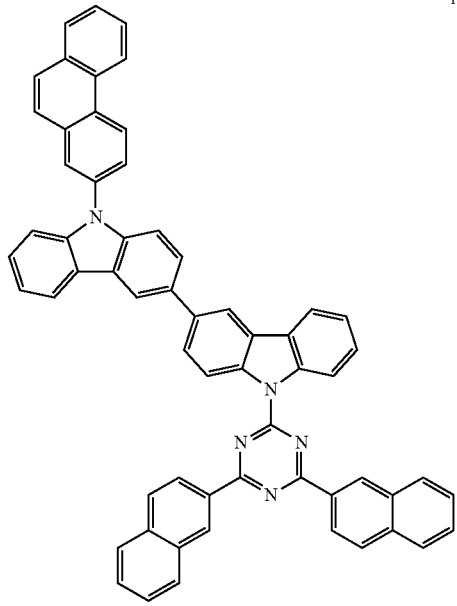
Compound 57
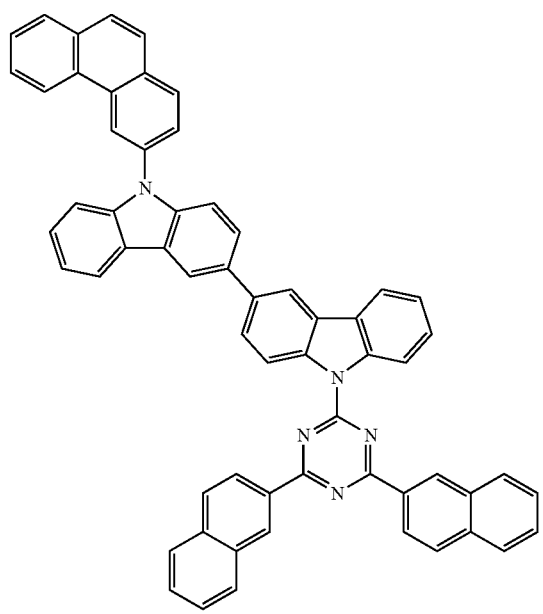
Compound 58
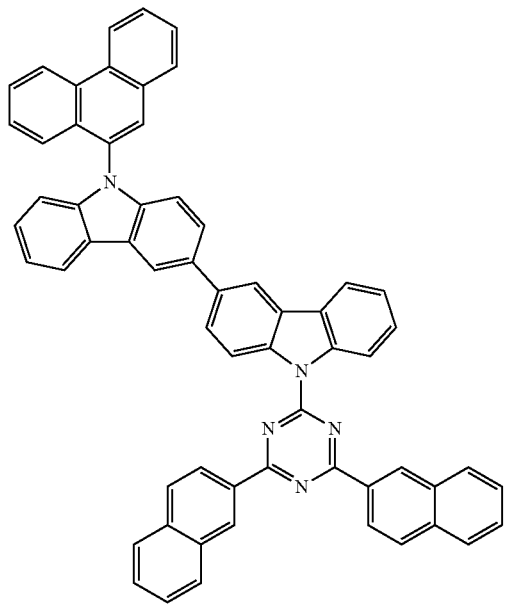
Compound 59
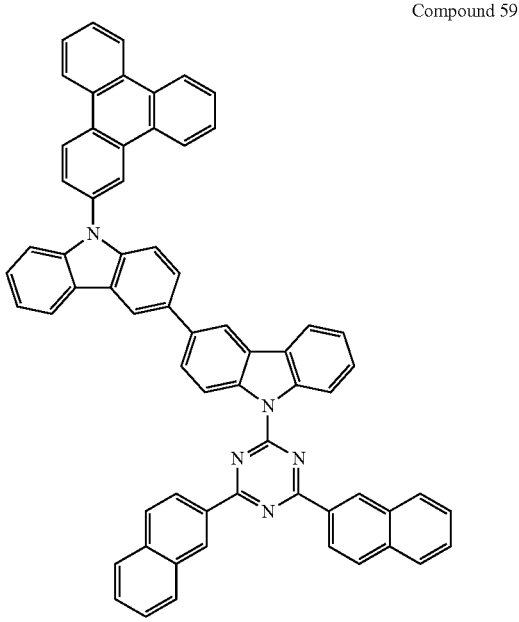

Compound 60
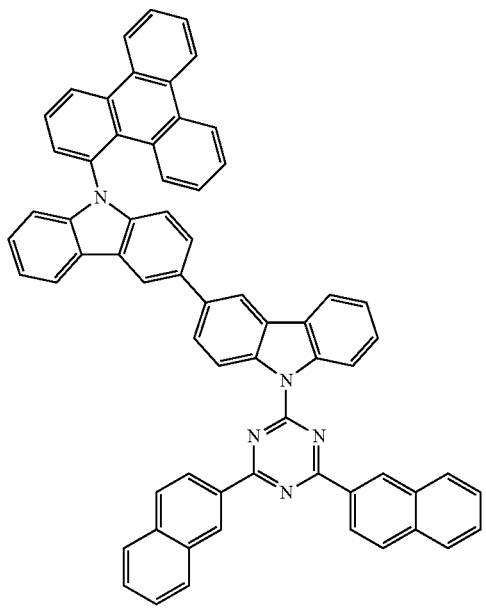
Compound 61
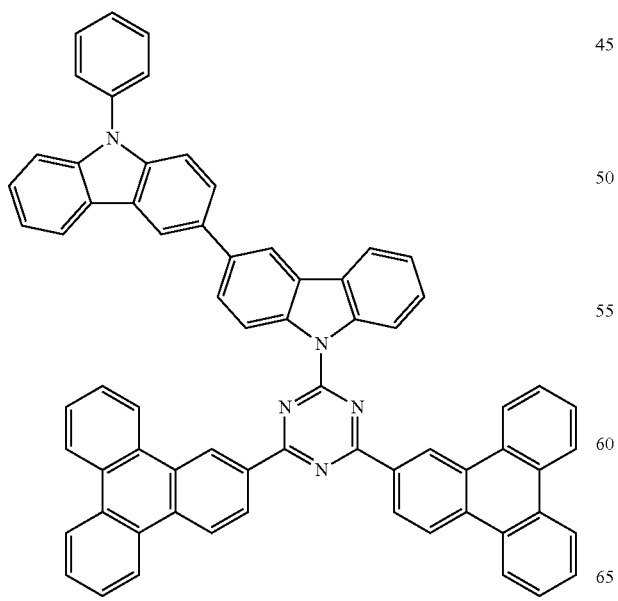
Compound 62
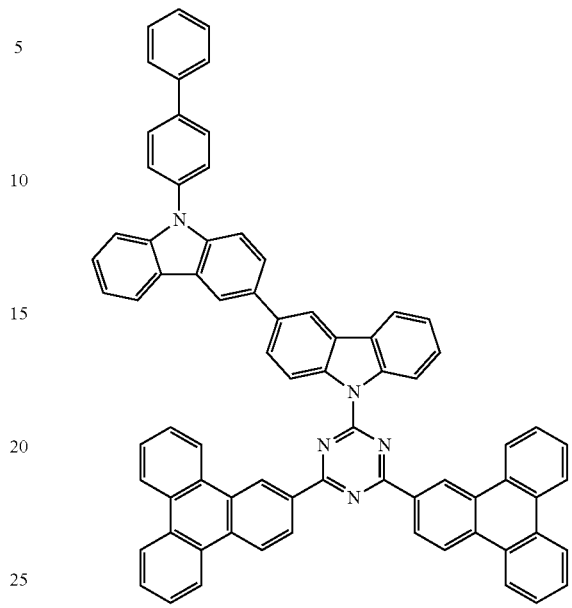
Compound 63
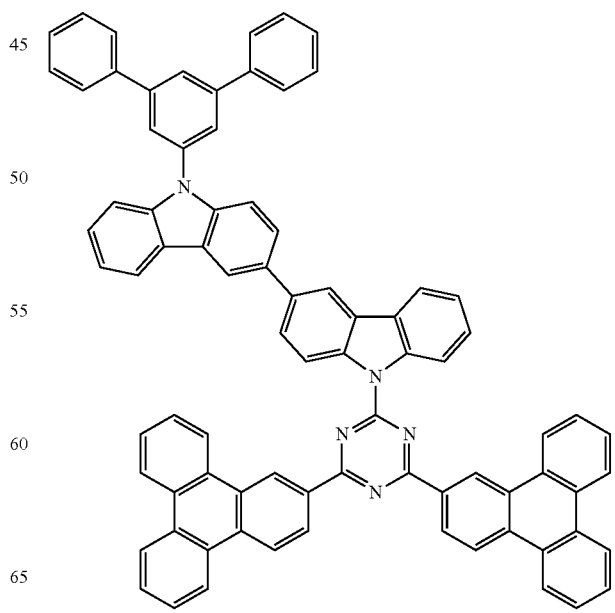

Compound 64
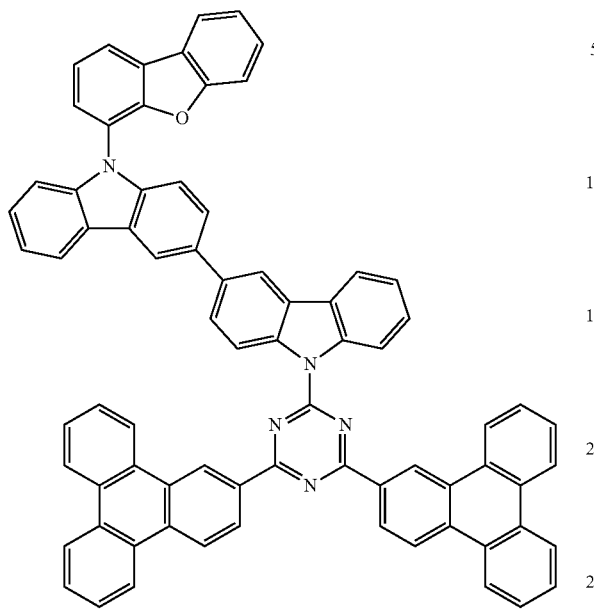
Compound 65
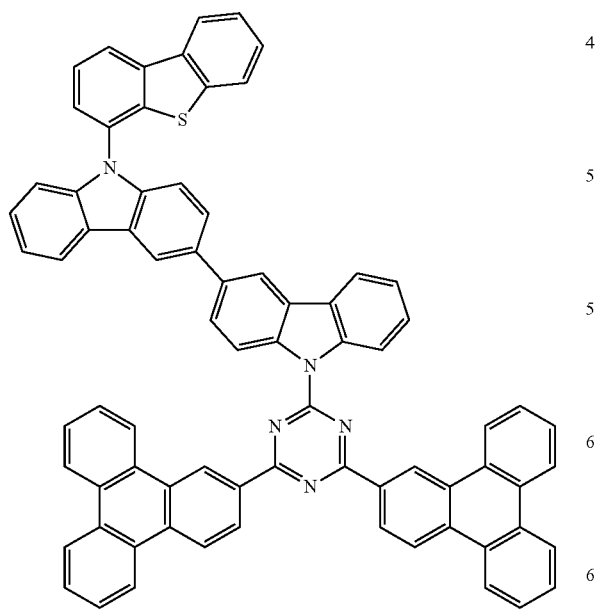
Compound 66
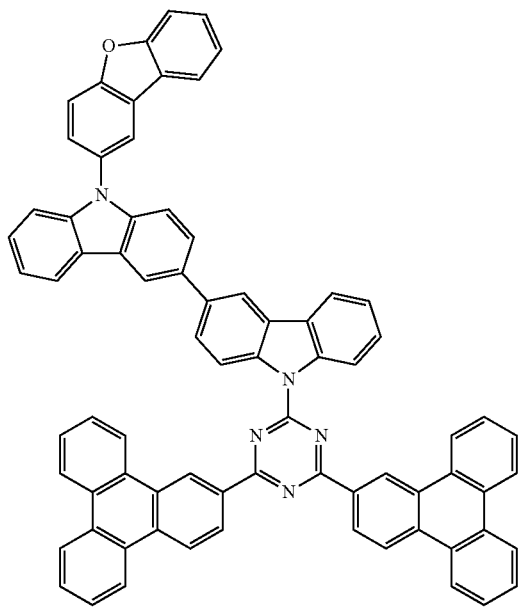
Compound 67
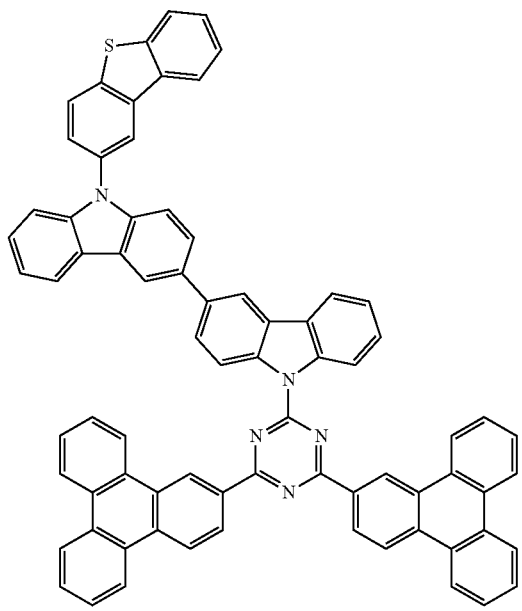

Compound 68
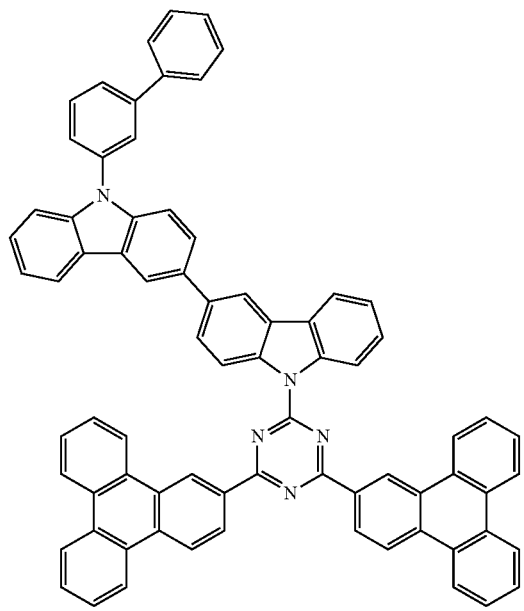
Compound 69
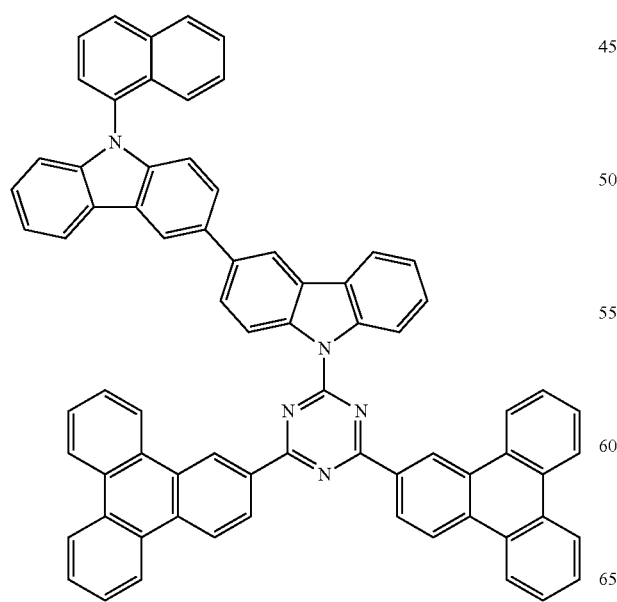
Compound 70
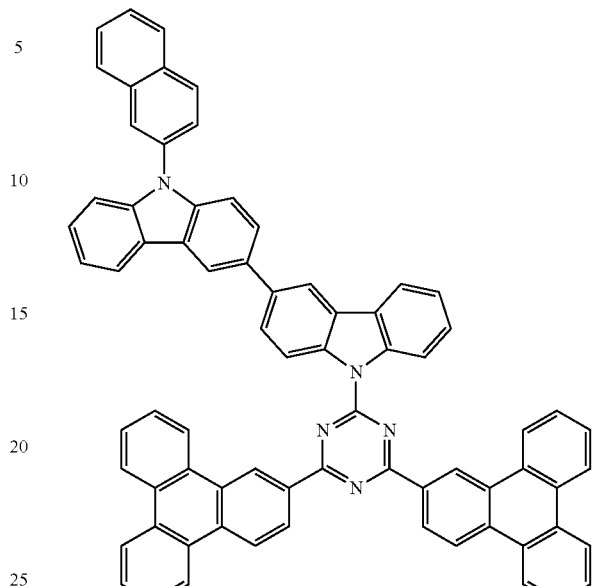
Compound 71
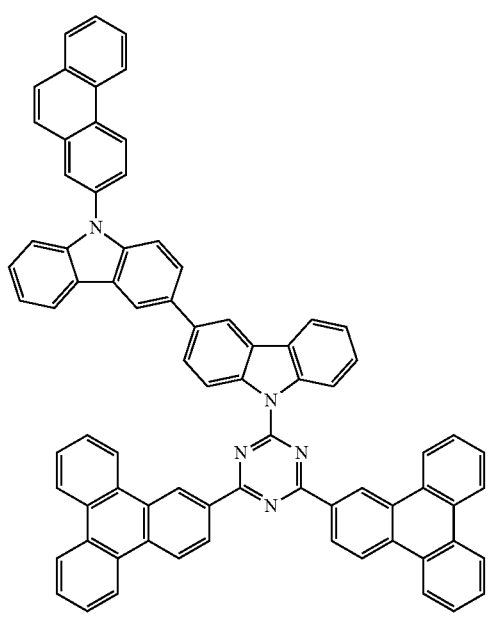

Compound 72
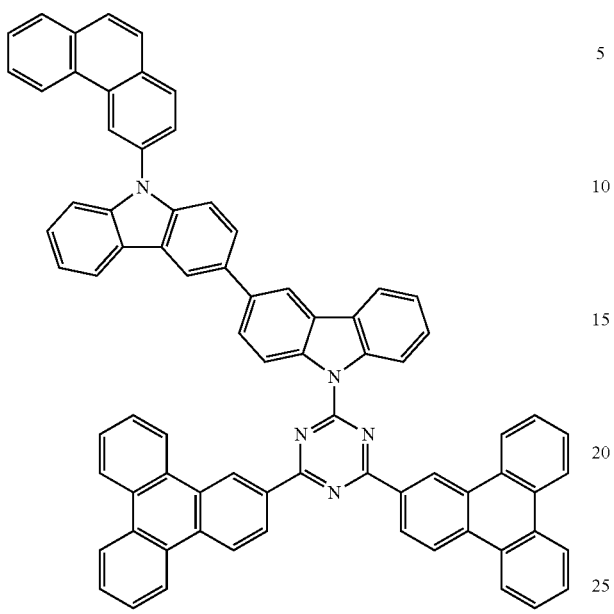
Compound 74
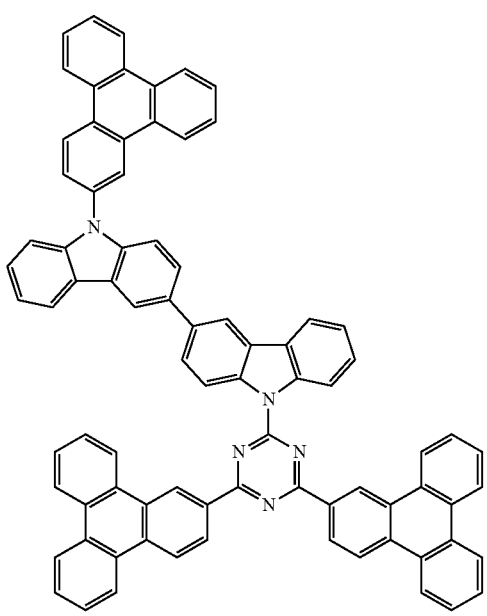
Compound 73
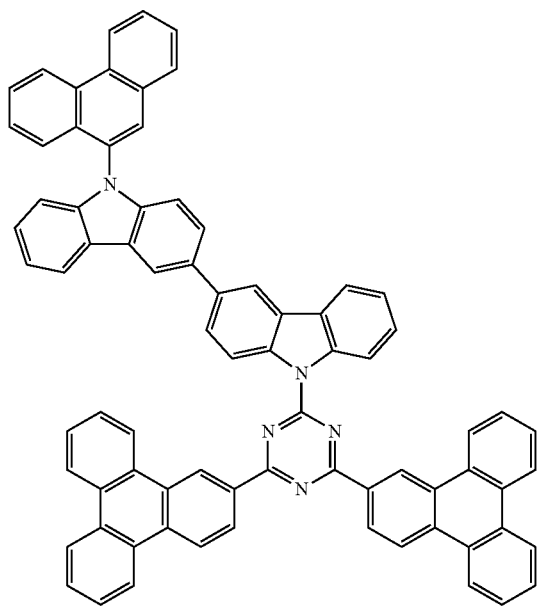
Compound 75
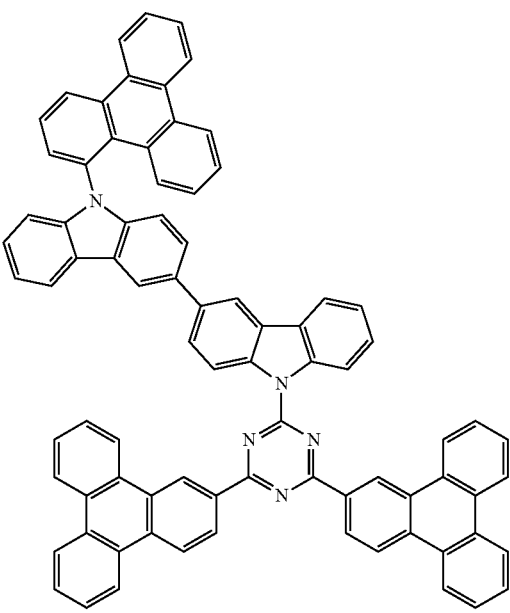

Compound 76
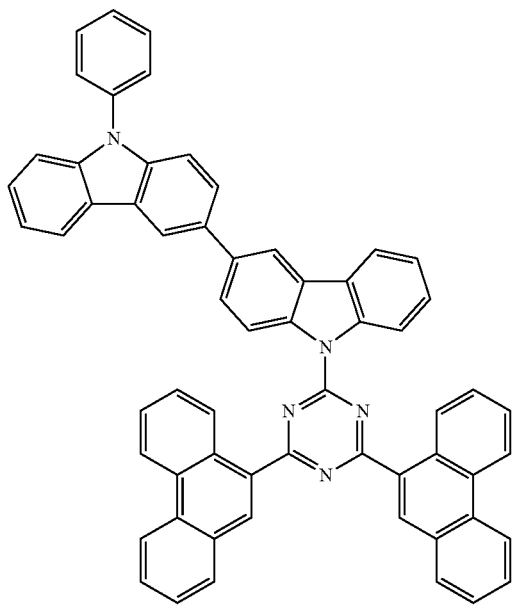
Compound 78
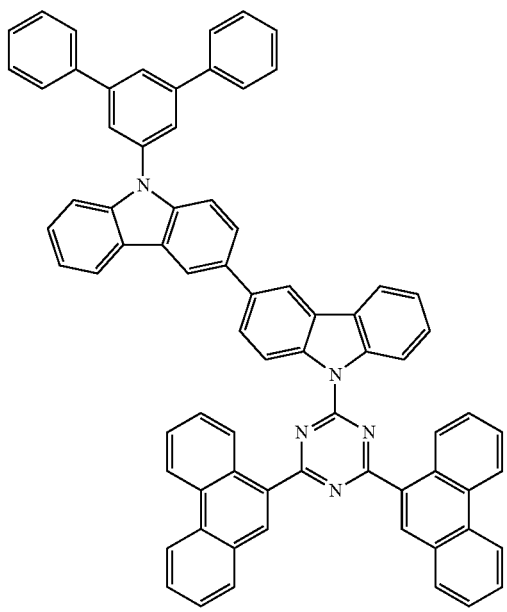
Compound 77
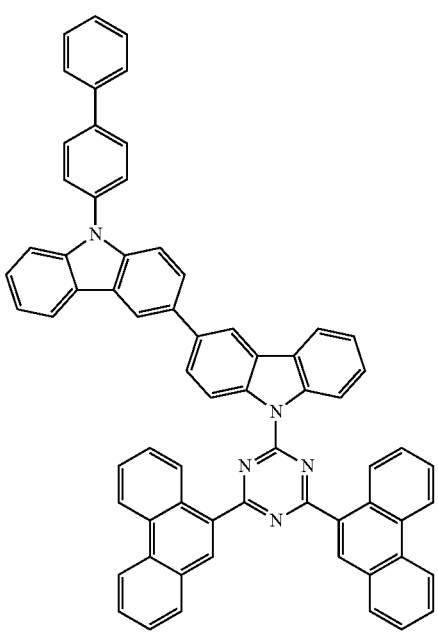
Compound 79

Compound 80
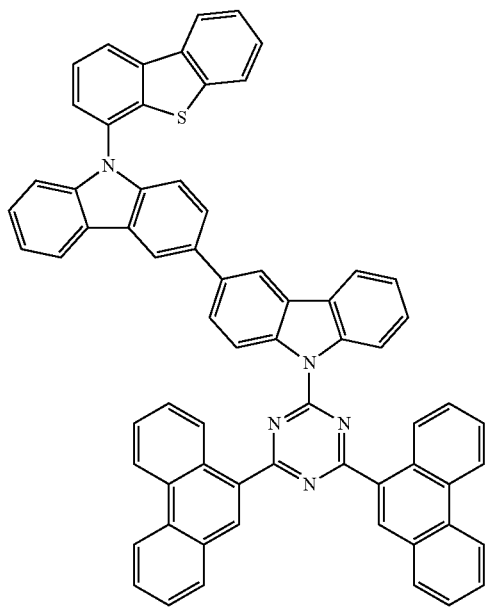
Compound 81
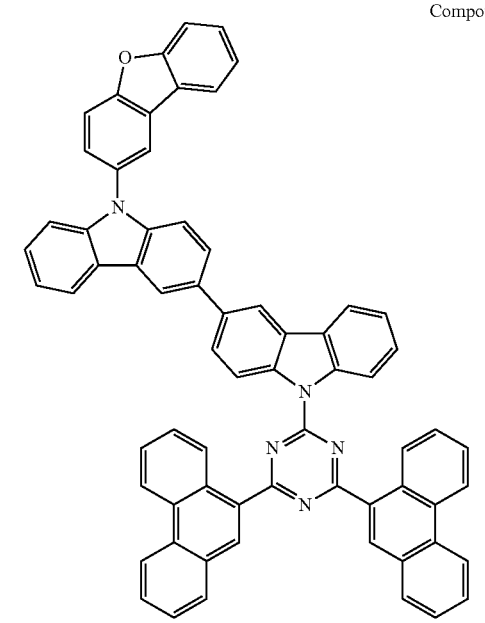
Compound 82
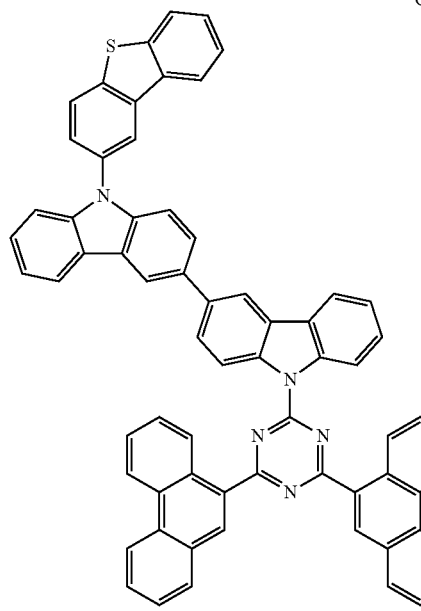
Compound 83
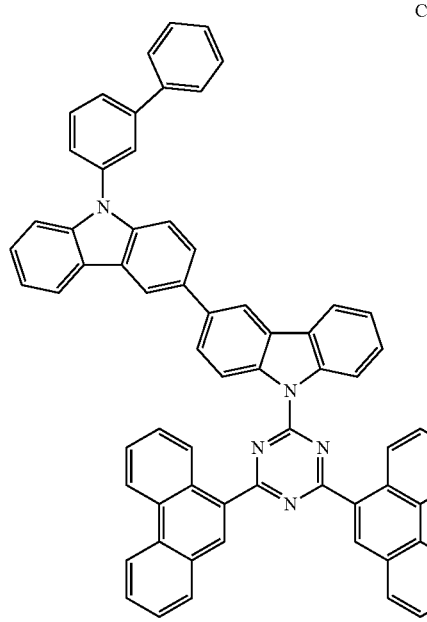

Compound 84
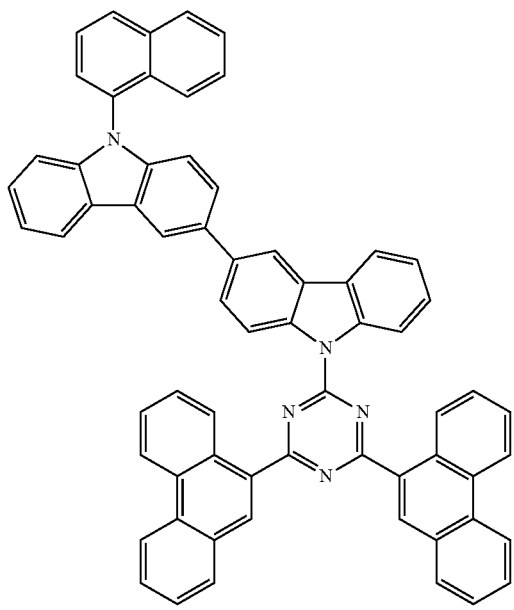
Compound 85
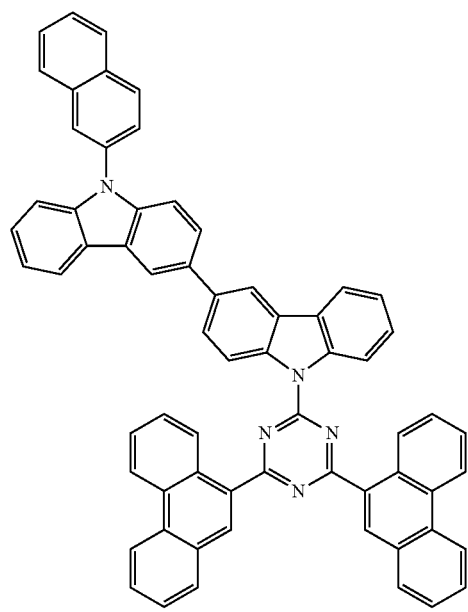
Compound 86
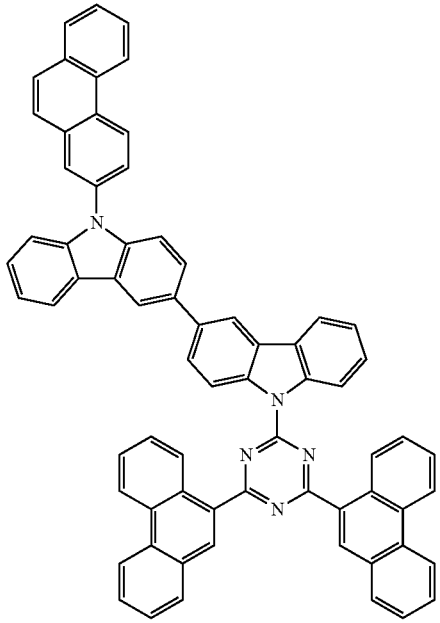
Compound 87
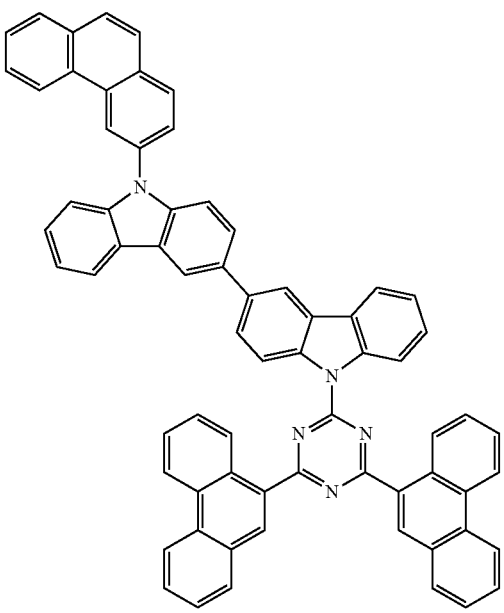

Compound 88
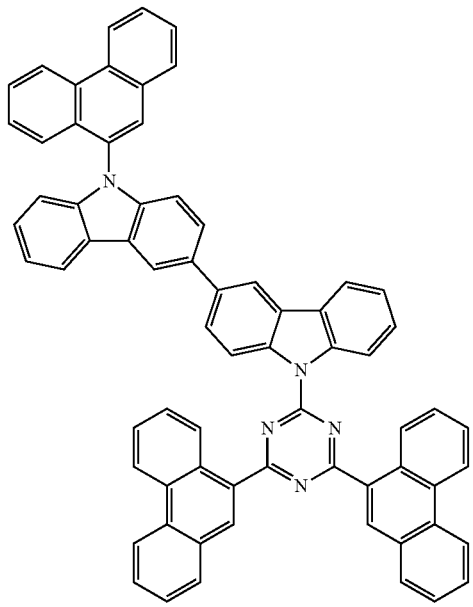
Compound 89
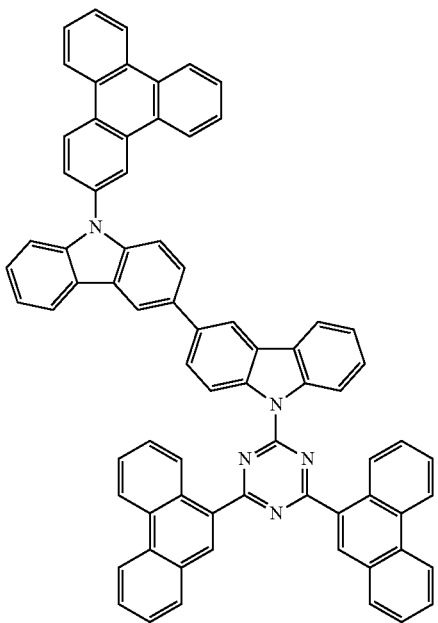
Compound 90
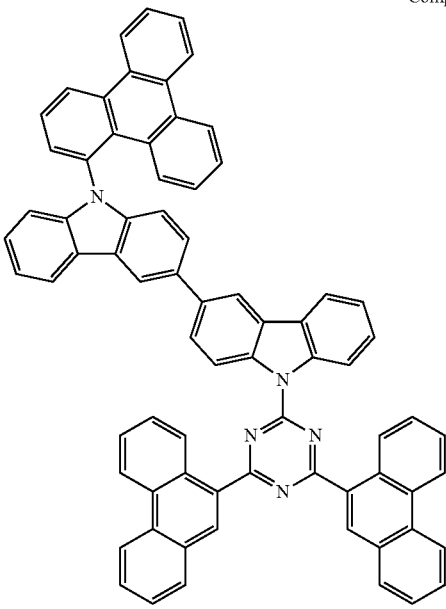
Compound 91
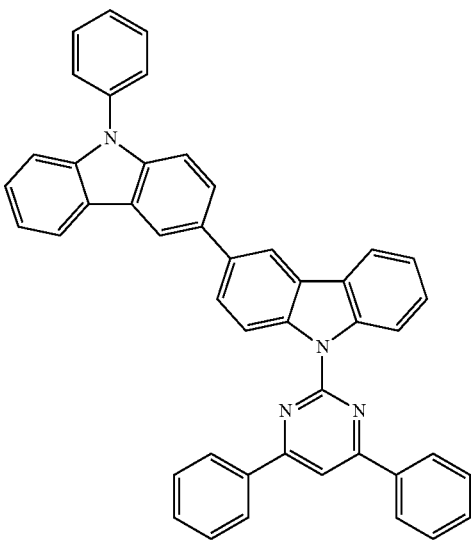

Compound 92
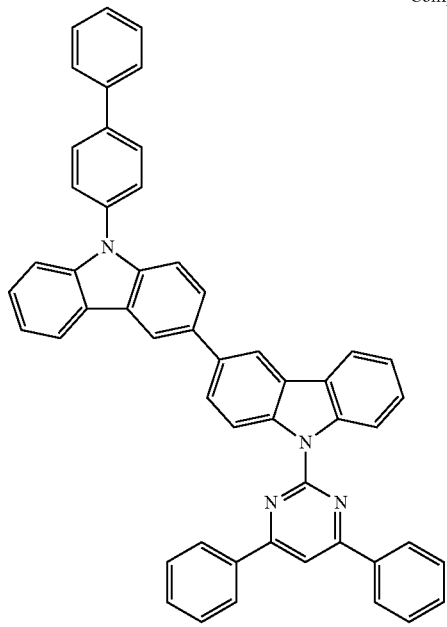
Compound 93
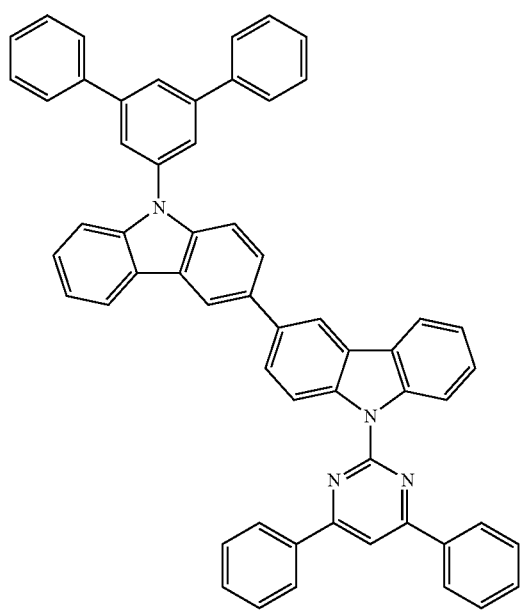
Compound 94
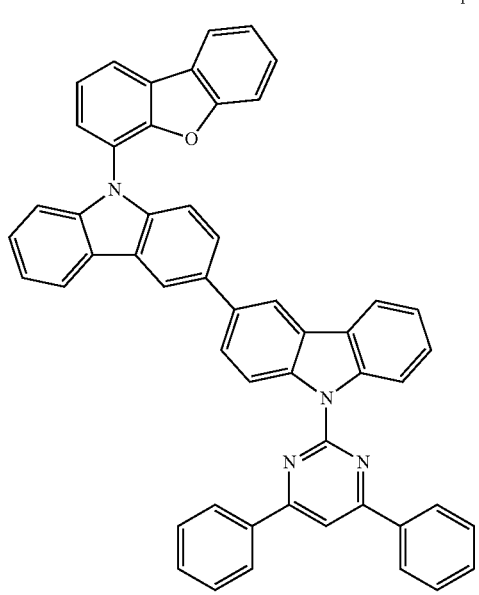
Compound 95
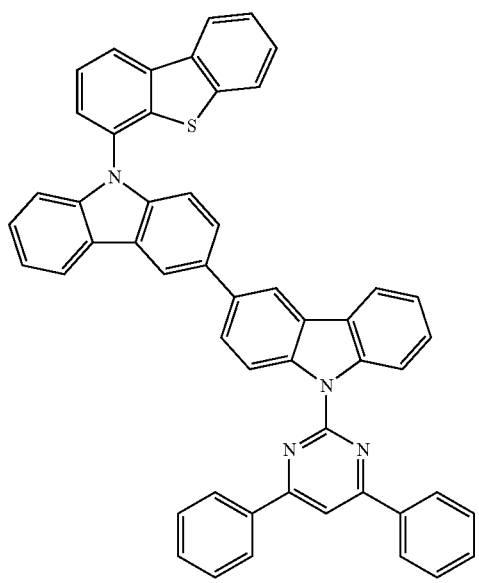

Compound 96
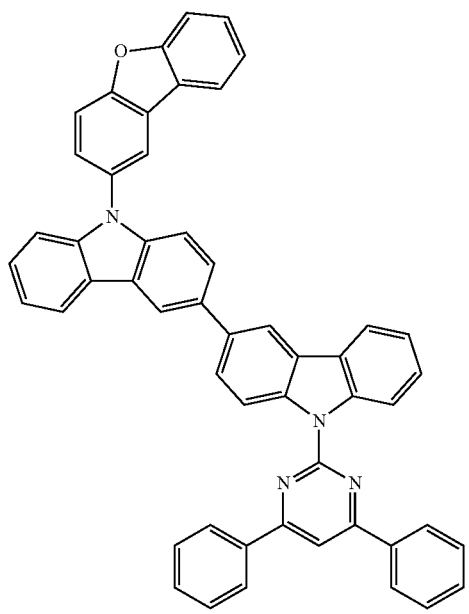
Compound 97
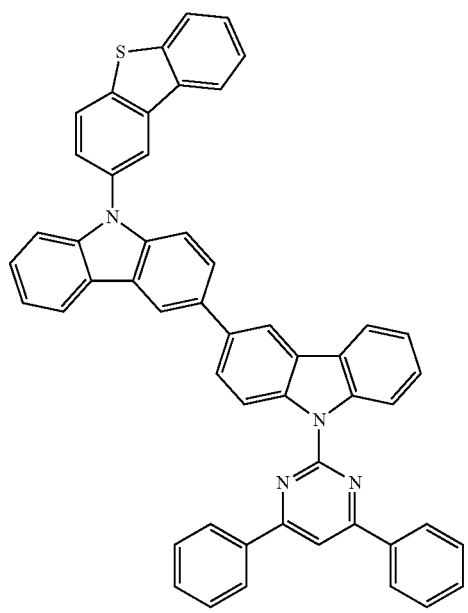
Compound 98
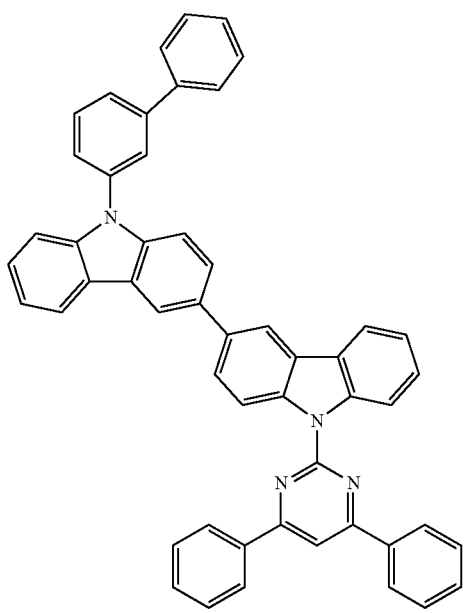
Compound 99
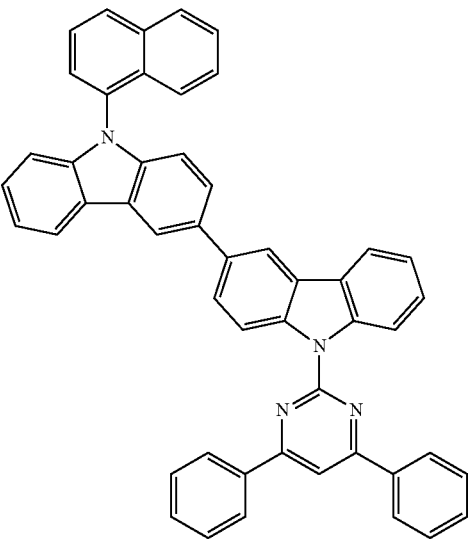

Compound 100
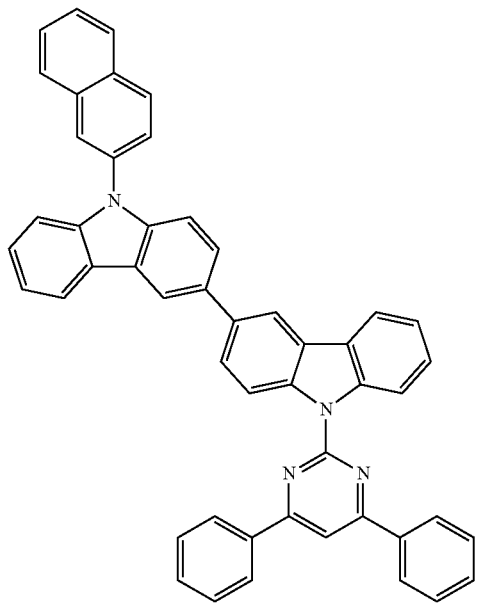
Compound 101
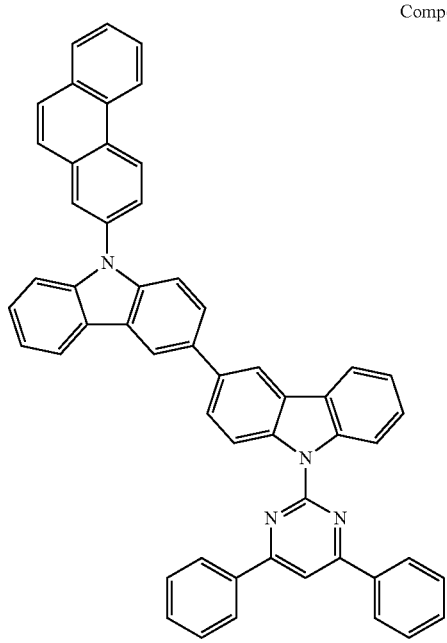
Compound 102
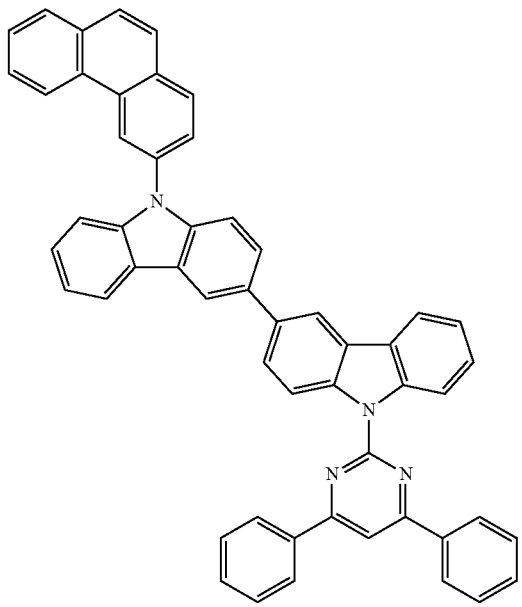
Compound 103
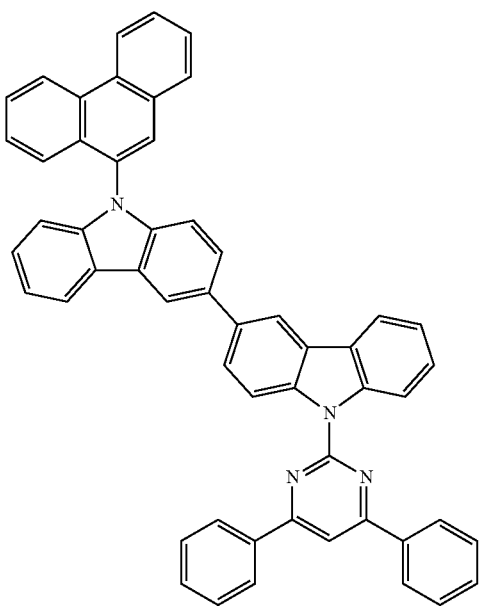

Compound 104
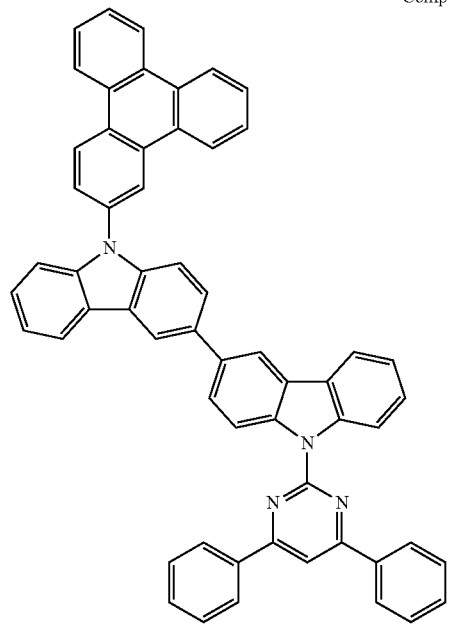
Compound 105
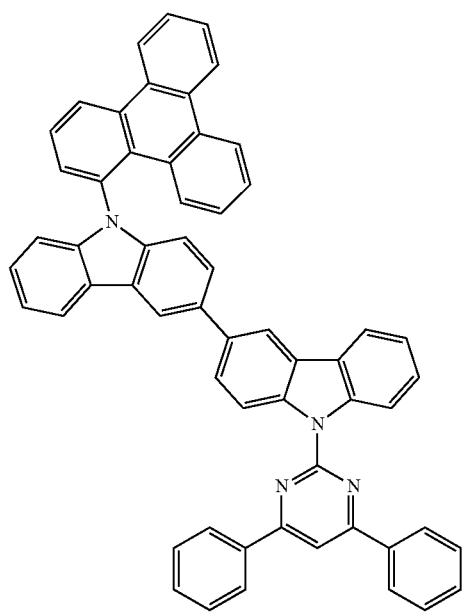
Compound 106
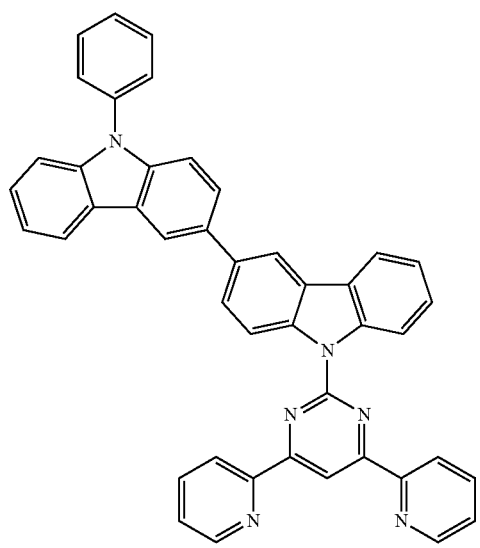
Compound 107
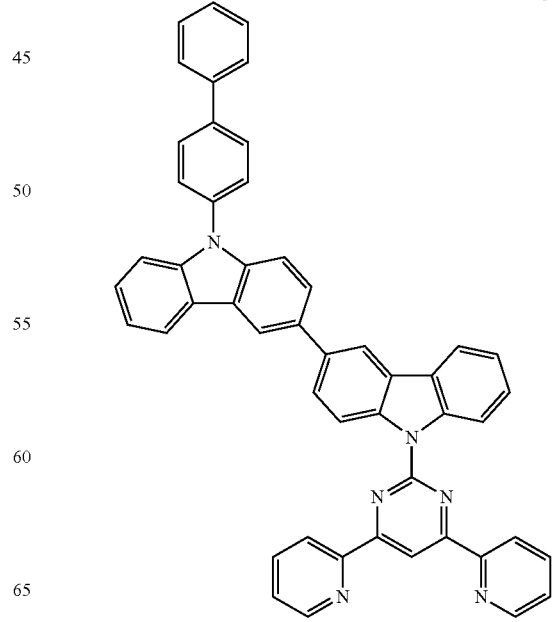

Compound 108
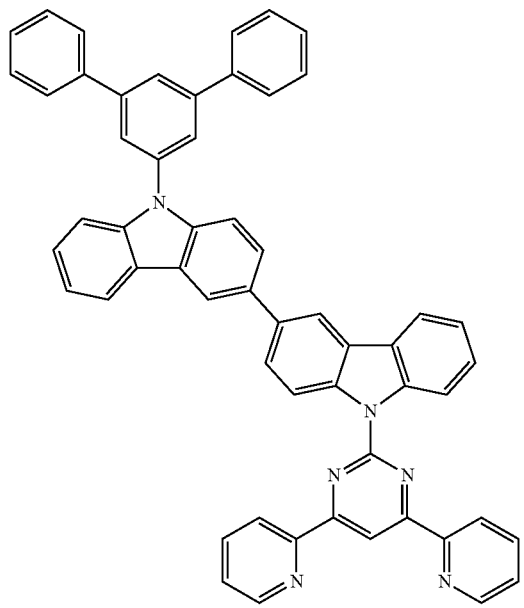
Compound 109
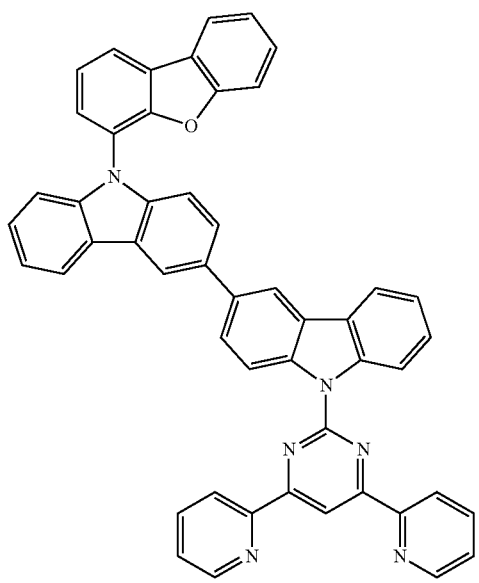
Compound 110
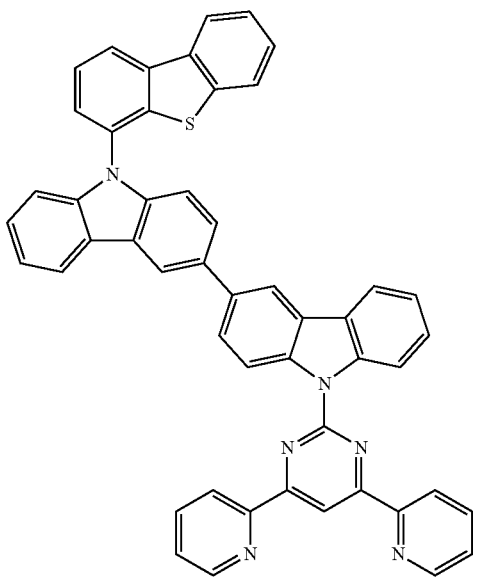
Compound 111
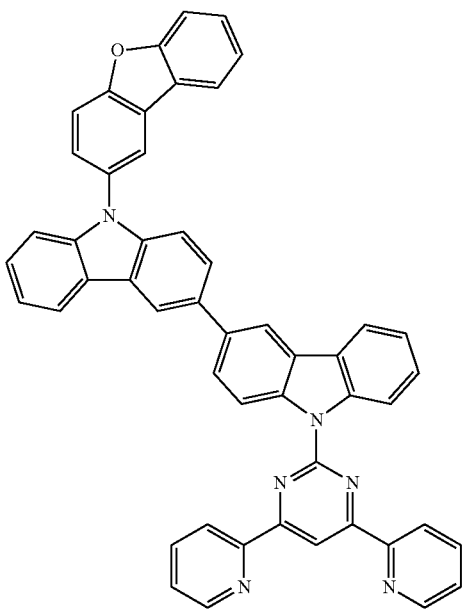

Compound 112
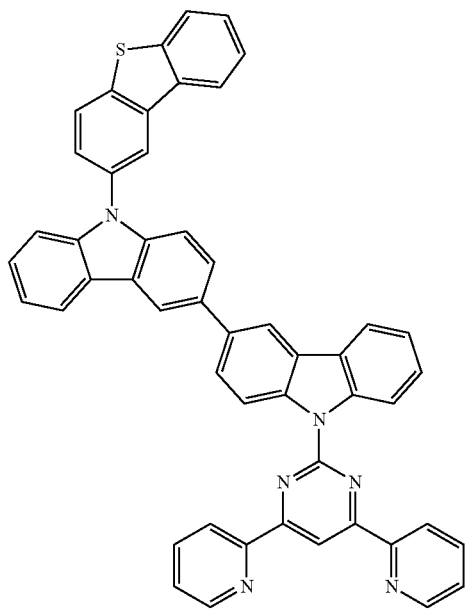
Compound 113
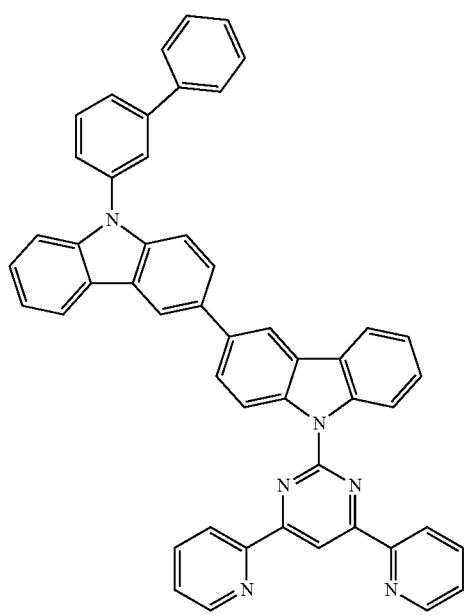
Compound 114
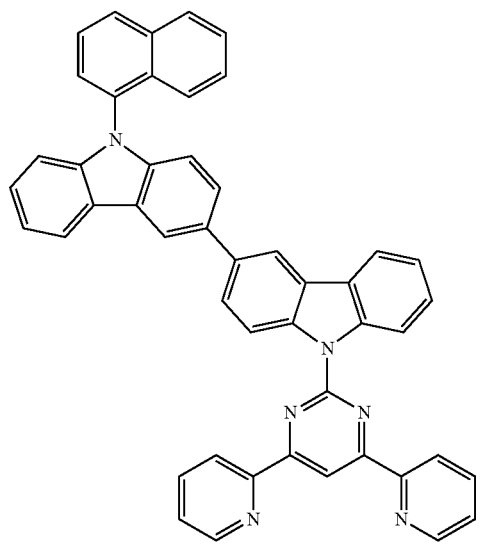
Compound 115
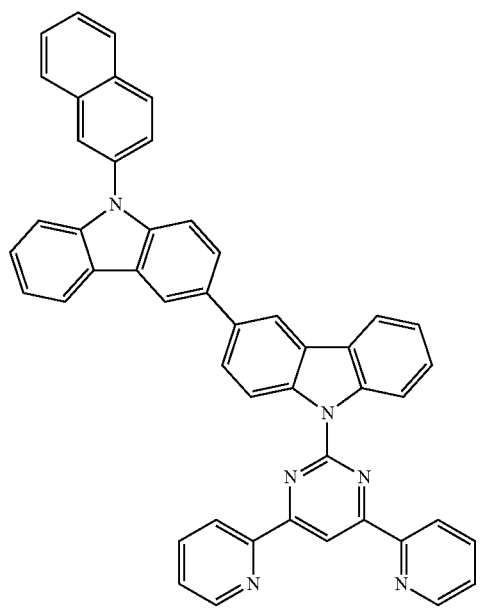

Compound 116
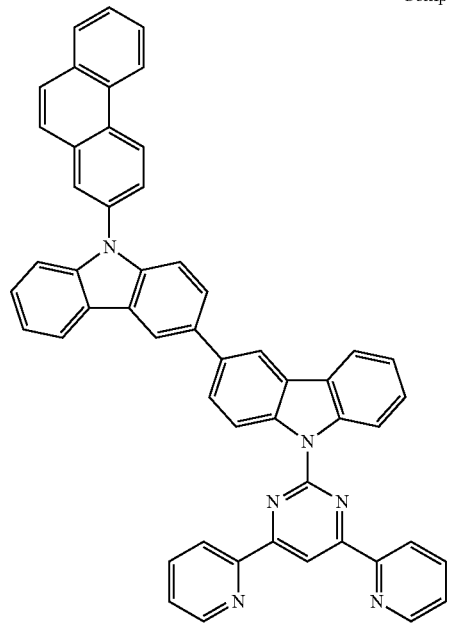
Compound 117
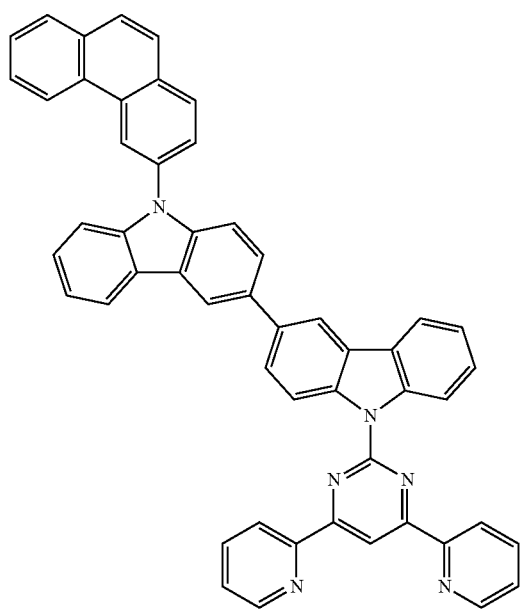
Compound 118
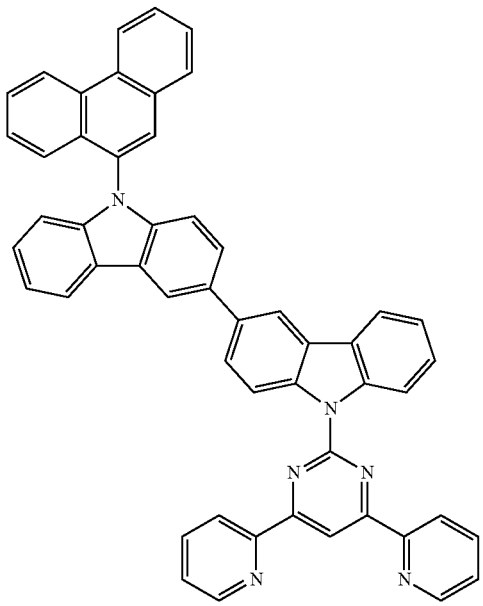
Compound 119
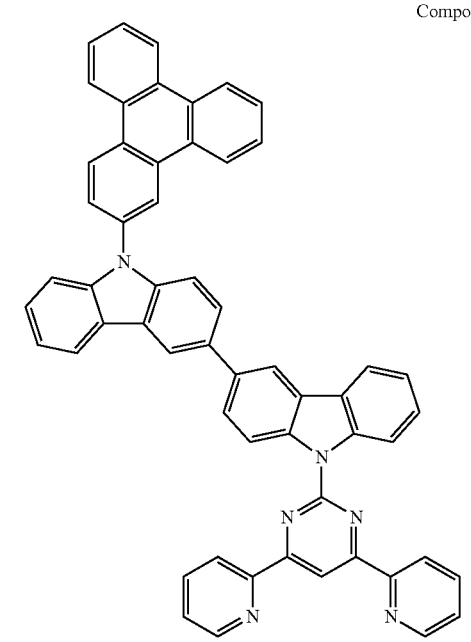

Compound 120
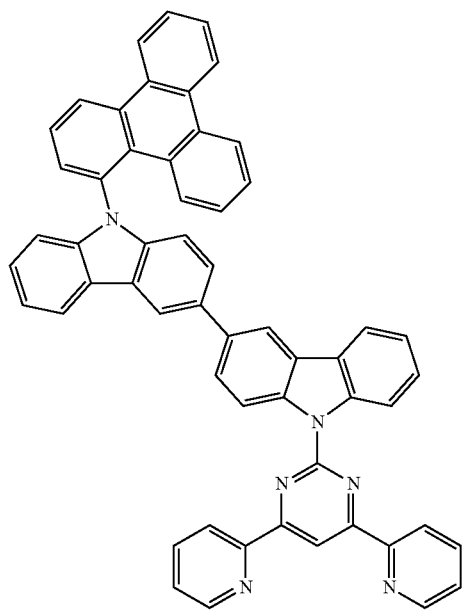
Compound 121
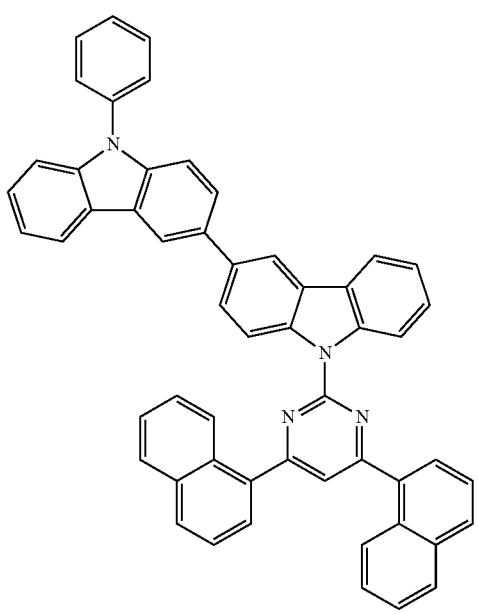
Compound 122
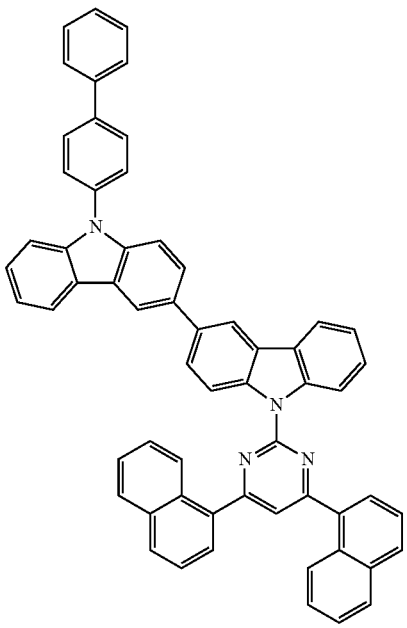
Compound 123
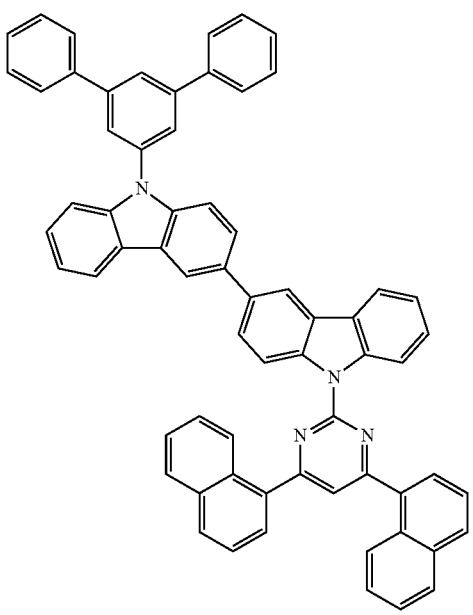

Compound 124
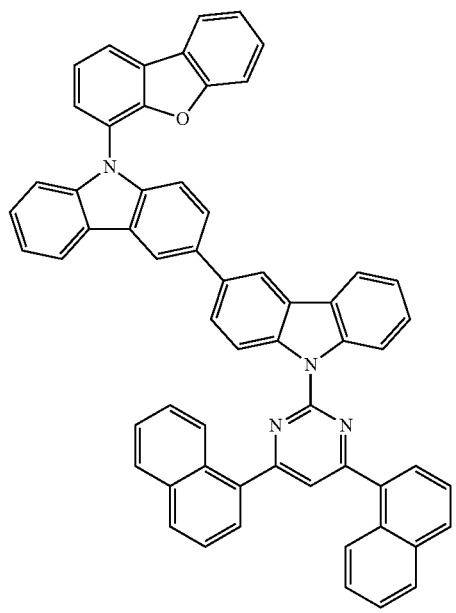
Compound 125
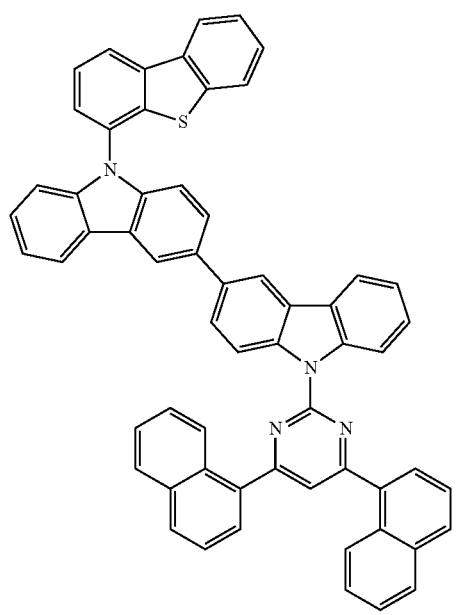
Compound 126
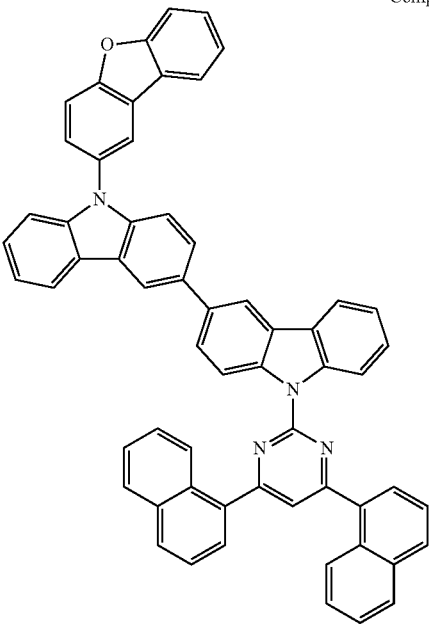
Compound 127
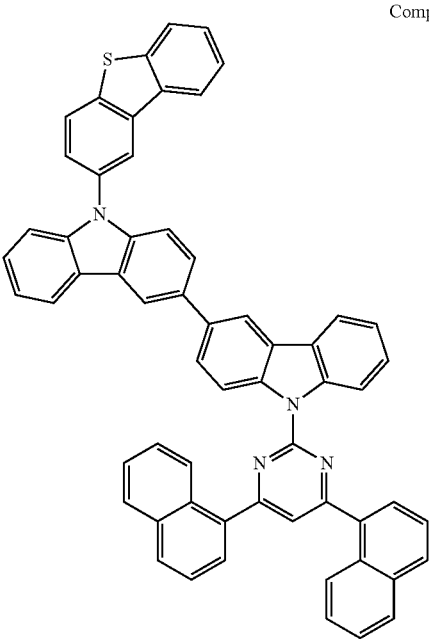

Compound 128
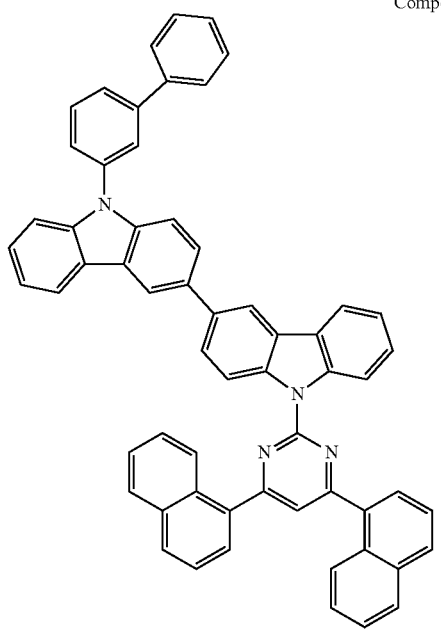
Compound 129
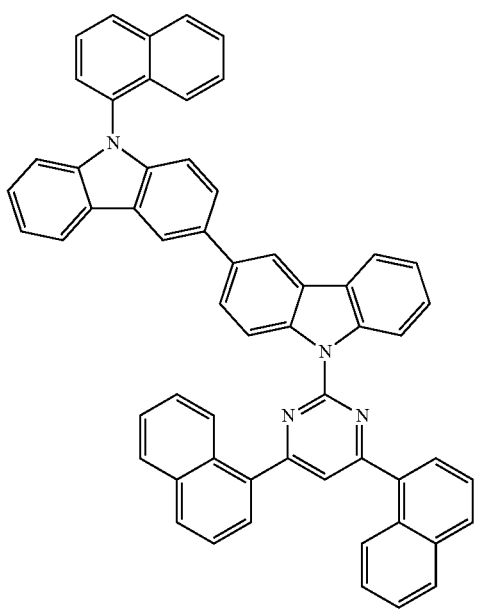
Compound 130
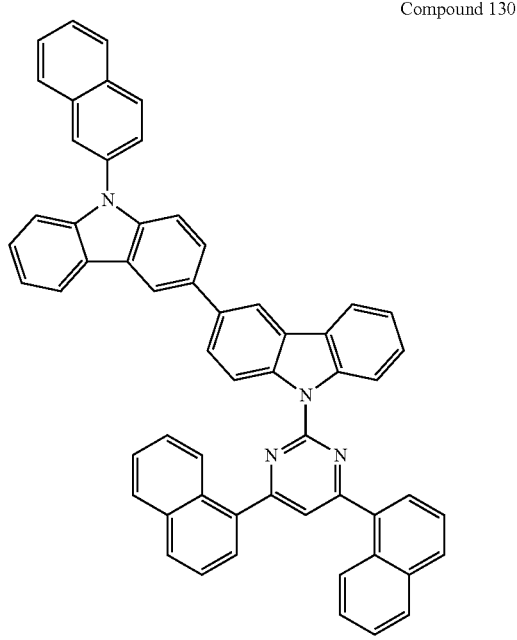
Compound 131

Compound 132
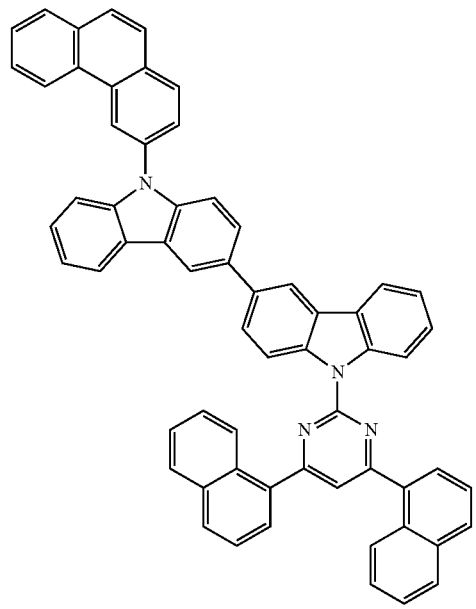
Compound 133
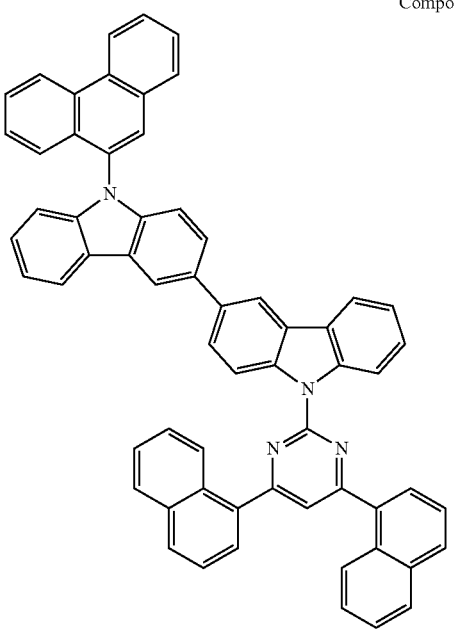
Compound 134
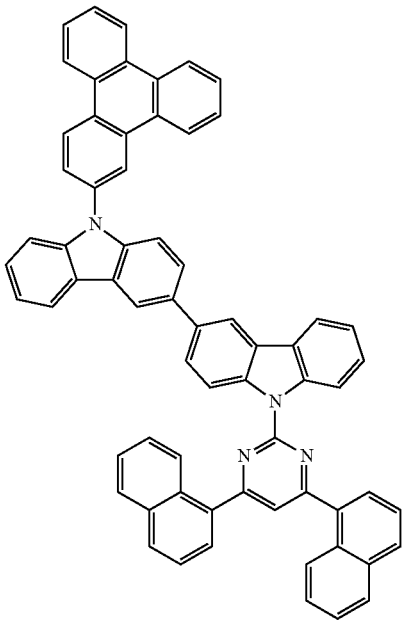
Compound 135
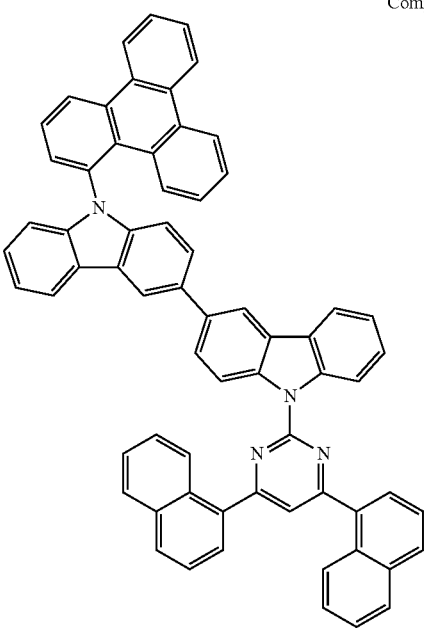

Compound 136
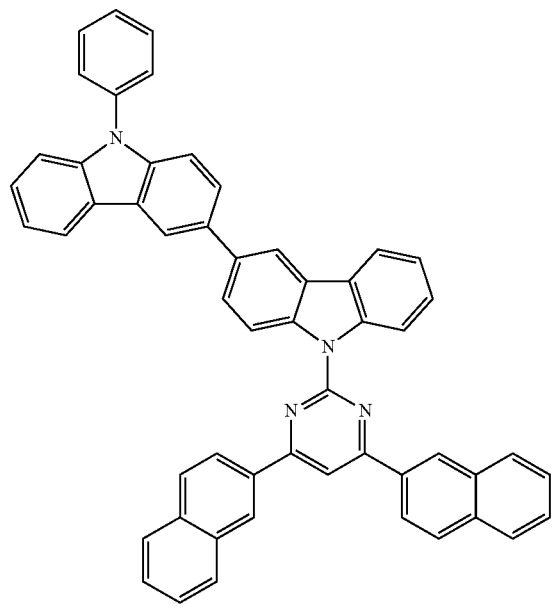
Compound 137
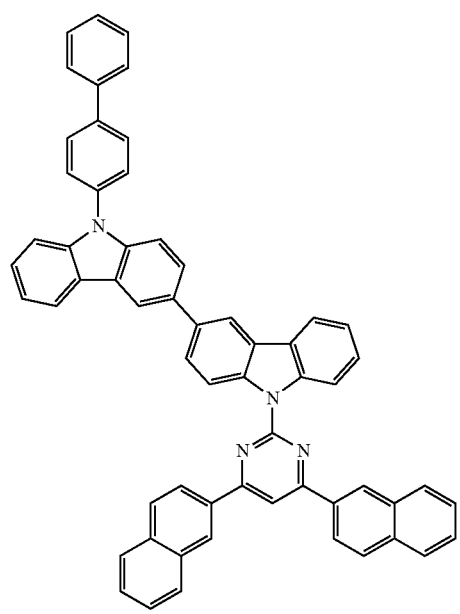
Compound 138
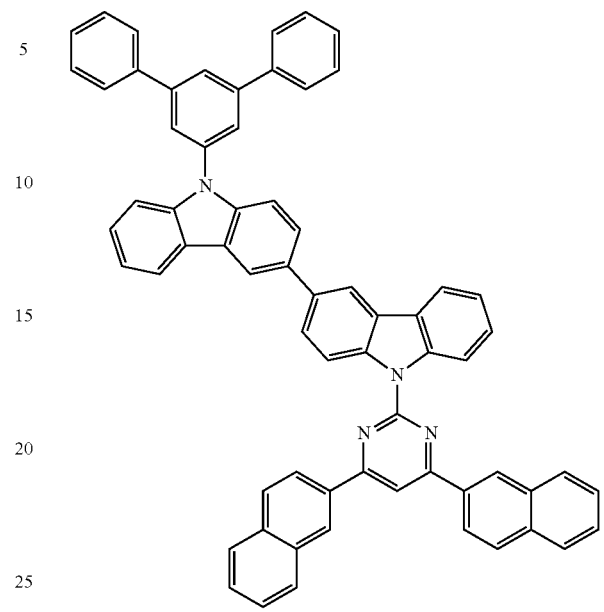
Compound 139
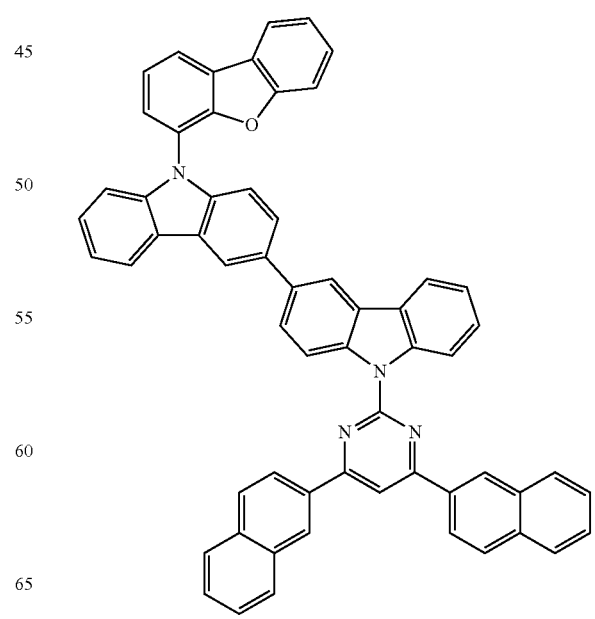

Compound 140
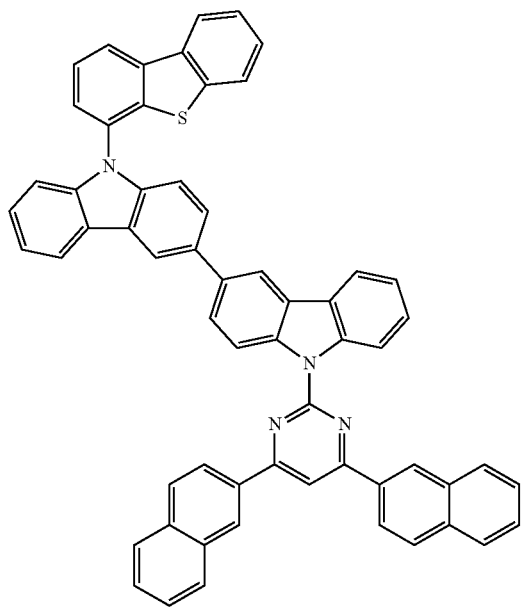
Compound 142
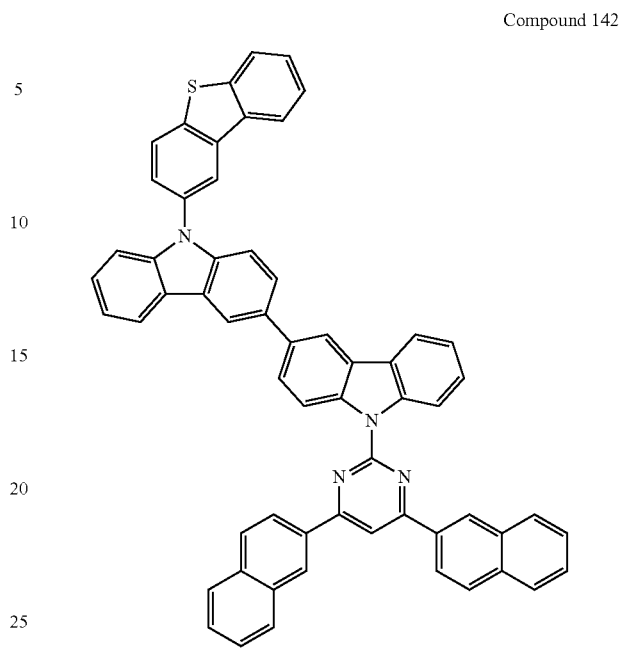
Compound 141
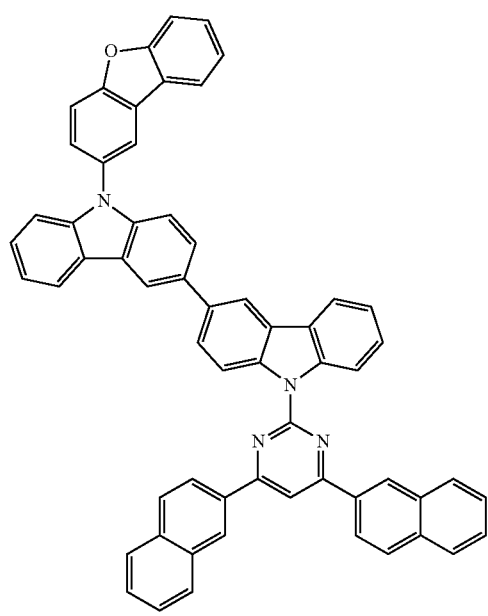
Compound 143
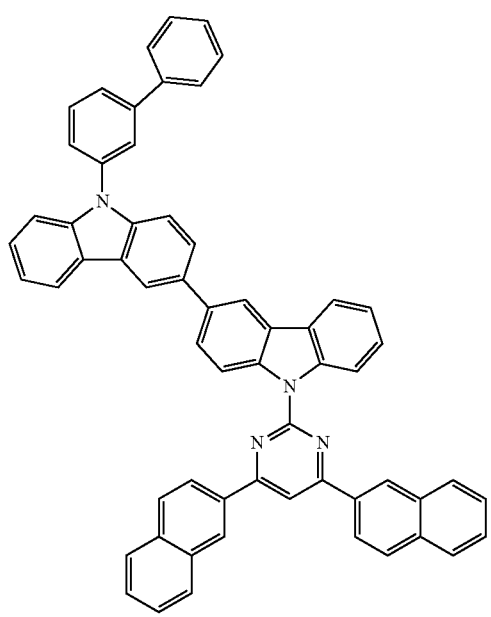

Compound 144
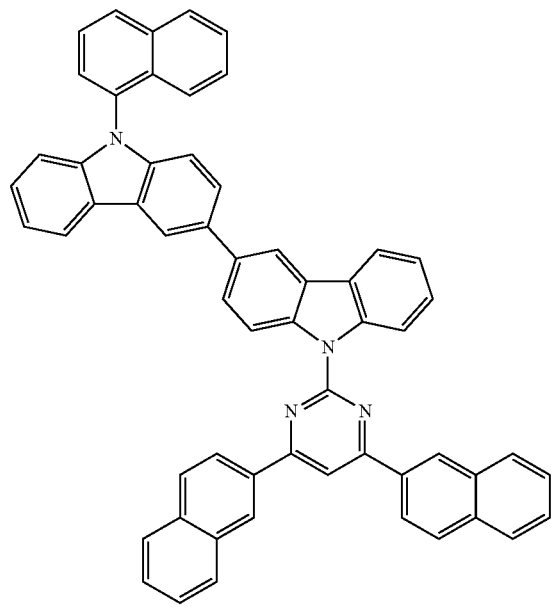
Compound 146
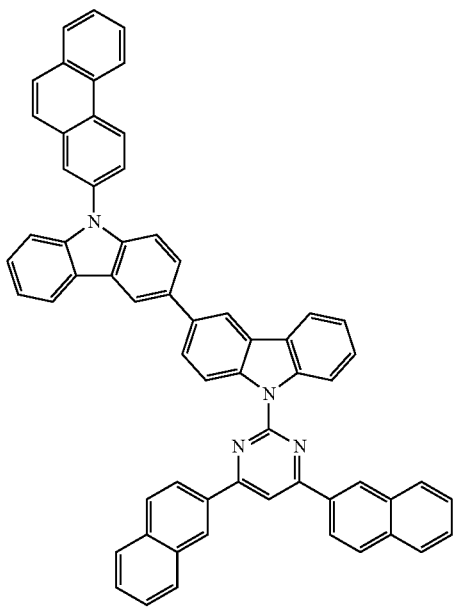
Compound 145
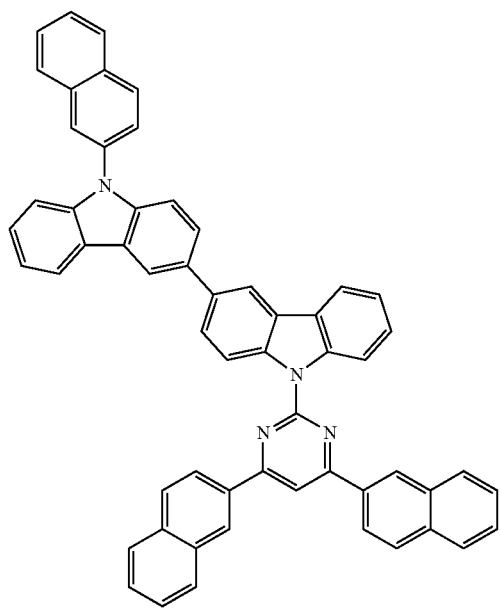
Compound 147
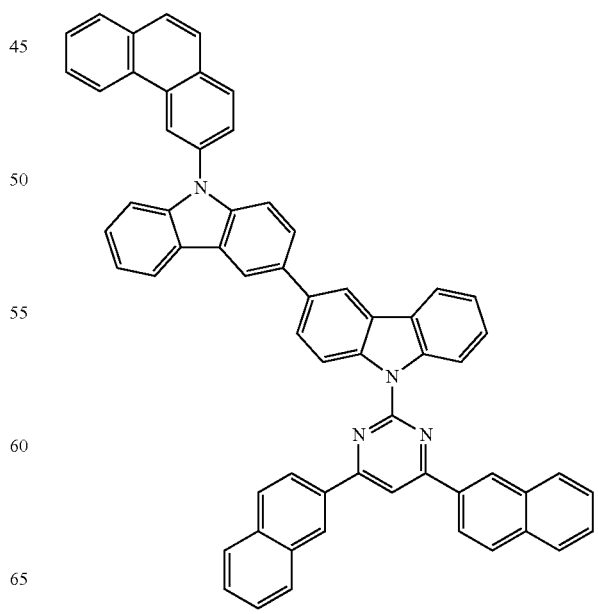

Compound 148
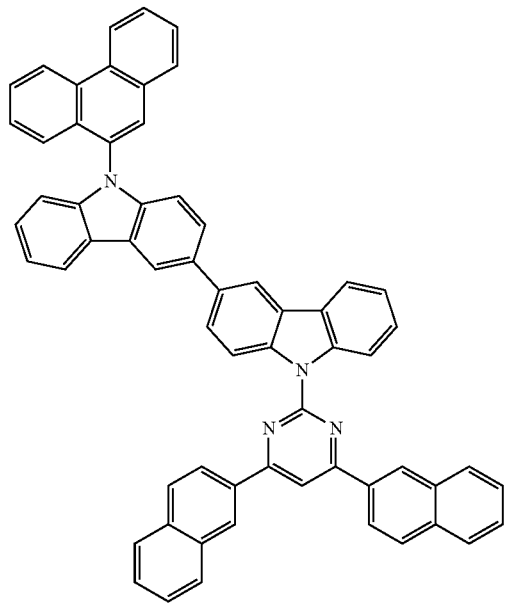
Compound 149
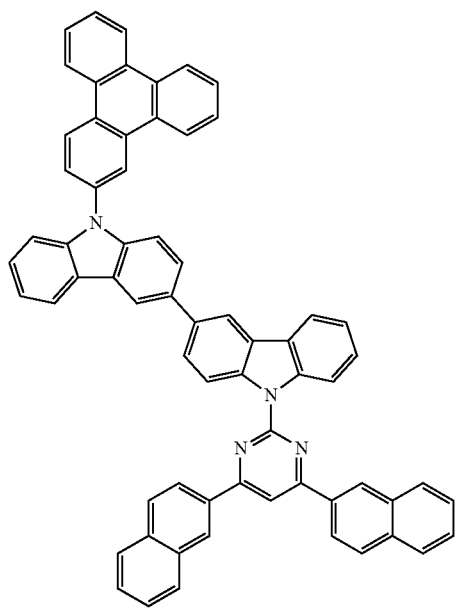
Compound 150
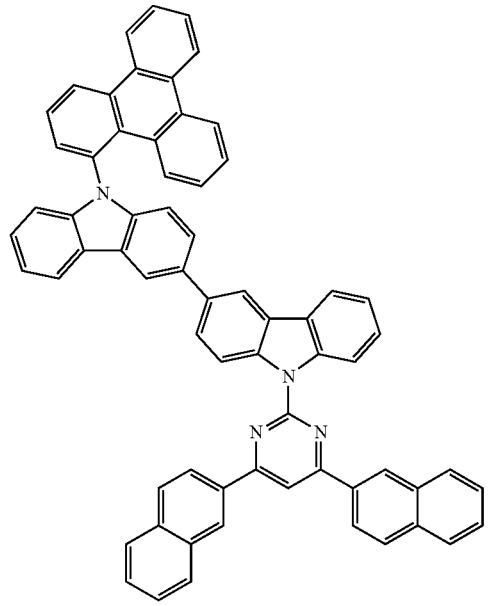
Compound 151
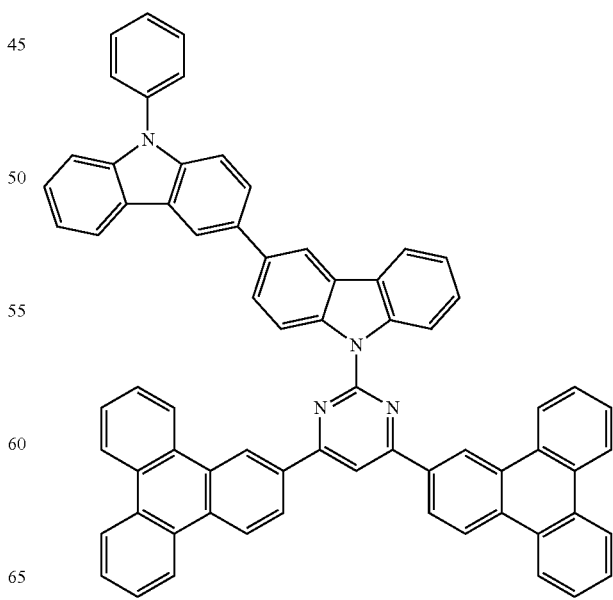

Compound 152
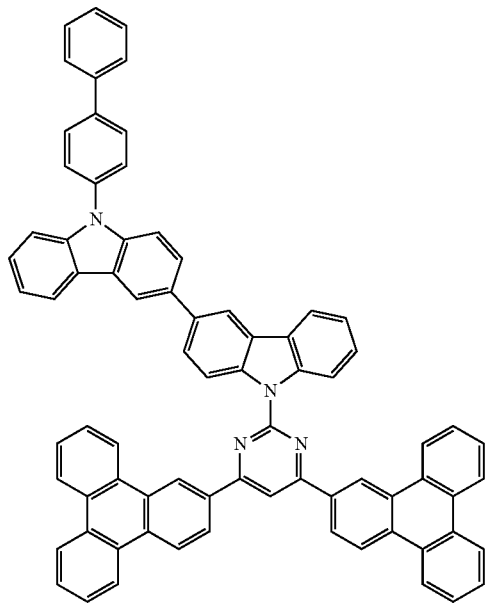
Compound 153
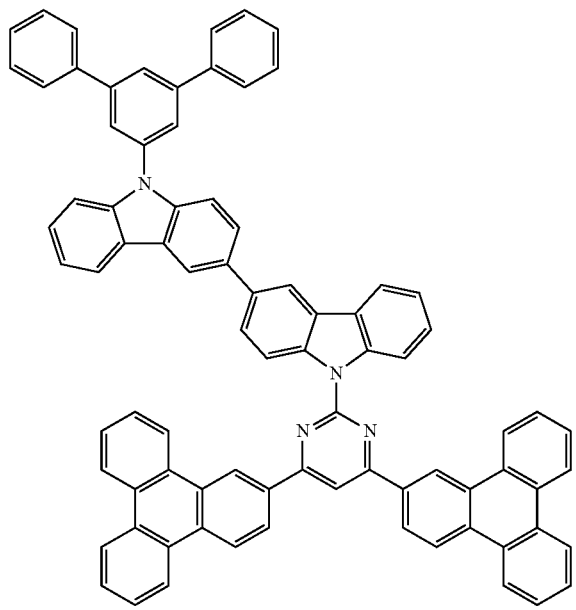
Compound 154
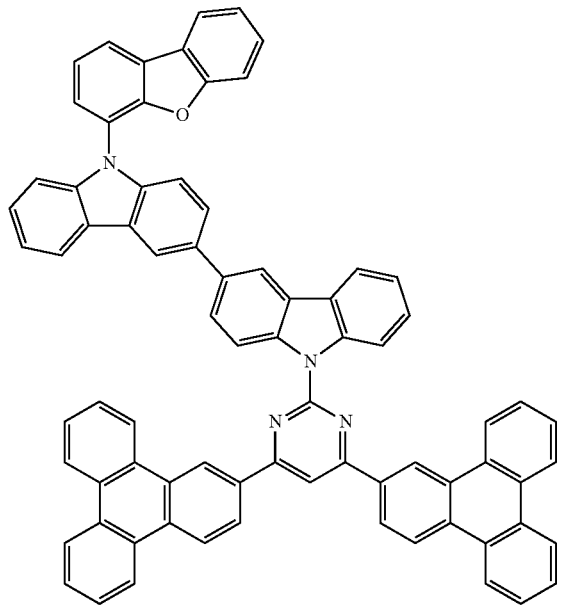
Compound 155
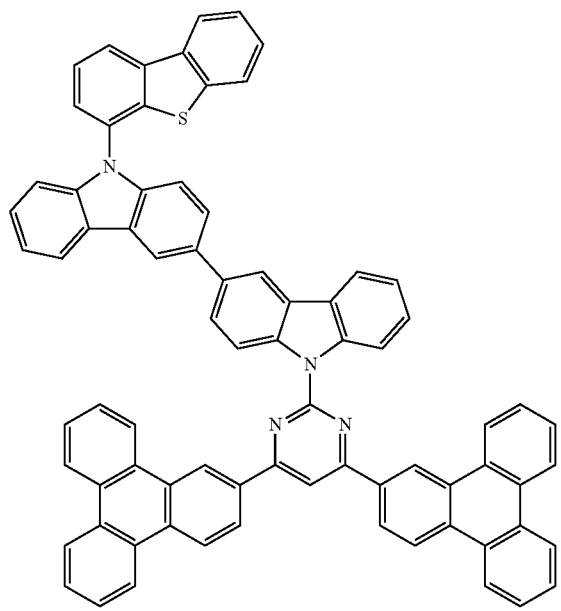

Compound 156
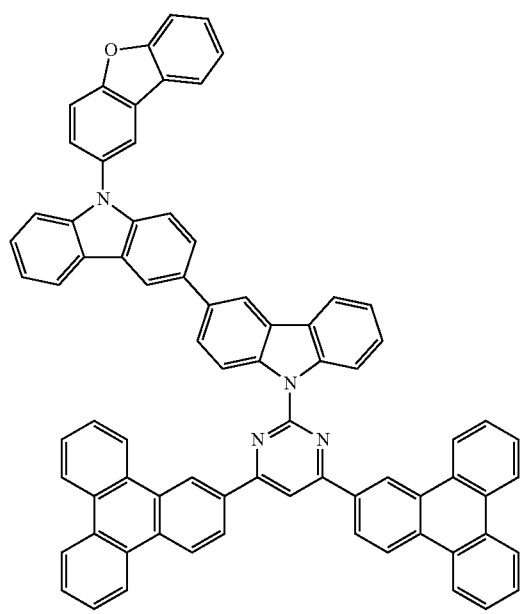
Compound 157
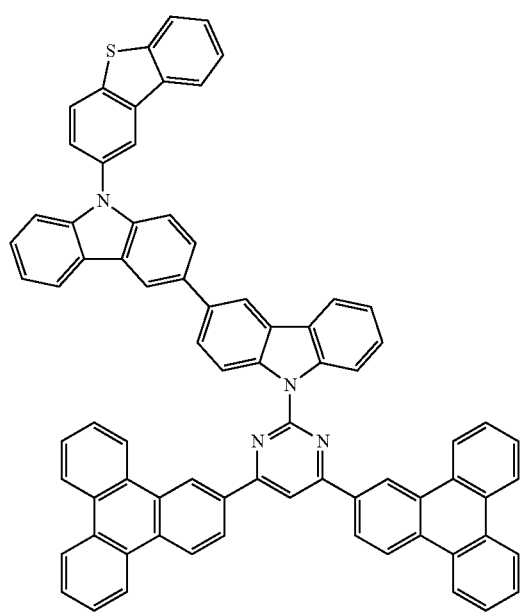
Compound 158
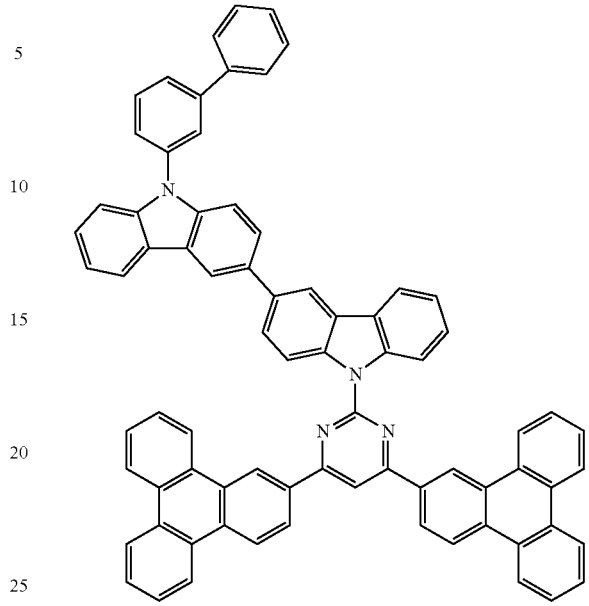
Compound 159
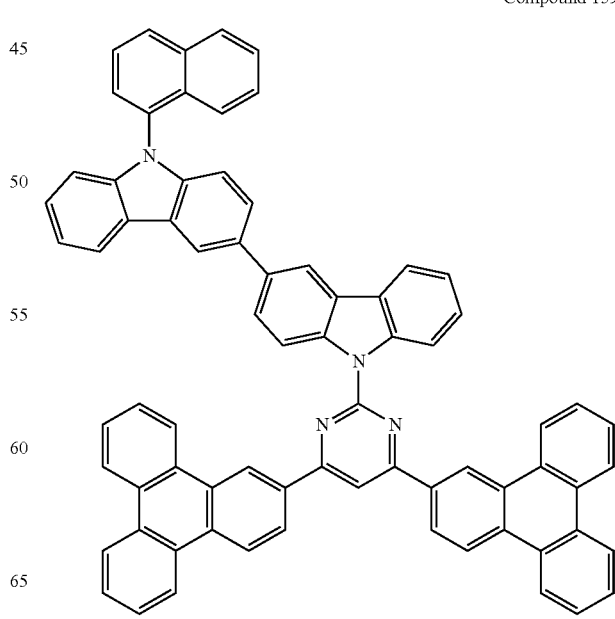

Compound 160
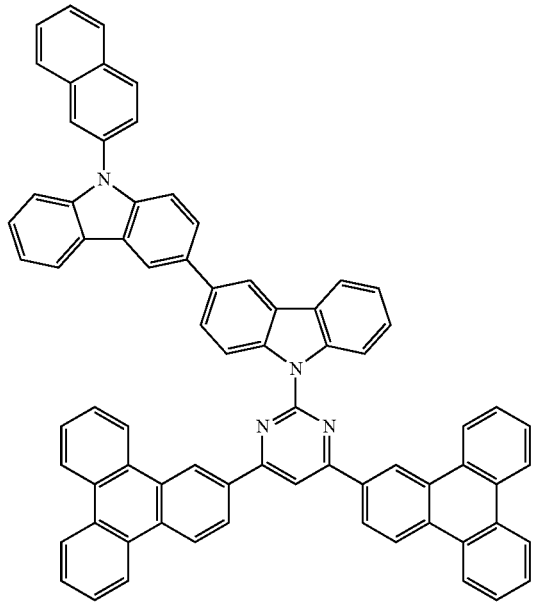
Compound 161
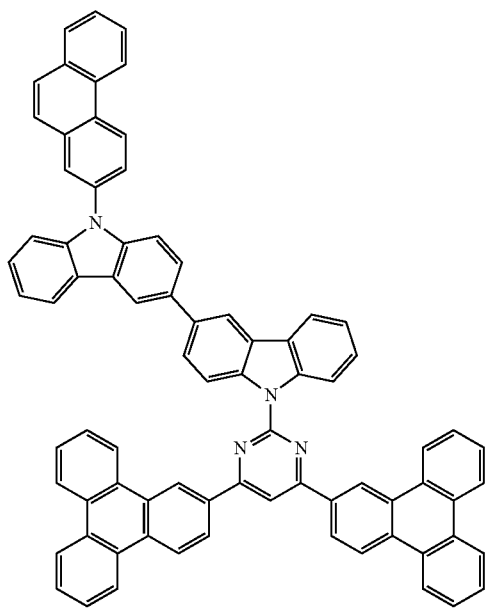
Compound 162
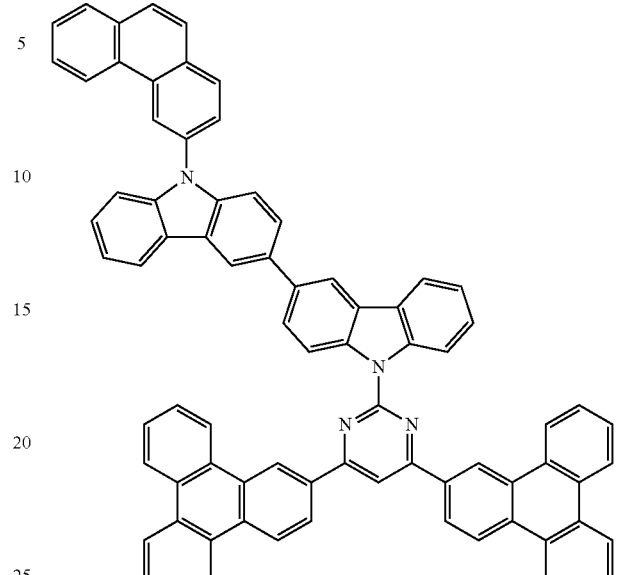
Compound 163
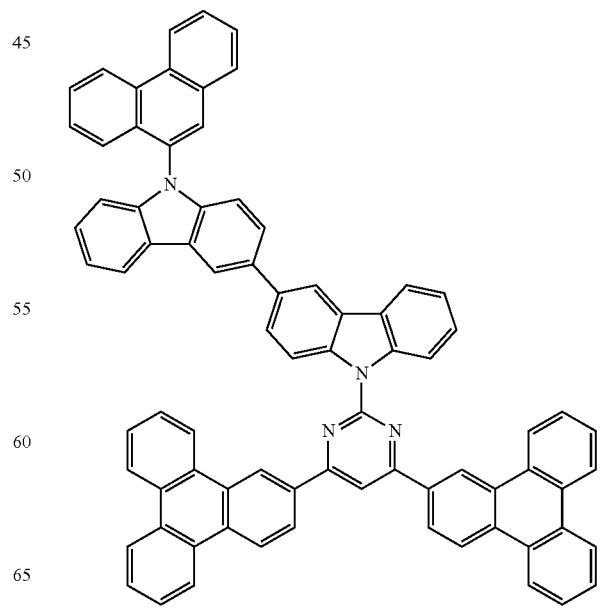

-continued
Compound 164
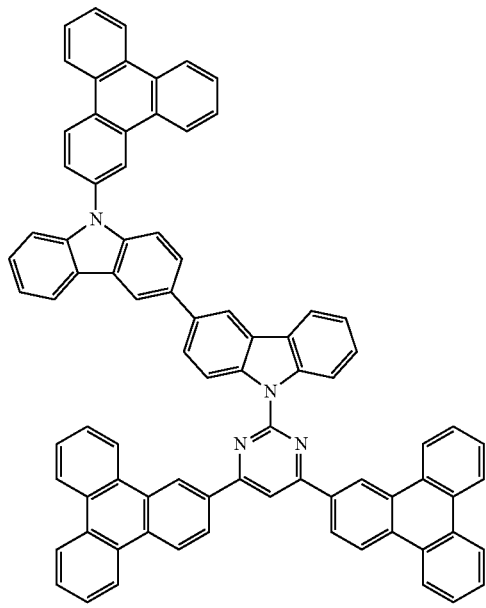
Compound 165
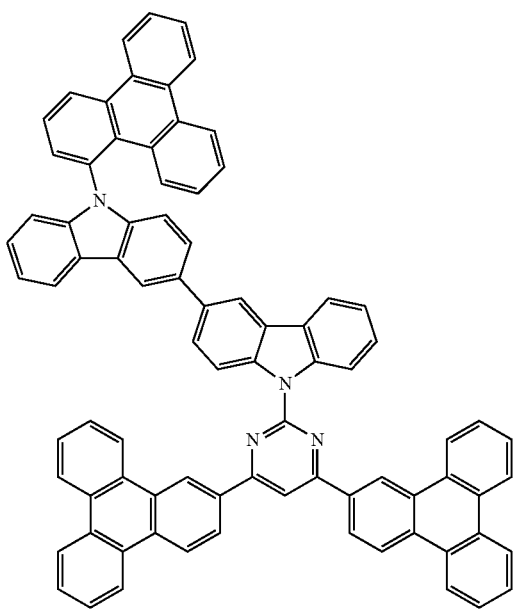
-continued
Compound 166
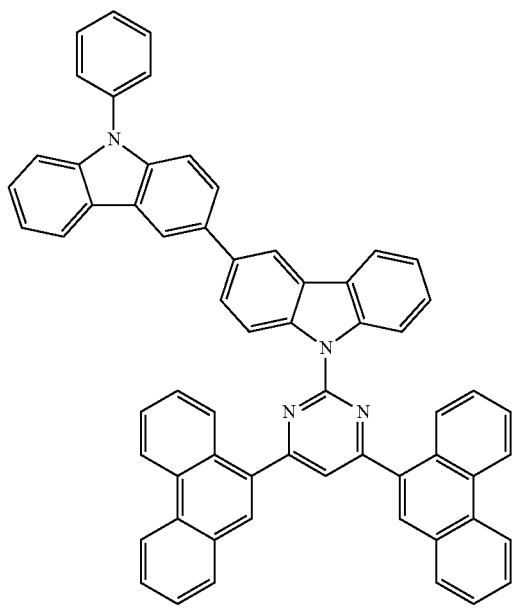
Compound 167
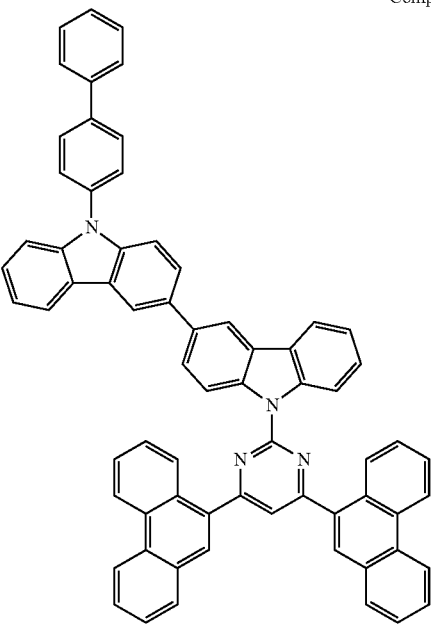

Compound 168
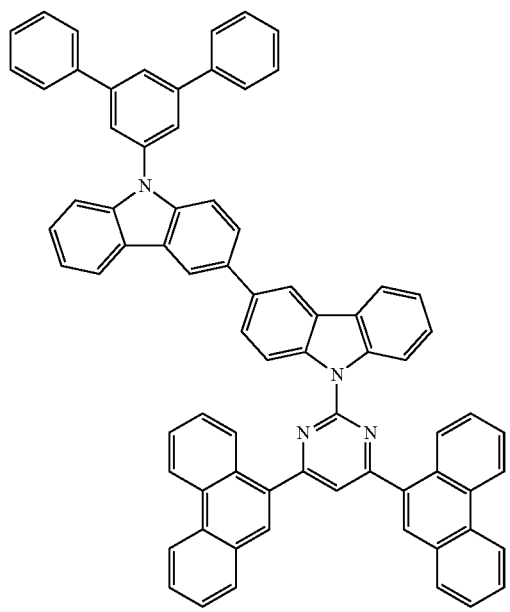
Compound 169
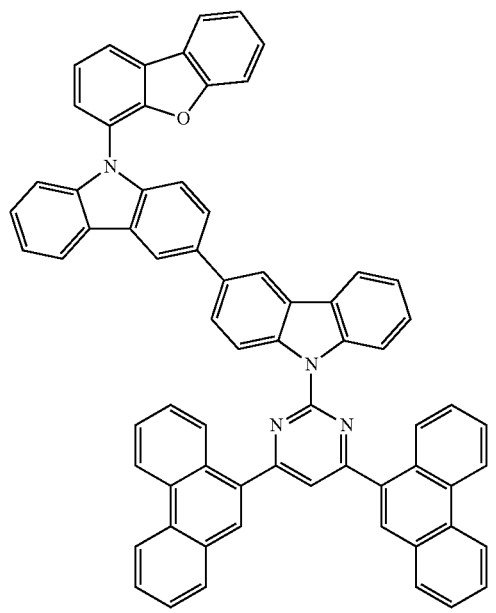
Compound 170
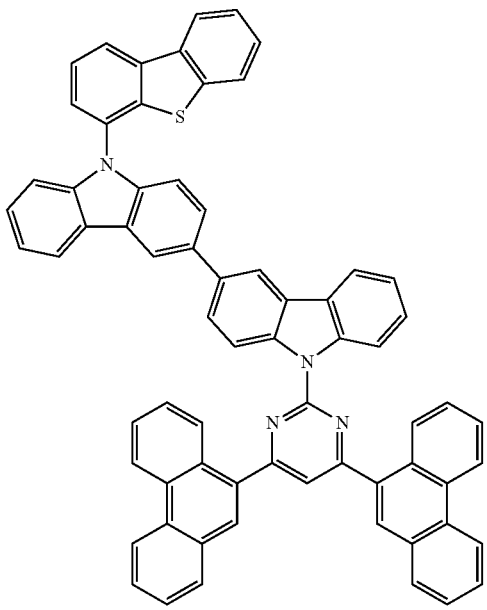
Compound 171
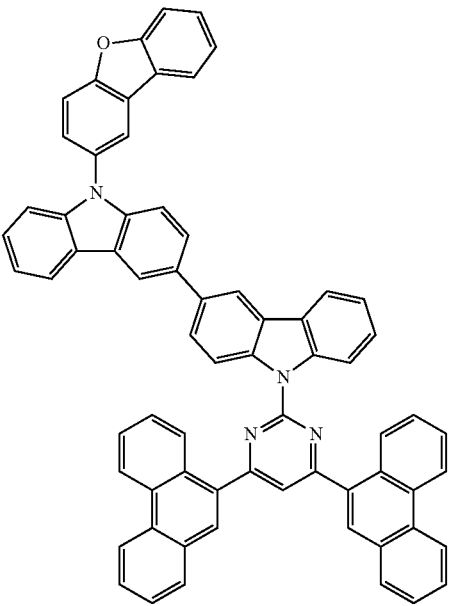

Compound 172
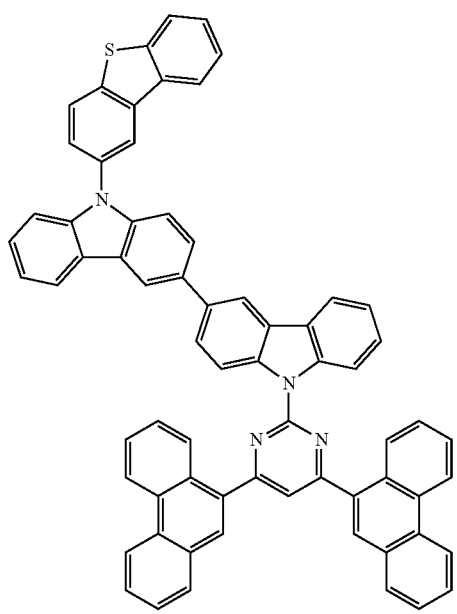
Compound 174
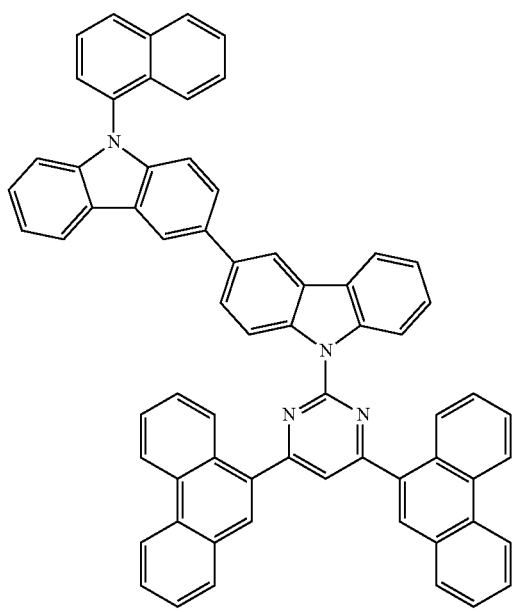
Compound 173
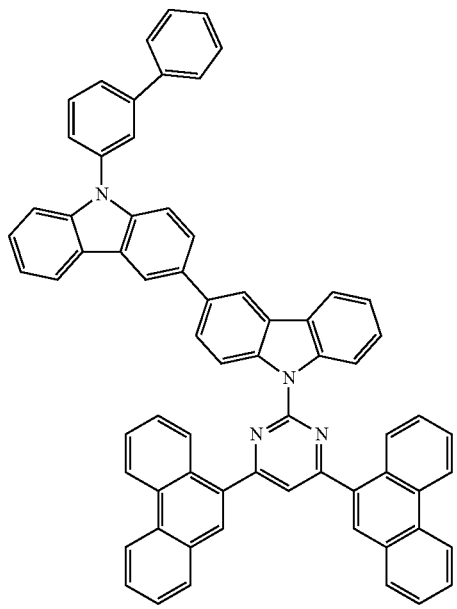
Compound 175
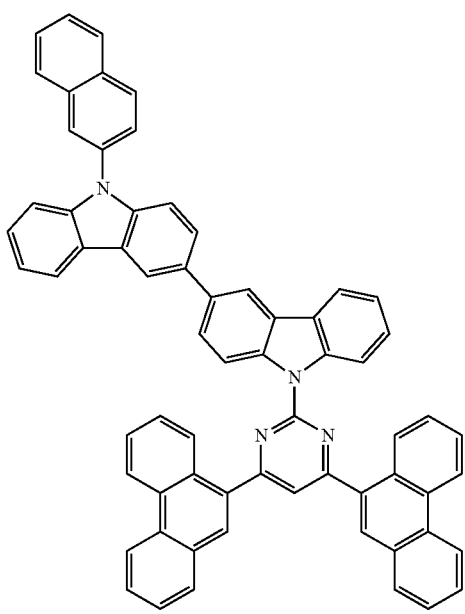

Compound 176
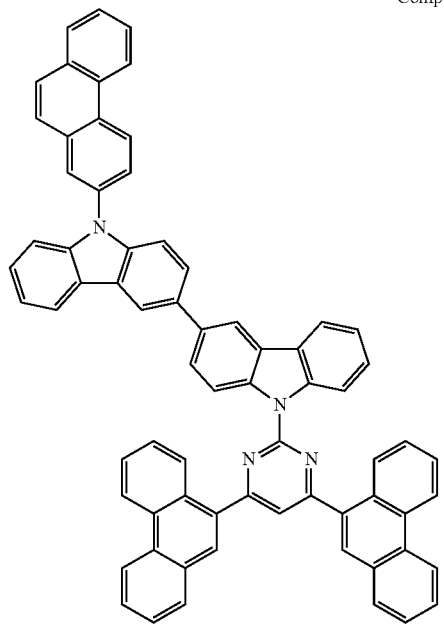
Compound 178
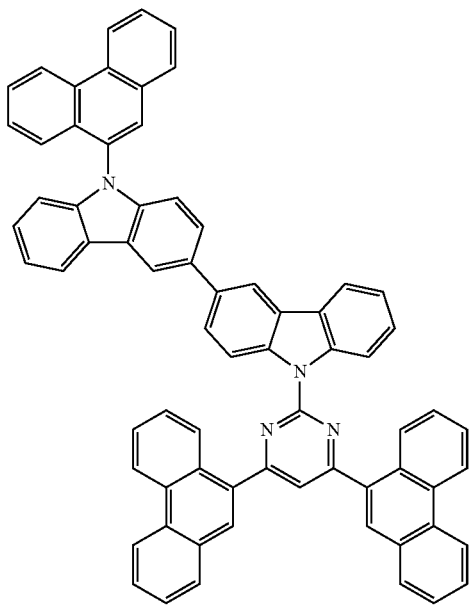
Compound 177
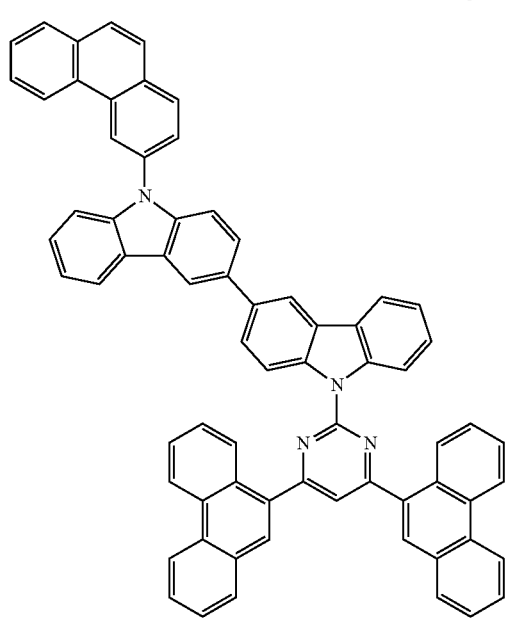
Compound 179
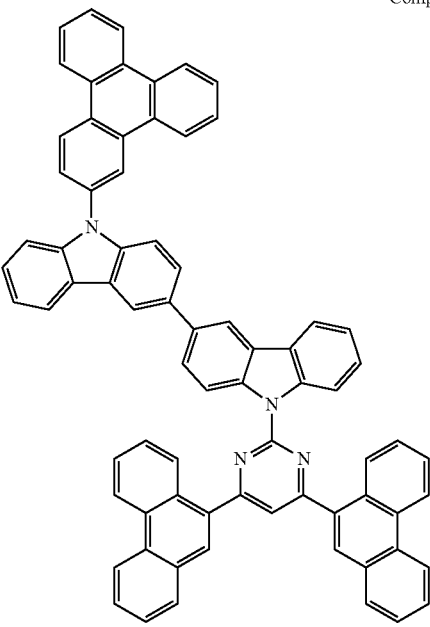

Compound 180
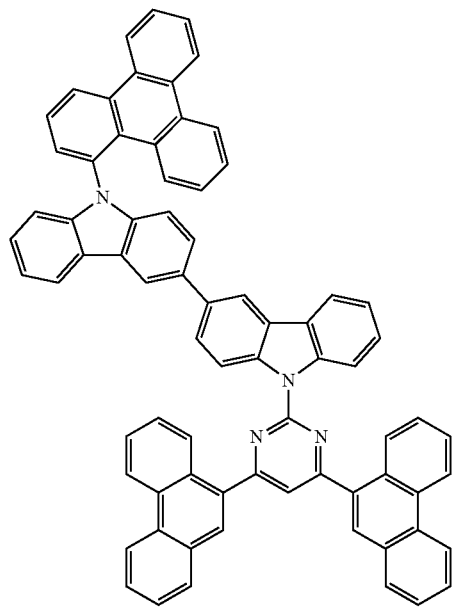
Compound 181
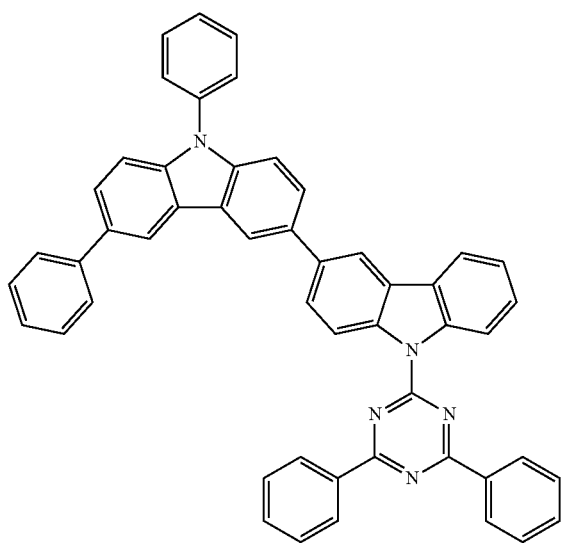
Compound 182
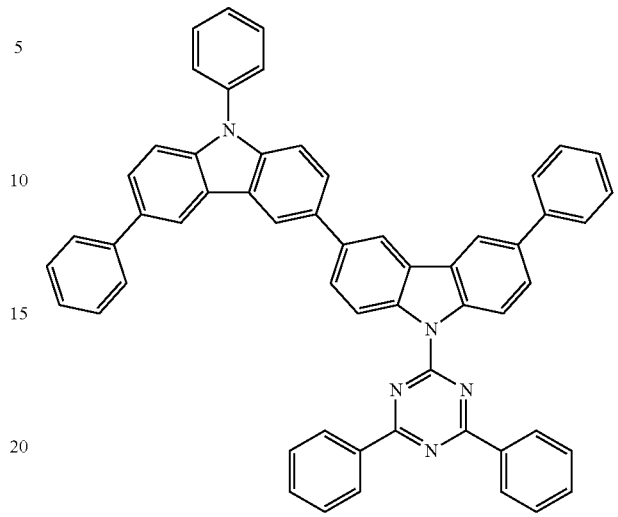
Compound 183
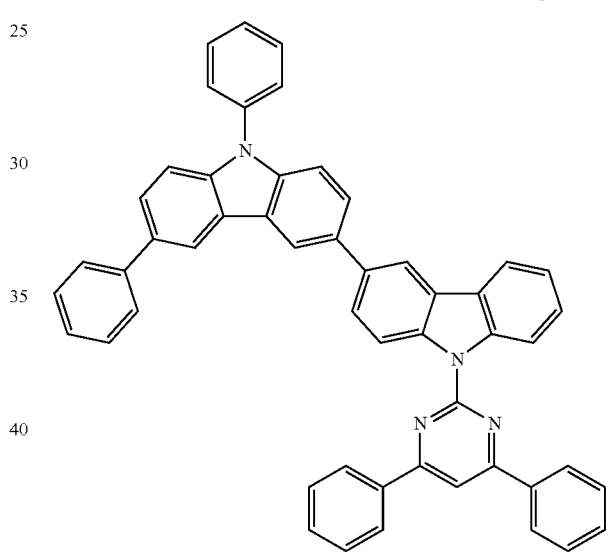
Compound 184
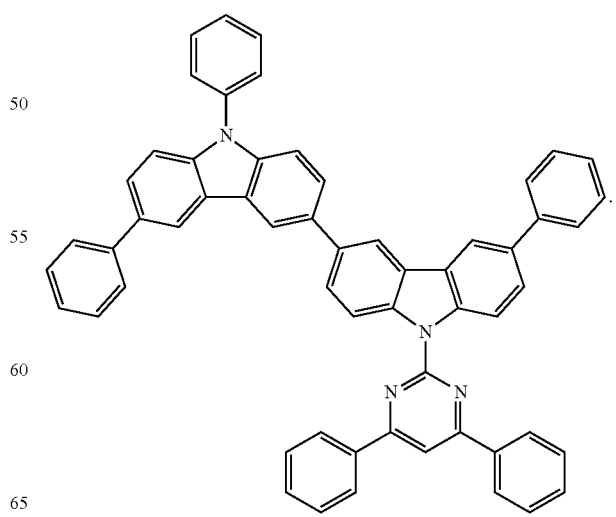

A first device comprising an organic light emitting device is also provided. The device further comprises an anode, a cathode, and an organic layer, disposed between the anode and the cathode. The organic layer comprises a compound having Formula I, as described above.

$R_1$, $R_2$, $R_3$, and $R_4$ may represent mono, di, tri, or tetra substitutions. $R_1$, $R_2$, $R_3$, and $R_4$ are independently selected from the group consisting of hydrogen, alkyl, alkoxy, amino, alkenyl, alkynyl, aryl and heteroaryl. $Ar_1$, $Ar_2$, and $Ar_3$ are independently selected from aryl or heteroaryl. $Ar_1$, $Ar_2$, and $Ar_3$ may be further substituted. X is C or N.

In one aspect, $Ar_1$, $Ar_2$, and $Ar_3$ are independently selected from the group consisting of phenyl, pyridine, naphthalene, biphenyl, terphenyl, fluorene, dibenzofuran, dibenzothiophene, phenanthrene, and triphenylene. $Ar_1$, $Ar_2$, and $Ar_3$ are independently further substituted with a substituent selected from the group consisting of hydrogen, alkyl, alkoxy, amino, alkenyl, alkynyl, aryl and heteroaryl, but the substituent is not an aryl or heteroaryl fused directly to $Ar_1$, $Ar_2$, and $Ar_3$. Preferably, $Ar_1$ and $Ar_2$ are independently selected from the group consisting of phenyl, pyridine, and naphthalene. Preferably, $Ar_3$ is selected from the group consisting of phenyl, biphenyl, dibenzofuran, and dibenzothiophene.

In another aspect, $R_1$, $R_2$, $R_3$, and $R_4$ are hydrogen.

Specific examples of devices containing compounds comprising bicarbazole are also provided. In particular, the compound is selected from the group consisting of Compound 1-Compound 184.

In one aspect, the organic layer is deposited using solution processing.

In one aspect, the organic layer is an emissive layer and the compound having Formula I is a host.

In another aspect, the organic layer further comprises an emissive dopant having the formula:

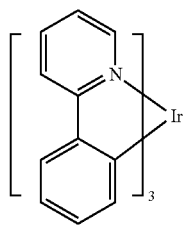

D1

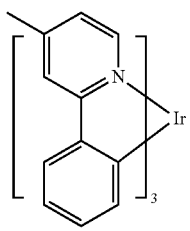

D2

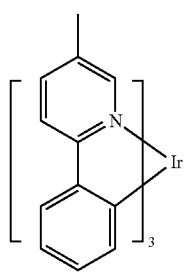

D3

-continued

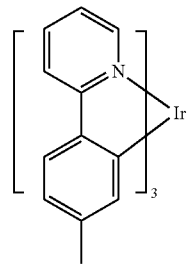

D4

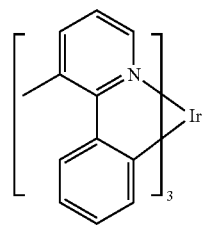

D5

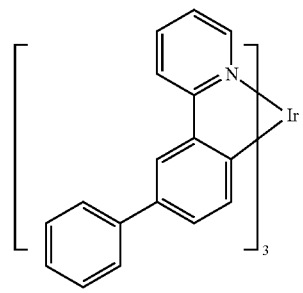

D6

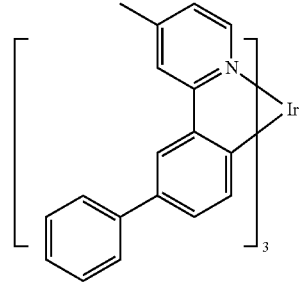

D7

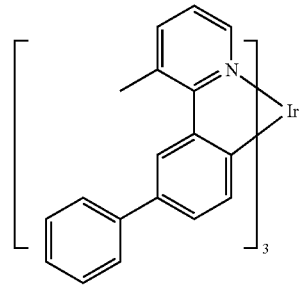

D8

D9
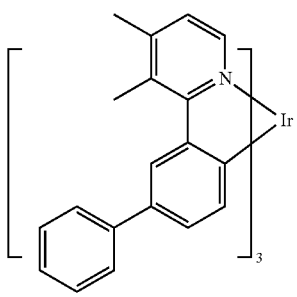
D10
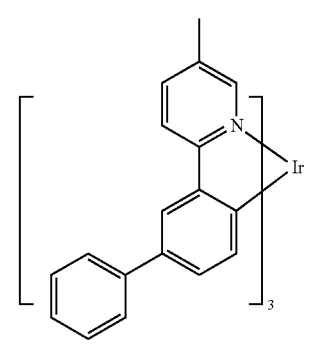
D11
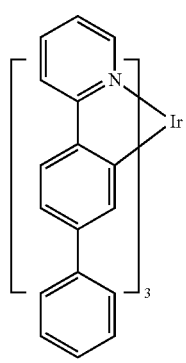
D12
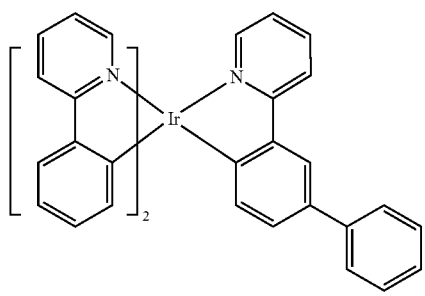
D13
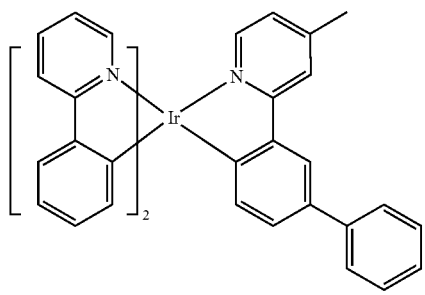
D14
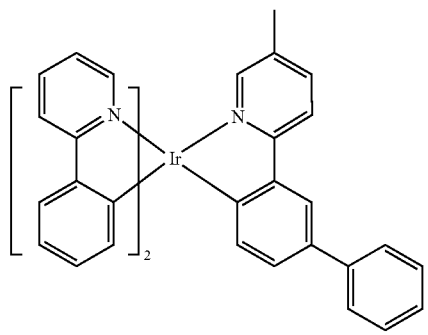
D15
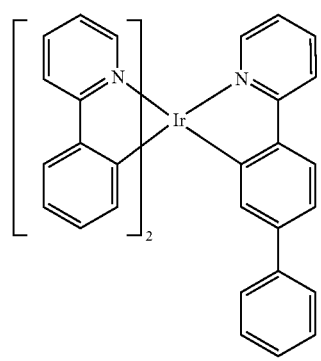
D16
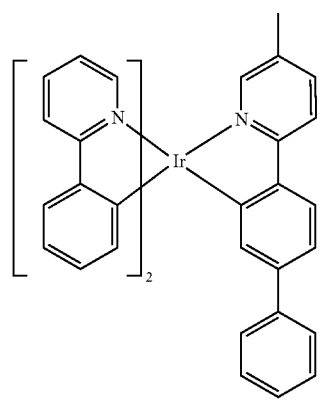
D17
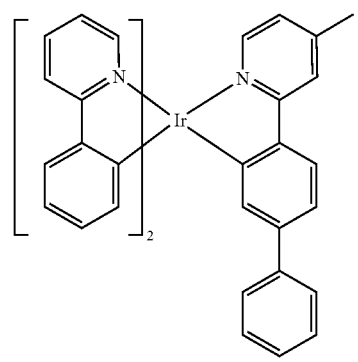

D18
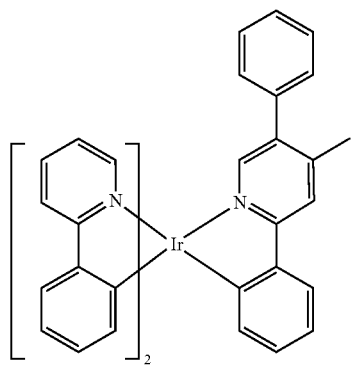
D19
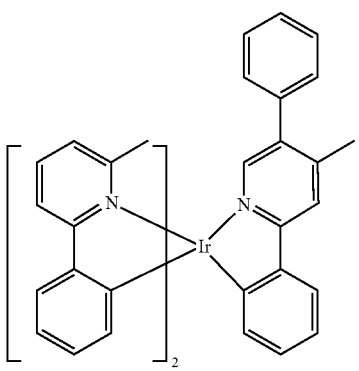
D20
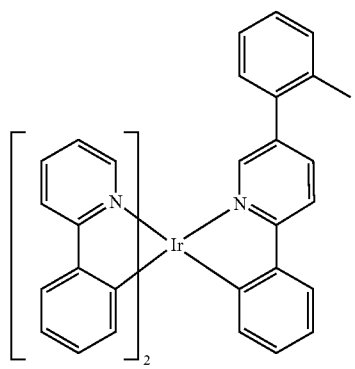
D21
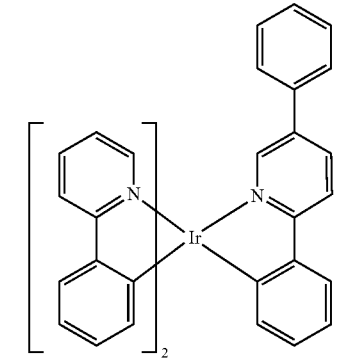
D22
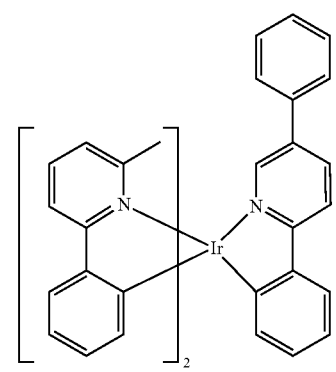
D23
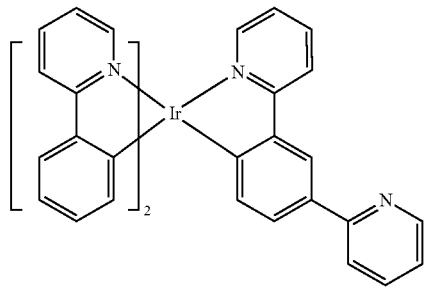
D24
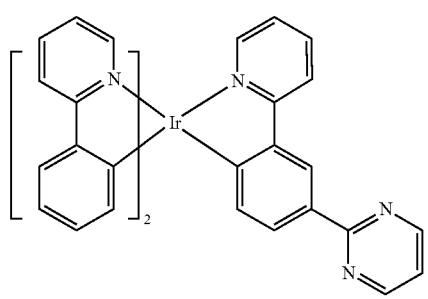
D25
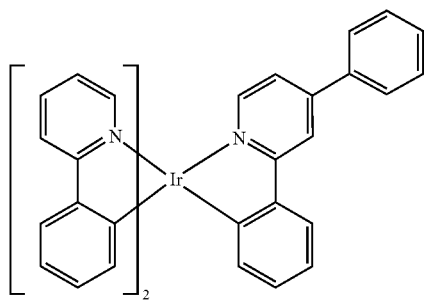
D26
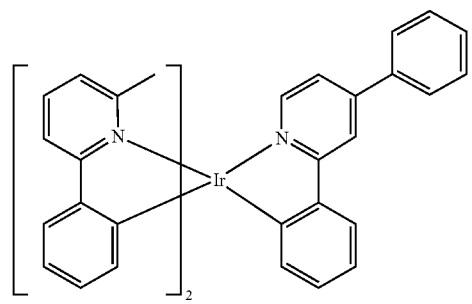

-continued
D27
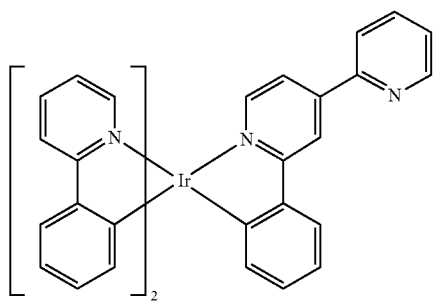
D28
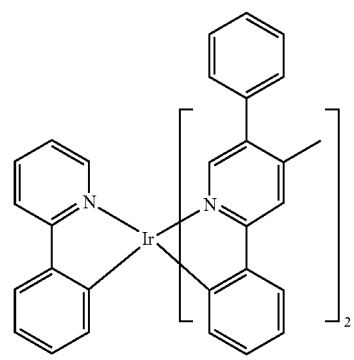
D29
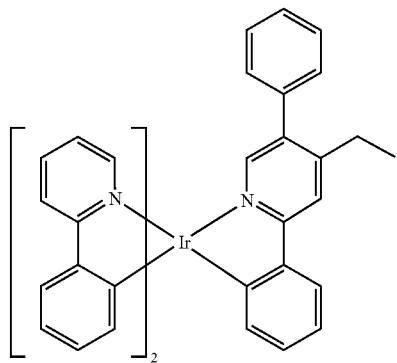
D30
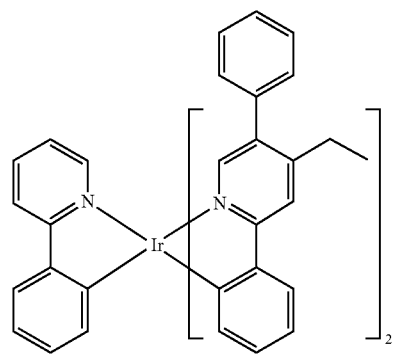
-continued
D31
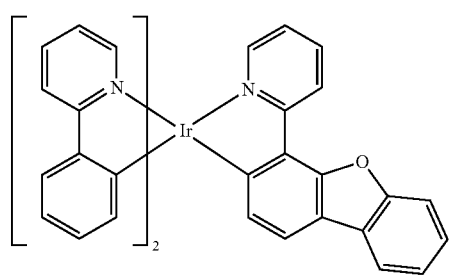
D32
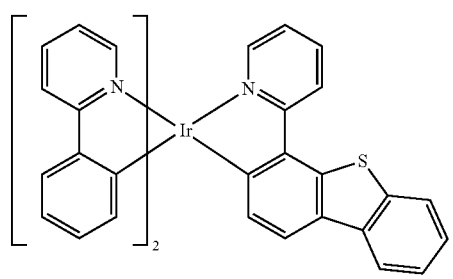
D33
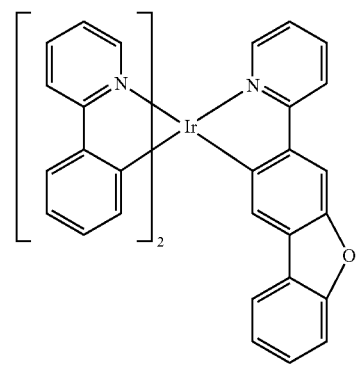
D34
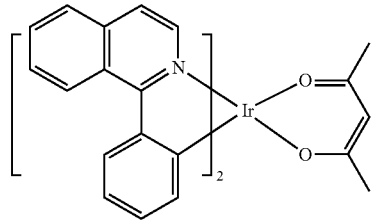
D35
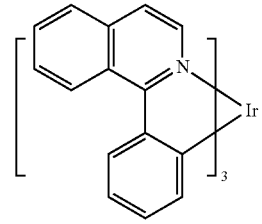

D36 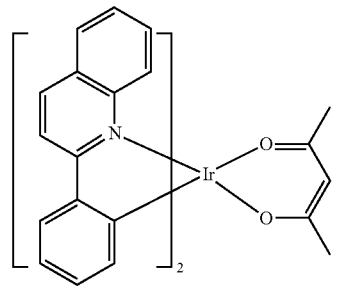
D37 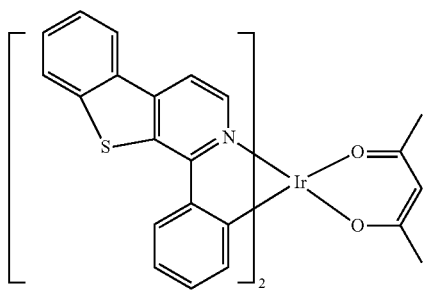
D38 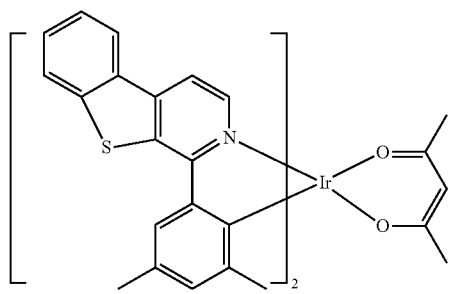
D39 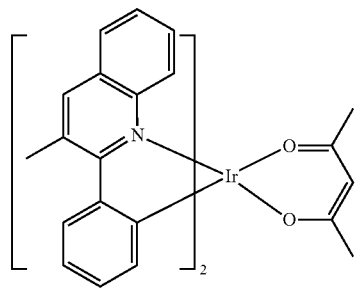
D40 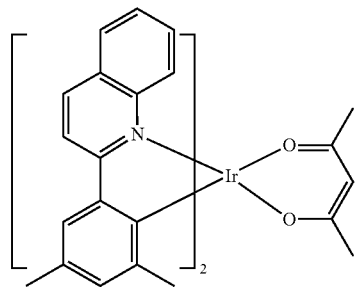
D41 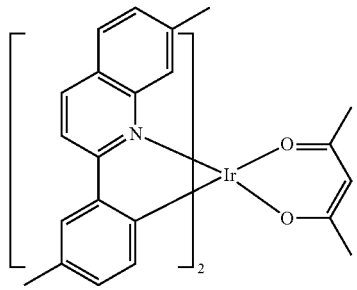
D42 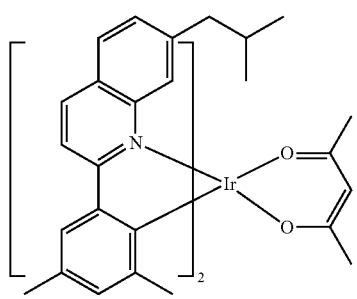
D43 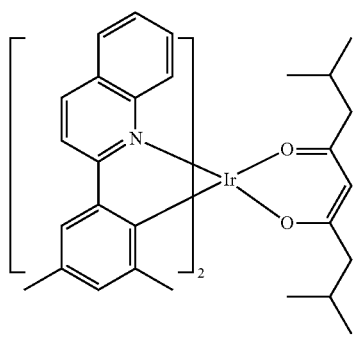
D44 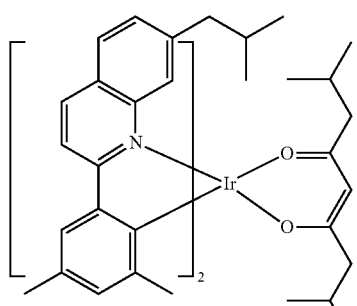
D45 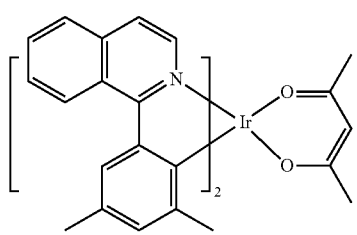

-continued

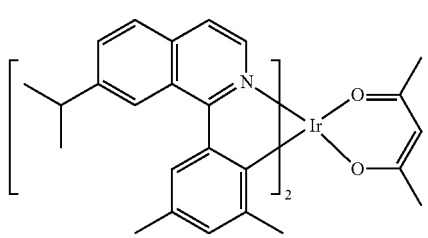
D46

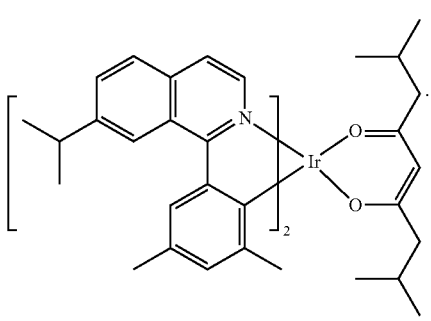
D47

In one aspect, the first device is a consumer product. In another aspect, the first device is an organic light emitting device.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and sliane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

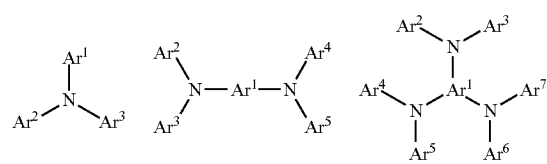

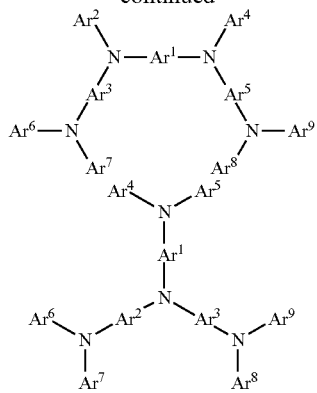

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, alkyl, alkoxy, amino, alkenyl, alkynyl, arylalkyl, heteroalkyl, aryl and heteroaryl.

In one aspect, $Ar^1$ to $Ar^9$ is independently selected from the group consisting of:

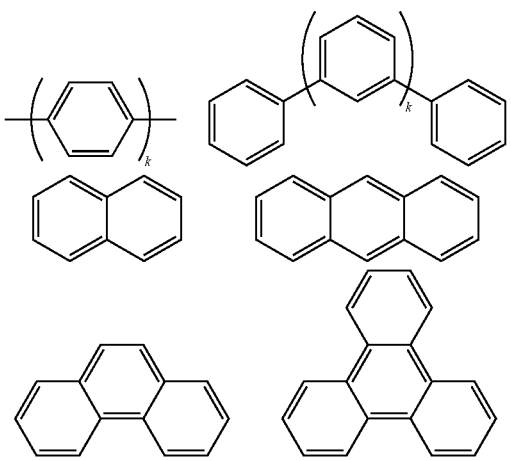

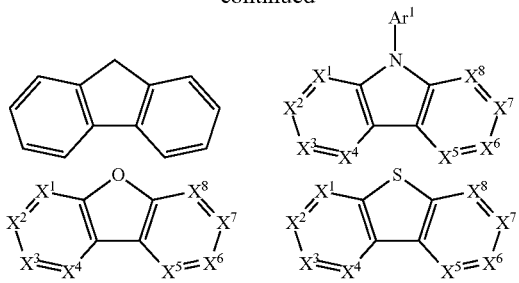

k is an integer from 1 to 20; $X^1$ to $X^8$ is CH or N; $Ar^1$ has the same group defined above.

Examples of metal complexes used in HIL or HTL include, but not limit to the following general formula:

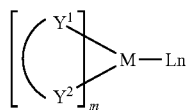

M is a metal, having an atomic weight greater than 40; $(Y^1\text{-}Y^2)$ is a bidentate ligand, Y1 and $Y^2$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, $(Y^1\text{-}Y^2)$ is a 2-phenylpyridine derivative.

In another aspect, $(Y^1\text{-}Y^2)$ is a carbene ligand.

In another aspect, M is selected from Ir, Pt, Os, and Zn.

In a further aspect, the metal complex has a smallest oxidation potential in solution vs. $Fc^+/Fc$ couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant.

Examples of metal complexes used as host are preferred to have the following general formula:

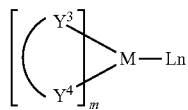

M is a metal; $(Y^3\text{-}Y^4)$ is a bidentate ligand, $Y^3$ and $Y^4$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, the metal complexes are:

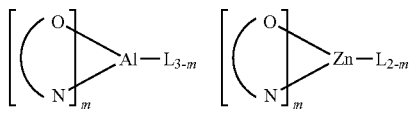

(O—N) is a bidentate ligand, having metal coordinated to atoms O and N.

In another aspect, M is selected from Ir and Pt.

In a further aspect, $(Y^3\text{-}Y^4)$ is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, alkyl, alkoxy, amino, alkenyl, alkynyl, arylalkyl, heteroalkyl, aryl and heteroaryl.

In one aspect, host compound contains at least one of the following groups in the molecule:

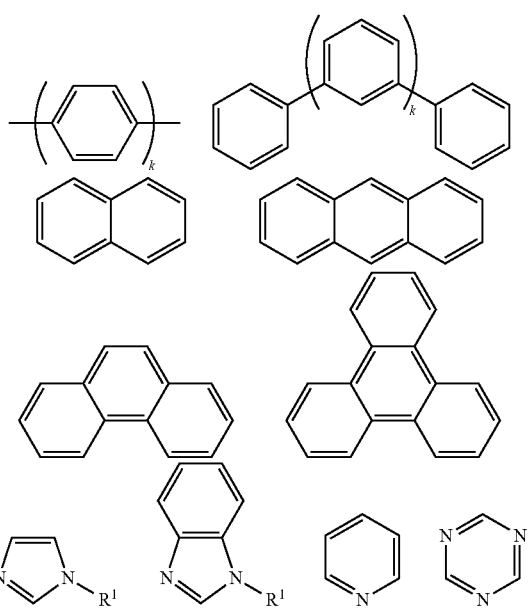

R¹ to R⁷ is independently selected from the group consisting of hydrogen, alkyl, alkoxy, amino, alkenyl, alkynyl, arylalkyl, heteroalkyl, aryl and heteroaryl, when it is aryl or heteroaryl, it has the similar definition as Ar's mentioned above.

k is an integer from 0 to 20.

X¹ to X⁸ is selected from CH or N.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule used as host described above.

In another aspect, compound used in HBL contains at least one of the following groups in the molecule:

k is an integer from 0 to 20; L is an ancillary ligand, m is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

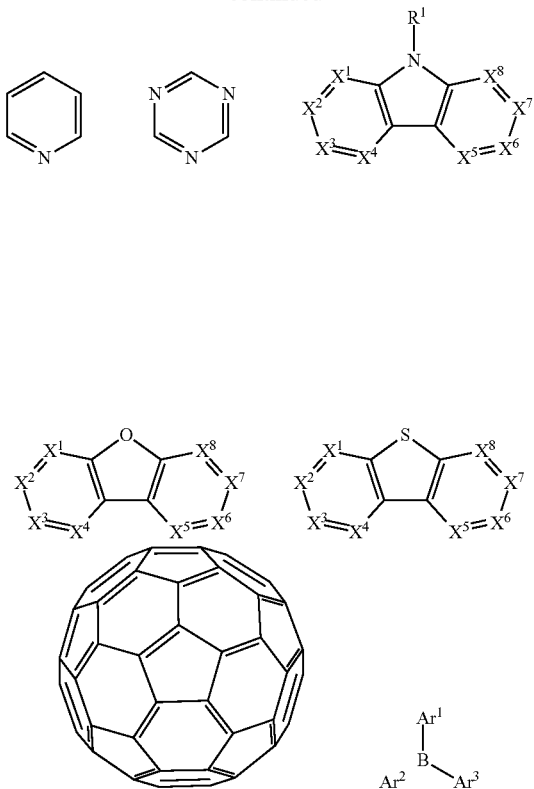

$R^1$ is selected from the group consisting of hydrogen, alkyl, alkoxy, amino, alkenyl, alkynyl, arylalkyl, heteroalkyl, aryl and heteroaryl, when it is aryl or heteroaryl, it has the similar definition as Ar's mentioned above.

$Ar^1$ to $Ar^3$ has the similar definition as Ar's mentioned above.

k is an integer from 0 to 20.

$X^1$ to $X^8$ is selected from CH or N.

In another aspect, the metal complexes used in ETL contains, but not limit to the following general formula:

(O—N) or (N—N) is a bidentate ligand, having metal coordinated to atoms O, N or N, N; L is an ancillary ligand; m is an integer value from 1 to the maximum number of ligands that may be attached to the metal.

In any above-mentioned compounds used in each layer of OLED device, the hydrogen atoms attached to conjugated rings can be partially or fully deuterated.

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 1 below. Table 1 lists non-limiting classes of materials, non-limiting examples of compounds for each class, and references that disclose the materials.

TABLE 1

| MATERIAL | EXAMPLES OF MATERIAL | PUBLICATIONS |
|---|---|---|
| | Hole injection materials | |
| Phthalocyanine and porphryin compounds | | Appl. Phys. Lett. 69, 2160 (1996) |

TABLE 1-continued

| MATERIAL | EXAMPLES OF MATERIAL | PUBLICATIONS |
| --- | --- | --- |
| Starburst triarylamines | | J. Lumin. 72-74, 985 (1997) |
| $CF_x$ Fluorohydrocarbon polymer | $-[CH_xF_y]_n-$ | Appl. Phys. Lett. 78, 673 (2001) |
| Conducting polymers (e.g., PEDOT:PSS, polyaniline, polypthiophene) | | Synth. Met. 87, 171 (1997) WO2007002683 |
| Phosphonic acid and sliane SAMs | | US20030162053 |
| Triarylamine or polythiophene polymers with conductivity dopants | and | EA01725079A1 |

TABLE 1-continued
| MATERIAL | EXAMPLES OF MATERIAL | PUBLICATIONS |
| --- | --- | --- |
|  | 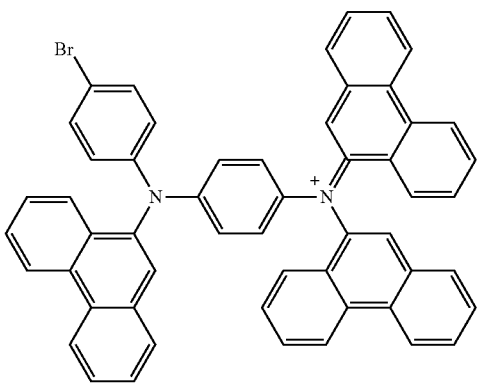 |  |
|  | 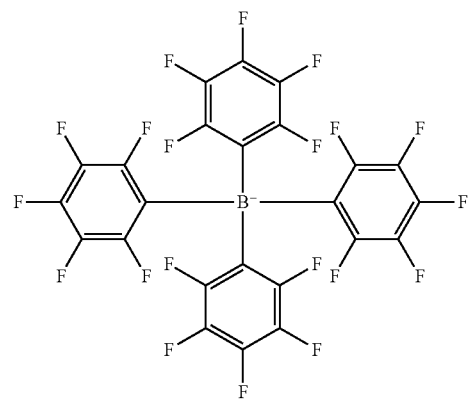 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] |  |
| Arylamines complexed with metal oxides such as molybdenum and tungsten oxides | 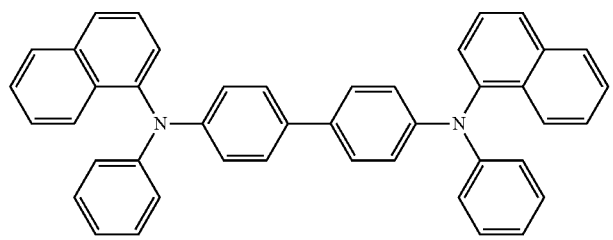 [SMILES: c1ccc(N(c2ccc(-c3ccc(N(c4ccccc4)c4cccc5ccccc45)cc3)cc2)c2cccc3ccccc23)cc1] | SID Symposium Digest, 37, 923 (2006) WO2009018009 |
| p-type semiconducting organic complexes | 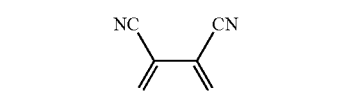 | US20020158242 |
| Metal organometallic complexes | 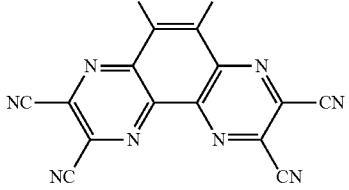 | US20060240279 |

TABLE 1-continued

| MATERIAL | EXAMPLES OF MATERIAL | PUBLICATIONS |
| --- | --- | --- |
| Cross-linkable compounds | | US20080220265 |

Hole transporting materials

| | | |
| --- | --- | --- |
| Triarylamines (e.g., TPD, α-NPD) | | Appl. Phys. Lett. 51, 913 (1987) |
| | | U.S. Pat. No. 5,061,569 |
| | | EP650955 |

TABLE 1-continued
| MATERIAL | EXAMPLES OF MATERIAL | PUBLICATIONS |
|---|---|---|
| | 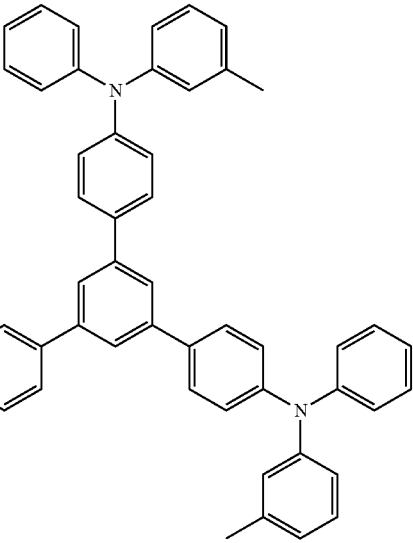 | J. Mater. Chem. 3, 319 (1993) |
| | 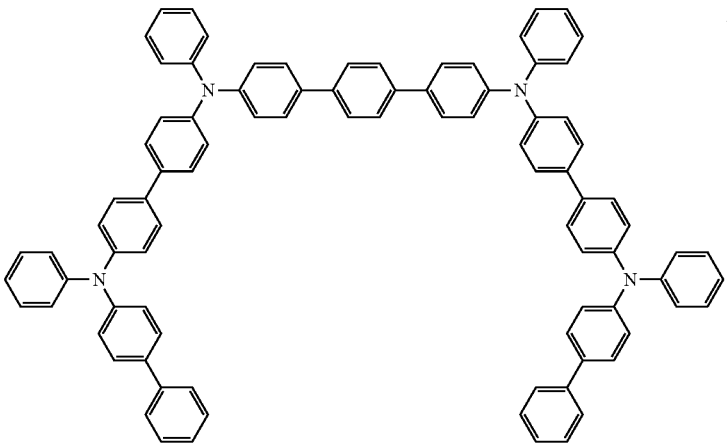 [SMILES: c1ccc(-c2ccc(N(c3ccccc3)c3ccc(-c4ccc(N(c5ccccc5)c5ccc(-c6ccc(-c7ccc(N(c8ccccc8)c8ccc(-c9ccc(N(c%10ccccc%10)c%10ccc(-c%11ccccc%11)cc%10)cc9)cc8)cc7)cc6)cc5)cc4)cc3)cc2)cc1] | Appl. Phys. Lett. 90, 183503 (2007) |
| | 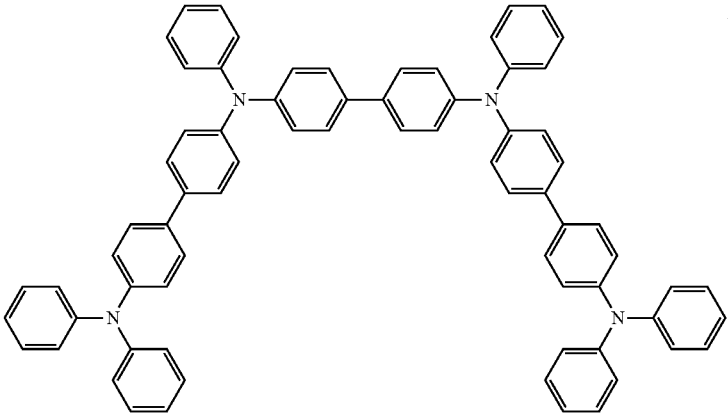 [SMILES: c1ccc(N(c2ccccc2)c2ccc(-c3ccc(N(c4ccccc4)c4ccc(-c5ccc(N(c6ccccc6)c6ccc(-c7ccc(N(c8ccccc8)c8ccccc8)cc7)cc6)cc5)cc4)cc3)cc2)cc1] | Appl. Phys. Lett. 90, 183503 (2007) |

TABLE 1-continued

| MATERIAL | EXAMPLES OF MATERIAL | PUBLICATIONS |
| --- | --- | --- |
| Triaylamine on spirofluorene core | | Synth. Met. 91, 209 (1997) |
| Arylamine carbazole compounds | | Adv. Mater. 6, 677 (1994), US20080124572 |
| Triarylamine with (di)benzothiophene/(di) benzofuran | | US20070278938, US20080106190 |
| Indolocarbazoles | | Synth. Met. 111, 421 (2000) |

TABLE 1-continued

| MATERIAL | EXAMPLES OF MATERIAL | PUBLICATIONS |
|---|---|---|
| Isoindole compounds | | Chem. Mater. 15, 3148 (2003) |
| Metal carbene complexes | | US20080018221 |

Phosphorescent OLED host materials

Red hosts

| | | |
|---|---|---|
| Arylcarbazoles | | Appl. Phys. Lett. 78, 1622 (2001) |
| Metal 8-hydroxyquinolates (e.g., Alq$_3$, BAlq) | | Nature 395, 151 (1998) |
| | | US20060202194 |

TABLE 1-continued
| MATERIAL | EXAMPLES OF MATERIAL | PUBLICATIONS |
|---|---|---|
| | 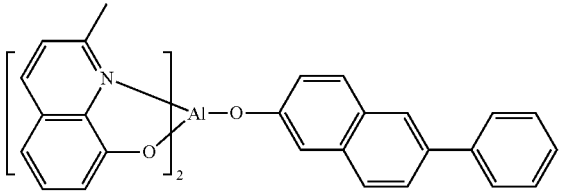 | WO2005014551 |
| | 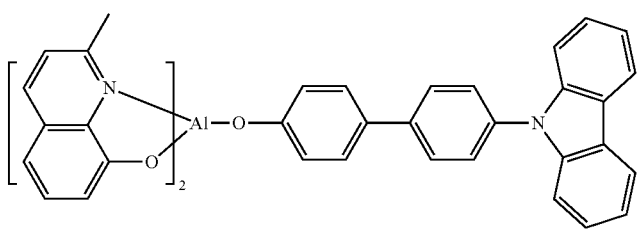 | WO2006072002 |
| Metal phenoxybenzothiazole compounds | 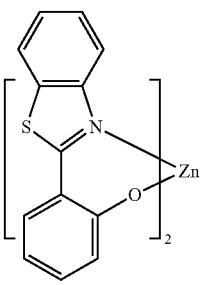 | Appl. Phys. Lett. 90, 123509 (2007) |
| Conjugated oligomers and polymers (e.g., polyfluorene) | 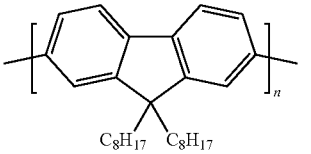 | Org. Electron. 1, 15 (2000) |
| Aromatic fused rings | 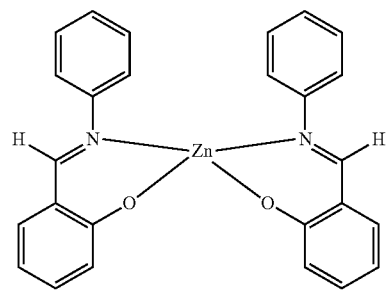 | WO2009066779, WO2009066778, WO2009063833, US20090045731, US20090045730, WO2009008311, US20090008605, US20090009065 |
| Zinc complexes | | WO2009062578 |

| MATERIAL | EXAMPLES OF MATERIAL | PUBLICATIONS |
|---|---|---|
| Green hosts | | |
| Arylcarbazoles | 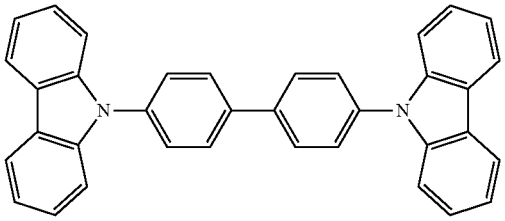 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| | 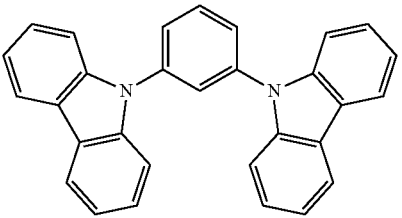 [SMILES: c1cc(-n2c3ccccc3c3ccccc32)cc(-n2c3ccccc3c3ccccc32)c1] | US20030175553 |
| | 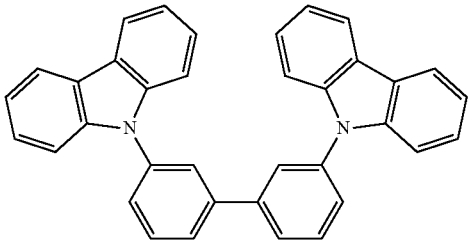 [SMILES: c1cc(-c2cccc(-n3c4ccccc4c4ccccc43)c2)cc(-n2c3ccccc3c3ccccc32)c1] | WO2001039234 |
| Aryltriphenylene compounds | 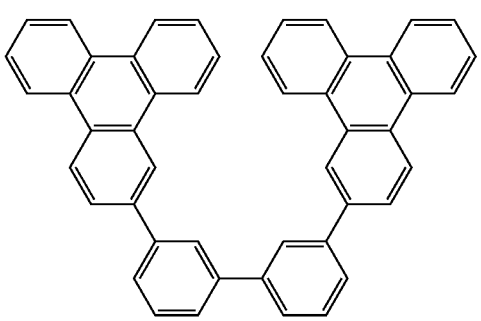 [SMILES: c1cc(-c2cccc(-c3ccc4c5ccccc5c5ccccc5c4c3)c2)cc(-c2ccc3c4ccccc4c4ccccc4c3c2)c1] | US20060280965 |
| | 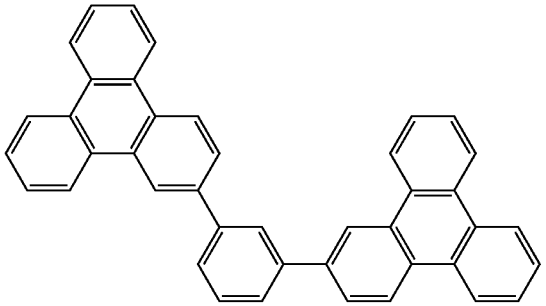 [SMILES: c1cc(-c2ccc3c4ccccc4c4ccccc4c3c2)cc(-c2ccc3c4ccccc4c4ccccc4c3c2)c1] | US20060280965 |
| | 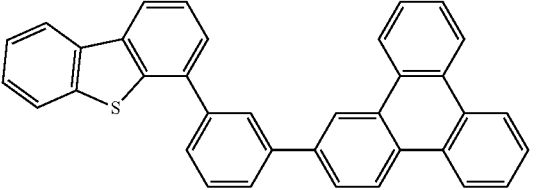 [SMILES: c1cc(-c2ccc3c4ccccc4c4ccccc4c3c2)cc(-c2cccc3c2sc2ccccc23)c1] | WO2009021126 |

TABLE 1-continued

| MATERIAL | EXAMPLES OF MATERIAL | PUBLICATIONS |
| --- | --- | --- |
| Donor acceptor type molecules | | WO2008056746 |
| Aza-carbazole/DBT/DBF | | JP2008074939 |
| Polymers (e.g., PVK) | | Appl. Phys. Lett. 77, 2280 (2000) |
| Spirofluorene compounds | | WO2004093207 |
| Metal phenoxybenzooxazole compounds | | WO2005089025 |

TABLE 1-continued
| MATERIAL | EXAMPLES OF MATERIAL | PUBLICATIONS |
|---|---|---|
| | 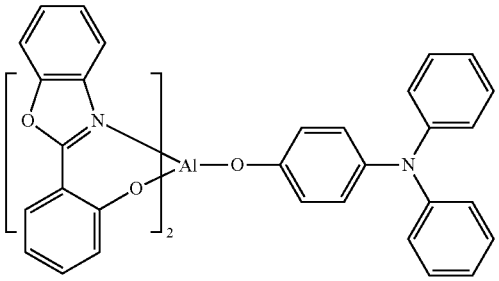 | WO2006132173 |
| | 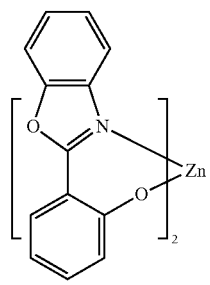 | JP200511610 |
| Spirofluorene-carbazole compounds | 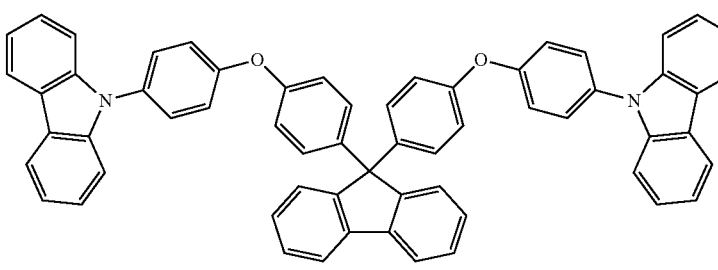 | JP2007254297 |
| | 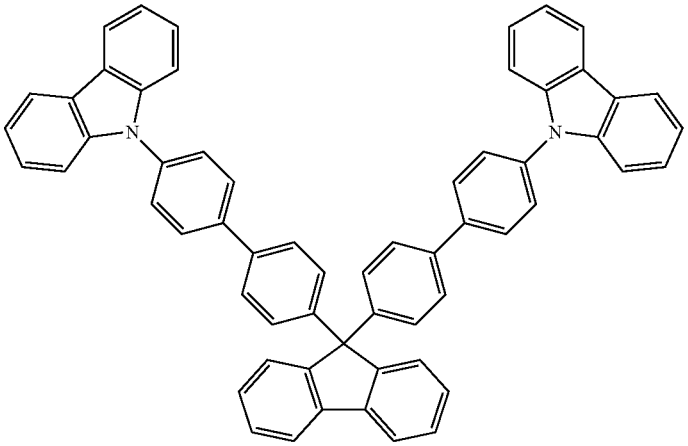 [SMILES: c1ccc2c(c1)-c1ccccc1C2(c1ccc(-c2ccc(-n3c4ccccc4c4ccccc43)cc2)cc1)c1ccc(-c2ccc(-n3c4ccccc4c4ccccc43)cc2)cc1] | JP2007254297 |
| Indolocabazoles | 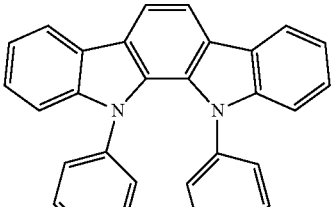 | WO2007063796 |

TABLE 1-continued

| MATERIAL | EXAMPLES OF MATERIAL | PUBLICATIONS |
|---|---|---|
|  |  | WO2007063754 |
| 5-member ring electron deficient heterocycles (e.g., triazole, oxadiazole) |  | J. Appl. Phys. 90, 5048 (2001) |
|  |  | WO2004107822 |
| Tetraphenylene complexes |  | US20050112407 |
| Metal phenoxypyridine compounds |  | WO2005030900 |

TABLE 1-continued

| MATERIAL | EXAMPLES OF MATERIAL | PUBLICATIONS |
|---|---|---|
| Metal coordination complexes (e.g., Zn, Al with N^N ligands) | | US20040137268, US20040137267 |
| Blue hosts | | |
| Arylcarbazoles | | Appl. Phys. Lett, 82, 2422 (2003) |
| | | US20070190359 |
| Dibenzothiophene/ Dibenzofuran-carbazole compounds | | WO2006114966, US20090167162 |
| | | US20090167162 |
| | | WO2009086028 |

TABLE 1-continued
| MATERIAL | EXAMPLES OF MATERIAL | PUBLICATIONS |
|---|---|---|
| | 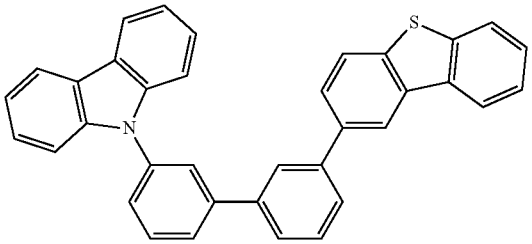 [SMILES: c1cc(-c2cccc(-n3c4ccccc4c4ccccc43)c2)cc(-c2ccc3sc4ccccc4c3c2)c1] | US20090030202, US20090017330 |
| Silicon aryl compounds | 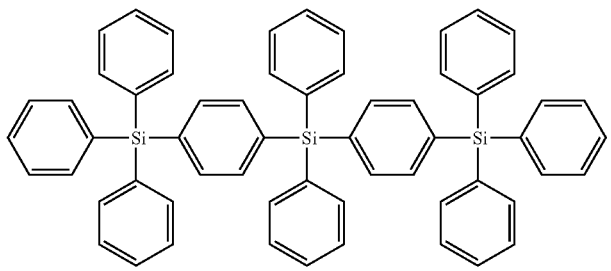 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 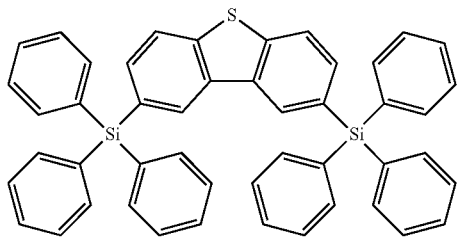 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |
| Silicon/Germanium aryl compounds | 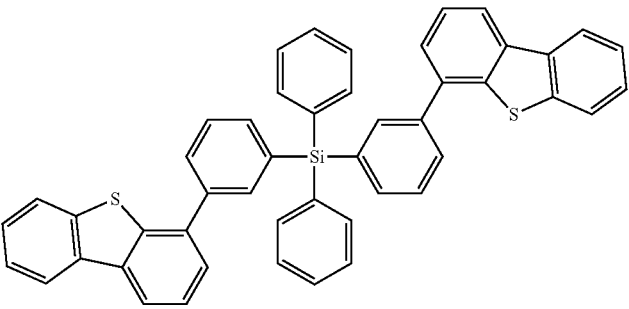 [SMILES: c1ccc([Si](c2ccccc2)(c2cccc(-c3cccc4c3sc3ccccc34)c2)c2cccc(-c3cccc4c3sc3ccccc34)c2)cc1] | EP2034538A |
| Aryl benzoyl ester | 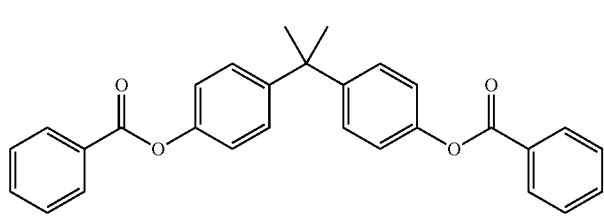 [SMILES: CC(C)(c1ccc(OC(=O)c2ccccc2)cc1)c1ccc(OC(=O)c2ccccc2)cc1] | WO2006100298 |
| High triplet metal organometallic complex | 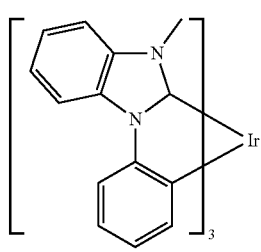 | U.S. Pat. No. 7,154,114 |

TABLE 1-continued

| MATERIAL | EXAMPLES OF MATERIAL | PUBLICATIONS |
|---|---|---|
| Phosphorescent dopants | | |
| Red dopants | | |
| Heavy metal porphyrins (e.g., PtOEP) | | Nature 395, 151 (1998) |
| Iridium(III) organometallic complexes | | Appl. Phys. Lett. 78, 1622 (2001) |
| | | US2006835469 |
| | | US2006835469 |
| | | US20060202194 |

TABLE 1-continued

| MATERIAL | EXAMPLES OF MATERIAL | PUBLICATIONS |
|---|---|---|
| | | US20060202194 |
| | | US20070087321 |
| | | US20070087321 |
| | | Adv. Mater. 19, 739 (2007) |
| | | WO2009100991 |

TABLE 1-continued
| MATERIAL | EXAMPLES OF MATERIAL | PUBLICATIONS |
|---|---|---|
| | 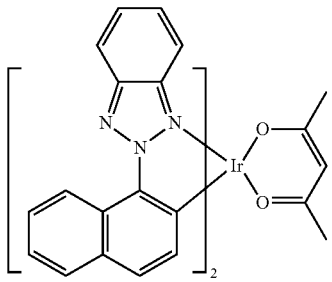 | WO2008101842 |
| Platinum(II) organometallic complexes | 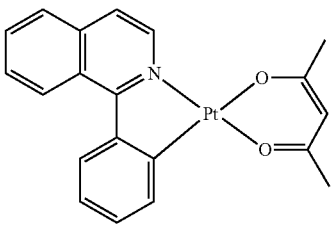 | WO2003040257 |
| Osminum(III) complexes | 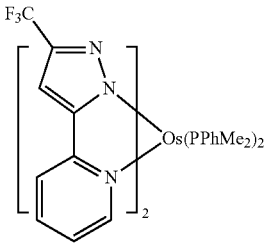 | Chem. Mater. 17, 3532 (2005) |
| Ruthenium(II) complexes | 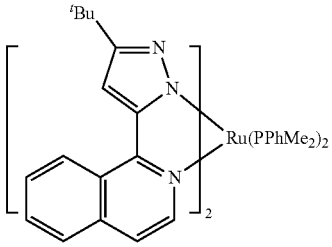 | Adv. Mater. 17, 1059 (2005) |
| Rhenium (I), (II), and (III) complexes | 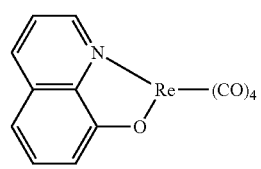 | US20050244673 |

TABLE 1-continued

| MATERIAL | EXAMPLES OF MATERIAL | PUBLICATIONS |
|---|---|---|
| Green dopants | | |
| Iridium(III) organometallic complexes | and its derivatives | Inorg. Chem. 40, 1704 (2001) |
| | | US20020034656 |
| | | U.S. Pat. No. 7,332,232 |

TABLE 1-continued

| MATERIAL | EXAMPLES OF MATERIAL | PUBLICATIONS |
|---|---|---|
| | | US20090108737 |
| | | US20090039776 |
| | | U.S. Pat. No. 6,921,915 |
| | | U.S. Pat. No. 6,687,266 |
| | | Chem. Mater. 16, 2480 (2004) |

TABLE 1-continued

| MATERIAL | EXAMPLES OF MATERIAL | PUBLICATIONS |
|---|---|---|
| | | US20070190359 |
| | | US20060008670<br>JP2007123392 |
| | | Adv. Mater. 16, 2003 (2004) |
| | | Angew. Chem. Int. Ed. 2006, 45, 7800 |
| | | WO2009050290 |
| | | US20090165846 |

TABLE 1-continued
| MATERIAL | EXAMPLES OF MATERIAL | PUBLICATIONS |
|---|---|---|
| | 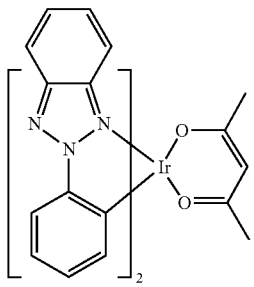 | US20080015355 |
| Monomer for polymeric metal organometallic compounds | 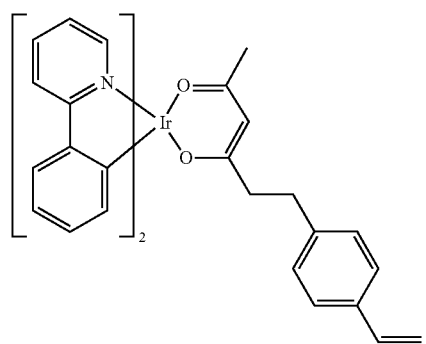 | U.S. Pat. No. 7,250,226, U.S. Pat. No. 7,396,598 |
| Pt(II) organometallic complexes, including polydentated ligands | 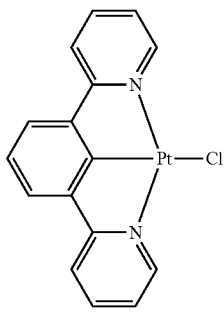 | Appl. Phys. Lett. 86, 153505 (2005) |
| | 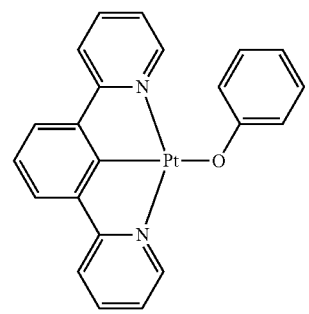 | Appl. Phys. Lett. 86, 153505 (2005) |
| | 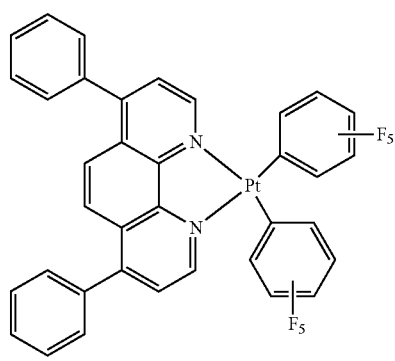 | Chem. Lett. 34, 592 (2005) |

TABLE 1-continued
| MATERIAL | EXAMPLES OF MATERIAL | PUBLICATIONS |
|---|---|---|
| | 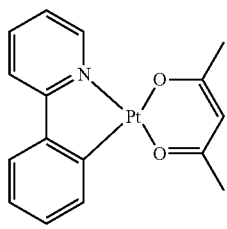 | WO2002015645 |
| | 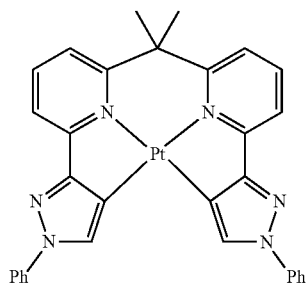 | US20060263635 |
| Cu complexes | 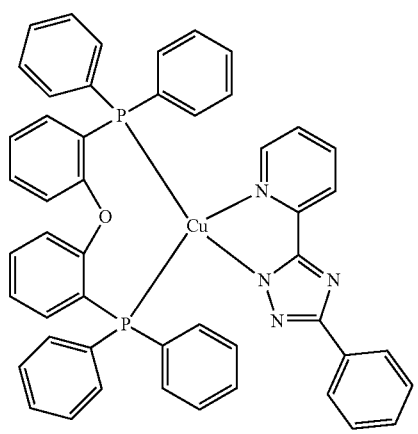 | WO2009000673 |
| Gold complexes | 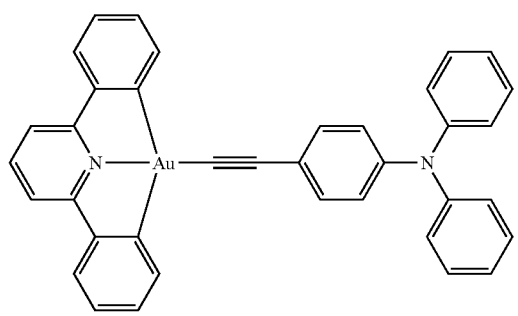 | Chem. Commun. 2906 (2005) |
| Rhenium(III) complexes | 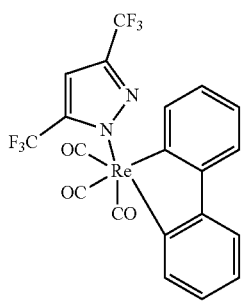 | Inorg. Chem. 42, 1248 (2003) |

TABLE 1-continued

| MATERIAL | EXAMPLES OF MATERIAL | PUBLICATIONS |
|---|---|---|
| Deuterated organometallic complexes | | US20030138657 |
| Organometallic complexes with two or more metal centers | | US20030152802 |
| | | U.S. Pat. No. 7,090,928 |

Blue dopants

| | | |
|---|---|---|
| Iridium(III) organometallic complexes | | WO2002002714 |

TABLE 1-continued

| MATERIAL | EXAMPLES OF MATERIAL | PUBLICATIONS |
| --- | --- | --- |
| | | WO2006009024 |
| | | US20060251923 |
| | | U.S. Pat. No. 7,393,599, WO2006056418, US20050260441, WO2005019373 |
| | | U.S. Pat. No. 7,534,505 |
| | | U.S. Pat. No. 7,445,855 |
| | | US20070190359, US20080297033 |

TABLE 1-continued
| MATERIAL | EXAMPLES OF MATERIAL | PUBLICATIONS |
|---|---|---|
| | 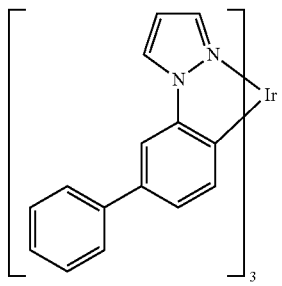 | U.S. Pat. No. 7,338,722 |
| | 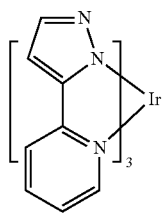 | US20020134984 |
| | 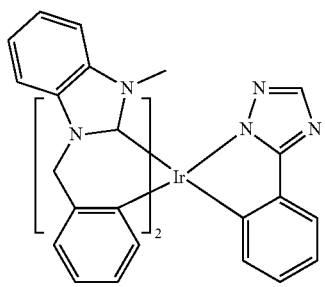 | Angew. Chem. Int. Ed. 47, 1 (2008) |
| | 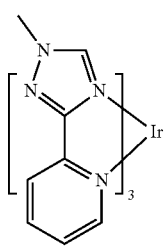 | Chem. Mater. 18, 5119 (2006) |
| | 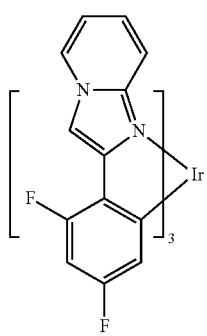 | Inorg. Chem. 46, 4308 (2007) |

TABLE 1-continued

| MATERIAL | EXAMPLES OF MATERIAL | PUBLICATIONS |
|---|---|---|
| | | WO2005123873 |
| | | WO2005123873 |
| | | WO2007004380 |
| | | WO2006082742 |
| Osmium(II) complexes | | U.S. Pat. No. 7,279,704 |

TABLE 1-continued

| MATERIAL | EXAMPLES OF MATERIAL | PUBLICATIONS |
| --- | --- | --- |
| | [Os(PPh₃) pyrazolyl-pyridine complex structure] | Organometallics 23, 3745 (2004) |
| Gold complexes | [Ph₂P-CH₂-PPh₂ bridged Au-Cl dimer structure] | Appl. Phys. Lett. 74, 1361 (1999) |
| Platinum(II) complexes | [Pt complex with thiophene and tris(pyrazolyl)borate structure] | WO2006098120, WO2006103874 |

Exciton/hole blocking layer materials

| MATERIAL | EXAMPLES OF MATERIAL | PUBLICATIONS |
| --- | --- | --- |
| Bathocuprine compounds (e.g., BCP, BPhen) | [BCP structure] | Appl. Phys. Lett. 75, 4 (1999) |
| | [BPhen structure] | Appl. Phys. Lett. 79, 449 (2001) |
| Metal 8-hydroxyquinolates (e.g., BAlq) | [BAlq structure] | Appl. Phys. Lett. 81, 162 (2002) |

TABLE 1-continued

| MATERIAL | EXAMPLES OF MATERIAL | PUBLICATIONS |
| --- | --- | --- |
| 5-member ring electron deficient heterocycles such as triazole, oxadiazole, imidazole, benzoimidazole | | Appl. Phys. Lett. 81, 162 (2002) |
| Triphenylene compounds | | US20050025993 |
| Fluorinated aromatic compounds | | Appl. Phys. Lett. 79, 156 (2001) |

TABLE 1-continued

| MATERIAL | EXAMPLES OF MATERIAL | PUBLICATIONS |
| --- | --- | --- |
| Phenothiazine-S-oxide | | WO2008132085 |

Electron transporting materials

| | | |
| --- | --- | --- |
| Anthracene-benzoimidazole compounds | | WO2003060956 |
| | | US20090179554 |
| Aza triphenylene derivatives | | US20090115316 |

TABLE 1-continued

| MATERIAL | EXAMPLES OF MATERIAL | PUBLICATIONS |
| --- | --- | --- |
| Anthracene-benzothiazole compounds | | Appl. Phys. Lett. 89, 063504 (2006) |
| Metal 8-hydroxyquinolates (e.g., Alq$_3$, Zrq$_4$) | | Appl. Phys. Lett. 51, 913 (1987)<br>U.S. Pat. No. 7,230,107 |
| Metal hydroxybenoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |
| 5-member ring electron deficient heterocycles (e.g., triazole, oxadiazole, imidazole, benzoimidazole) | | Appl. Phys. Lett. 74, 865 (1999) |

TABLE 1-continued
| MATERIAL | EXAMPLES OF MATERIAL | PUBLICATIONS |
|---|---|---|
| | 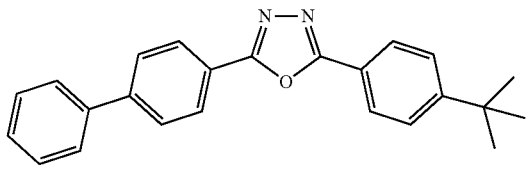 [SMILES: CC(C)(C)c1ccc(-c2nnc(-c3ccc(-c4ccccc4)cc3)o2)cc1] | Appl. Phys. Lett. 55, 1489 (1989) |
| | 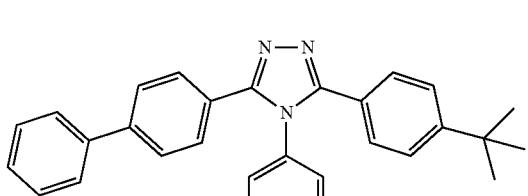 | Jpn. J. Apply. Phys. 32, L917 (1993) |
| Silole compounds | 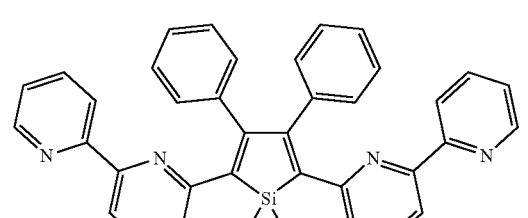 | Org. Electron. 4, 113 (2003) |
| Arylborane compounds | 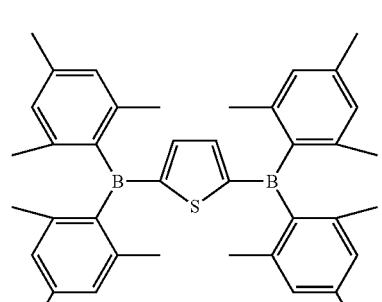 | J. Am. Chem. Soc. 120, 9714 (1998) |
| Fluorinated aromatic compounds | 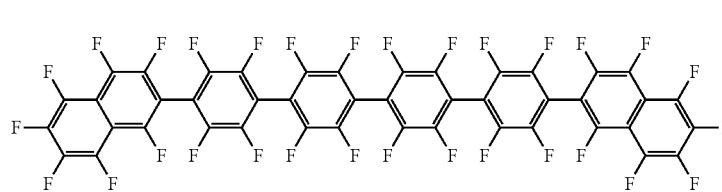 | J. Am. Chem. Soc. 122, 1832 (2000) |
| Fullerene (e.g., C60) | 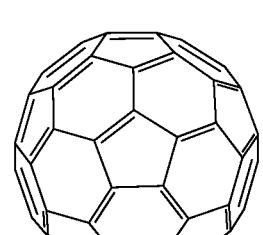 | US20090101870 |

TABLE 1-continued

| MATERIAL | EXAMPLES OF MATERIAL | PUBLICATIONS |
|---|---|---|
| Triazine complexes | | US20040036077 |
| Zn (N^N) complexes | | U.S. Pat. No. 6,528,187 |

EXPERIMENTAL

Compound Examples

Example 1. Synthesis of Compound 1

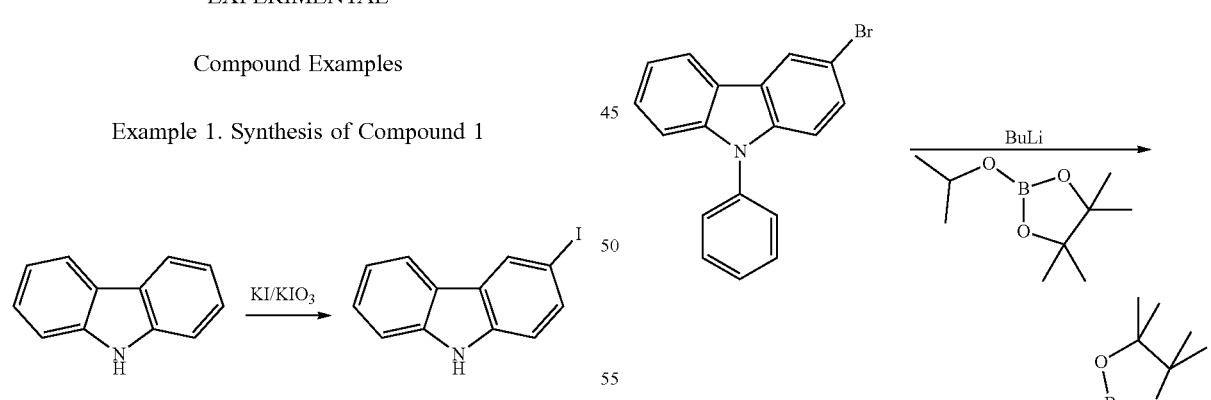

Synthesis of 3-iodo-9H-carbazole.

To a solution of 9H-carbazole (5.57 g, 33.3 mmol) and KI (3.68 g, 22.2 mmol) in AcOH (92 mL) was heated to 100° C. for 1 h. KIO$_3$ (3.57 g, 16.7 mmol) was added in portions to the solution, and the resulting mixture was stirred for another 2 h at 100° C. The mixture was poured into water (500 mL) and the precipitation was collected by filtration and washed with hot water. Recrystallization was made in DCM to afford 6.8 g (70%) of product as a white solid.

Synthesis of 9-phenyl-3-(4,4,5,5-tetramethyl-1,3,2-dioxaborolan-2-yl)-9H-carbazole To a solution of 3-bromo-9-phenyl-9H-carbazole (20.3 g, 63 mmol) in THF (150 mL) at −78° C. was added 47.25 mL (75.8 mmol) of n-butyllithium (1.6 M in hexane). The mixture was stirred at −78° C. for 1 h. 21 mL (100 mmol) of 2-isopropoxy-4,4,5,5-tetramethyl-[1,3,2]-dioxaborolane was added to the solution, and the resulting mixture was warmed to room temperature and stirred for 8 h. The mixture was poured into water and extracted with dichloromethane. The organic extracts were washed with brine and dried over magnesium sulfate. The solvent was removed by rotary evaporation, and recrystallization was made in hexane to afford 19.3 g (83%) of product as a white solid.

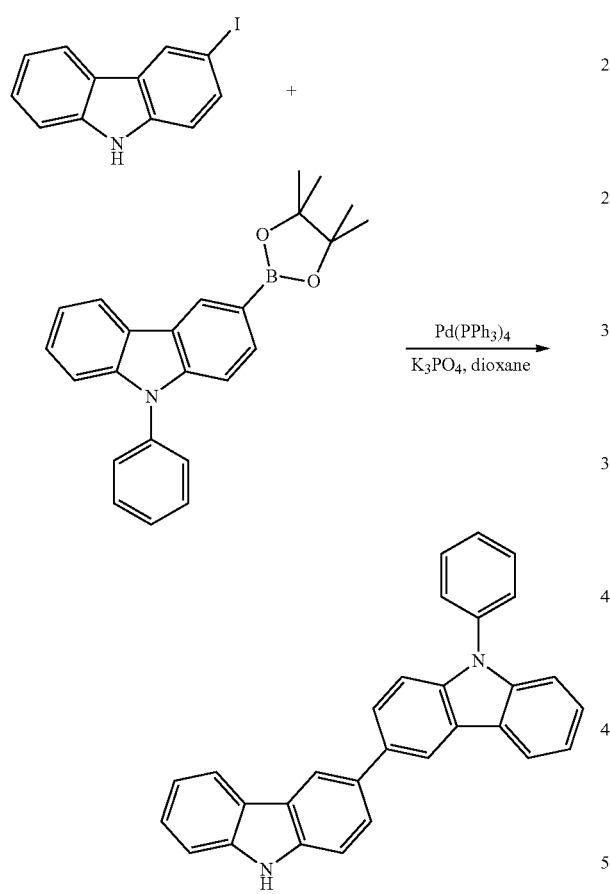

Synthesis of 3-(9-phenyl-9H-carbazol-3-yl)-9H-carbazole

To a solution of 3-iodo-9H-carbazole (879 mg, 3.0 mmol), Pd(PPh$_3$)$_4$ (165 mg, 0.15 mmol), 9-phenyl-3-(4,4,5,5-tetramethyl-1,3,2-dioxaborolan-2-yl)-9H-carbazole (1.29 g, 4.5 mmol) and K$_3$PO$_4$ (1.8 g, 18.0 mmol) in dioxane (5 mL). The solution was heated to 85° C. with vigorous stirring for 48 h under argon atmosphere. The mixture was poured into water and extracted with DCM. The organic extracts were washed with brine and dried over MgSO$_4$. The solvent was removed by rotary evaporation, and recrystallization was made in DCM to afford 900 mg (74%) of product.

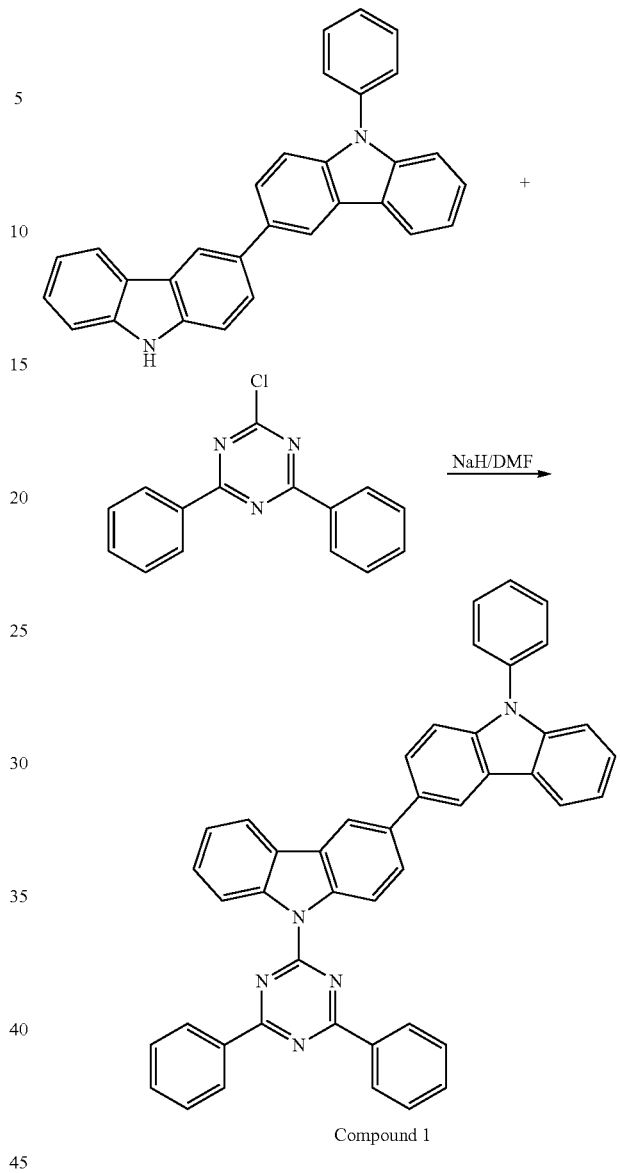

Compound 1

Synthesis of 9-(4,6-diphenyl-1,3,5-triazin-2-yl)-3-(9-phenyl-9H-carbazol-3-yl)-9H-carbazole (Compound 1)

To a solution of sodium hydride (100 mg, 3.0 mmol) and 3-(9-phenyl-9H-carbazol-3-yl)-9H-carbazole (816 mg, 2.0 mmol) in dry DMF (40 mL) was stirred at room temperature for 1 h under argon atmosphere. 2-Chloro-4,6-diphenyl-1,3,5-triazine (448 mg, 1.67 mmol) was added to the solution at room temperature, then refluxed overnight. The mixture was poured into water and the precipitation was collected by filtration and washed with water, methanol and DCM to get 800 mg (75%) yellow solid.

Device Examples

All device examples were fabricated by high vacuum (<10$^{-7}$ Torr) thermal evaporation. The anode electrode is 800 Å of indium tin oxide (ITO). The cathode consisted of 10 Å of LiF followed by 1000 Å of Al. All devices were encapsulated with a glass lid sealed with an epoxy resin in a nitrogen glove box (<1 ppm of $H_2O$ and $O_2$) immediately after fabrication, and a moisture getter was incorporated inside the package.

As used herein, the following compounds have the following structures:

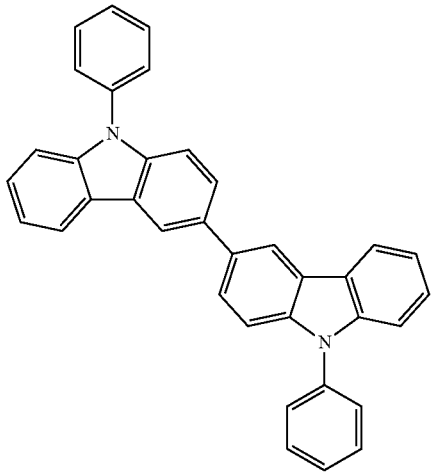

H1

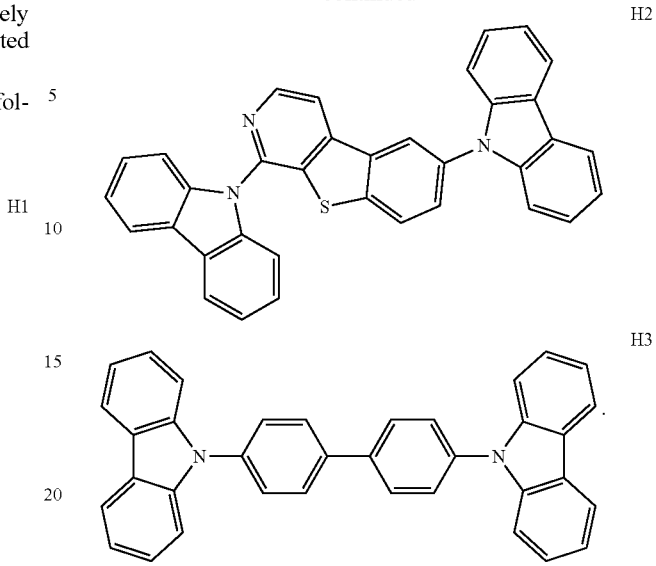

H2

H3

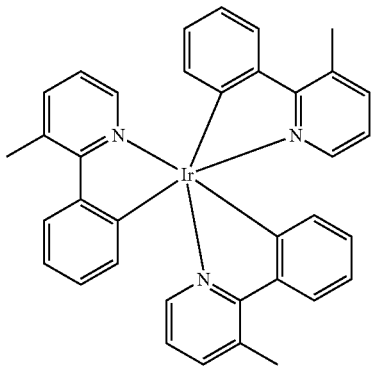

E1

Particular devices are provided. The organic stack of the Device Examples 1 and 2 consisted of sequentially, from the ITO surface, 100 Å of E1 as the hole injection layer (HIL), 300 Å of 4,4'-bis[N-(1-naphthyl)-N-phenylamino]biphenyl (α-NPD) as the hole transporting layer (HTL), 300 Å of host doped with E1 as the emissive layer (EML), 100 Å of H2 as the blocking layer (BL), and 400 Å of Alq as the electron transporting layer (ETL).

Comparative Device Examples 1 and 2 were fabricated similarly to Device Examples 1 and 2, except H3 was used as host.

Device structures for Device Examples 1 and 2 are provided in Table 2 and the corresponding measured device data is provided in Table 3.

TABLE 2

| VTE PHOLEDs | | | | | | |
|---|---|---|---|---|---|---|
| Example | HIL | HTL | EML | (doping %) | BL | ETL |
| Example 1 | E1 | NPD | Compound 1 | E1 5% | H2 | Alq |
| Example 2 | E1 | NPD | Compound 1 | E1 10% | H2 | Alq |
| Comparative Example 1 | E1 | NPD | H3 | E1 5% | H2 | Alq |
| Comparative Example 2 | E1 | NPD | H3 | E1 10% | H2 | Alq |

TABLE 3

| | VTE device data | | | | | | | | |
|---|---|---|---|---|---|---|---|---|---|
| | 1931 CIE | | | FWHM | Voltage | At 1000 nits | | | At 40 mA/cm$^2$ |
| Example | x | y | $\lambda_{max}$ | (nm) | (V) | LE (Cd/A) | EQE (%) | PE (lm/W) | $L_0$ (nits) | LT80% (h) |
| Example 1 | 0.324 | 0.623 | 520 | 66 | 5.7 | 40.6 | 11.3 | 22.2 | 12,769 | 86 |
| Example 2 | 0.336 | 0.619 | 522 | 69 | 5.6 | 47.4 | 13.2 | 26.4 | 15,048 | 83 |
| Comp. Example 1 | 0.316 | 0.628 | 520 | 64 | 5.7 | 45.5 | 12.7 | 25.1 | 12,635 | 46 |
| Comp. Example 2 | 0.317 | 0.630 | 520 | 64 | 5.2 | 54.4 | 15.1 | 32.6 | 16,264 | 29 |

Device Examples 1 and 2 showed green PHOLEDs with Compound 1 as host with different E1 doping concentrations. The comparative examples used H3 (i.e., CBP, a commonly used PHOLED host) as the host. As can be seen from the table, devices with Compound 1 as host had comparative operating voltage, slightly lower efficiency than devices with H3 as the host. However, the device operating lifetime was much higher than comparative examples. Device Example 1 almost doubled the lifetime of Comparative Example 1 (86 h vs 46 h) and Device Example 2 almost tripled the lifetime of Comparative Example 2 (83 h vs. 29 h). Therefore, Compound 1 is an excellent host material for phosphorescent OLEDs.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore includes variations from the particular examples and preferred embodiments described herein, as will be apparent to one of skill in the art. It is understood that various theories as to why the invention works are not intended to be limiting.

The invention claimed is:

1. A compound having the formula:

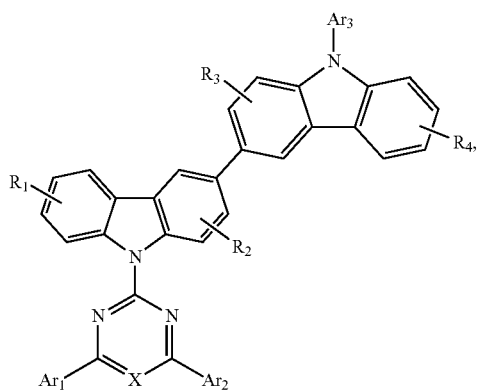

wherein $R_1$, $R_2$, $R_3$, and $R_4$ may represent mono up to the maximum available substitutions, or no substitutions;
wherein $R_1$, $R_2$, $R_3$, and $R_4$ are independently selected from the group consisting of hydrogen, alkyl, alkoxy, amino, alkenyl, alkynyl, aryl and heteroaryl;
wherein $Ar_2$ and $Ar_3$ are independently selected from aryl or heteroaryl;
wherein $Ar_1$ is selected from the group consisting of pyridine, naphthalene, fluorene, phenanthrene, and triphenylene;
wherein $Ar_2$ and $Ar_3$ are independently optionally substituted; and
wherein X is C or N.

2. The compound of claim 1, wherein at least one of $Ar_1$, $Ar_2$, and $Ar_3$ is further substituted.

3. The compound of claim 1, wherein $Ar_2$, and $Ar_3$ are independently selected from the group consisting of phenyl, pyridine, naphthalene, biphenyl, terphenyl, fluorene, dibenzofuran, dibenzothiophene, phenanthrene, and triphenylene; and
wherein at least one of $Ar_2$ and $Ar_3$ is further substituted with a substituent selected from the group consisting of hydrogen, alkyl, alkoxy, amino, alkenyl, alkynyl, aryl and heteroaryl, wherein the substituent is not an aryl or heteroaryl fused directly to $Ar_2$ and $Ar_3$.

4. The compound of claim 1, wherein $Ar_1$ is pyridine and $Ar_2$ is selected from the group consisting of phenyl, pyridine, and naphthalene.

5. The compound of claim 1, wherein $Ar_3$ is selected from the group consisting of phenyl, biphenyl, dibenzofuran, and dibenzothiophene.

6. The compound of claim 1, wherein $R_1$, $R_2$, $R_3$, and $R_4$ are hydrogen.

7. The compound of claim 1, wherein the compound is selected from the group consisting of:

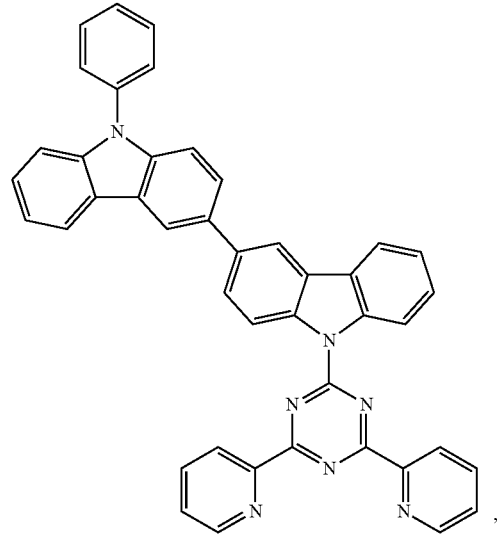

Compound 16

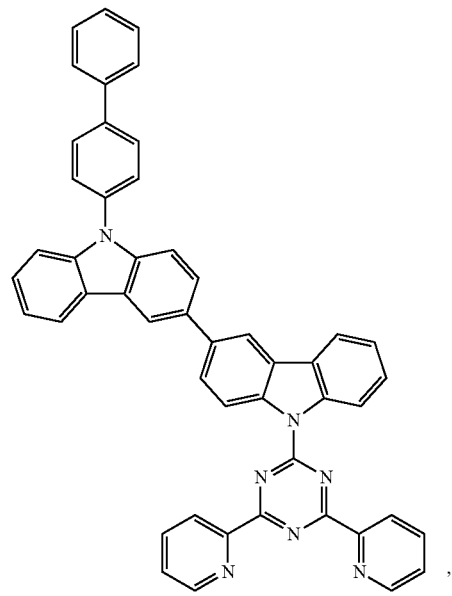

Compound 17

Compound 18
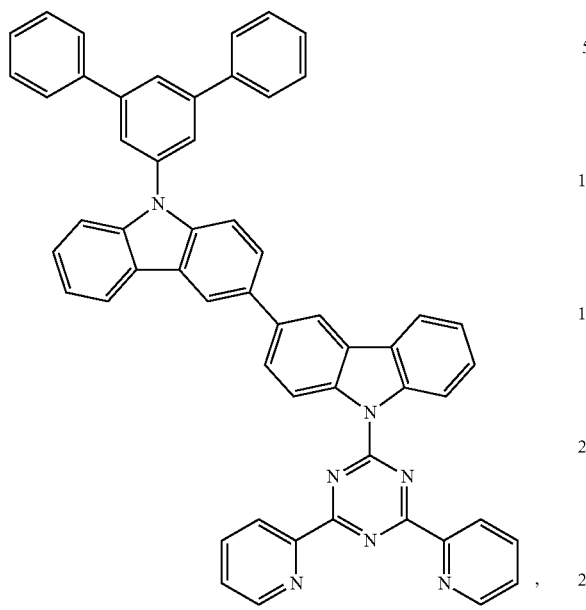
Compound 19
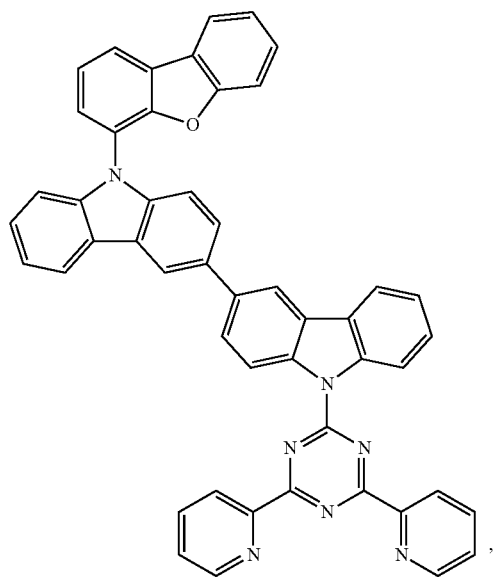
Compound 20
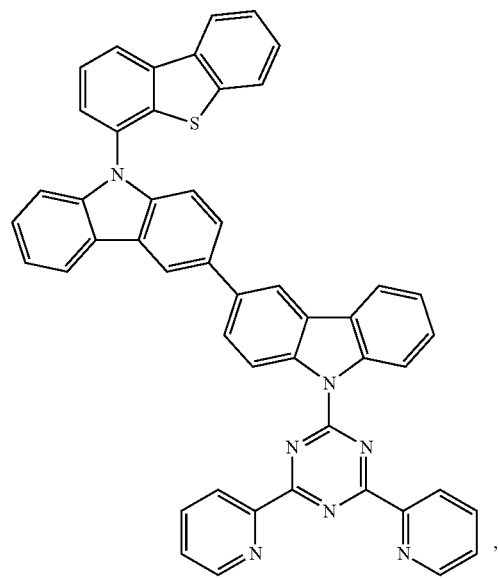
Compound 21
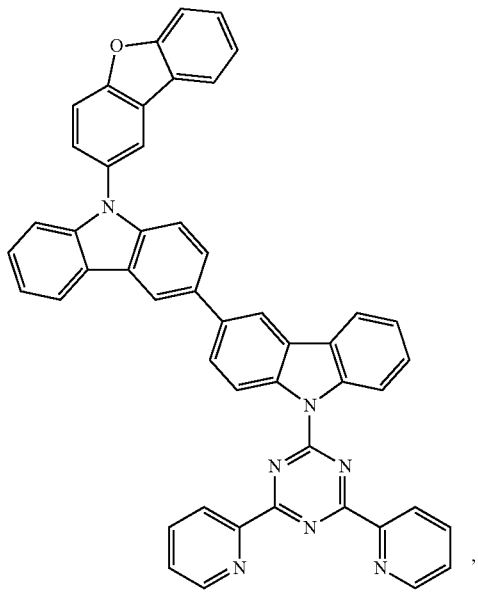

Compound 22
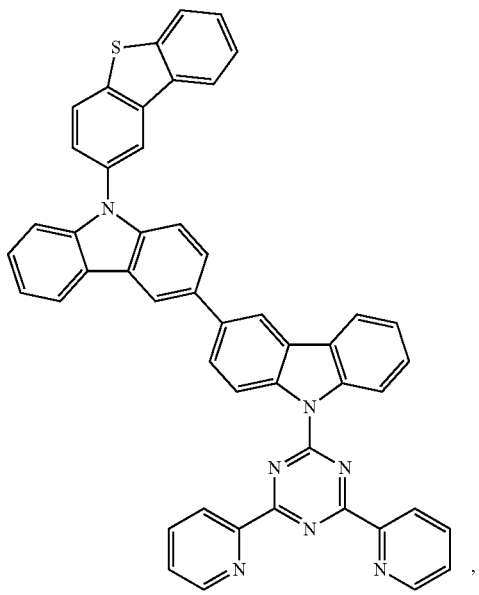
Compound 23
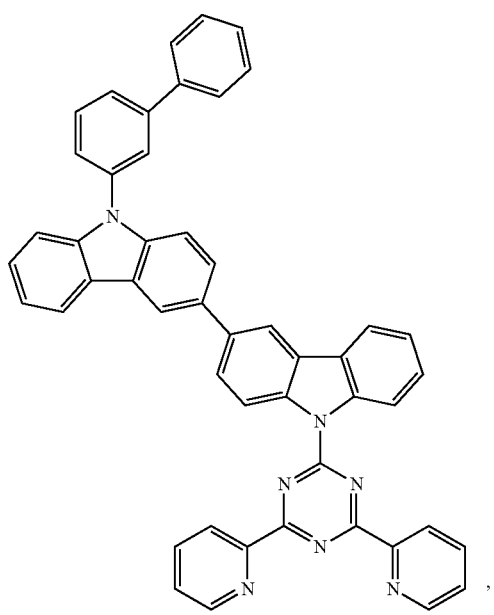
Compound 24
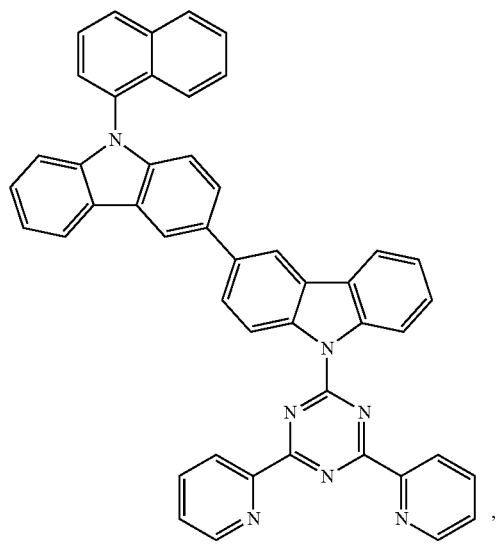
Compound 25
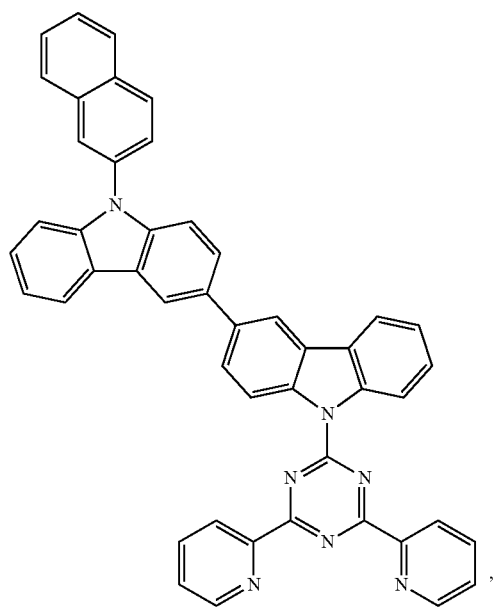

Compound 26
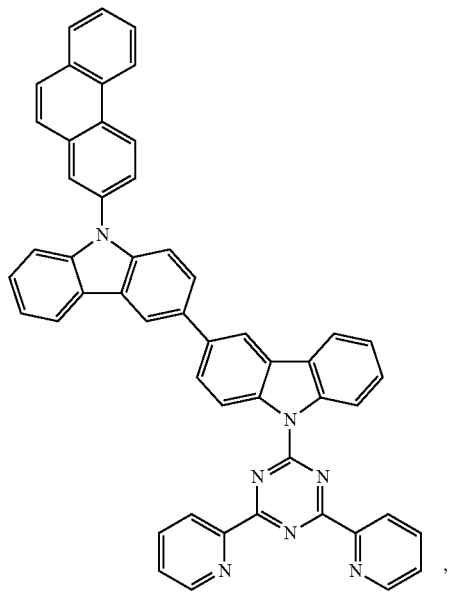
Compound 27
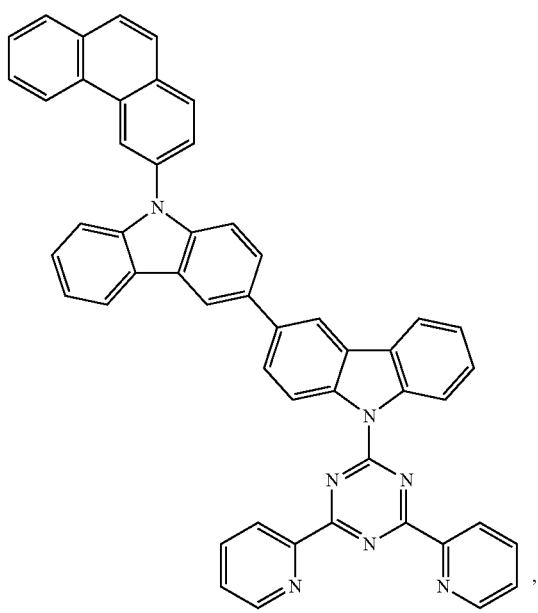
Compound 28
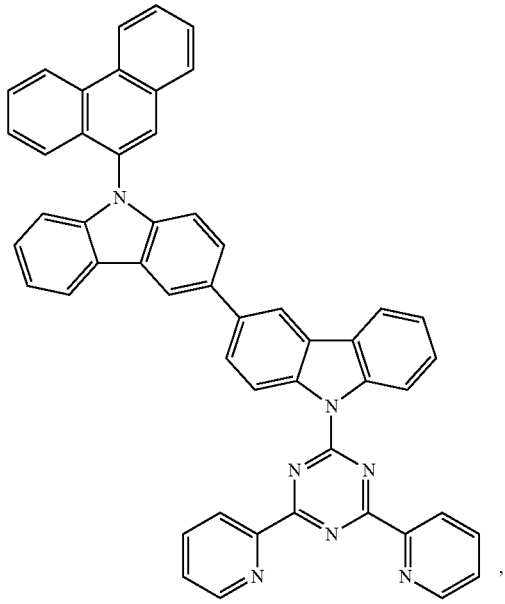
Compound 29
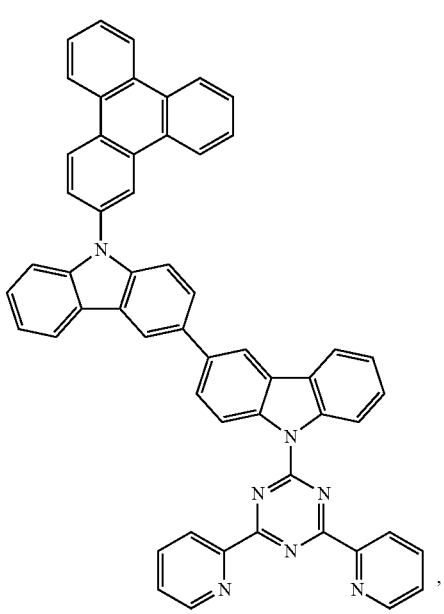

Compound 30
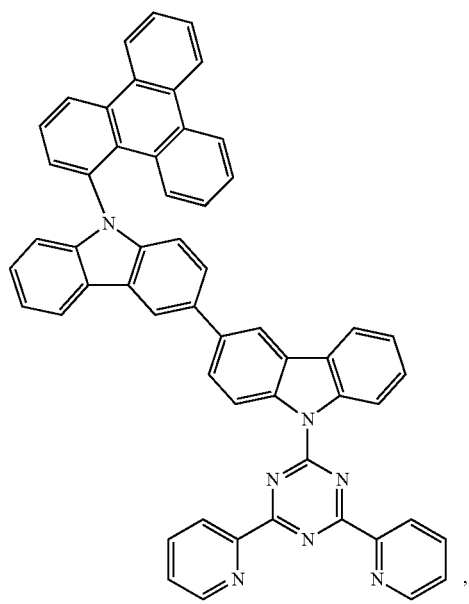
Compound 31
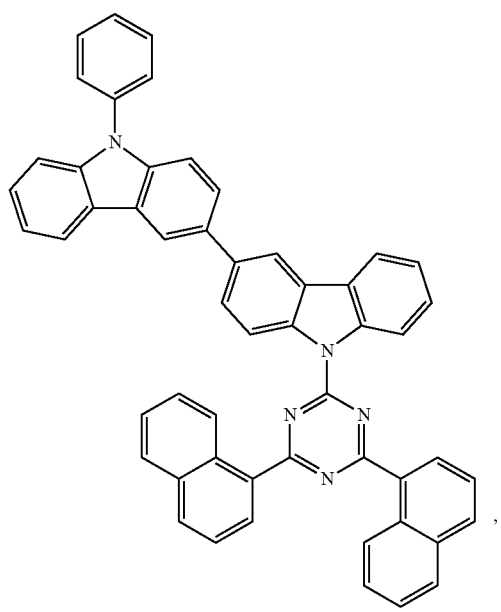
Compound 32
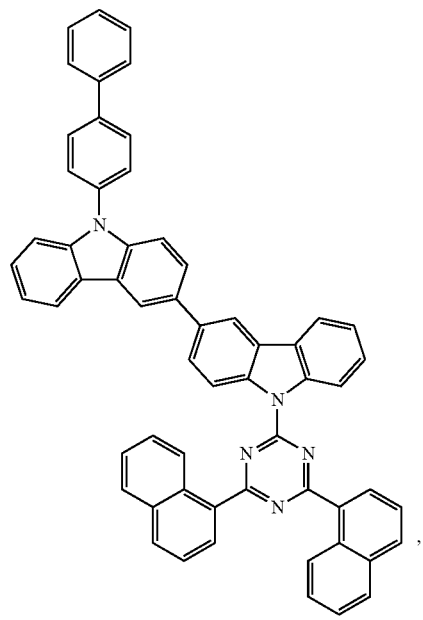
Compound 33
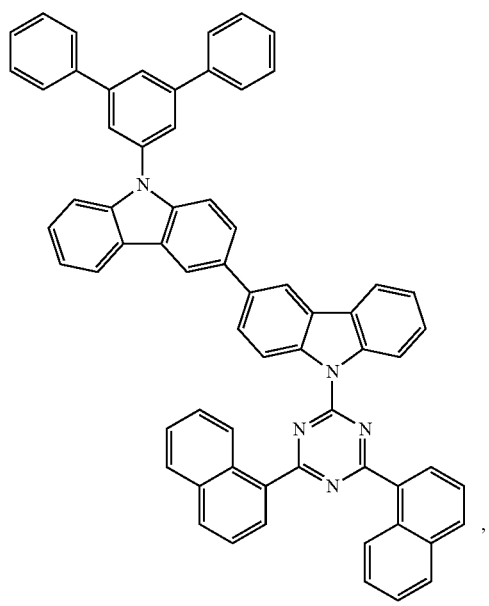

Compound 34
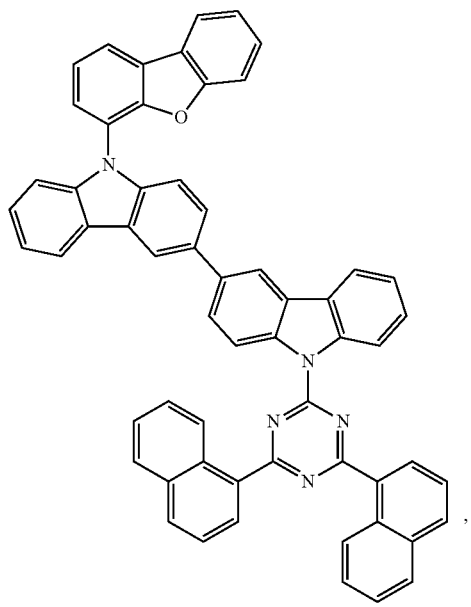
Compound 35
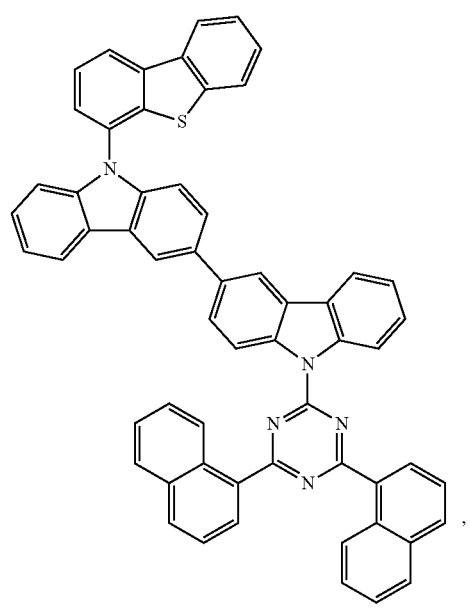
Compound 36
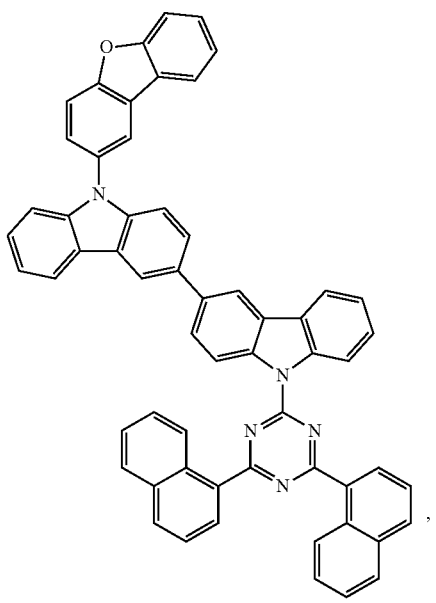
Compound 37
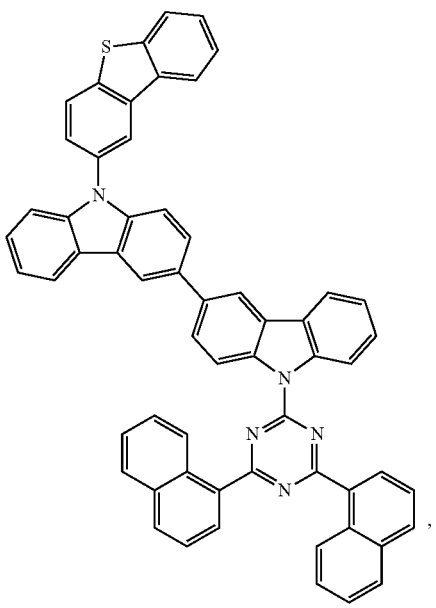

Compound 38
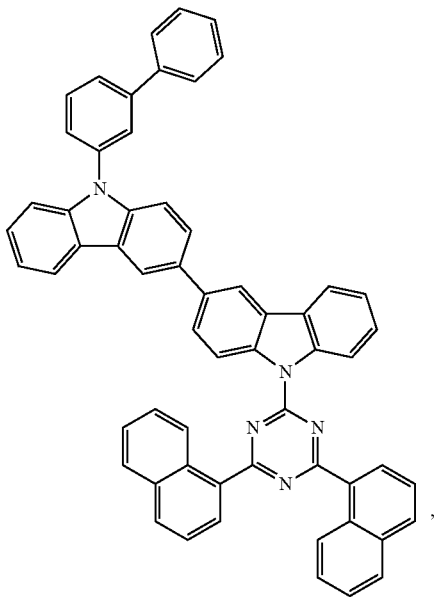
Compound 40
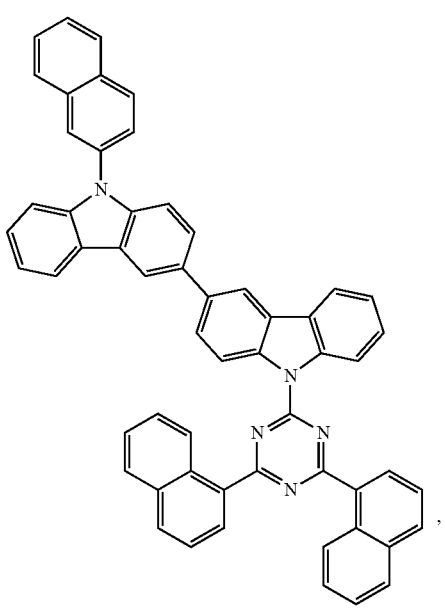
Compound 39
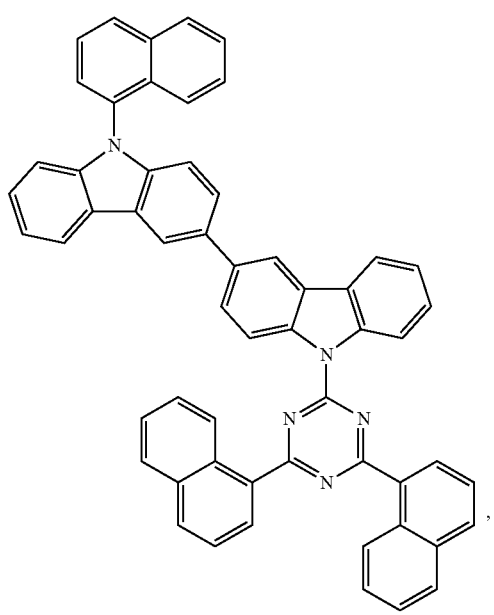
Compound 41

Compound 42
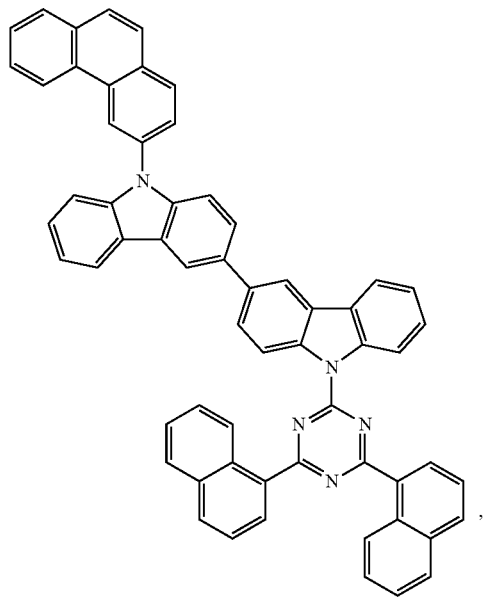
Compound 43
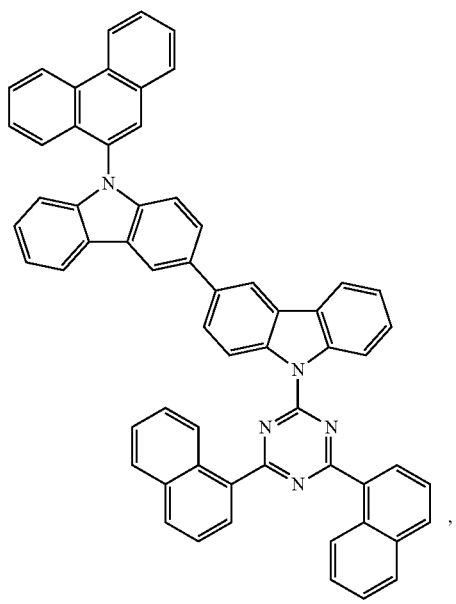
Compound 44
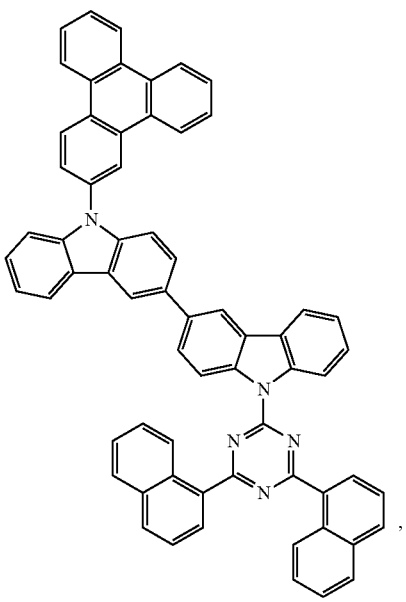
Compound 45
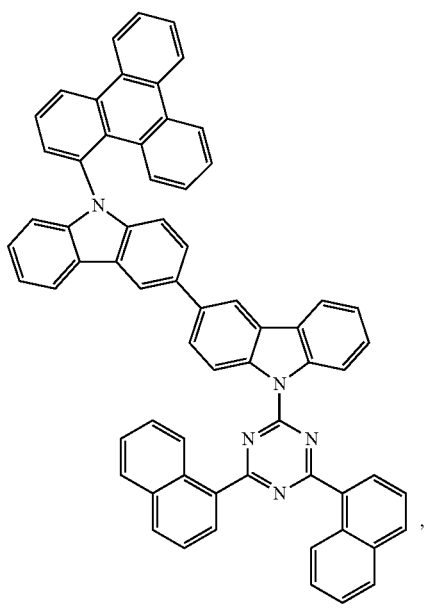

Compound 46
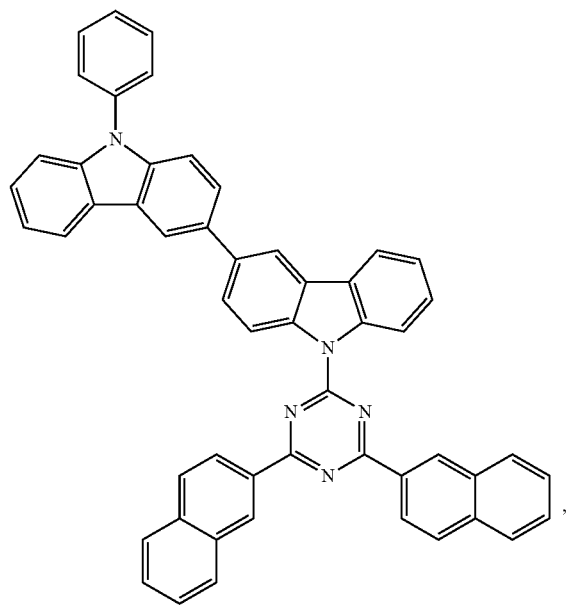
Compound 48
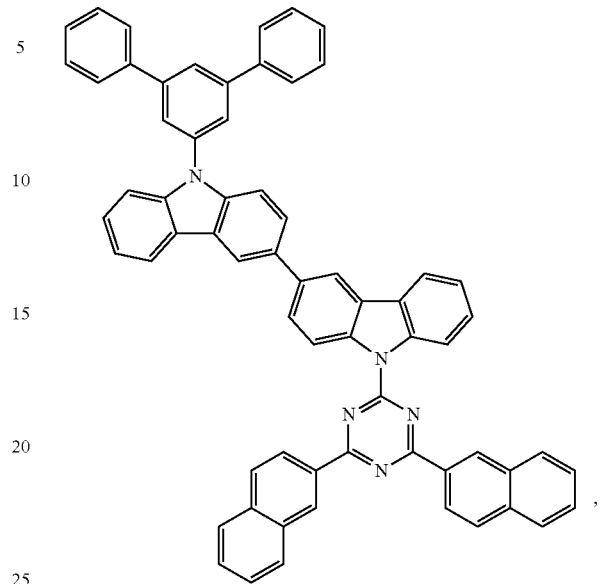
Compound 47
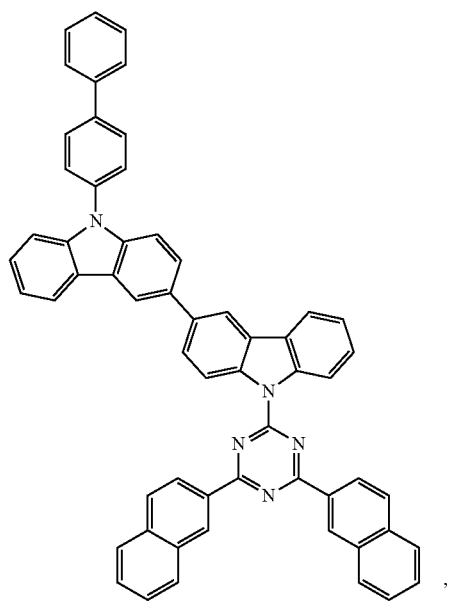
Compound 49
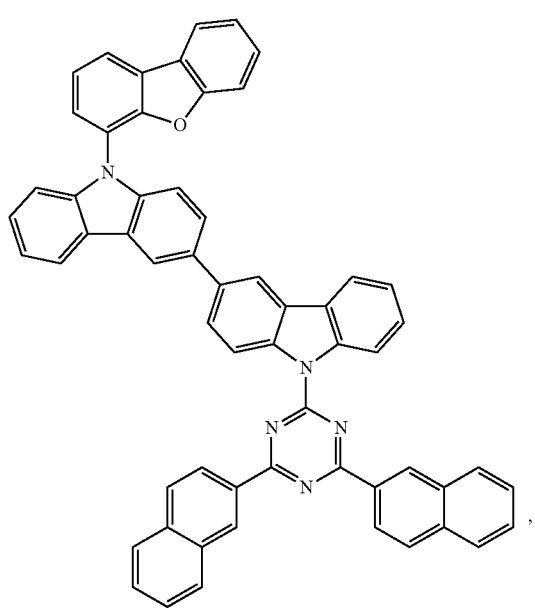

Compound 50
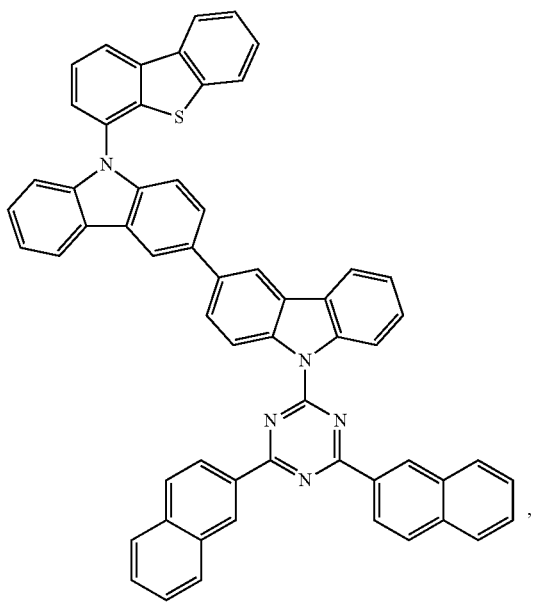
Compound 51
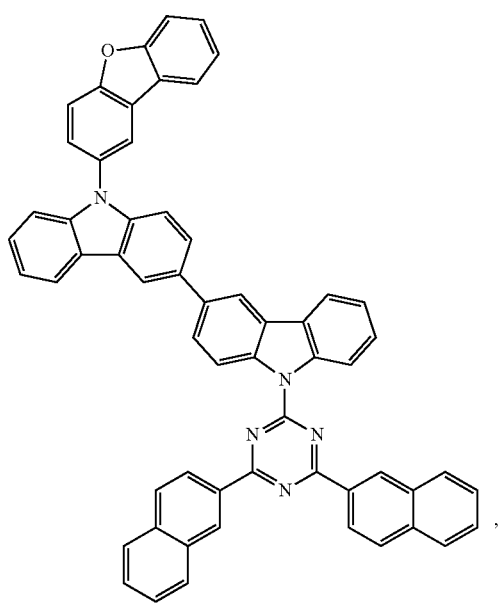
Compound 52
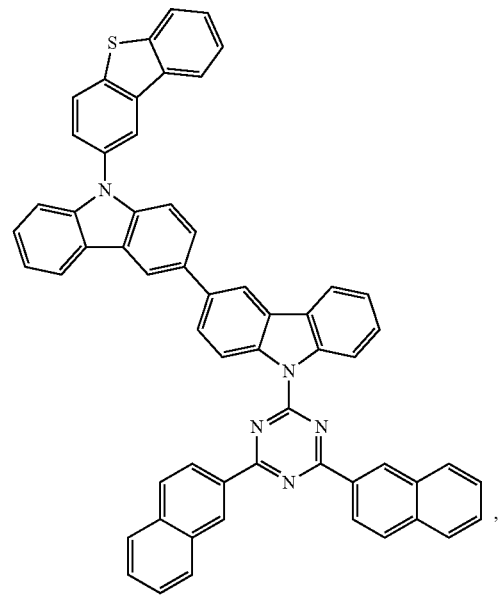
Compound 53
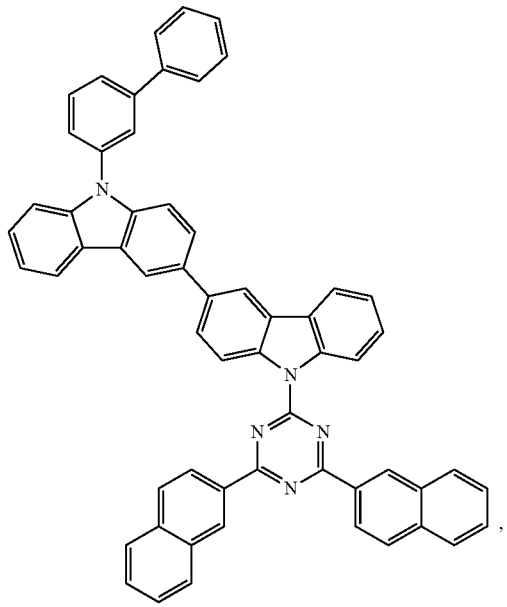

Compound 54
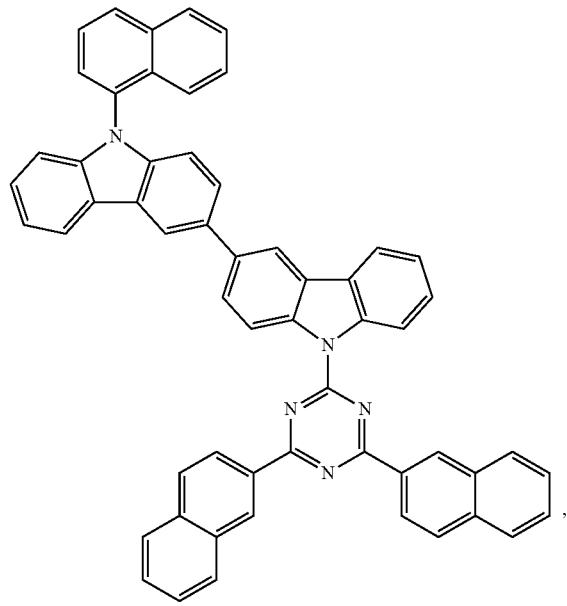
Compound 56
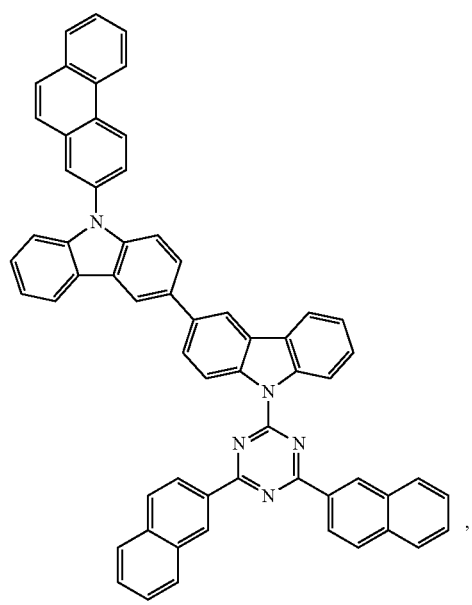
Compound 55
Compound 57

Compound 58
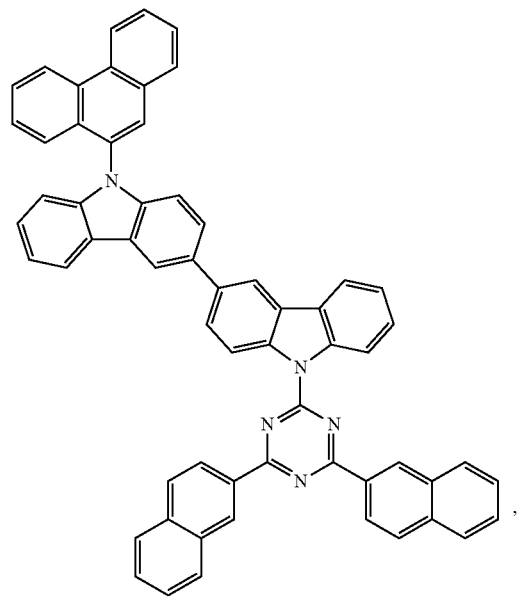
Compound 59
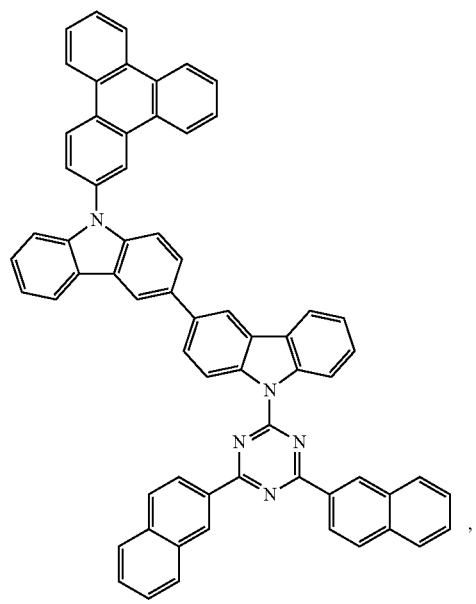
Compound 60
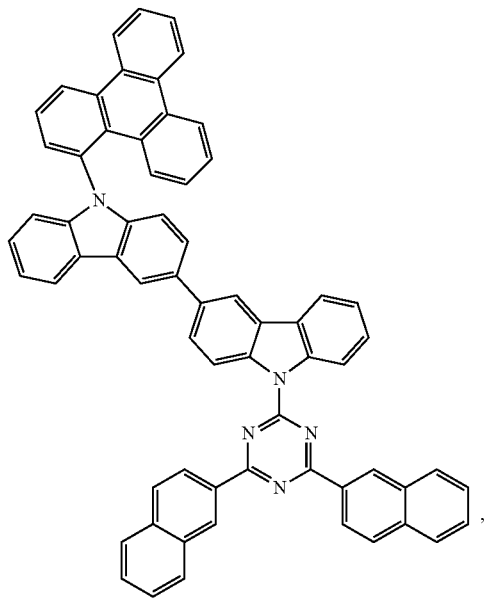
Compound 61
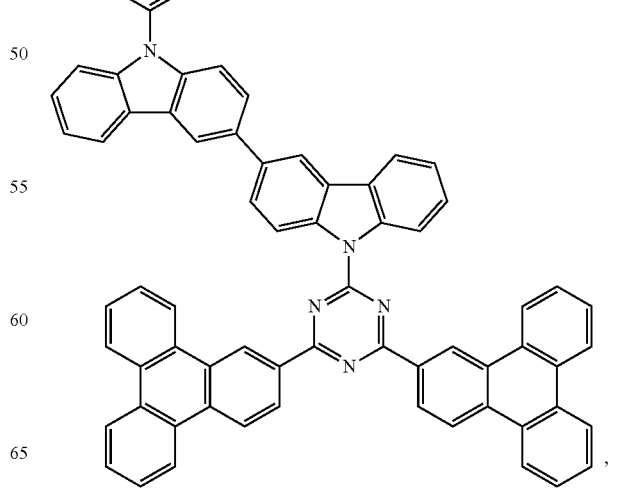

Compound 62
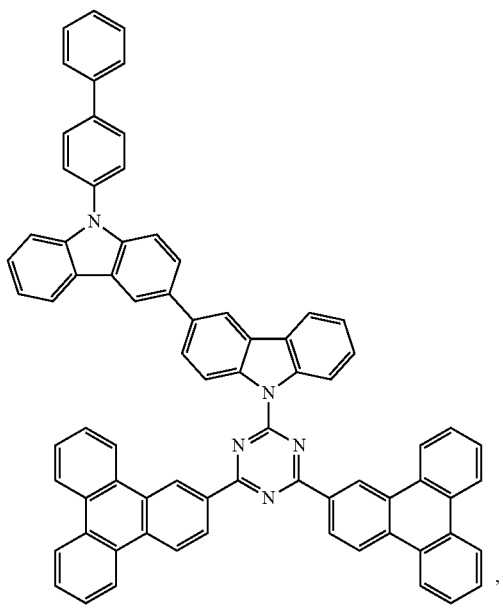
Compound 63
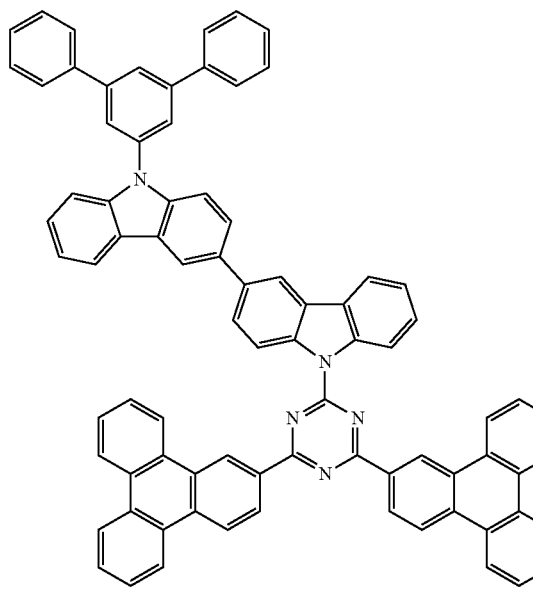
Compound 64
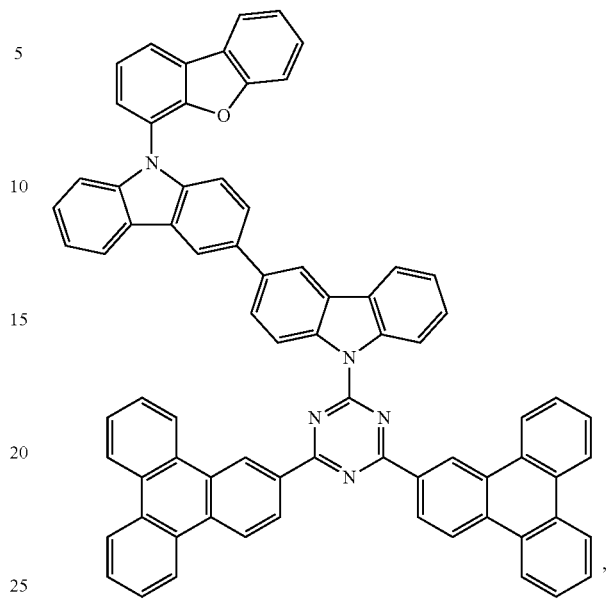
Compound 65
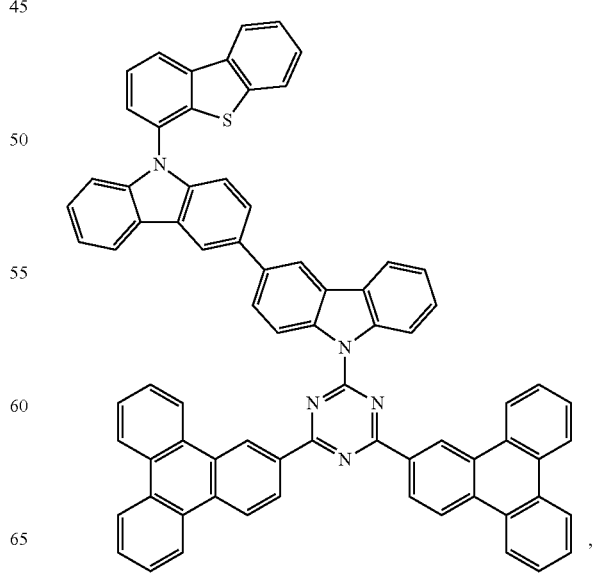

Compound 66
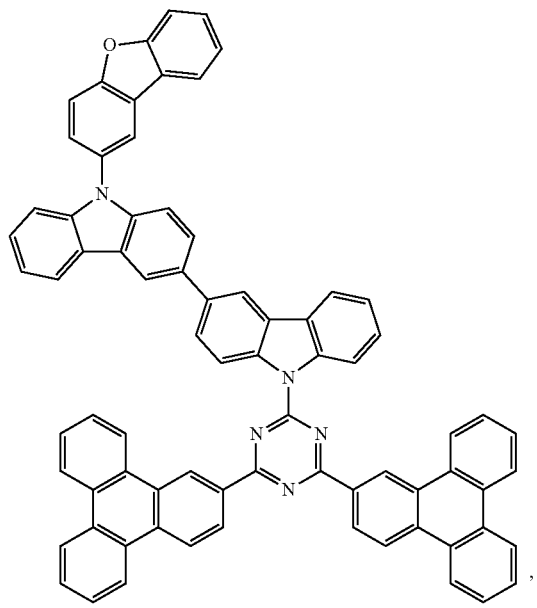
Compound 67
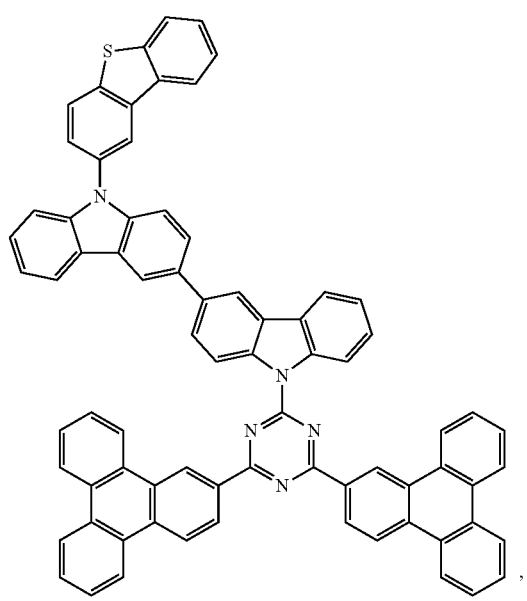
Compound 68
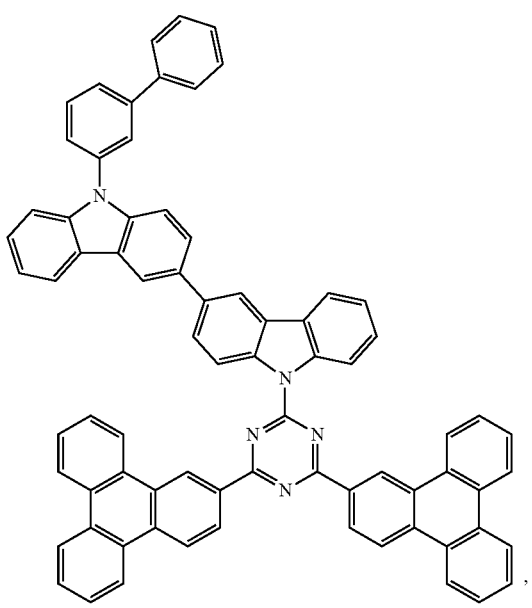
Compound 69
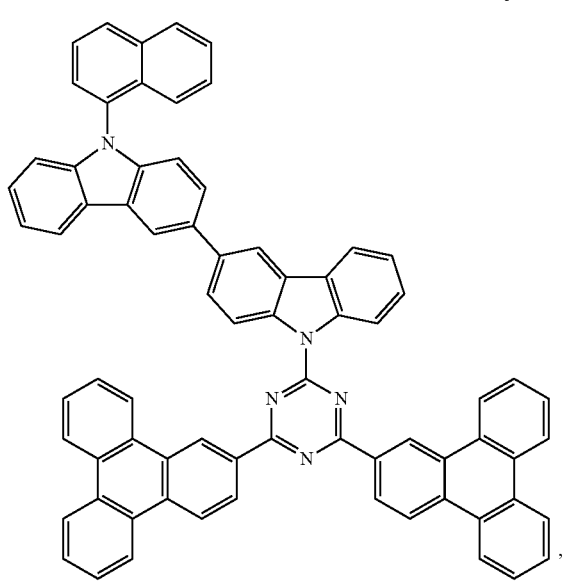

Compound 70
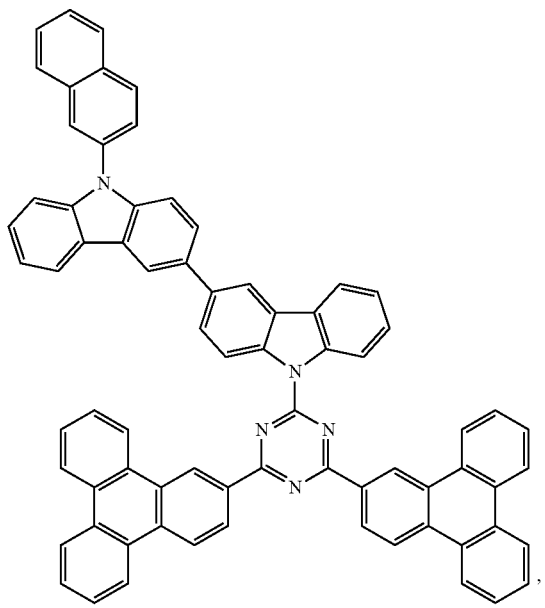
Compound 72
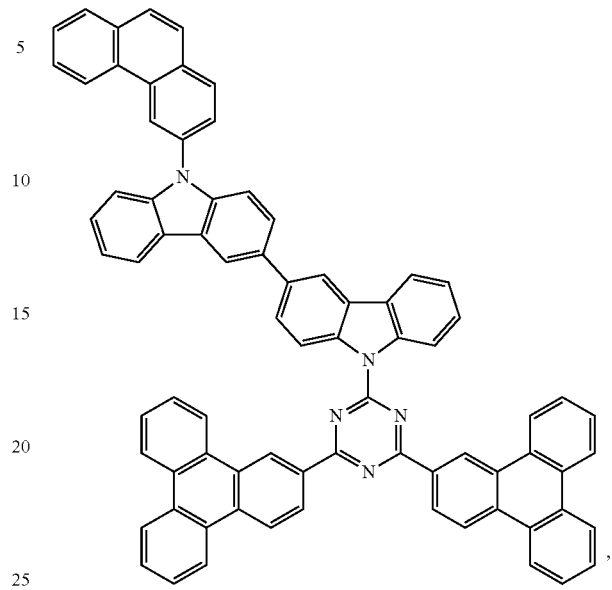
Compound 71
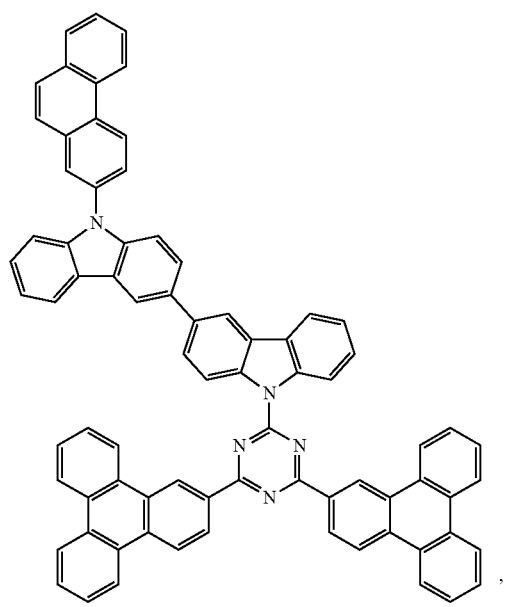
Compound 73
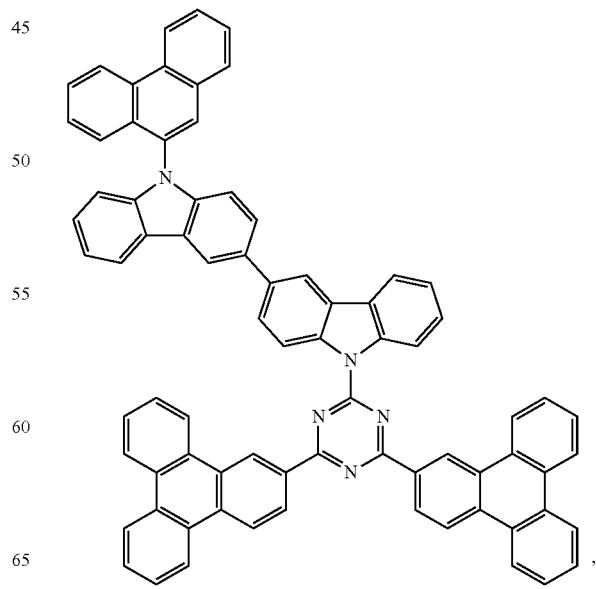

Compound 74
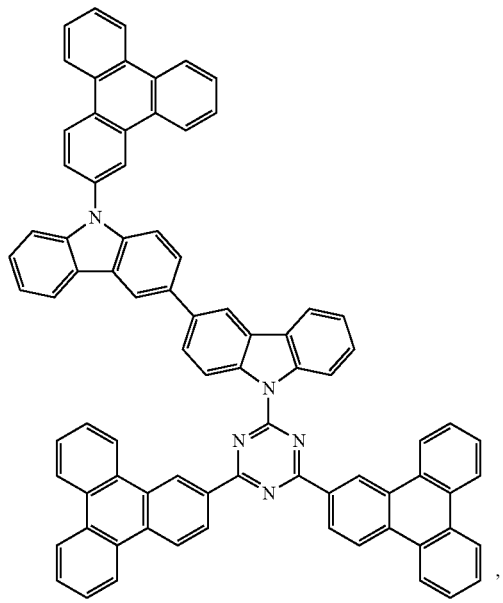
Compound 75
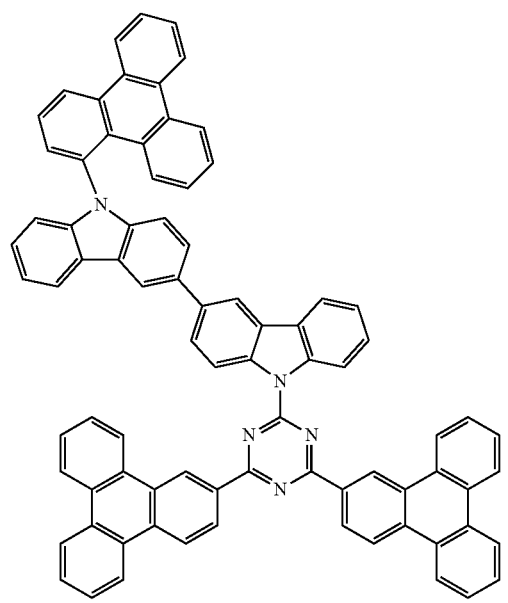
Compound 76
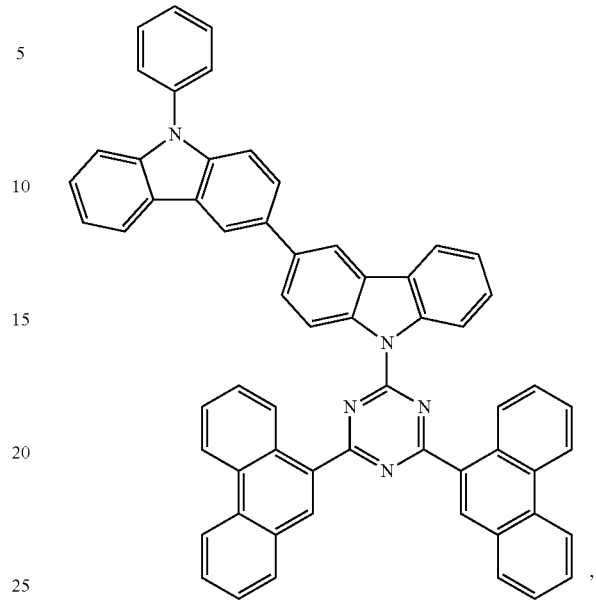
Compound 77
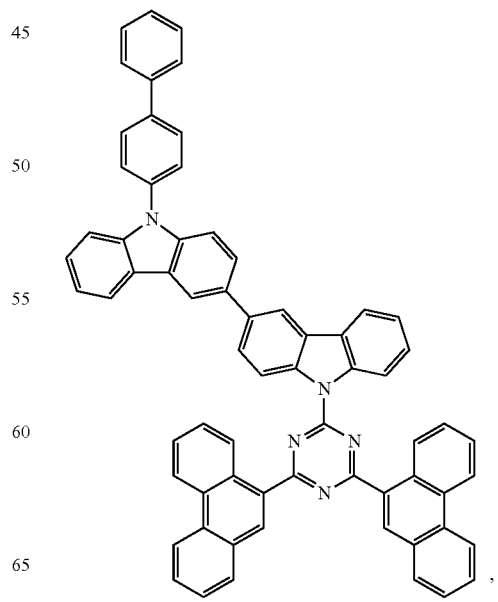

Compound 78
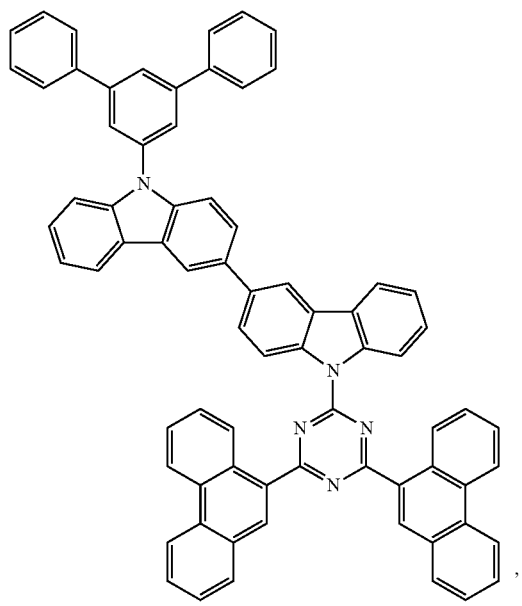
Compound 79
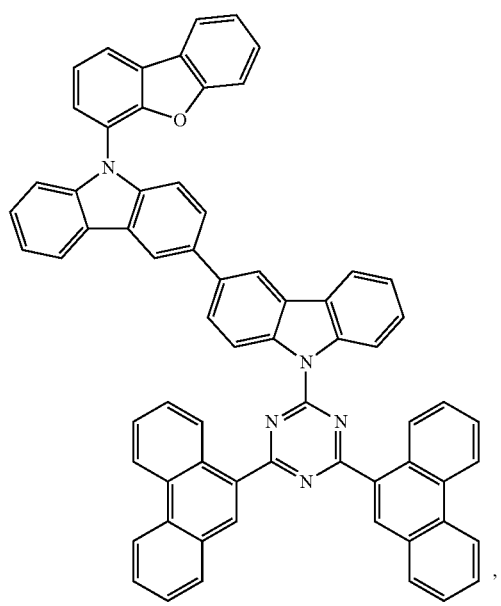
Compound 80
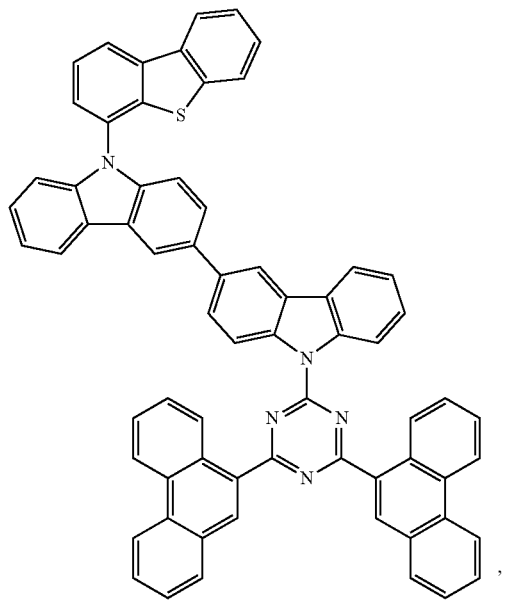
Compound 81
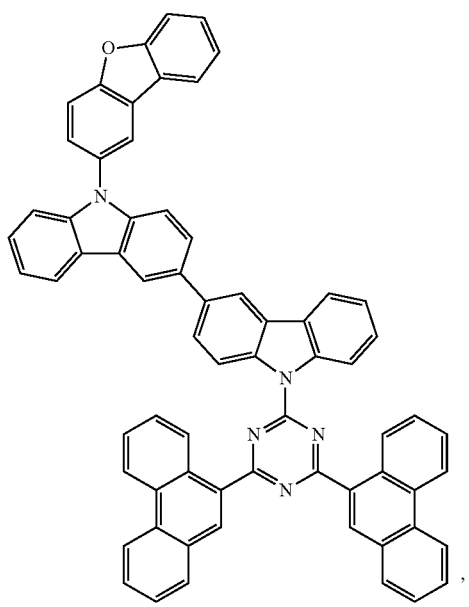

Compound 82
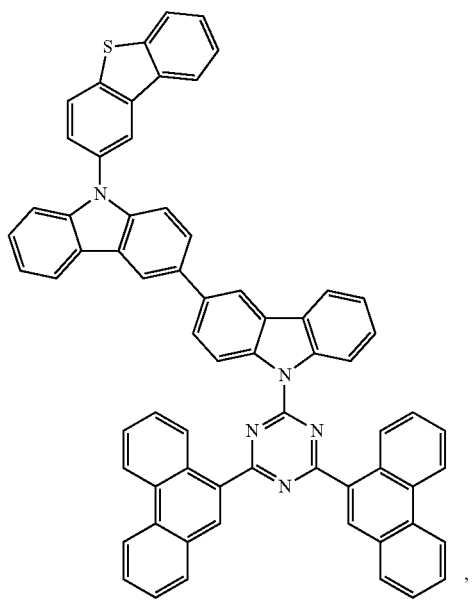
Compound 83
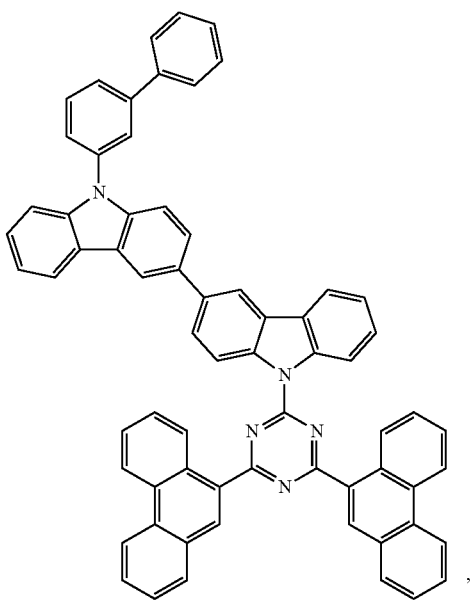
Compound 84
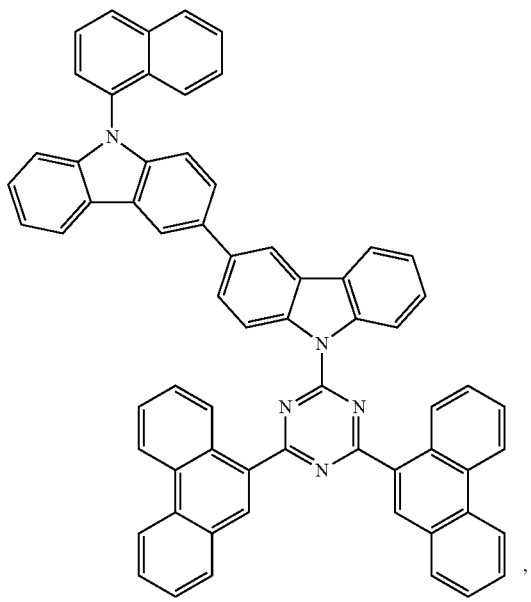
Compound 85
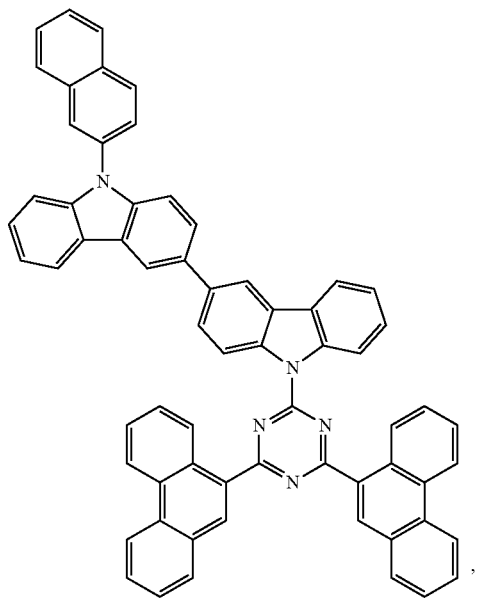

Compound 86
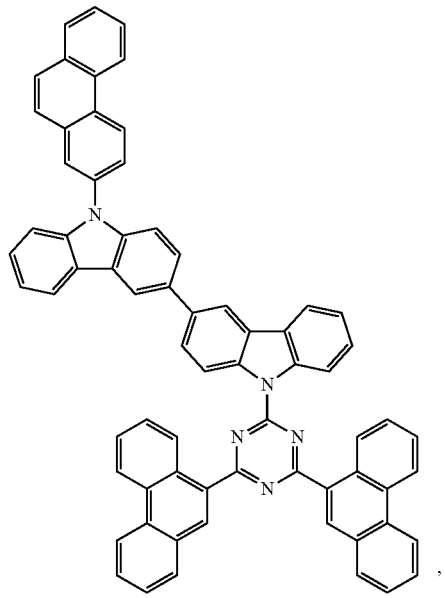
Compound 87
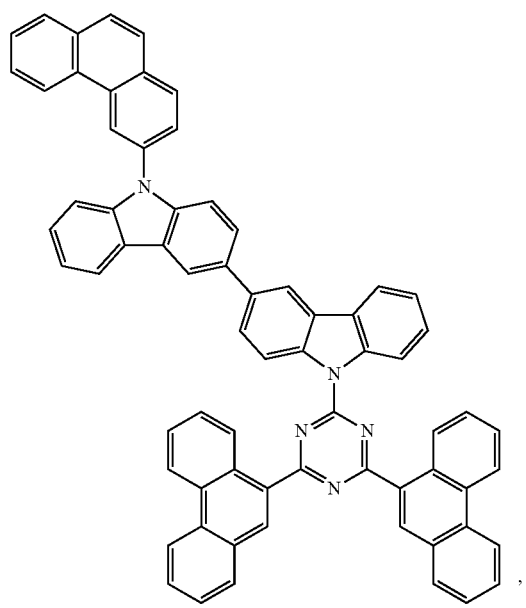
Compound 88
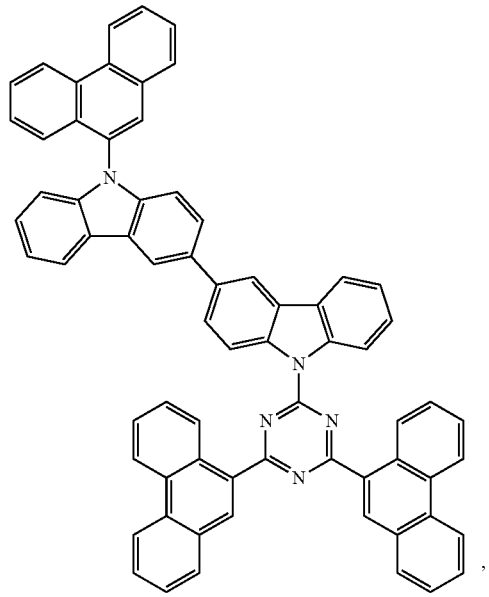
Compound 89
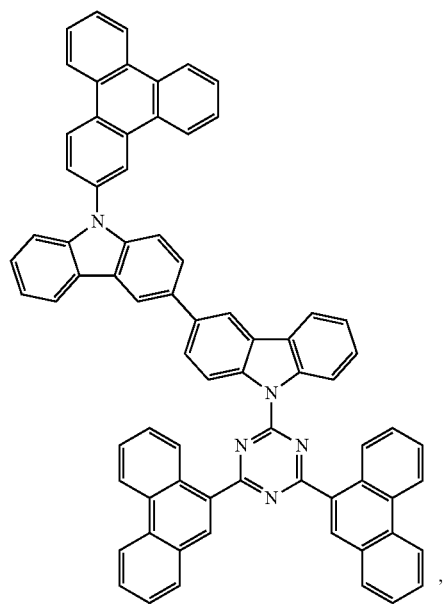

Compound 90
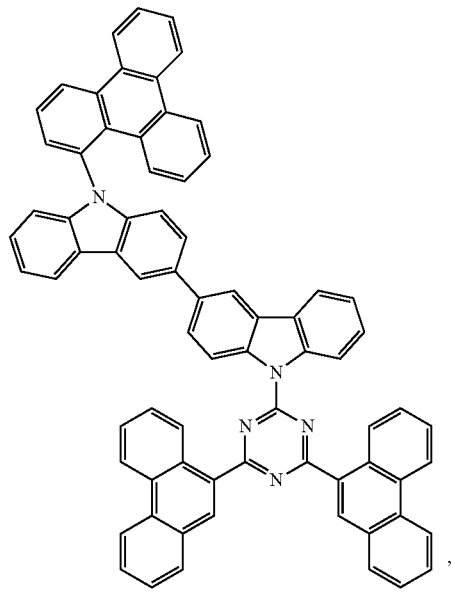
Compound 107
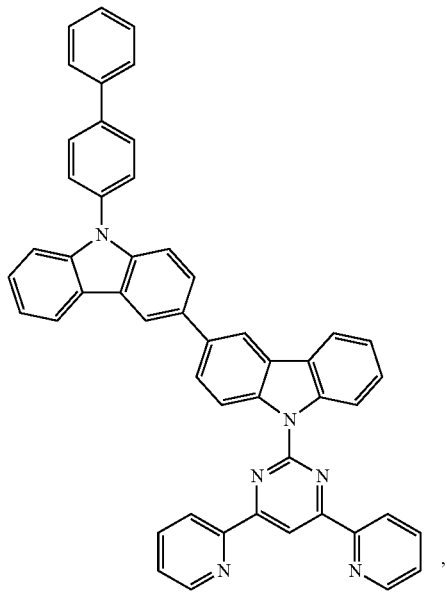
Compound 106
Compound 108
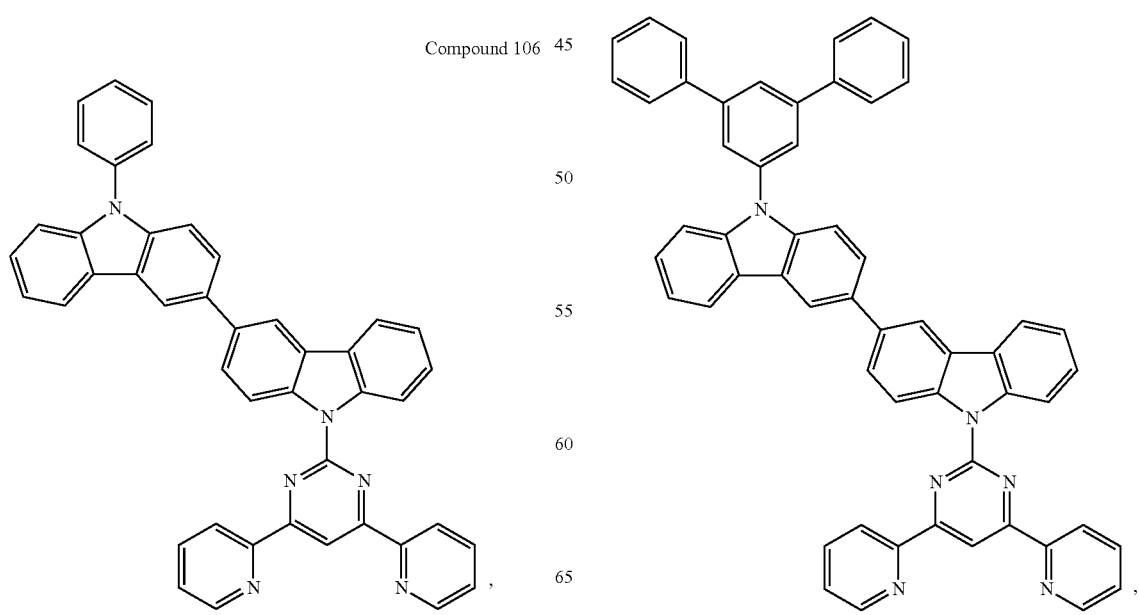

Compound 109
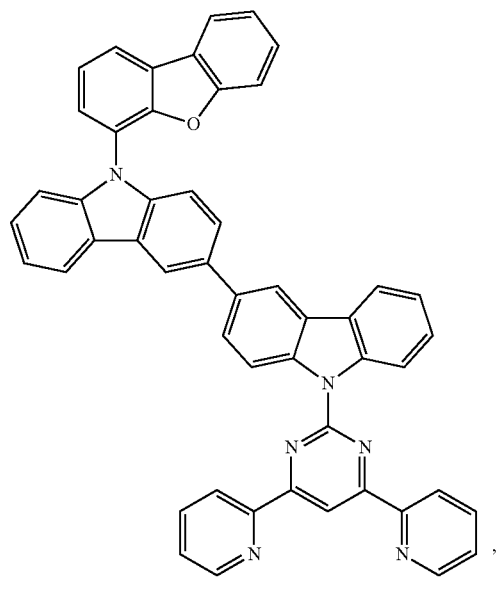
Compound 110
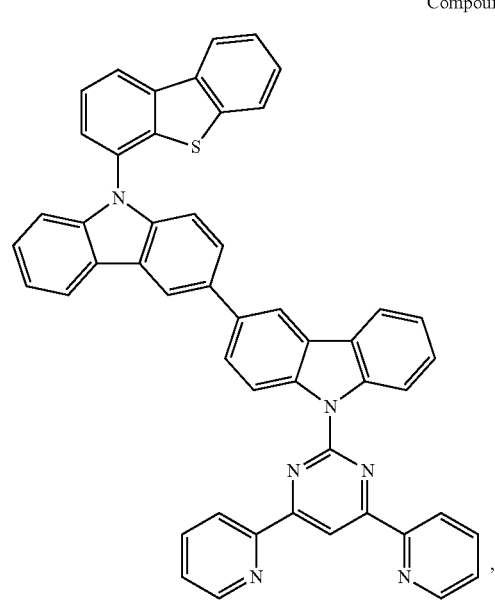
Compound 111
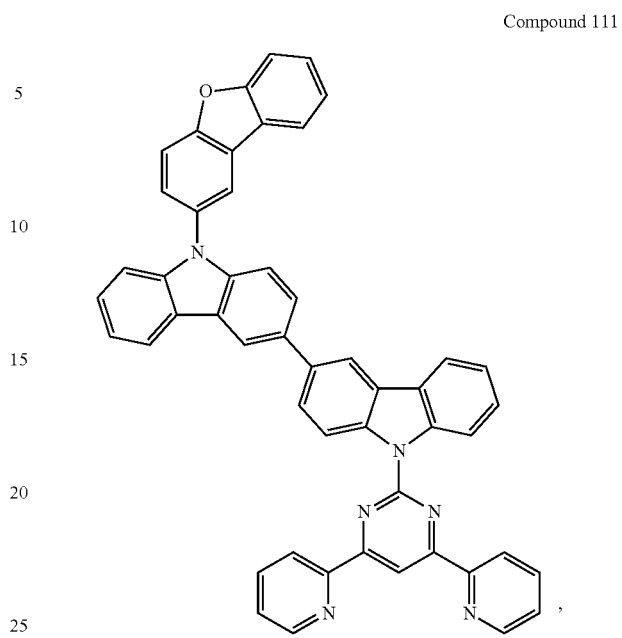
Compound 112
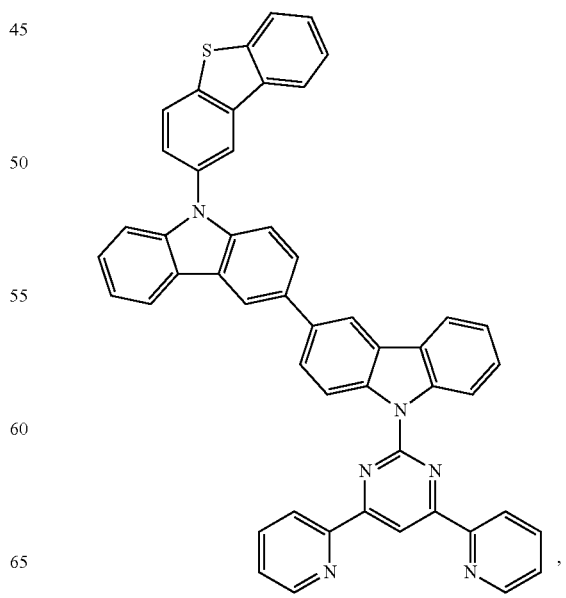

Compound 113
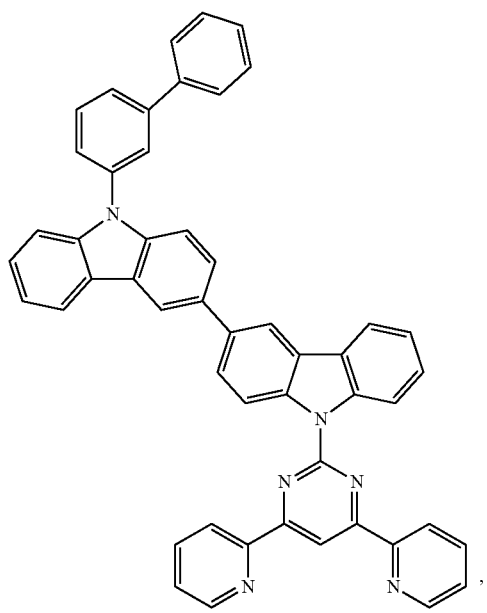
Compound 114
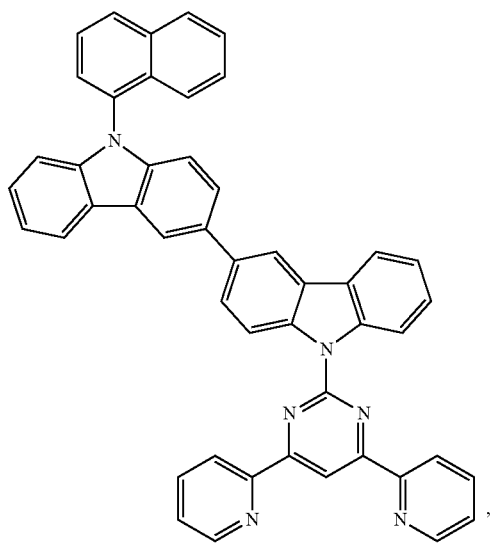
Compound 115
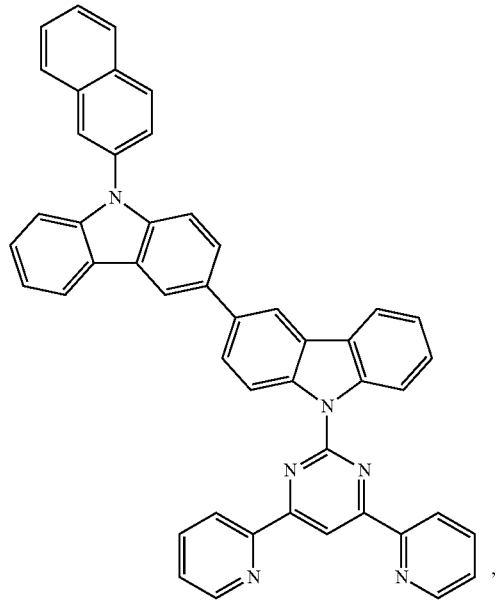
Compound 116
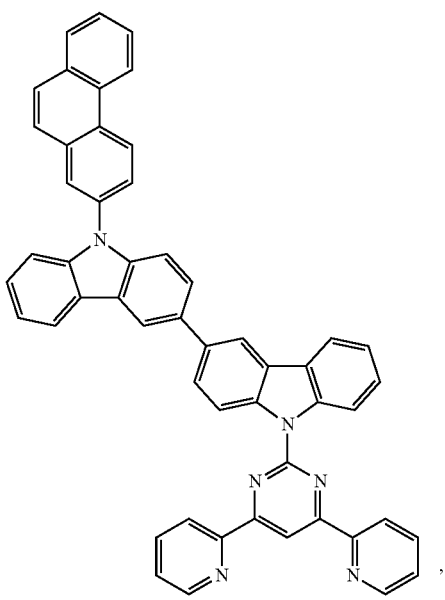

Compound 117
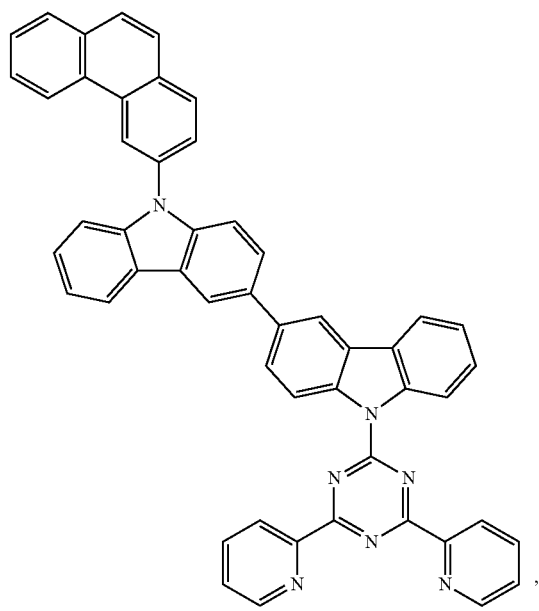
Compound 118
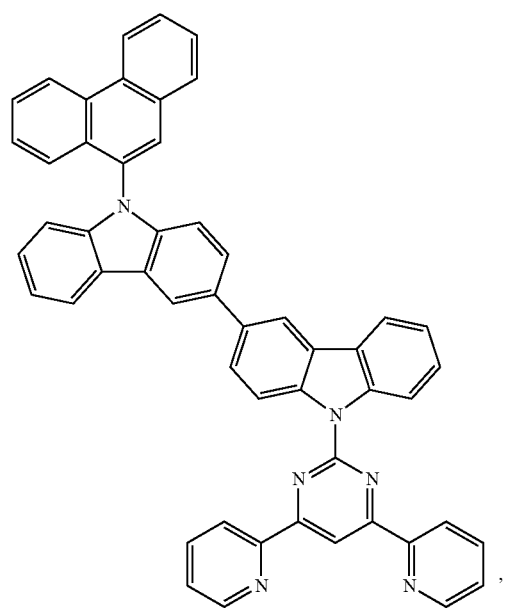
Compound 119
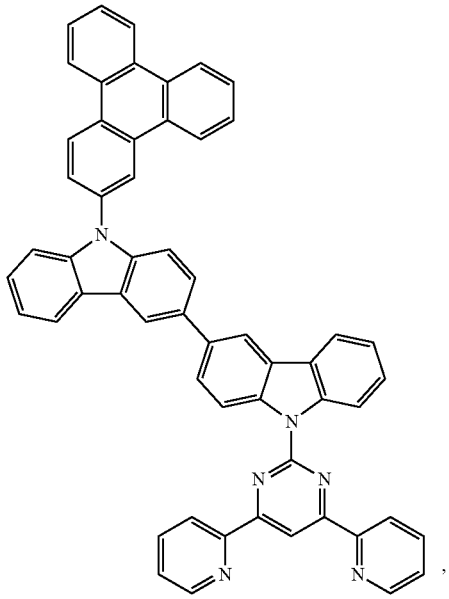
Compound 120
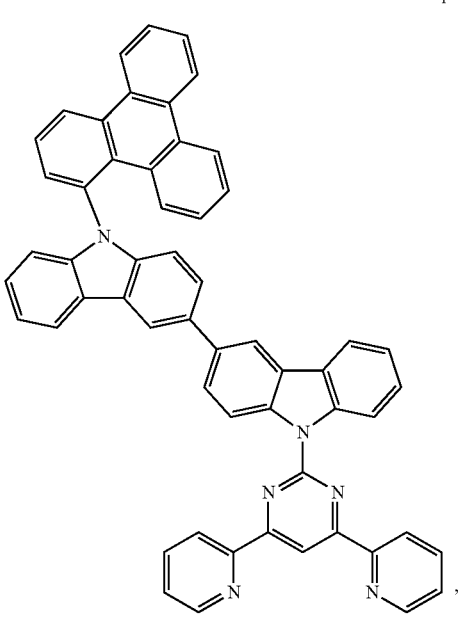

-continued
Compound 121
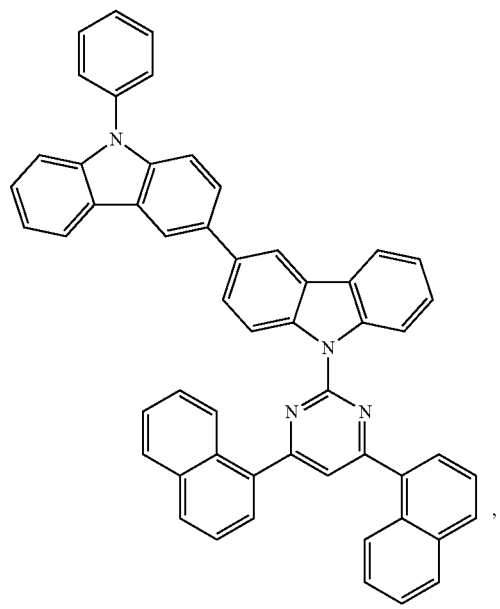
Compound 122
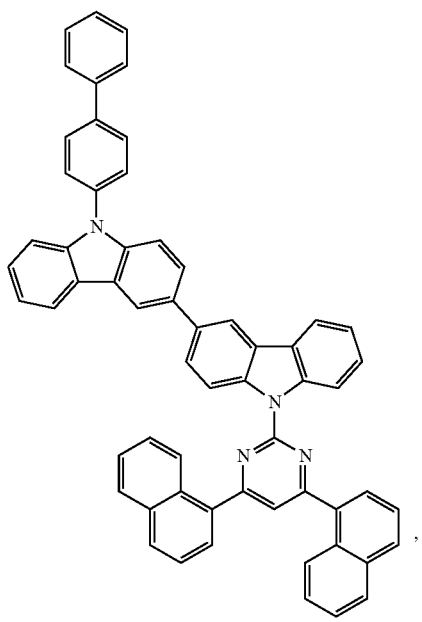
Compound 123
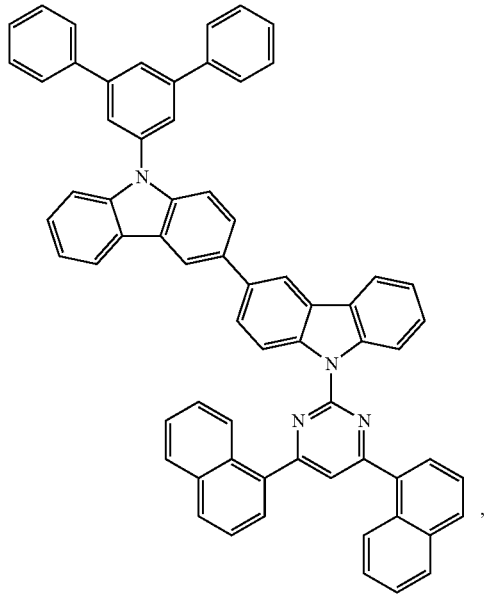
Compound 124
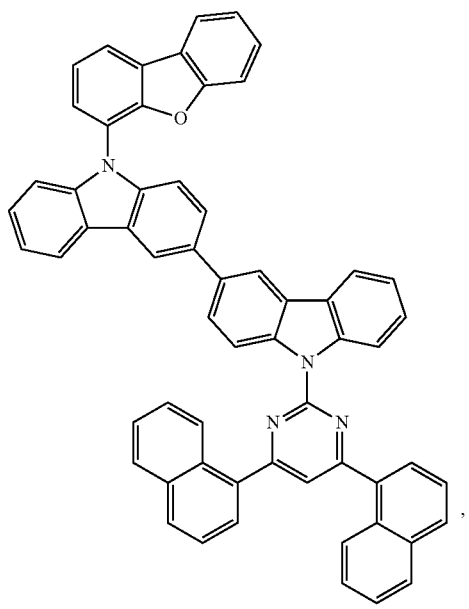

Compound 125
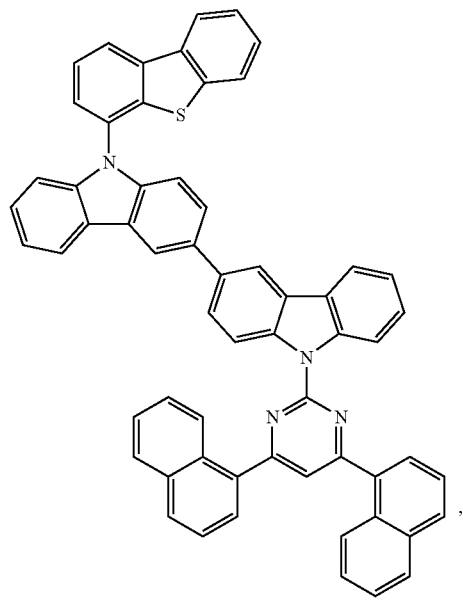
Compound 127
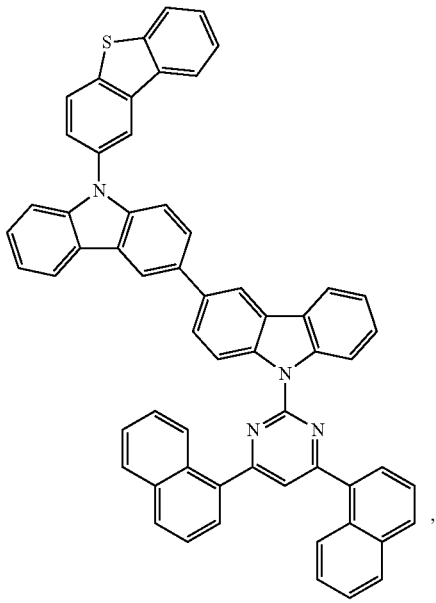
Compound 126
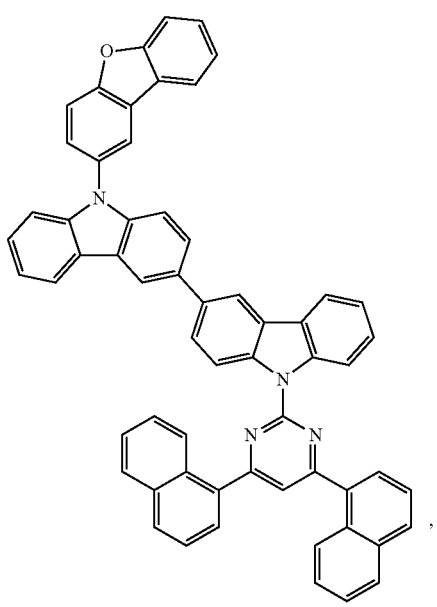
Compound 128
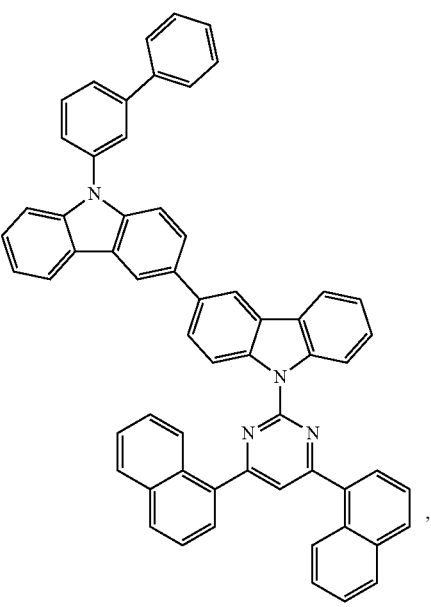

Compound 129
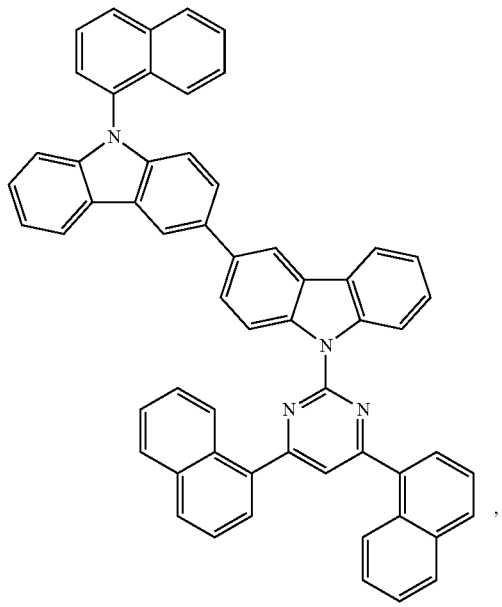
Compound 130
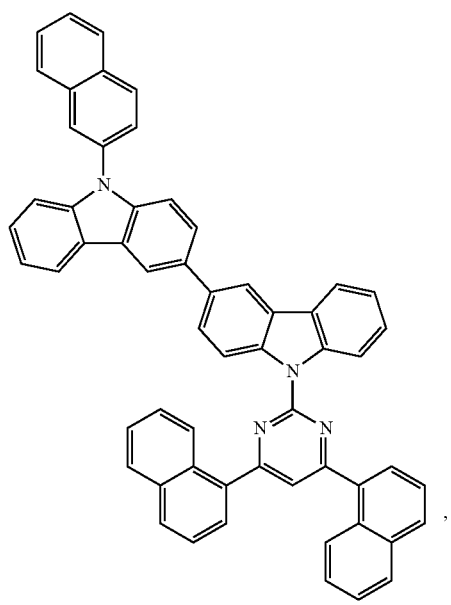
Compound 131
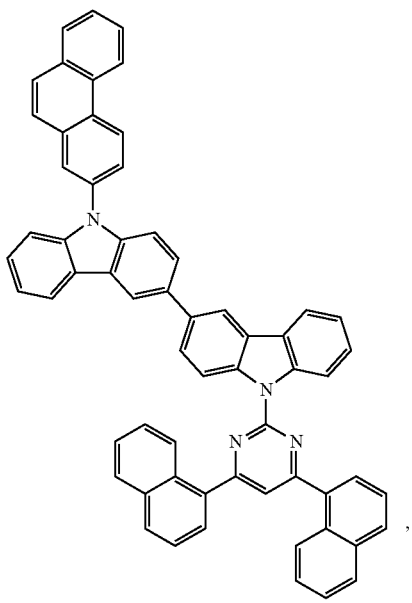
Compound 132
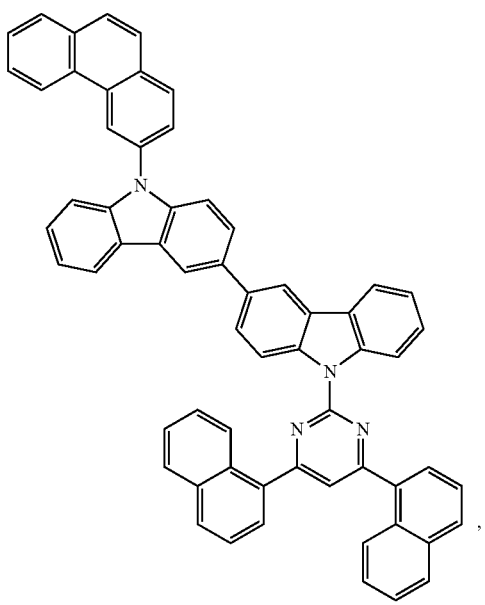

Compound 133
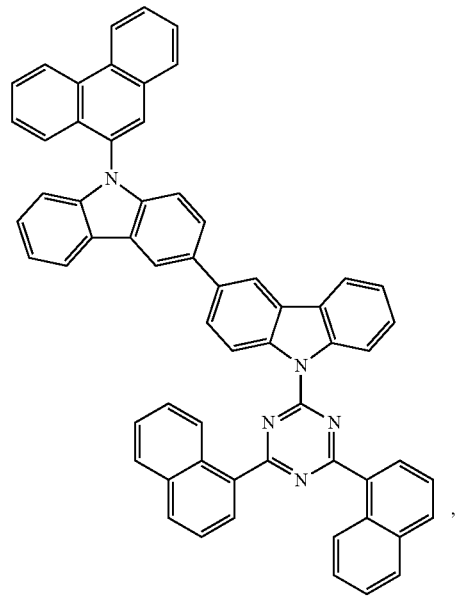
Compound 135
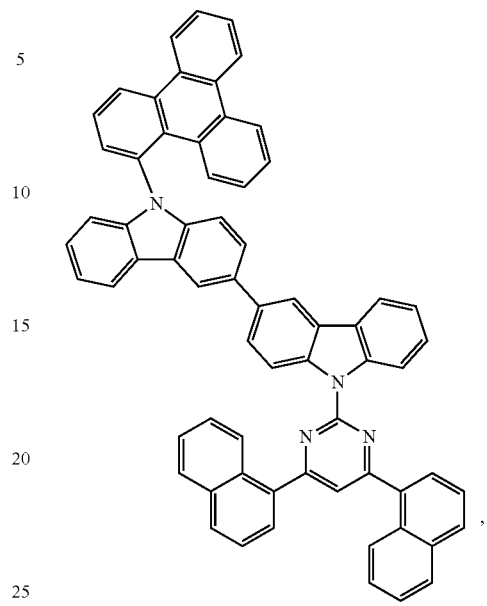
Compound 134
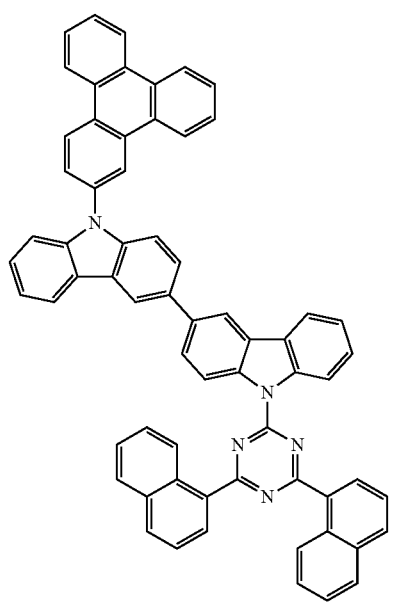
Compound 136
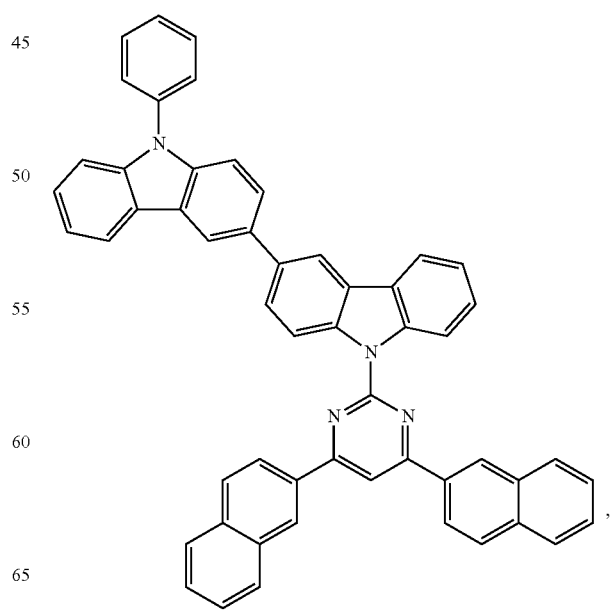

Compound 137
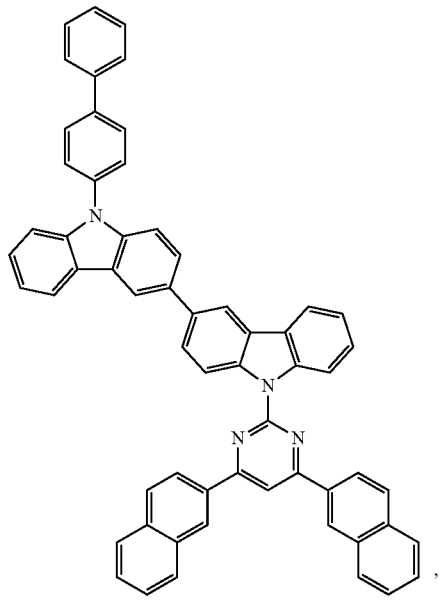
Compound 138
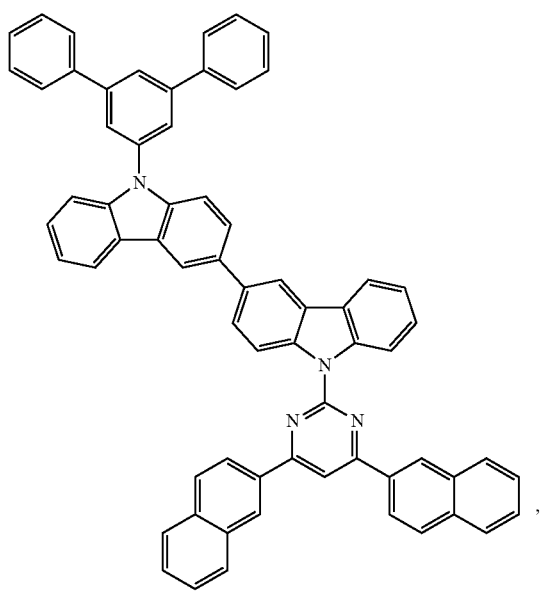
Compound 139
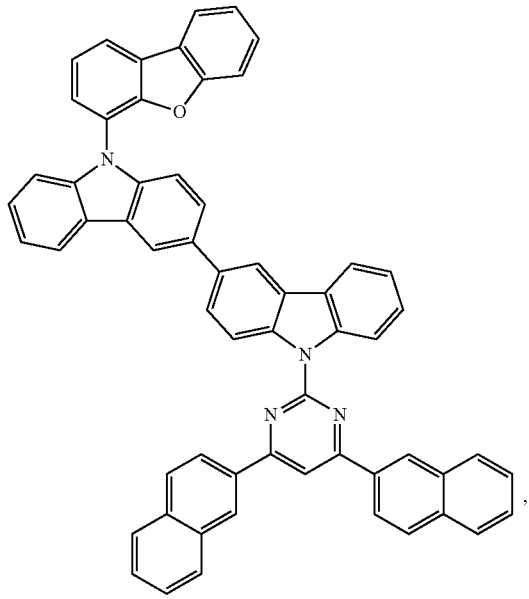
Compound 140
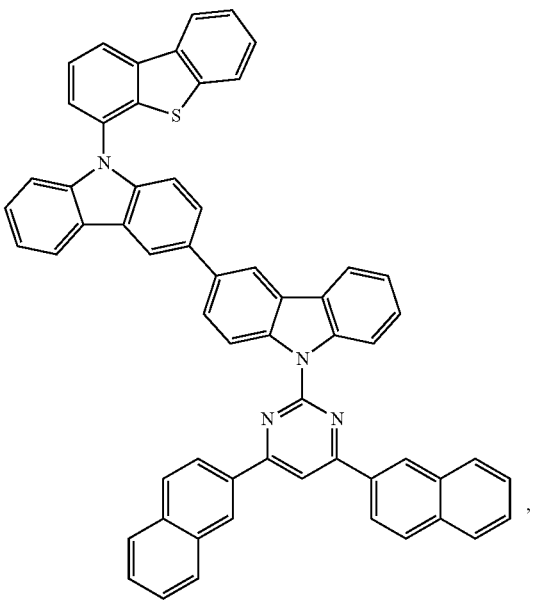

Compound 141
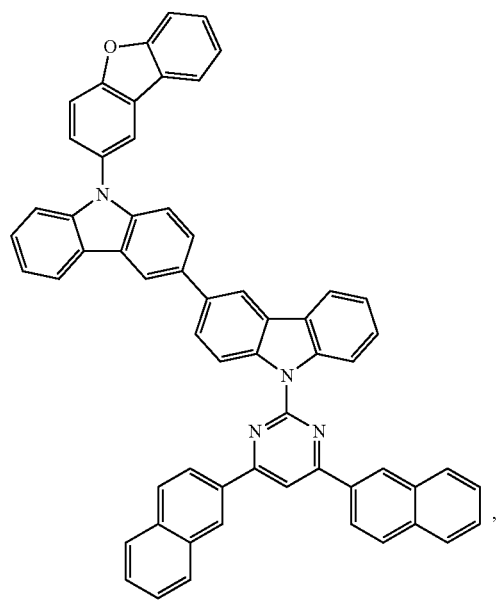
Compound 143
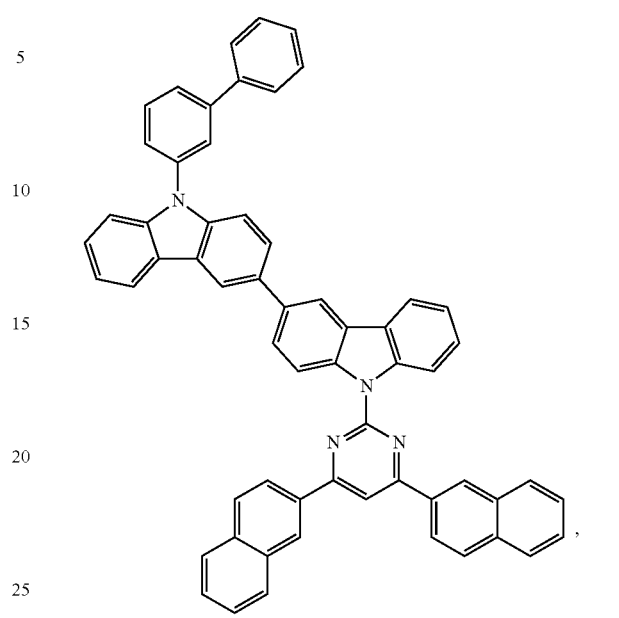
Compound 142
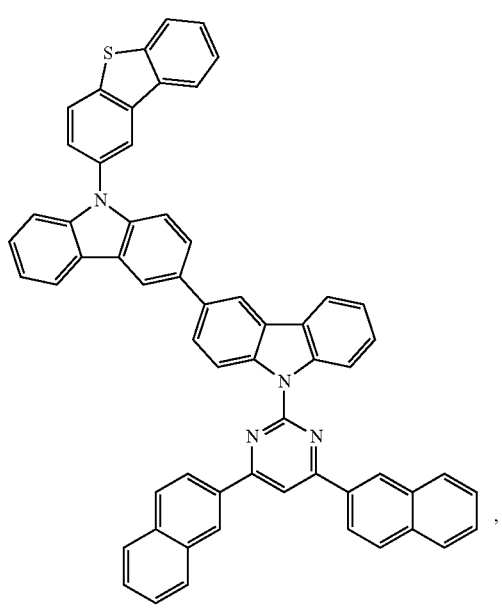
Compound 144
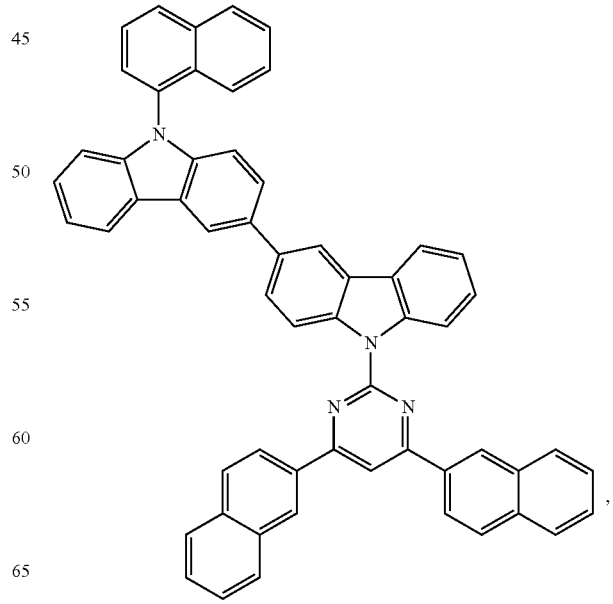

Compound 145
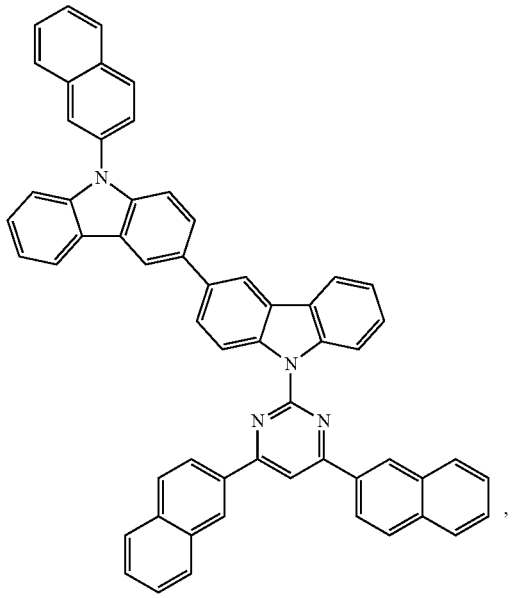
Compound 147
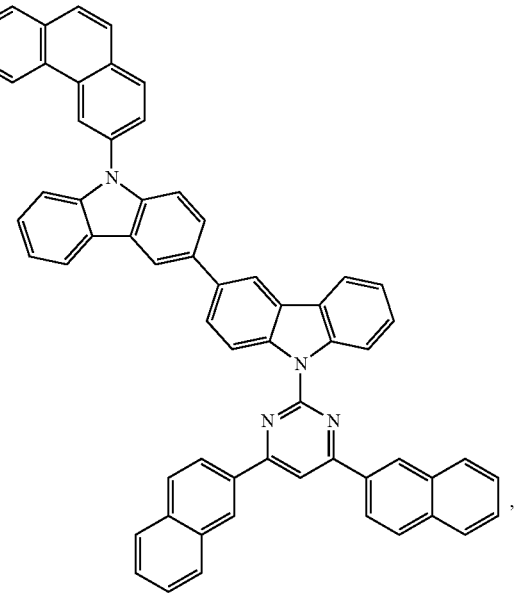
Compound 146
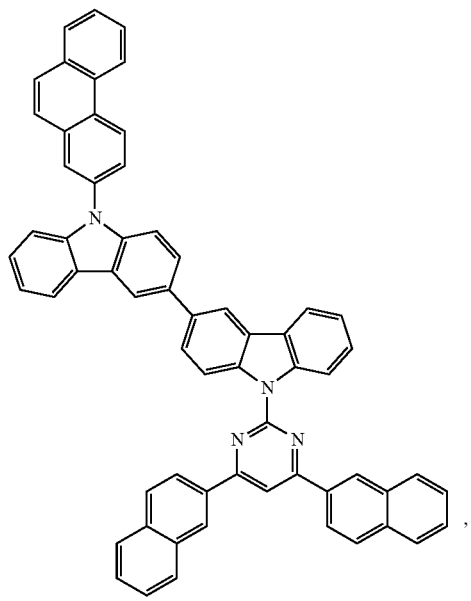
Compound 148

Compound 149
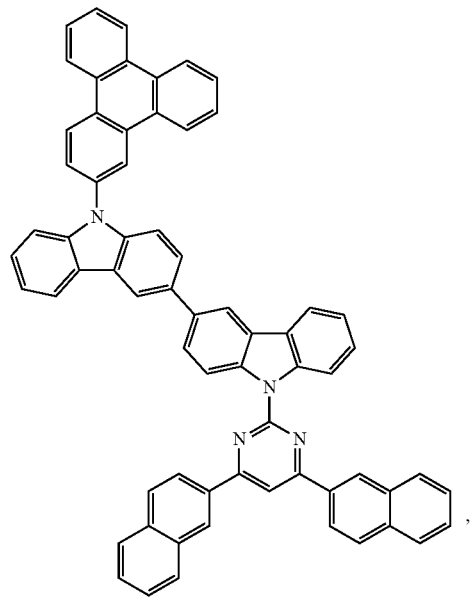
Compound 150
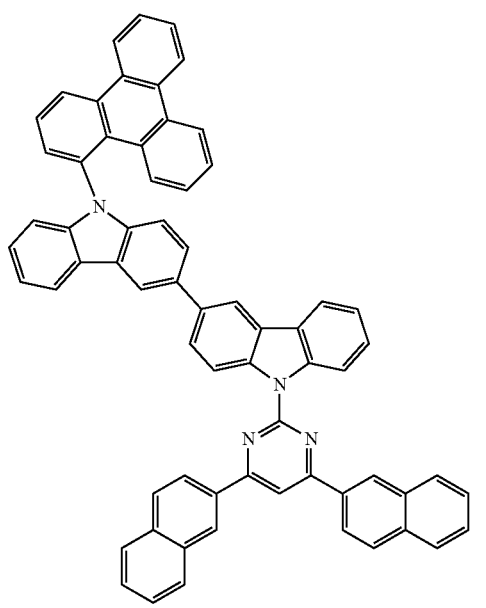
Compound 151
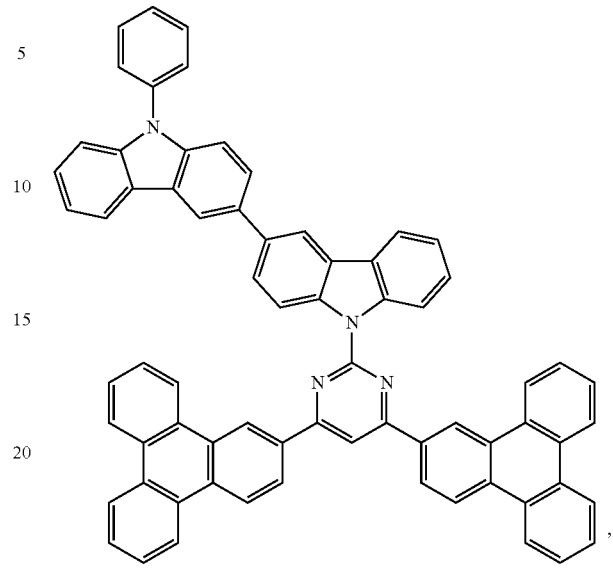
Compound 152
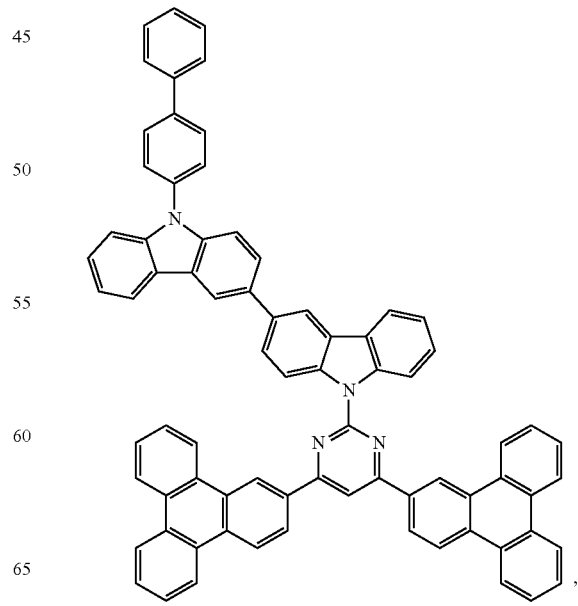

Compound 153
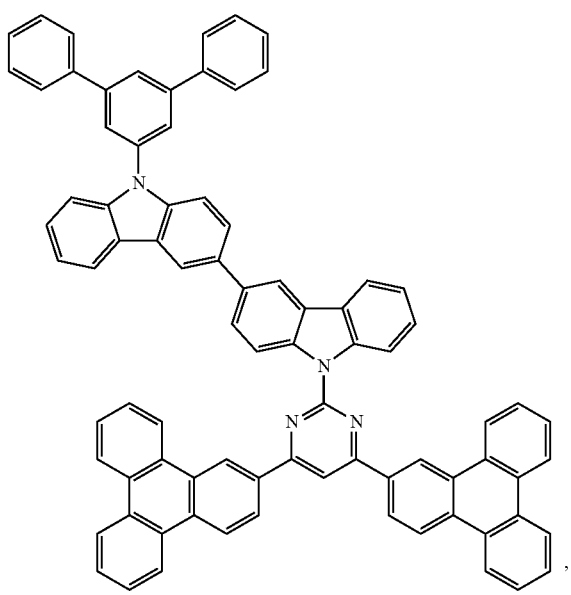
Compound 154
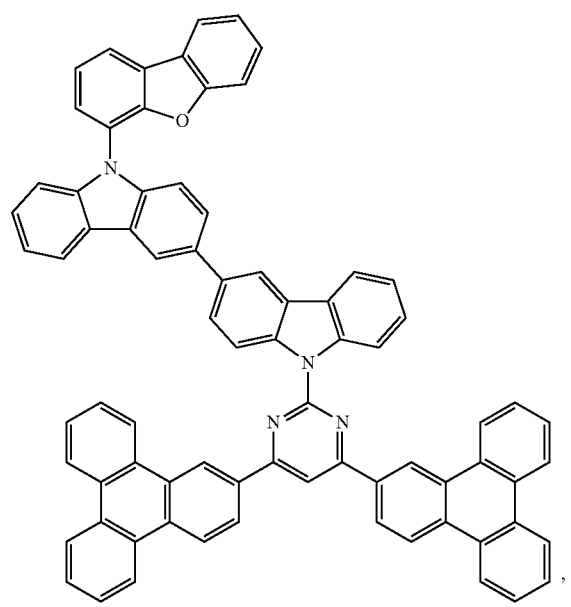
Compound 155
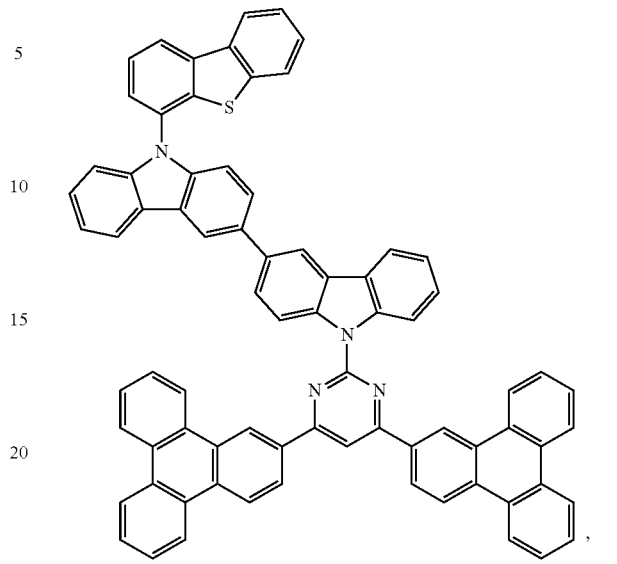
Compound 156
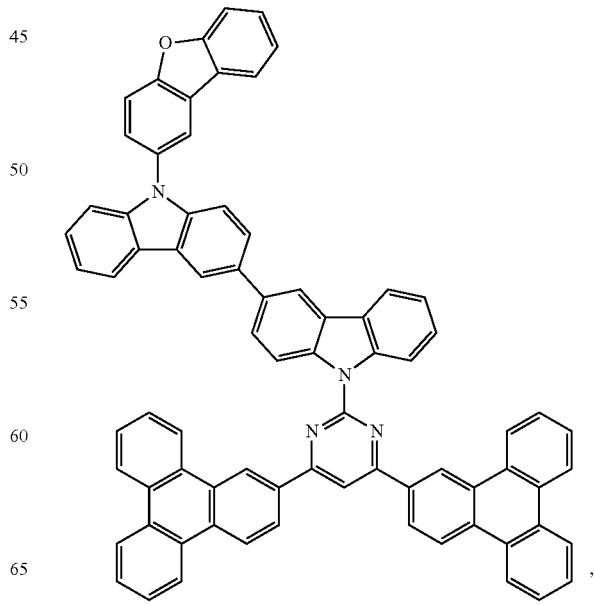

Compound 157
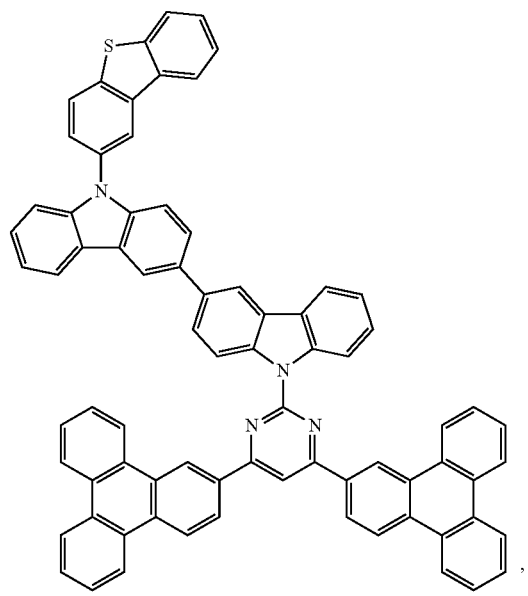
Compound 158
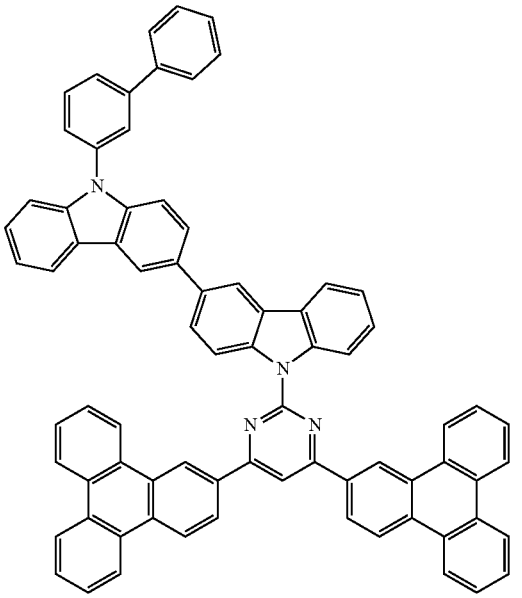
Compound 159
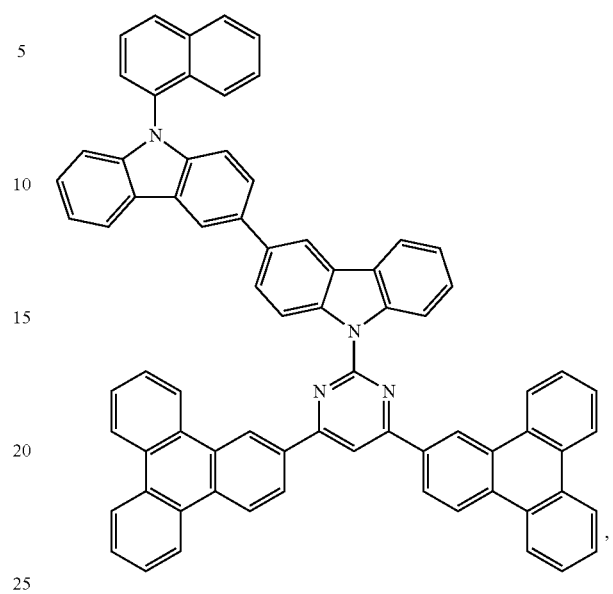
Compound 160
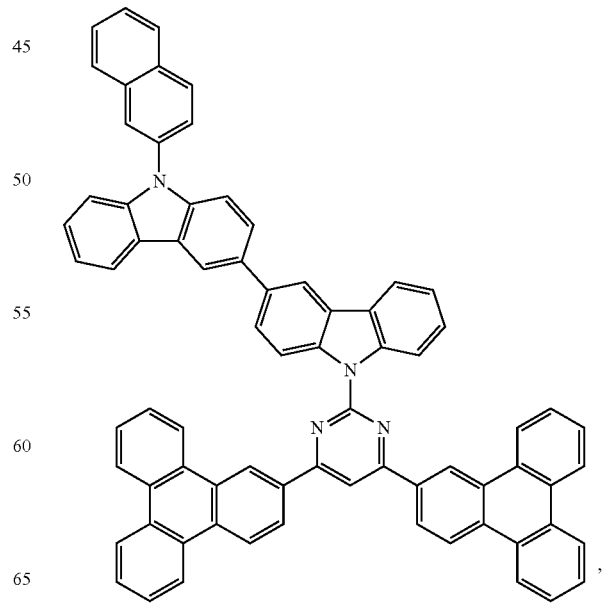

Compound 161
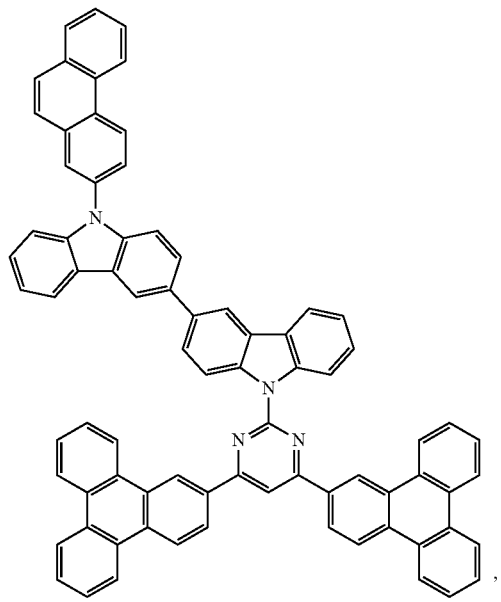
Compound 163
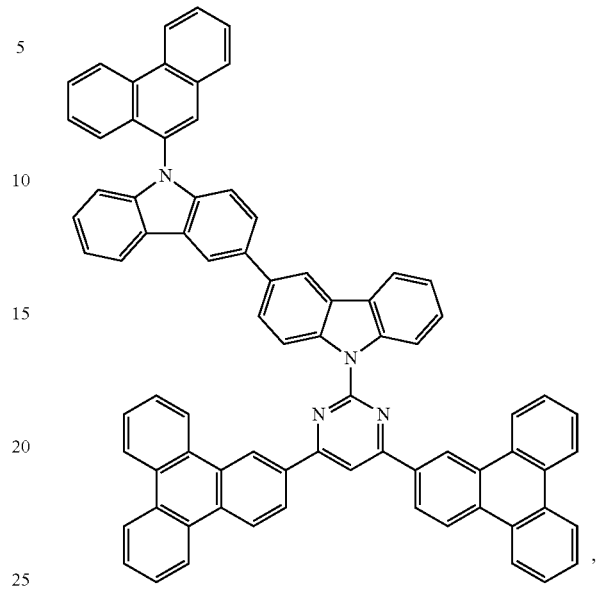
Compound 162
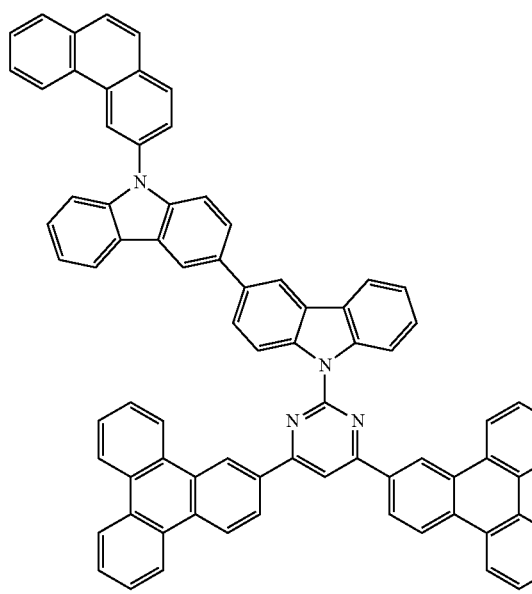
Compound 164
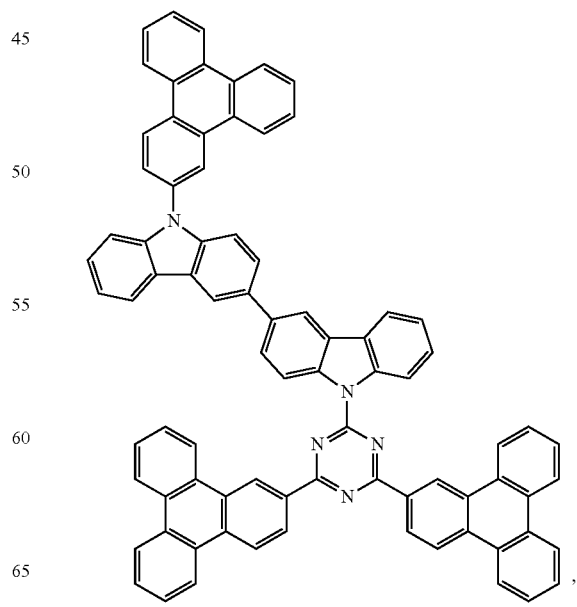

Compound 165
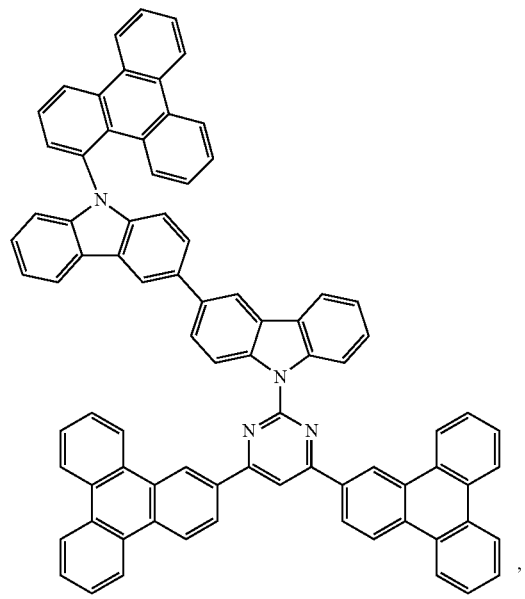
Compound 167
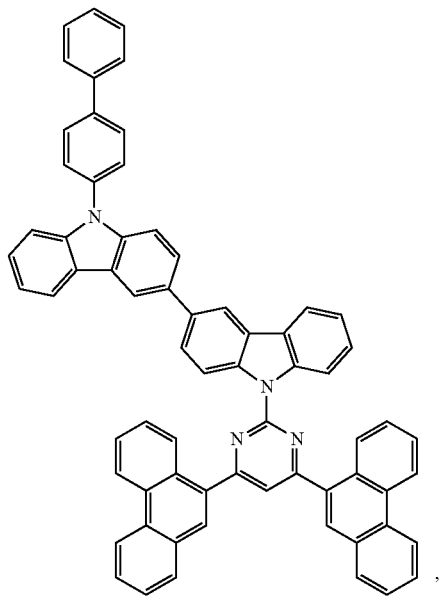
Compound 166
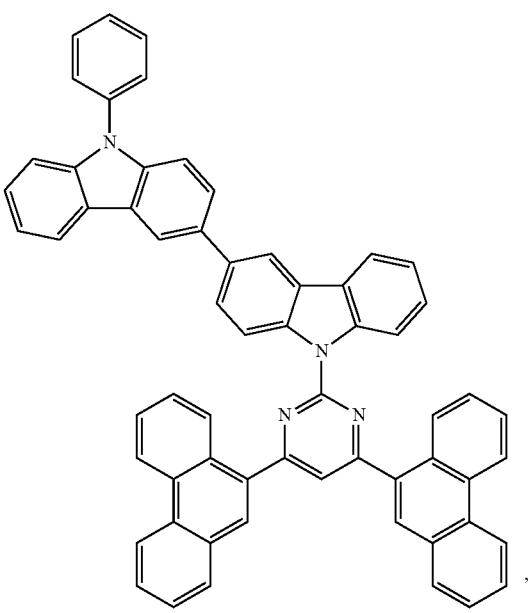
Compound 168
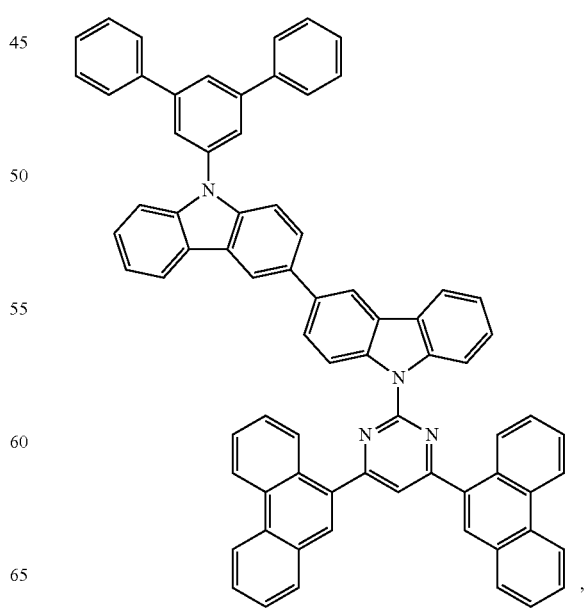

Compound 169
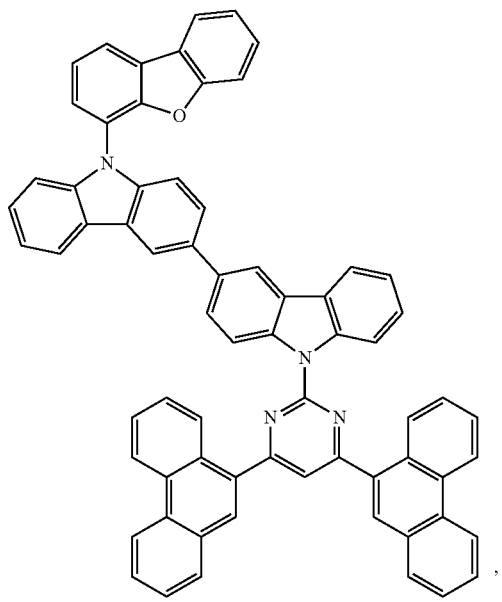
Compound 171
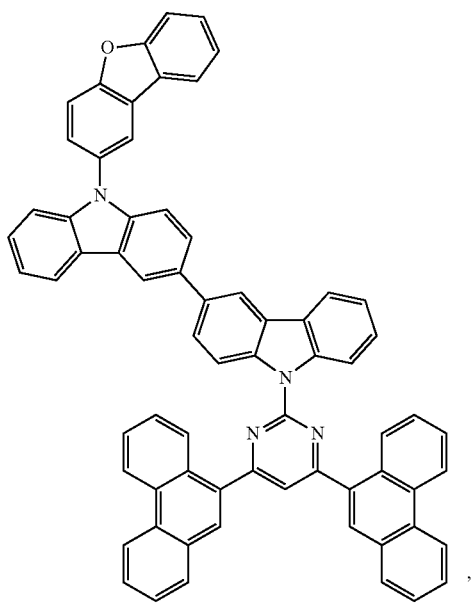
Compound 170
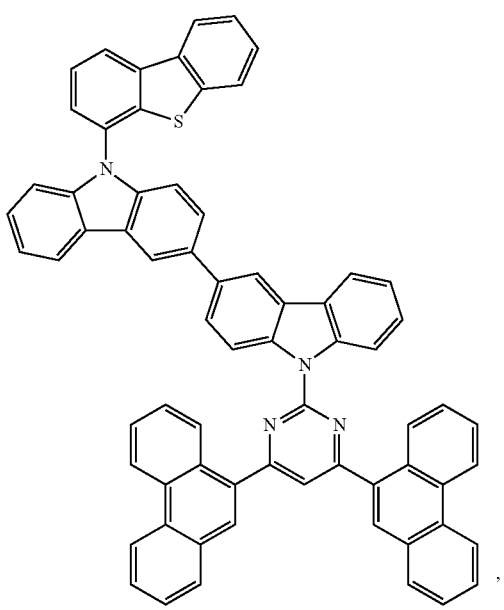
Compound 172
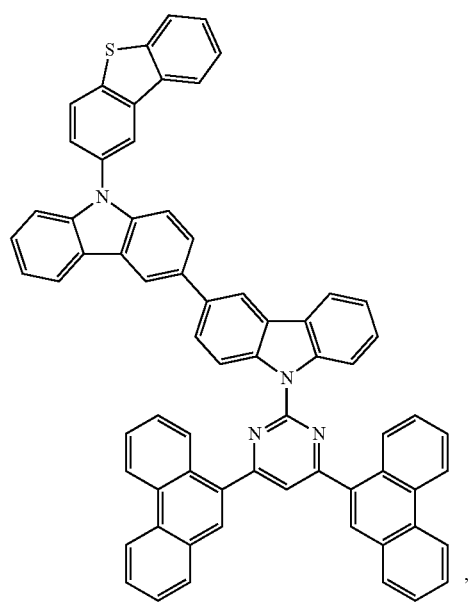

-continued
Compound 173
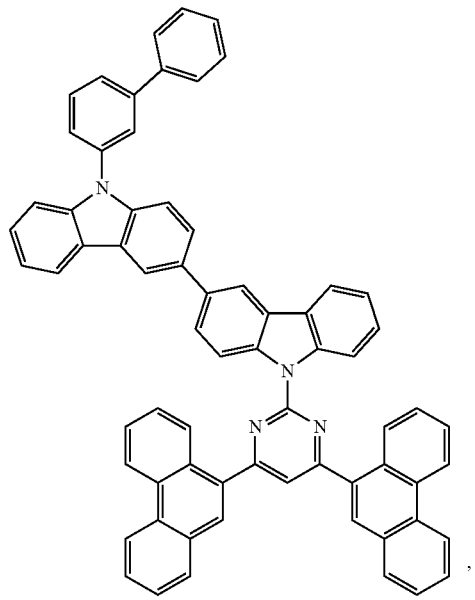
Compound 174
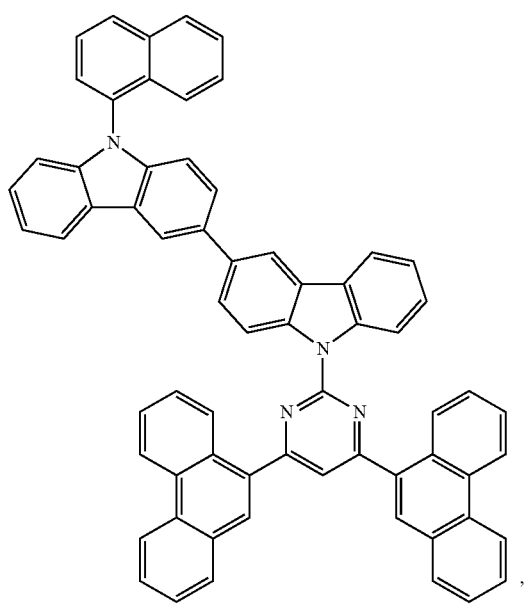
-continued
Compound 175
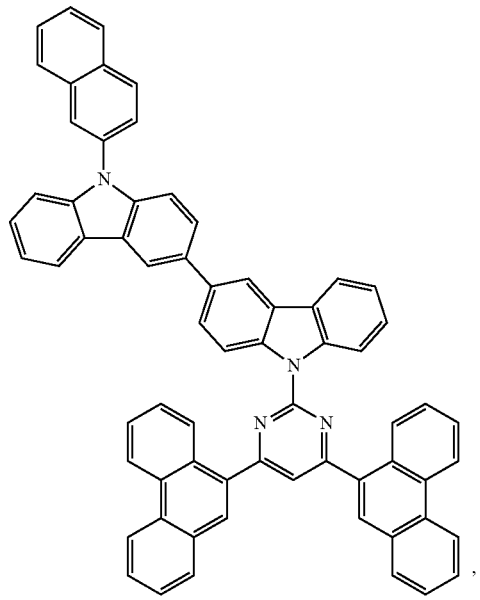
Compound 176
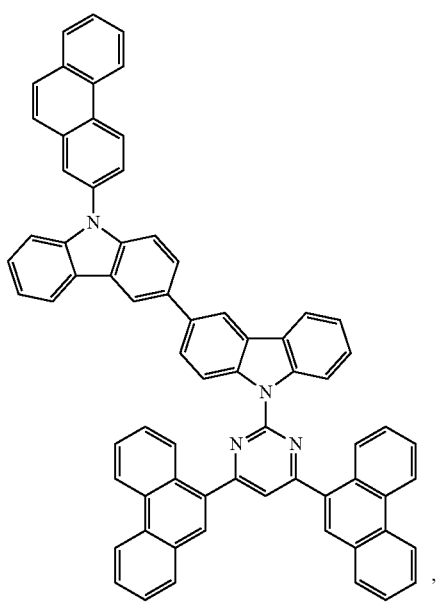

Compound 177
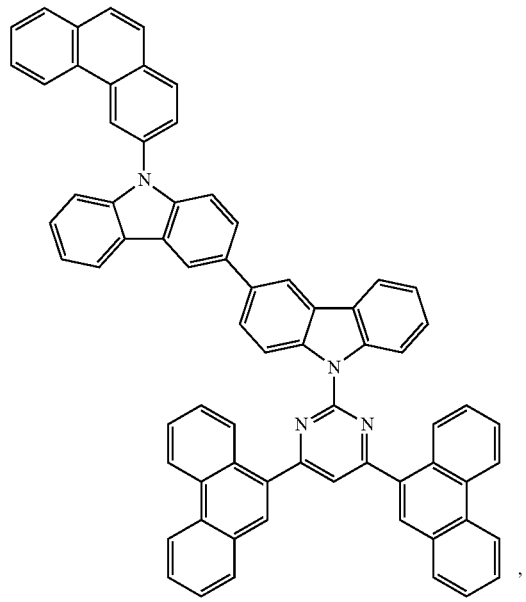
Compound 178
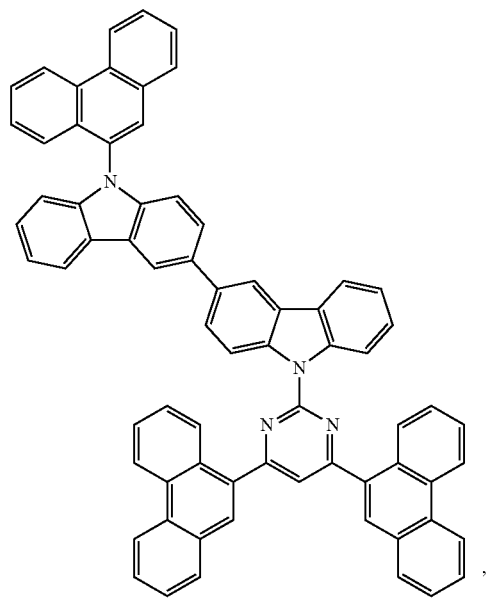
Compound 179
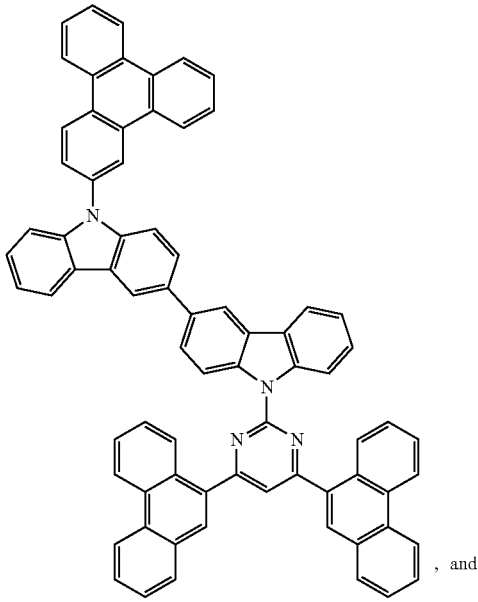
, and
Compound 180
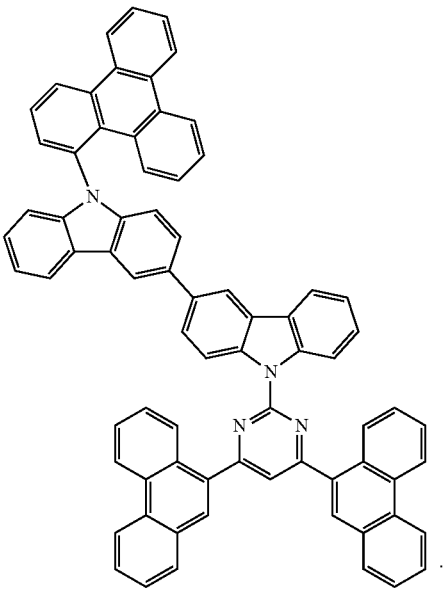
.
8. A first device comprising an organic light emitting device, the organic light emitting device further comprising:
   an anode;
   a cathode; and
   an organic layer, disposed between the anode and the cathode, wherein the organic layer comprises a compound having the formula:

Formula I

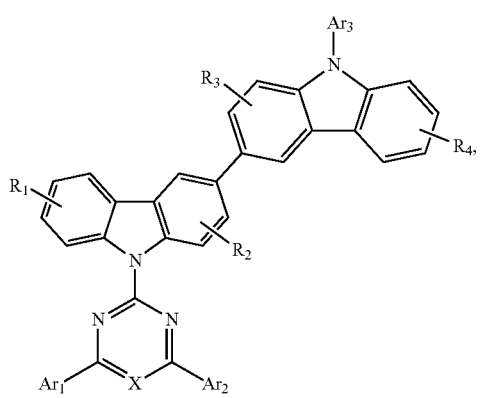

wherein $R_1$, $R_2$, $R_3$, and $R_4$ may represent mono up to the maximum available substitutions, or no substitutions;
wherein $R_1$, $R_2$, $R_3$, and $R_4$ are independently selected from the group consisting of hydrogen, alkyl, alkoxy, amino, alkenyl, alkynyl, aryl and heteroaryl;
wherein $Ar_2$ and $Ar_3$ are independently selected from aryl or heteroaryl;
wherein $Ar_1$ is selected from the group consisting of pyridine, naphthalene, fluorene, phenanthrene, and triphenylene;
wherein $Ar_2$ and $Ar_3$ are independently optionally substituted; and
wherein X is C or N.

9. The device of claim 8, wherein at least one of $Ar_1$, $Ar_2$, and $Ar_3$ is further substituted.

10. The device of claim 8, wherein $Ar_2$, and $Ar_3$ are independently selected from the group consisting of phenyl, pyridine, naphthalene, biphenyl, terphenyl, fluorene, dibenzofuran, dibenzothiophene, phenanthrene, and triphenylene; and
wherein at least one of $Ar_2$ and $Ar_3$ is further substituted with a substituent selected from the group consisting of hydrogen, alkyl, alkoxy, amino, alkenyl, alkynyl, aryl and heteroaryl, wherein the substituent is not an aryl or heteroaryl fused directly to $Ar_2$ and $Ar_3$.

11. The device of claim 8, wherein $Ar_1$ is pyridine and $Ar_2$ is selected from the group consisting of phenyl, pyridine, and naphthalene.

12. The device of claim 8, wherein $Ar_3$ is selected from the group consisting of phenyl, biphenyl, dibenzofuran, and dibenzothiophene.

13. The device of claim 8, wherein $R_1$, $R_2$, $R_3$, and $R_4$ are hydrogen.

14. The device of claim 8, wherein the organic layer is an emissive layer and the compound having Formula I is a host.

15. The device of claim 14, wherein the organic layer further comprises an emissive dopant having the structure:

D1
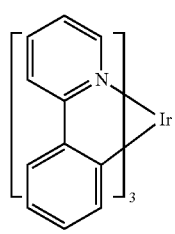

D2
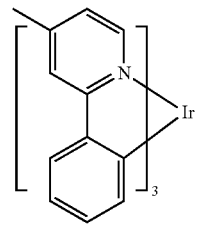

D3
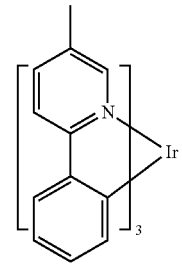

D4
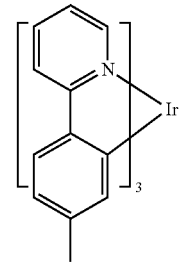

D5
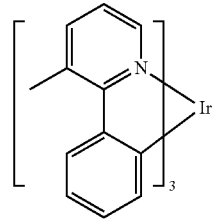

D6
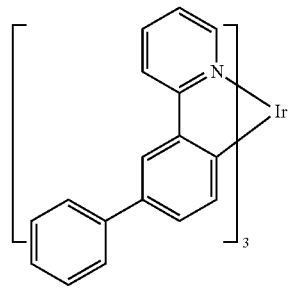

D7
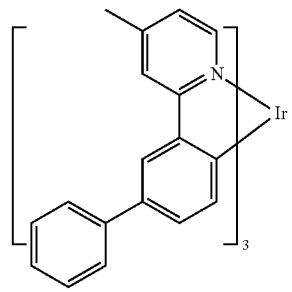

-continued
D8
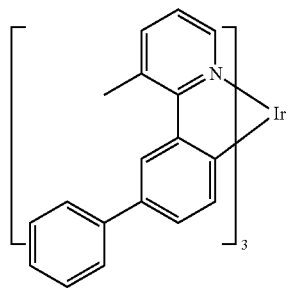
D9
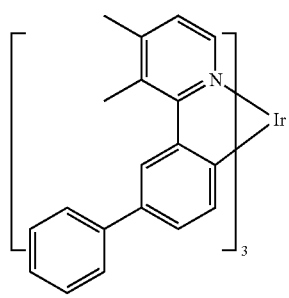
D10
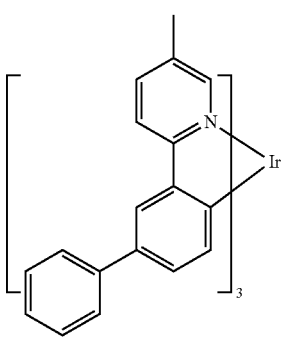
D11
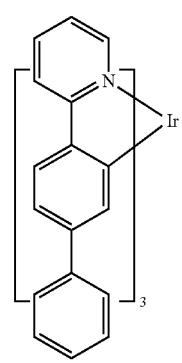
D12
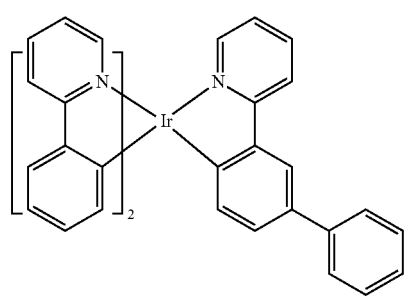
-continued
D13
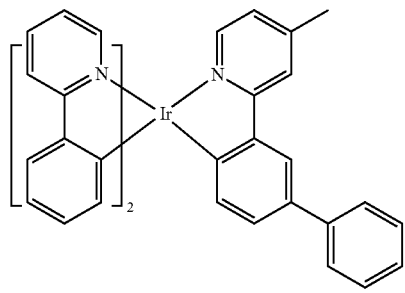
D14
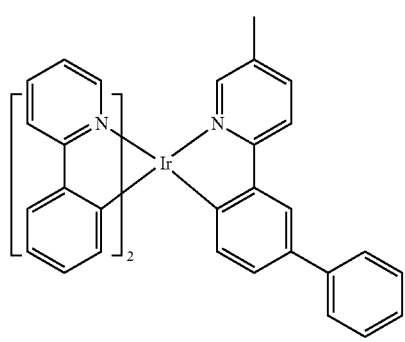
D15
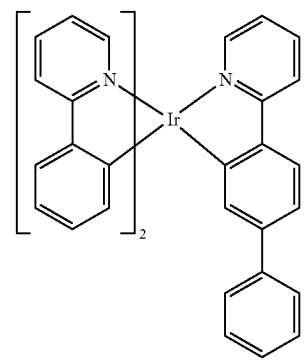
D16
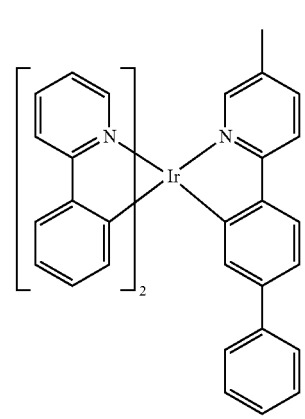

D17
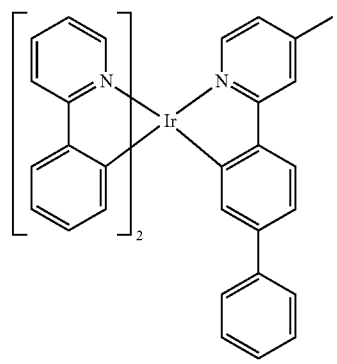
D18
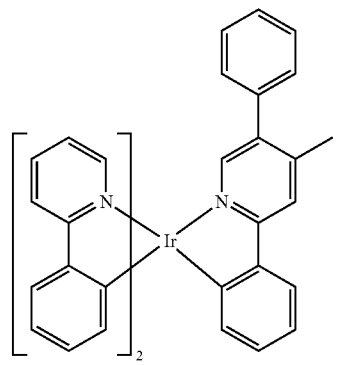
D19
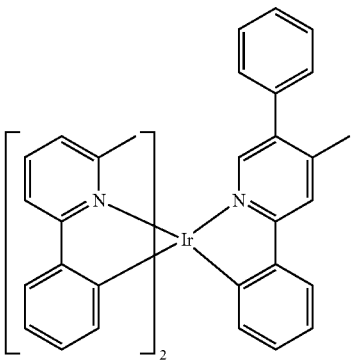
D20
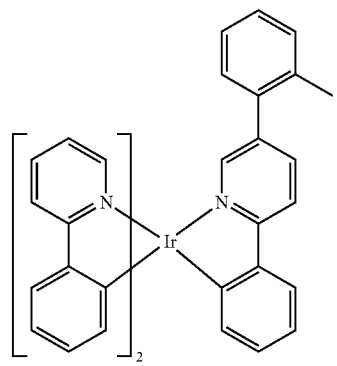
D21
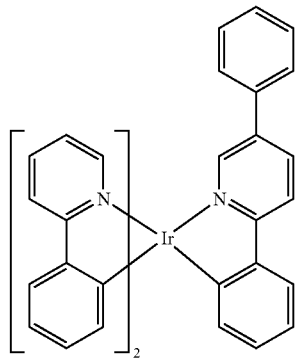
D22
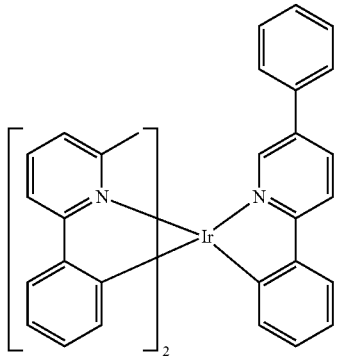
D23
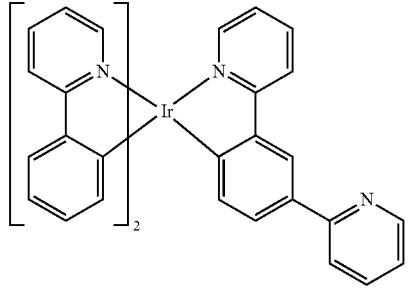
D24
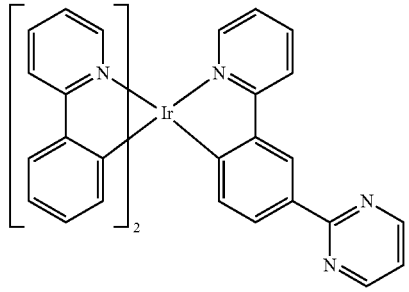
D25
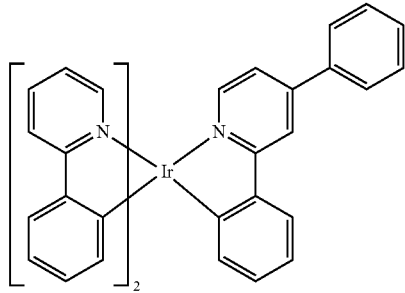

D26 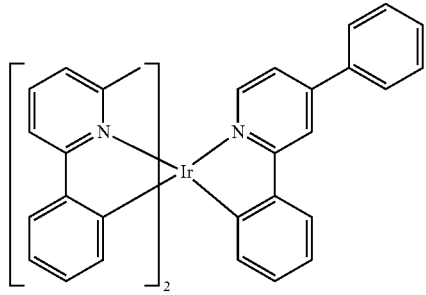
D27 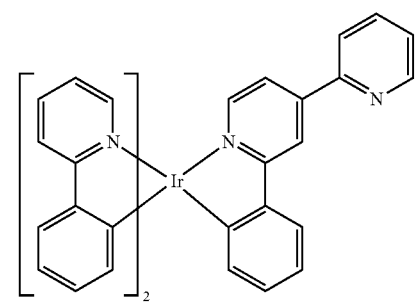
D28 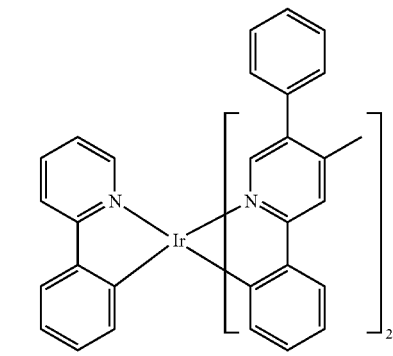
D29 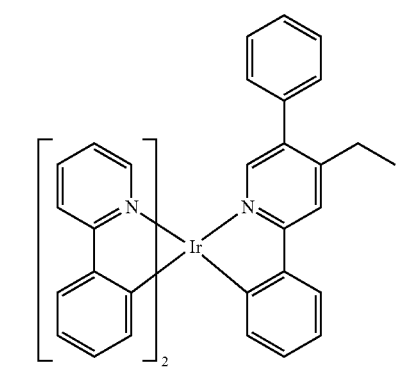
D30 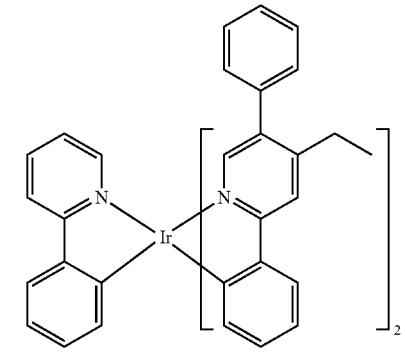
D31 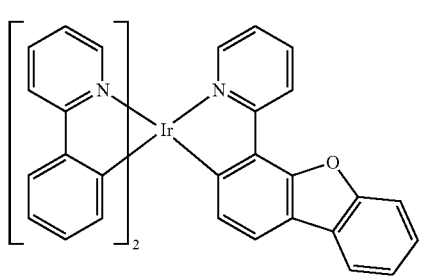
D32 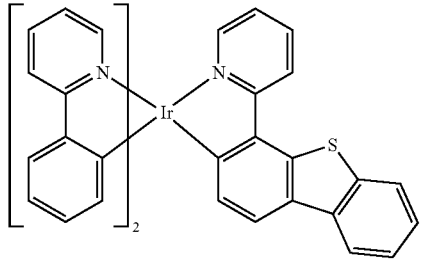
D33 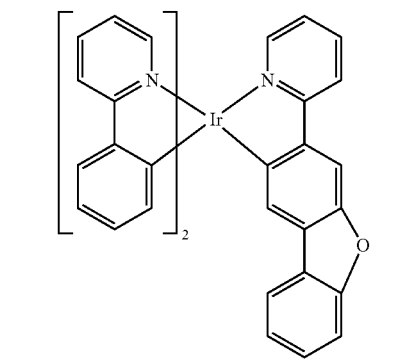
D34 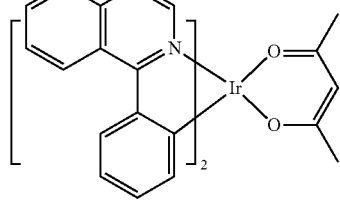

D35 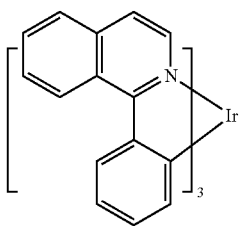
D36 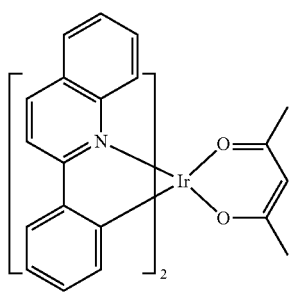
D37 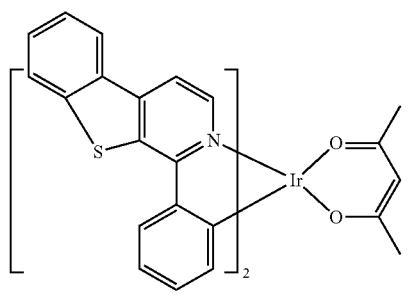
D38 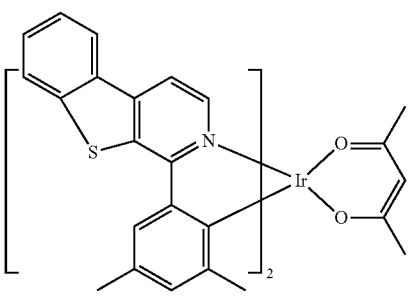
D39 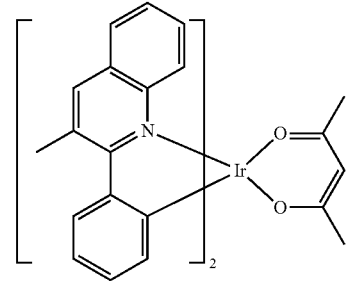
D40 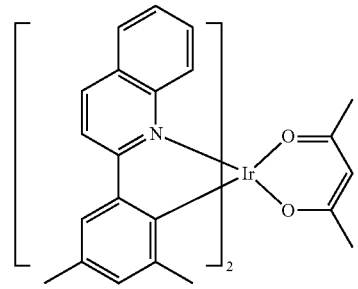
D41 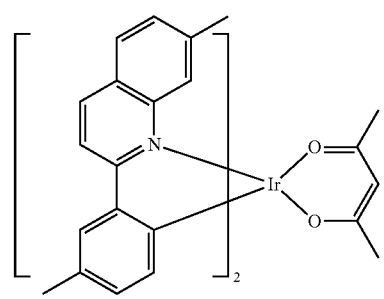
D42 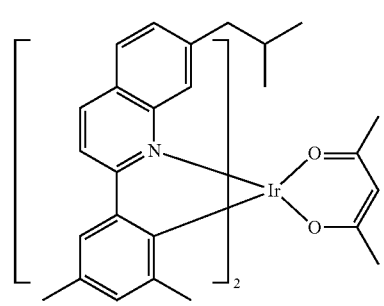
D43 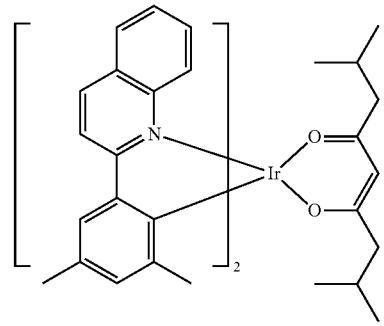
D44 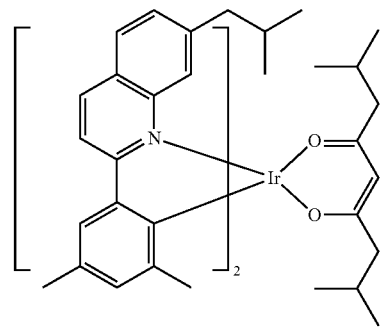

-continued
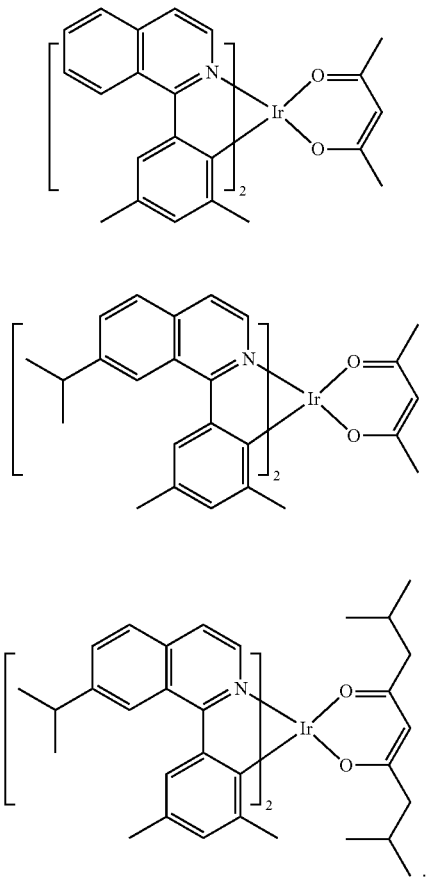
D45
D46
D47
16. The device of claim 8, wherein the first device is an organic light emitting device.
17. The device of claim 8, wherein the compound is selected from the group consisting of:
-continued
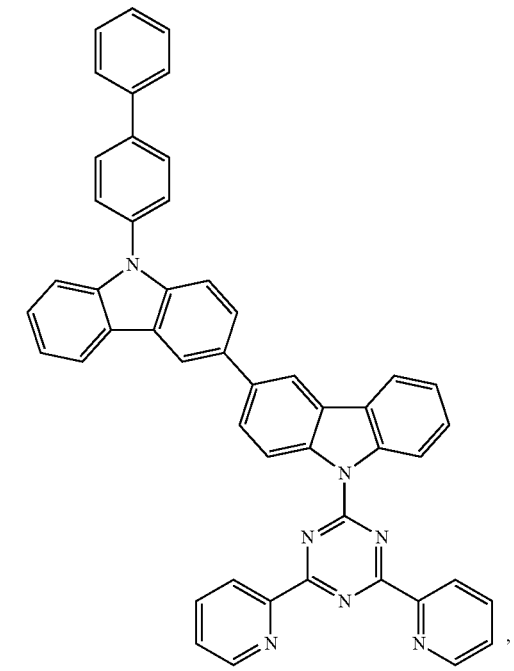
Compound 17
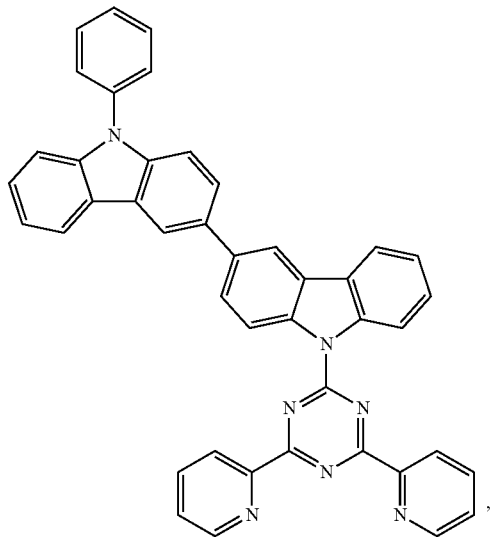
Compound 16
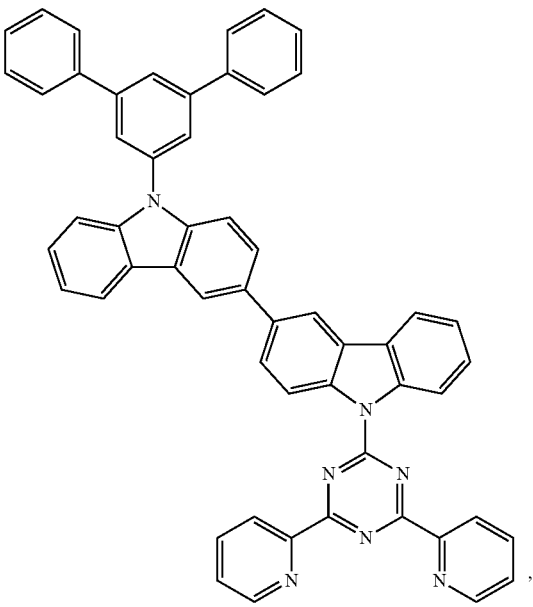
Compound 18

Compound 19
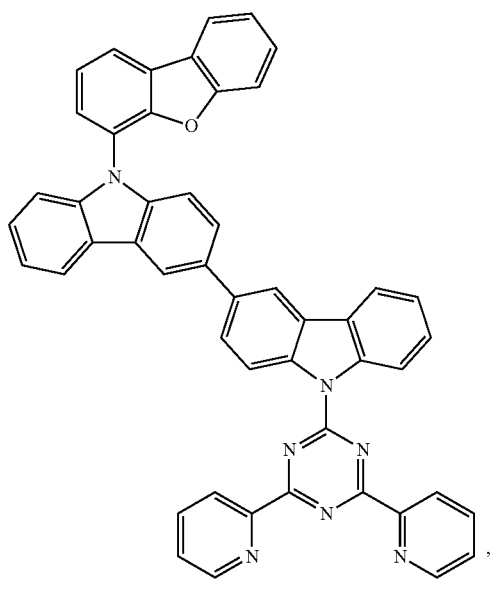
Compound 20
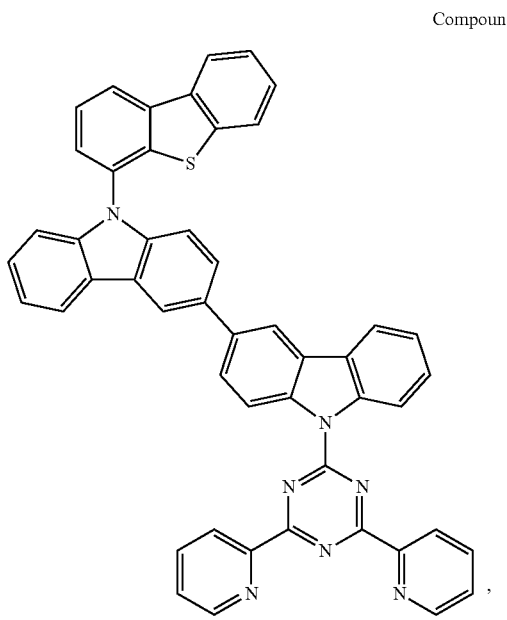
Compound 21
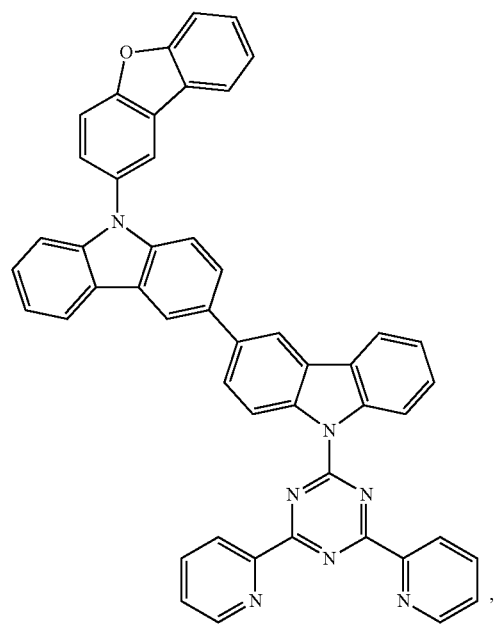
Compound 22
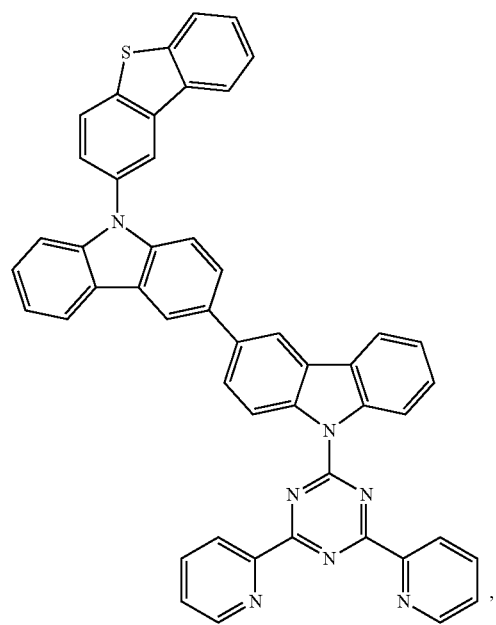

Compound 23
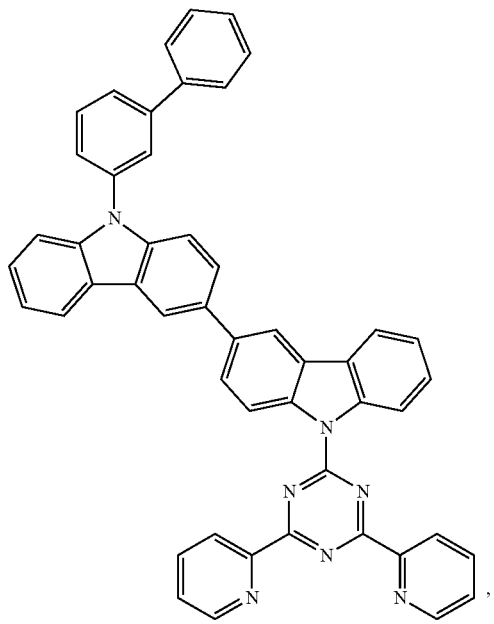
Compound 24
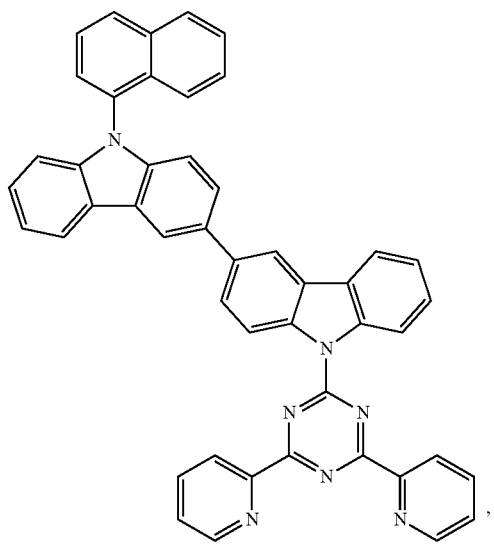
Compound 25
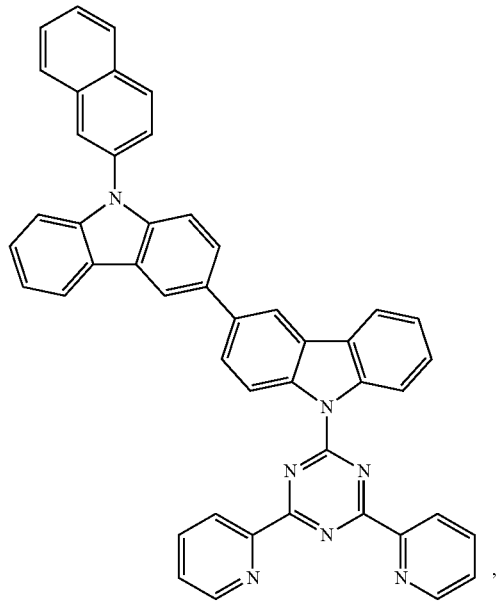
Compound 26
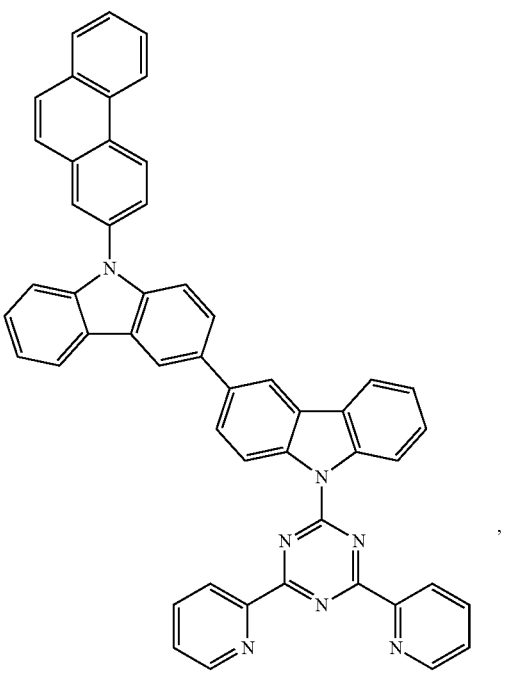

Compound 27
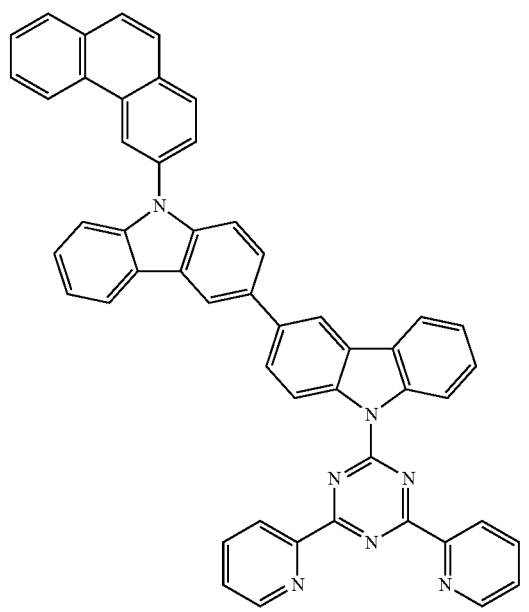
Compound 28
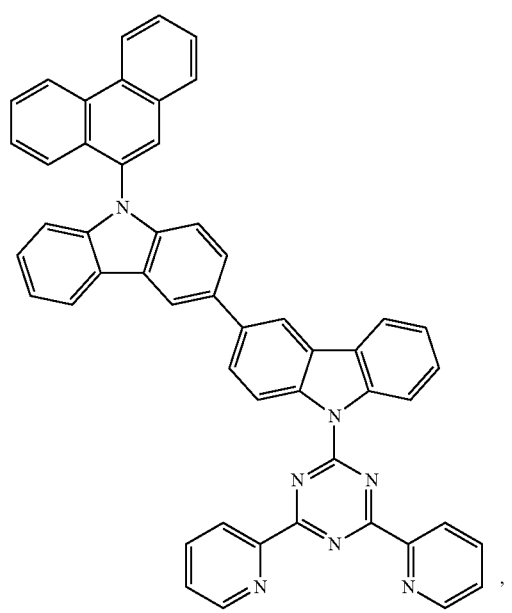
Compound 29
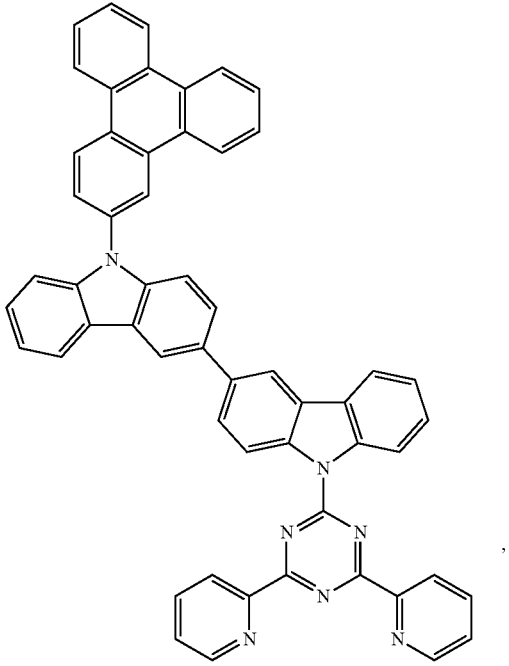
Compound 30
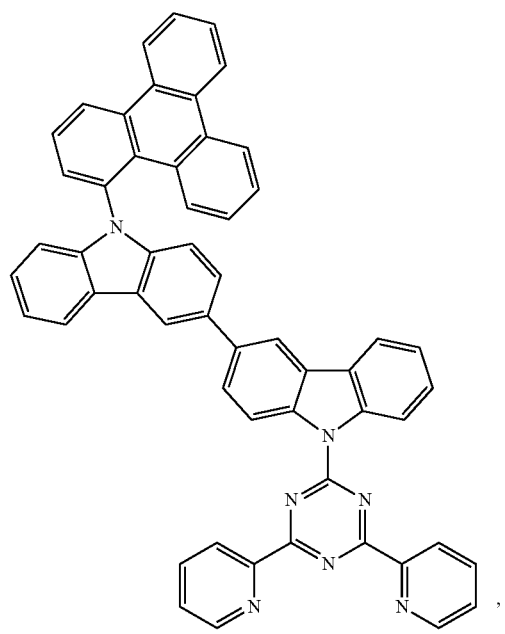

Compound 31
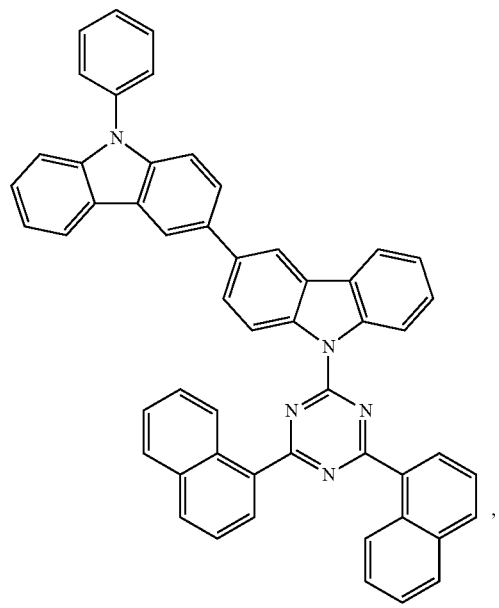
Compound 32
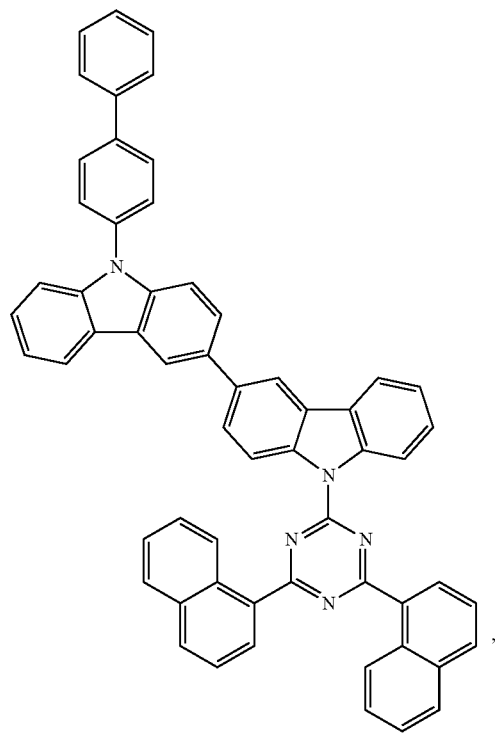
Compound 33
Compound 34

Compound 35
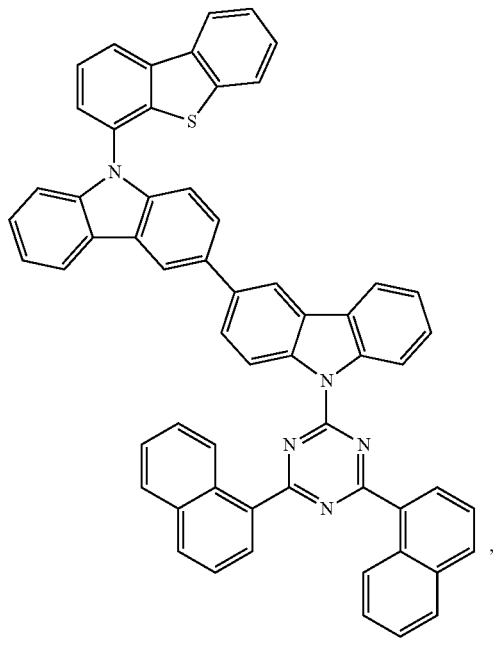
Compound 36
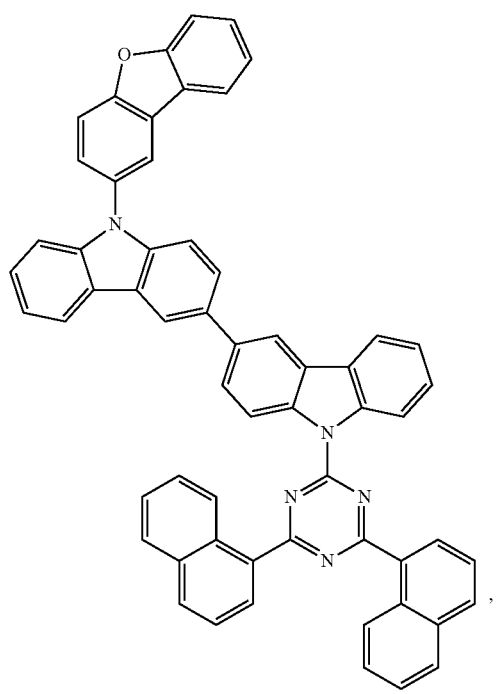
Compound 37
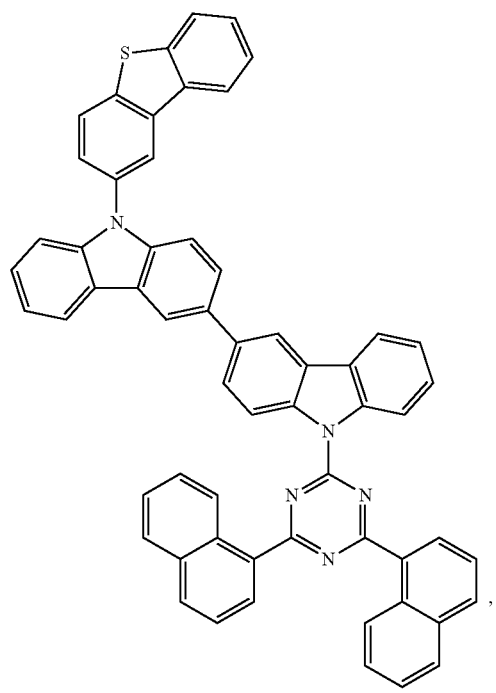
Compound 38
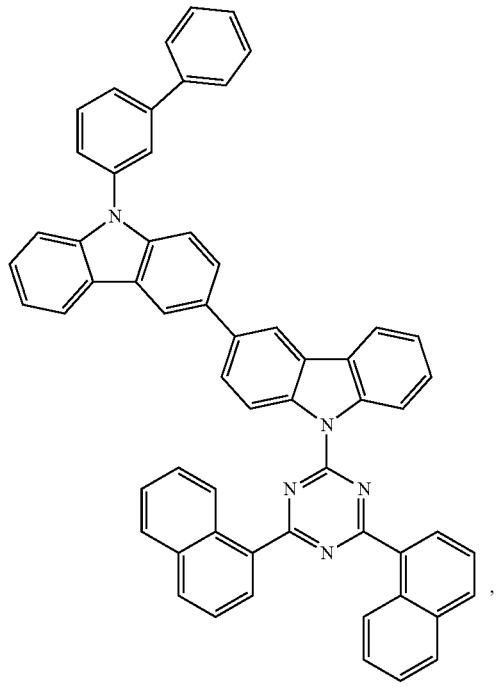

Compound 39
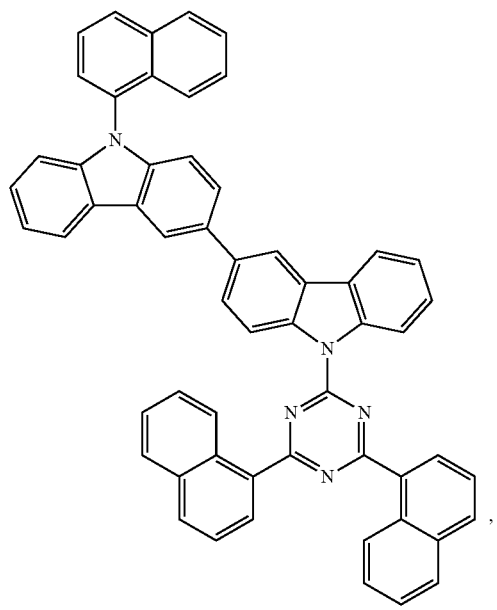
Compound 40
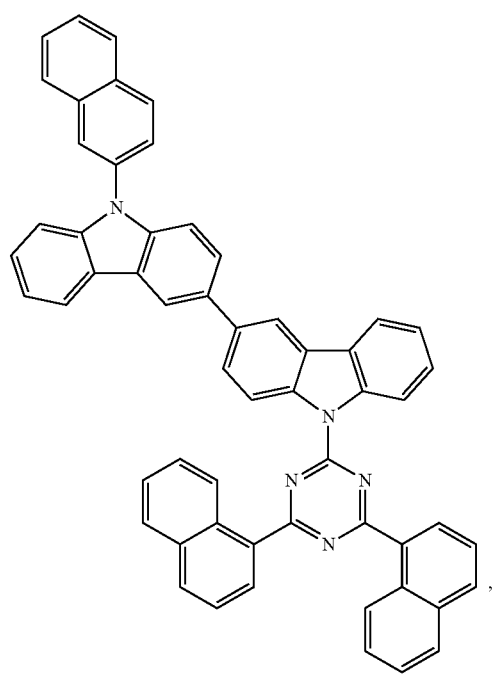
Compound 41
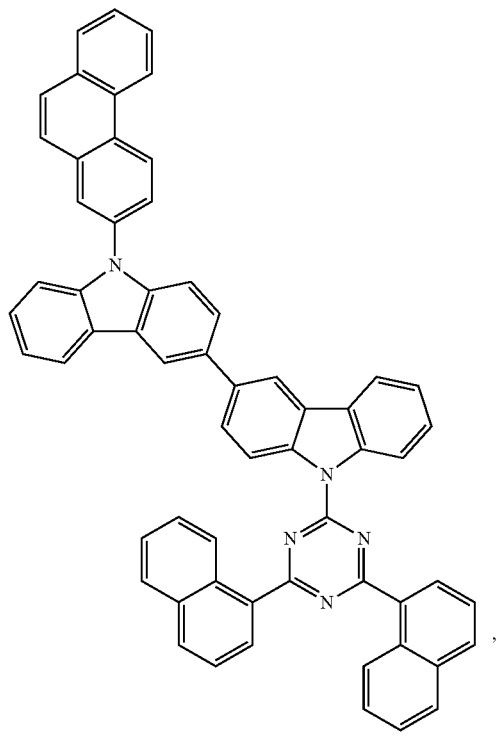
Compound 42
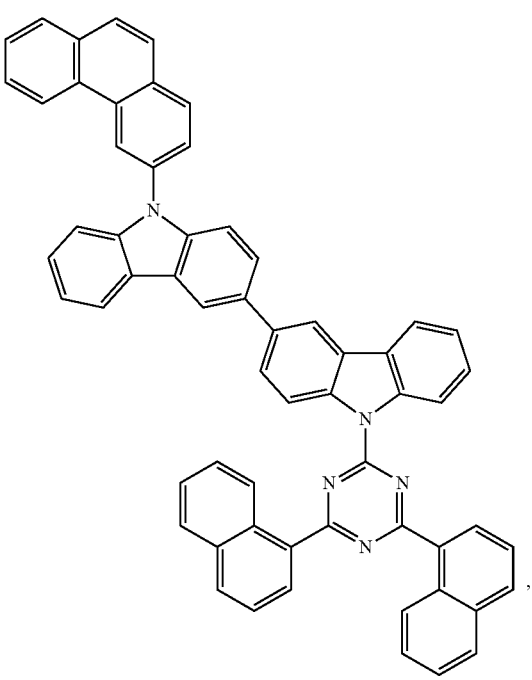

-continued
Compound 43
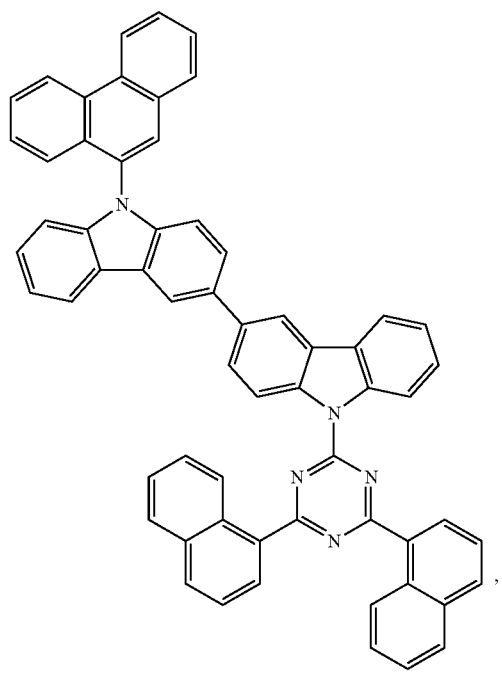
Compound 44
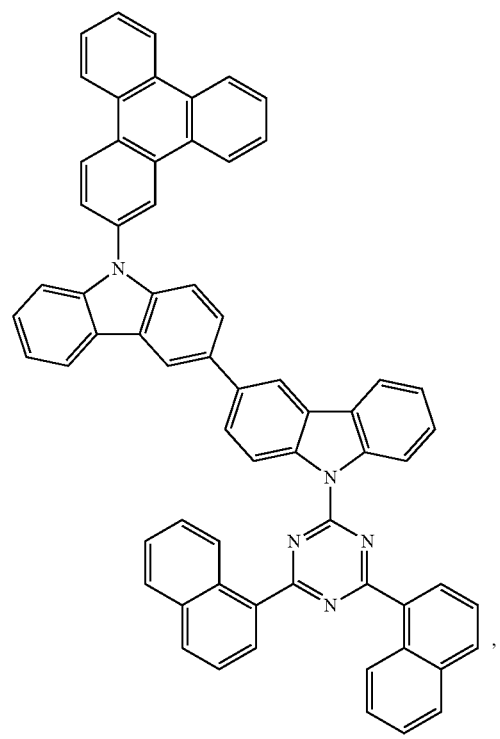
Compound 45
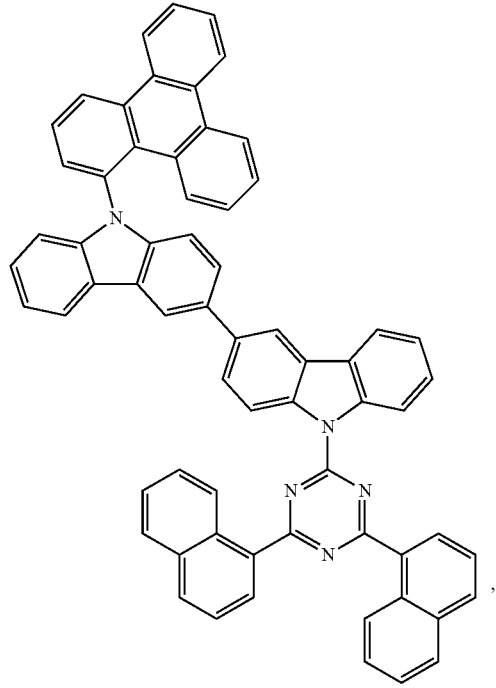
Compound 46
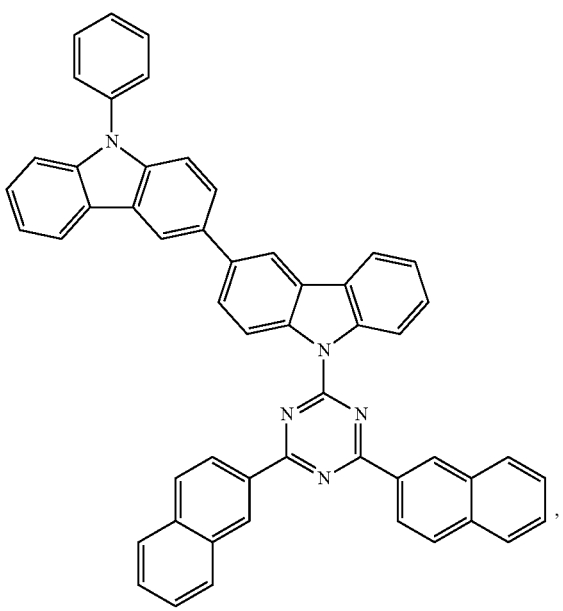

Compound 47
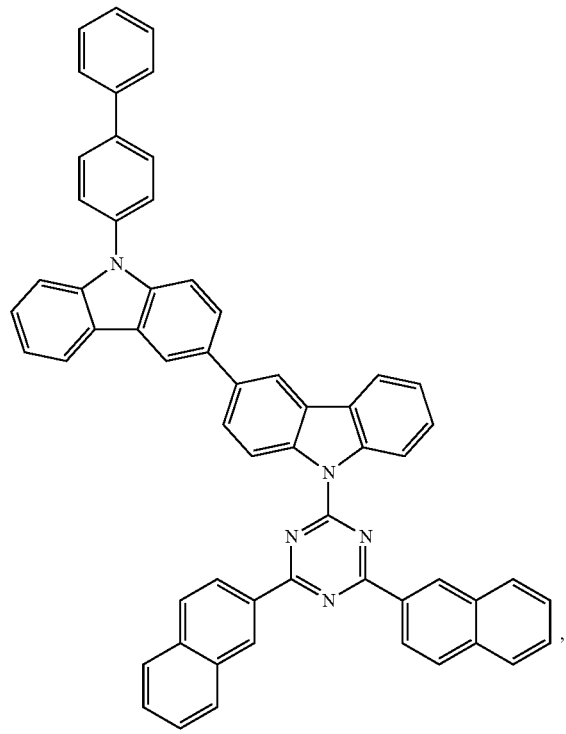
Compound 49
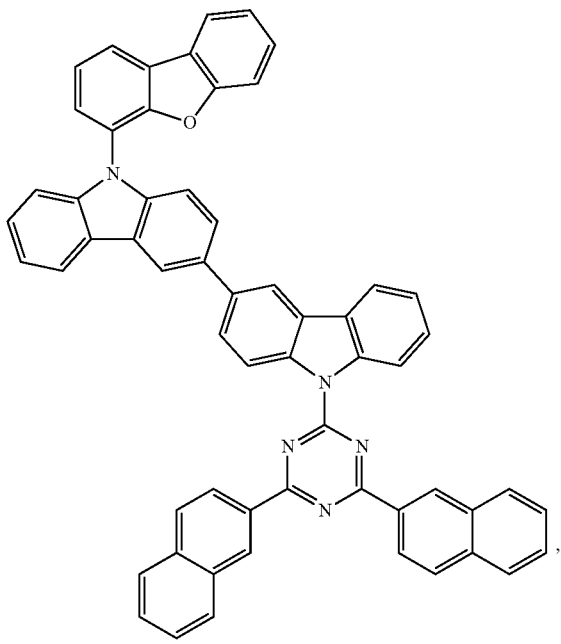
Compound 48
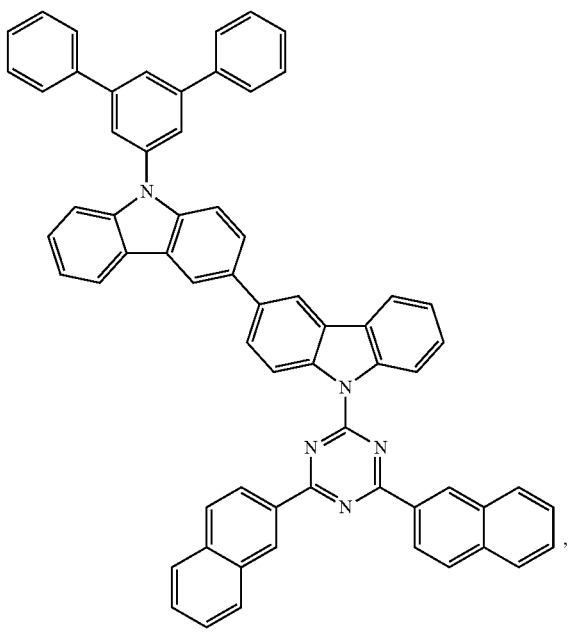
Compound 50

Compound 51
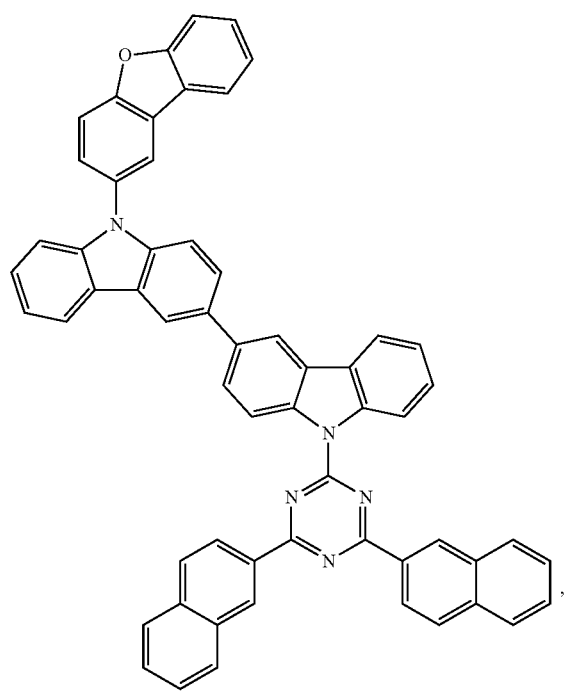
,
Compound 52
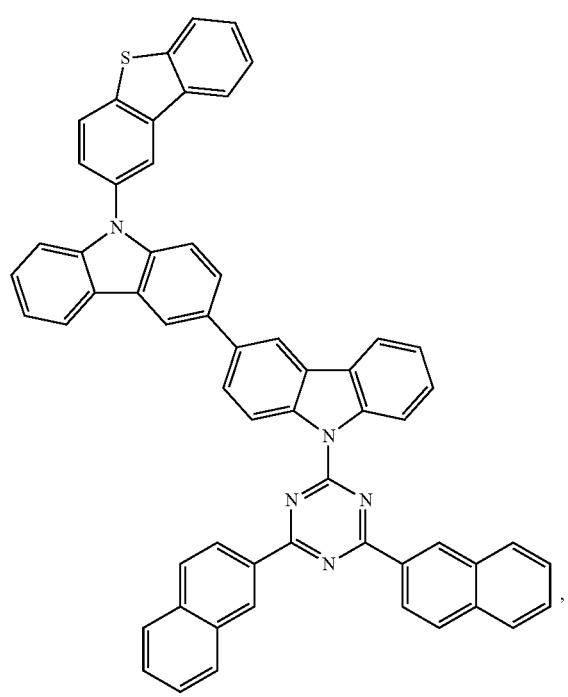
,
Compound 53
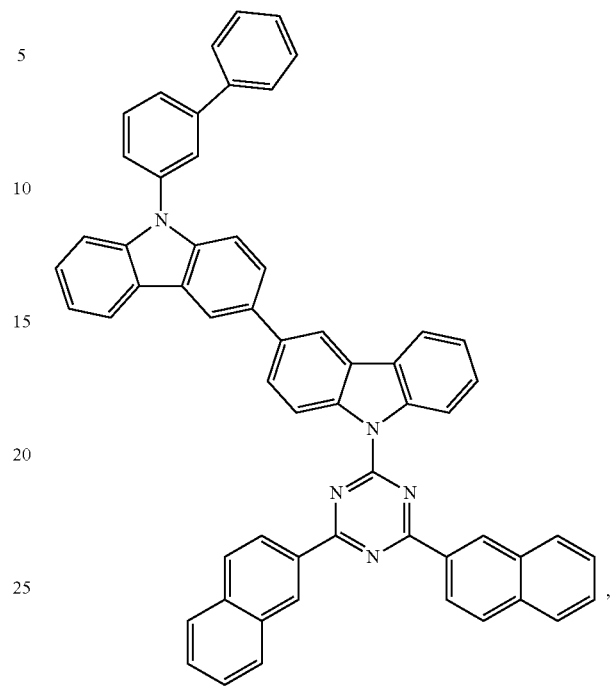
,
Compound 54
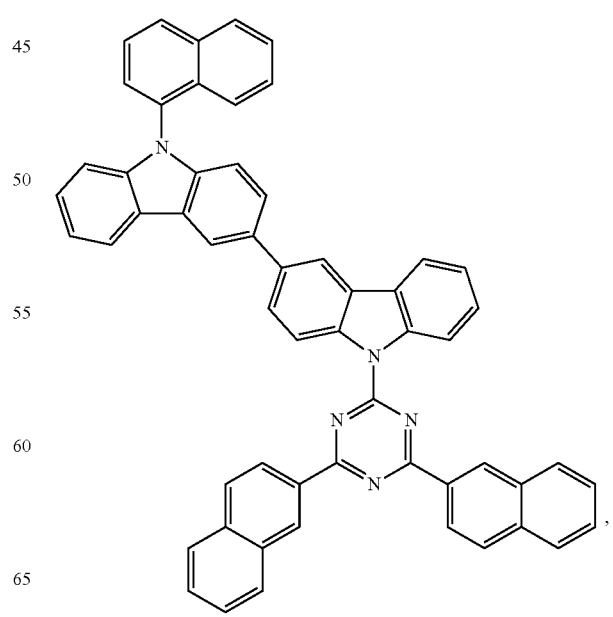
, Compound 55
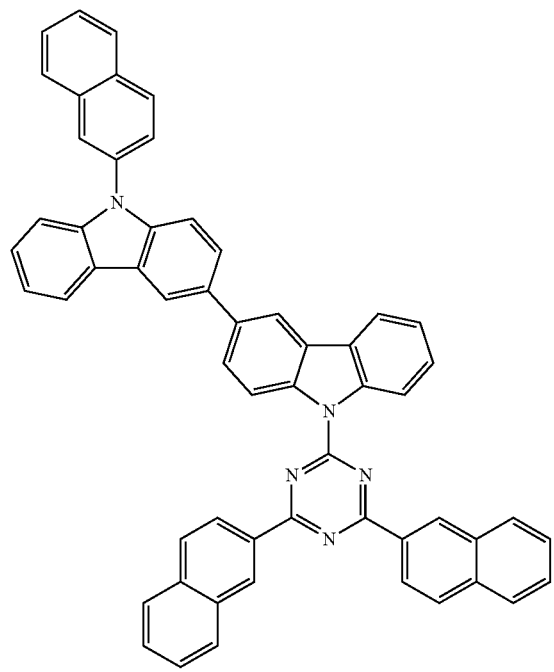
Compound 57
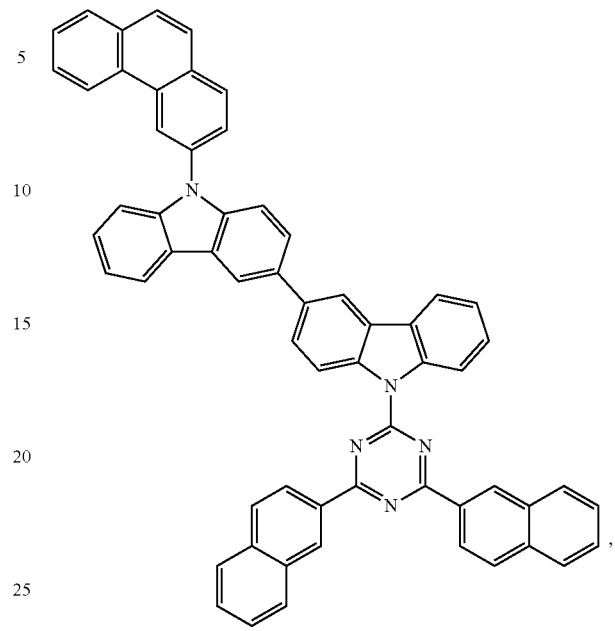
Compound 56
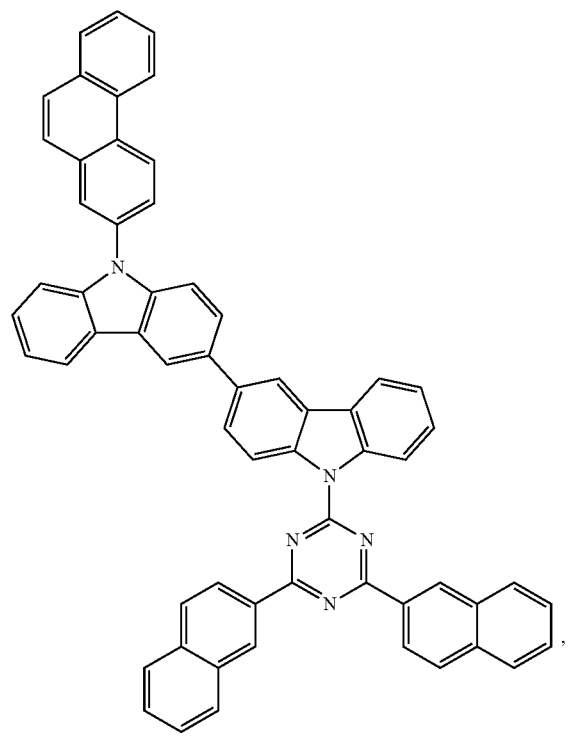
Compound 58
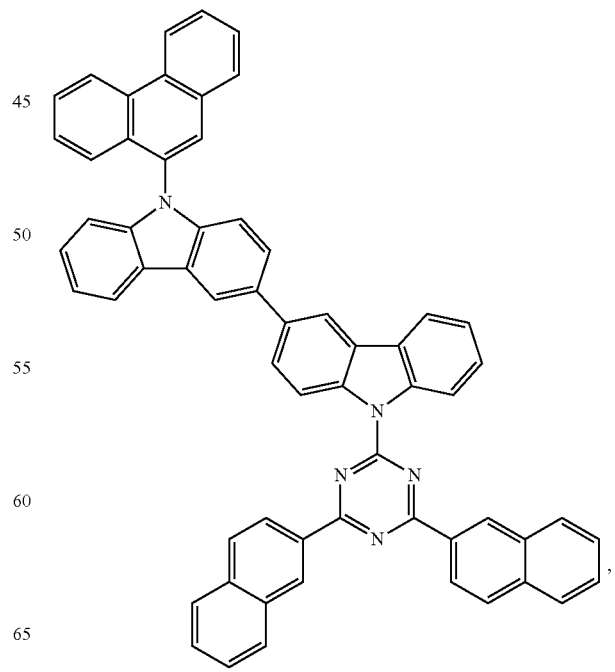

Compound 59
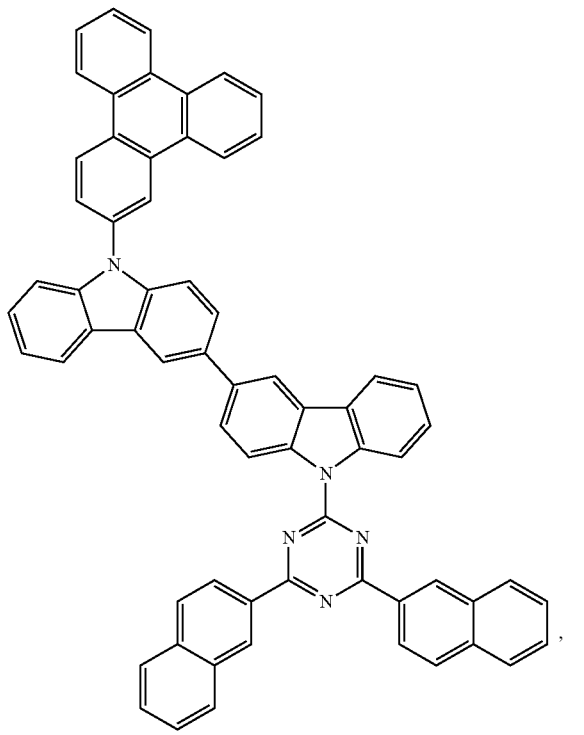
Compound 60
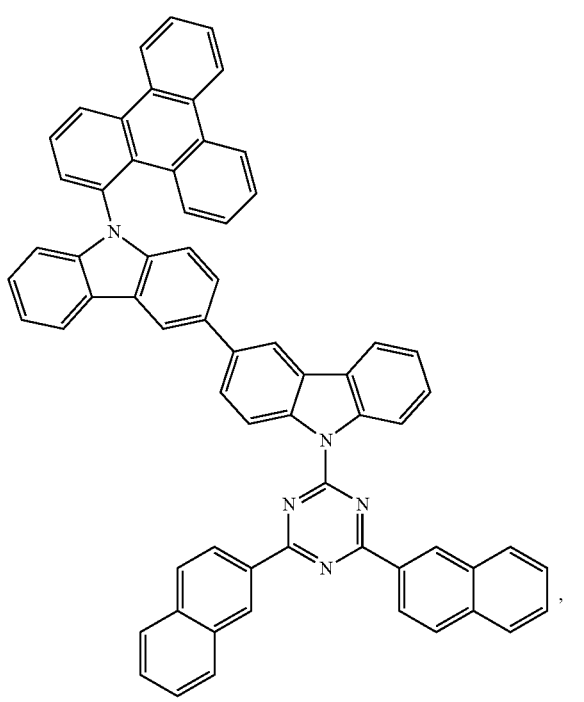
Compound 61
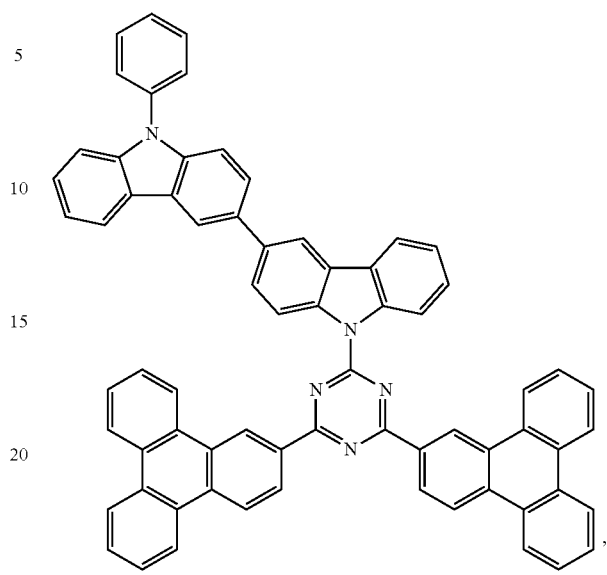
Compound 62
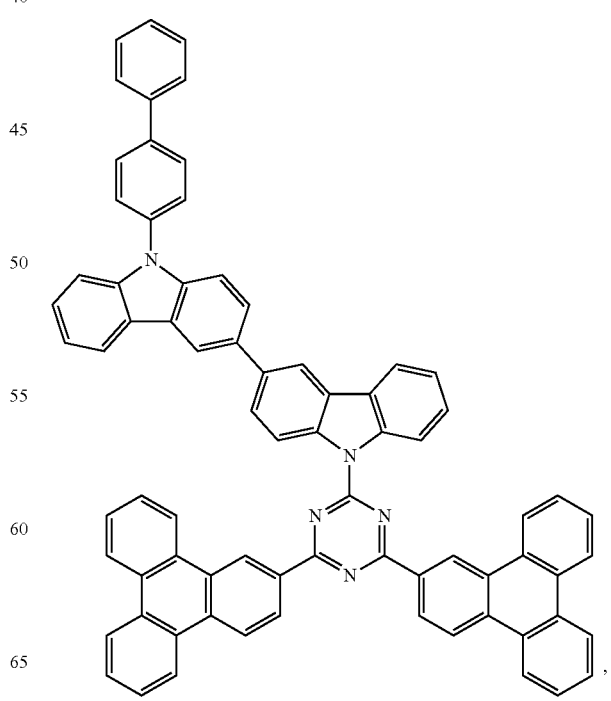

Compound 63
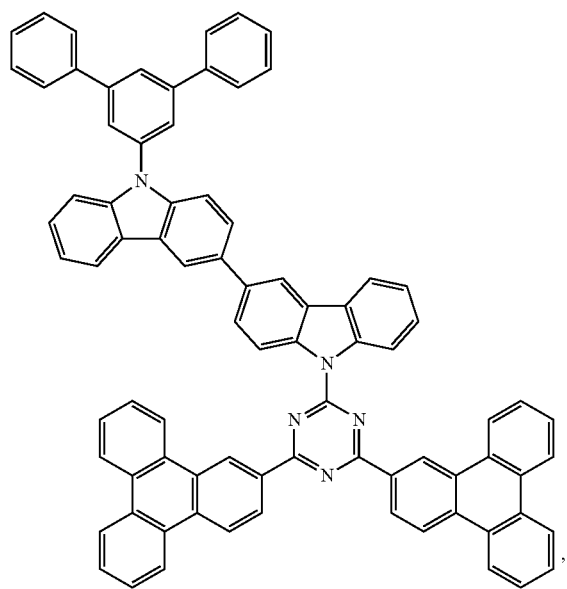
Compound 65
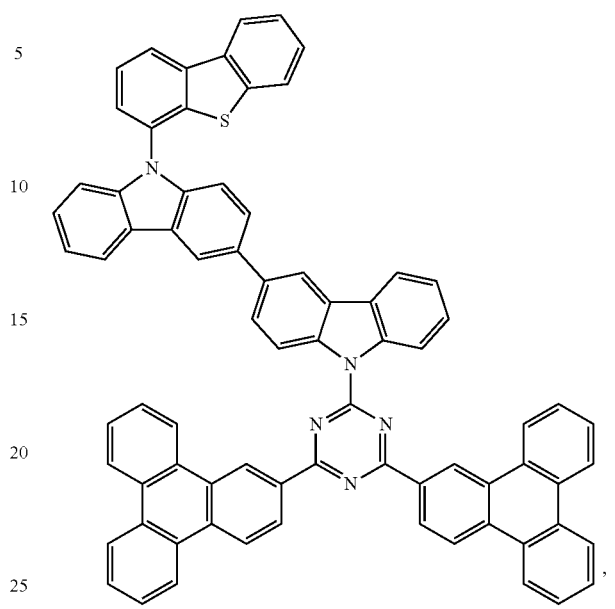
Compound 64
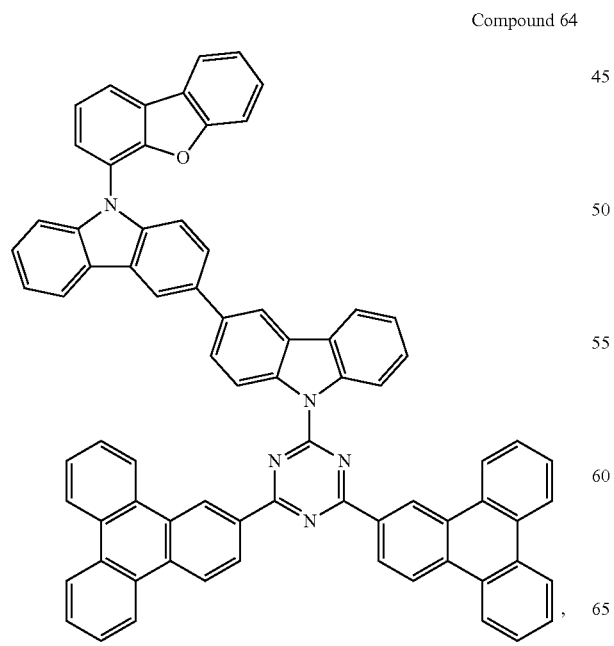
Compound 66
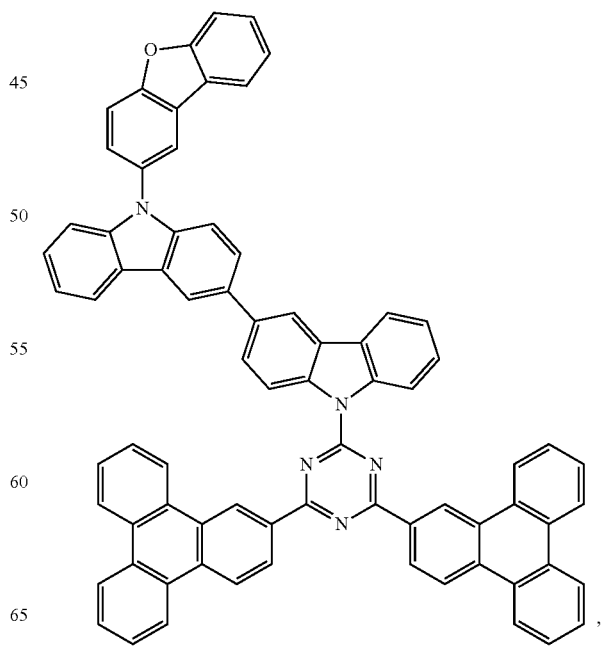

Compund 67
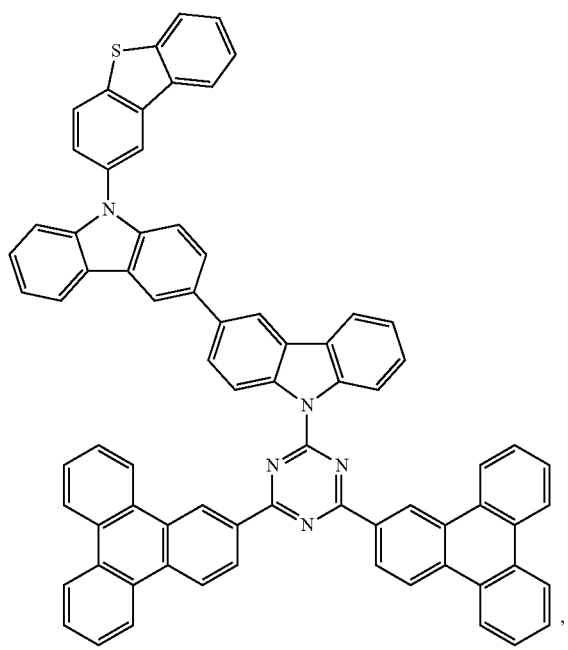
Compound 68
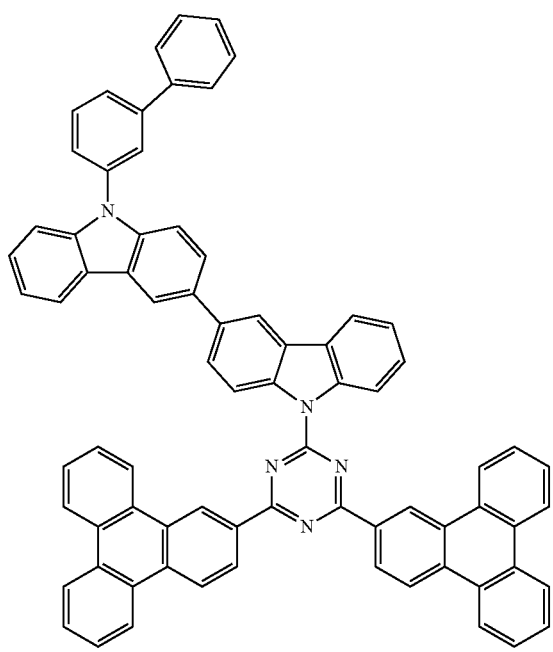
Compound 69
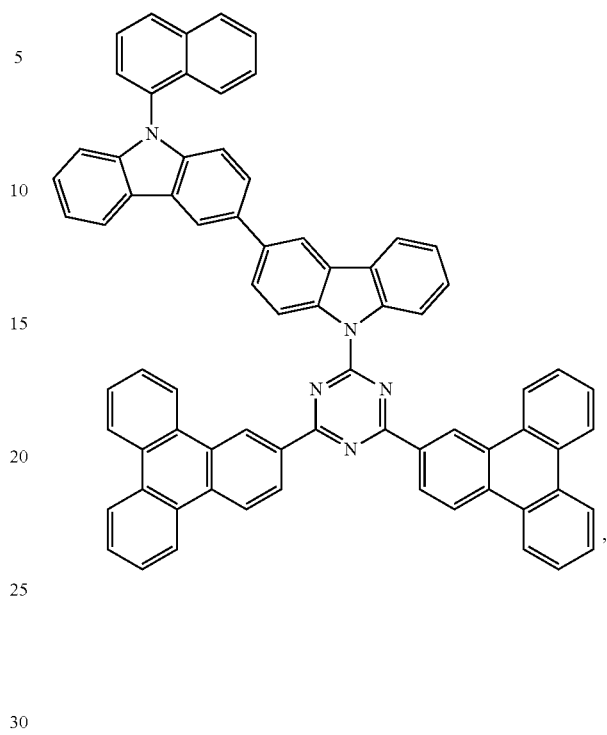
Compound 70
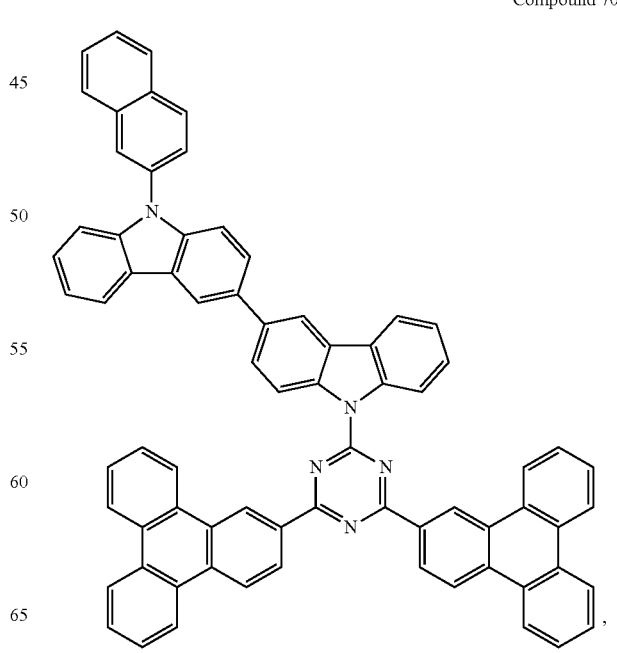

Compound 71
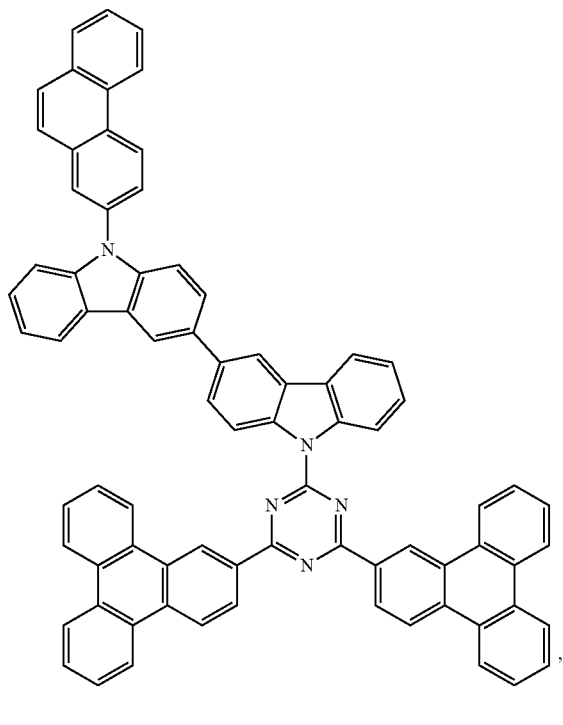
Compound 72
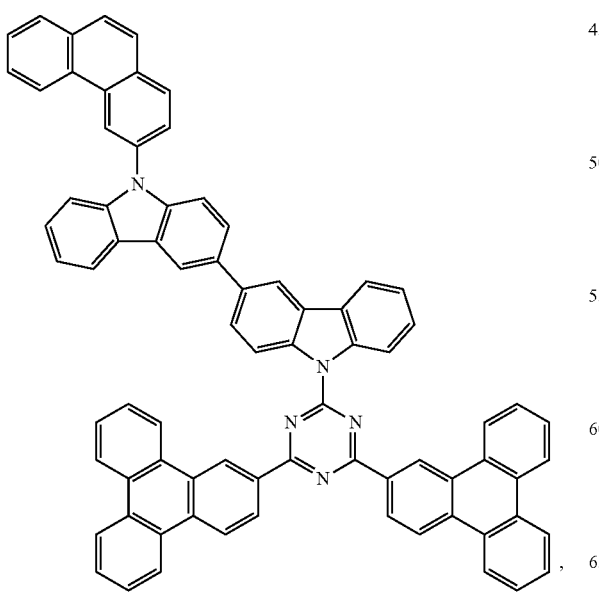
Compound 73
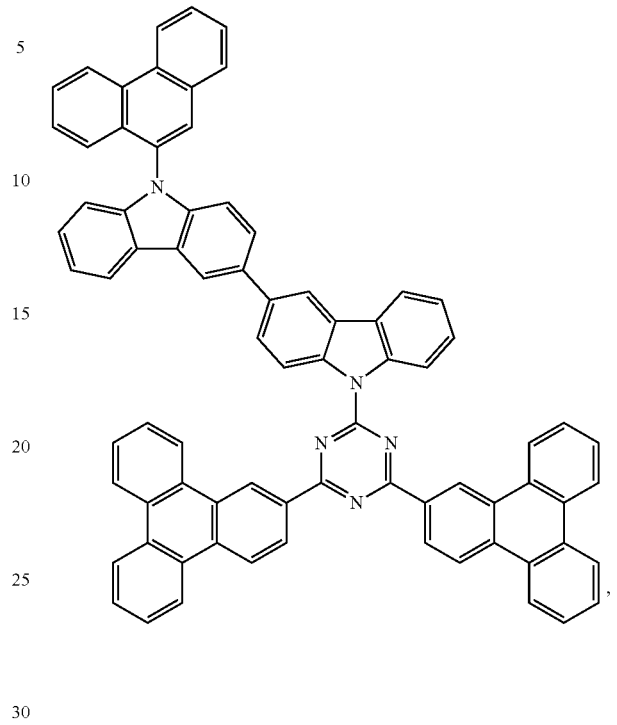
Compound 74
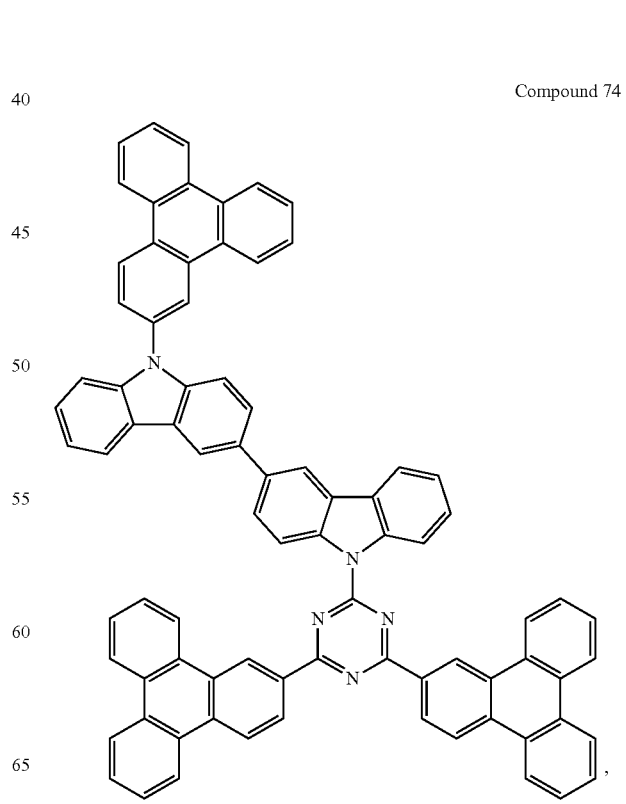

Compound 75
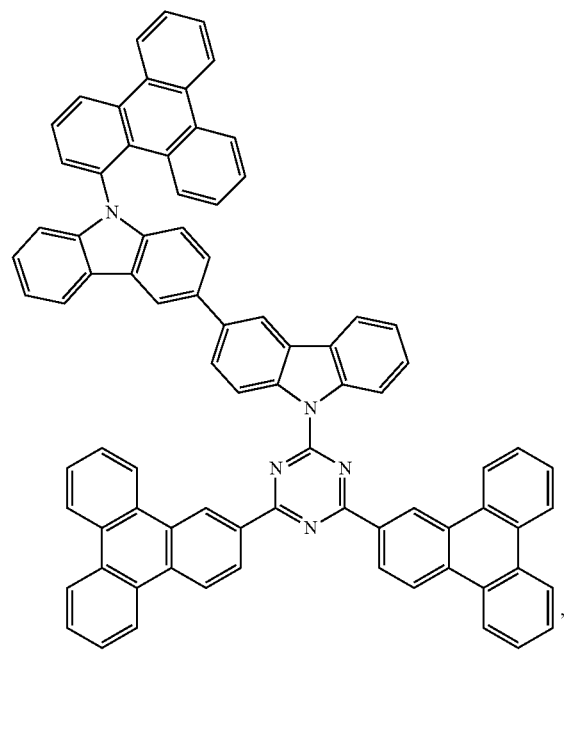
Compound 76
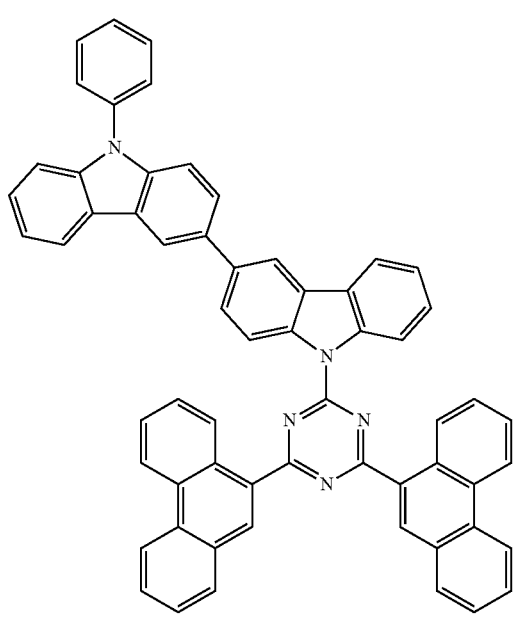
Compound 77
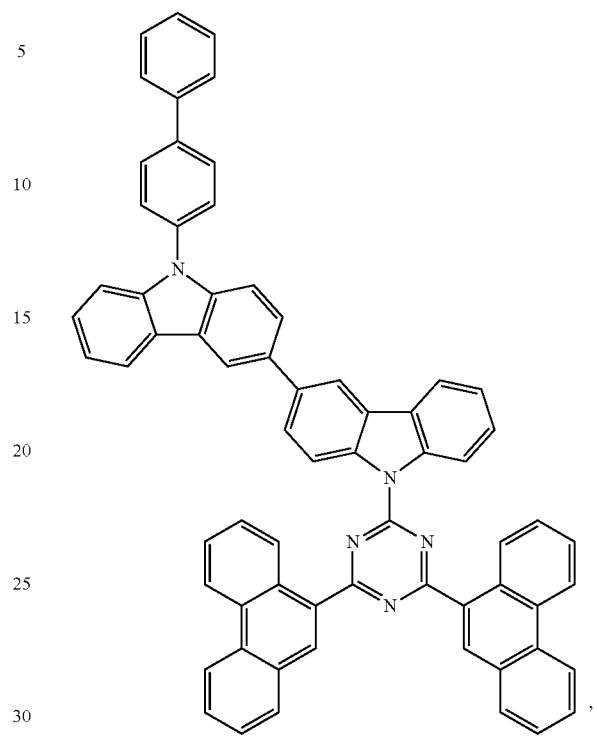
Compound 78
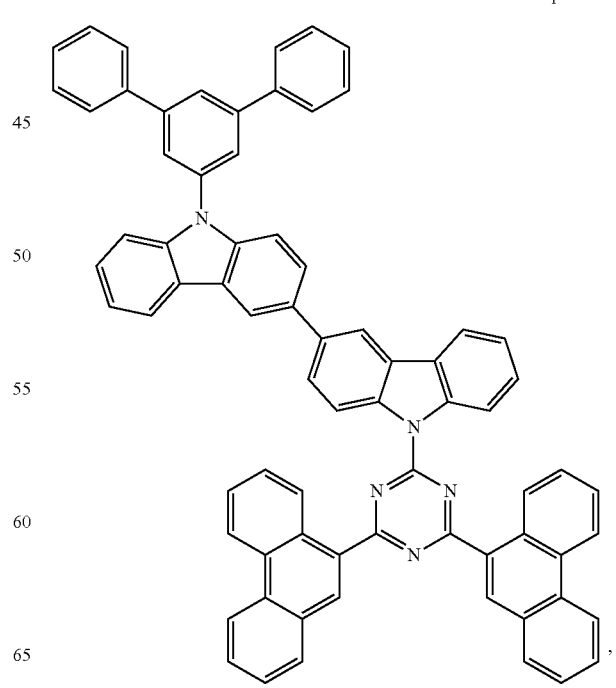

Compound 79
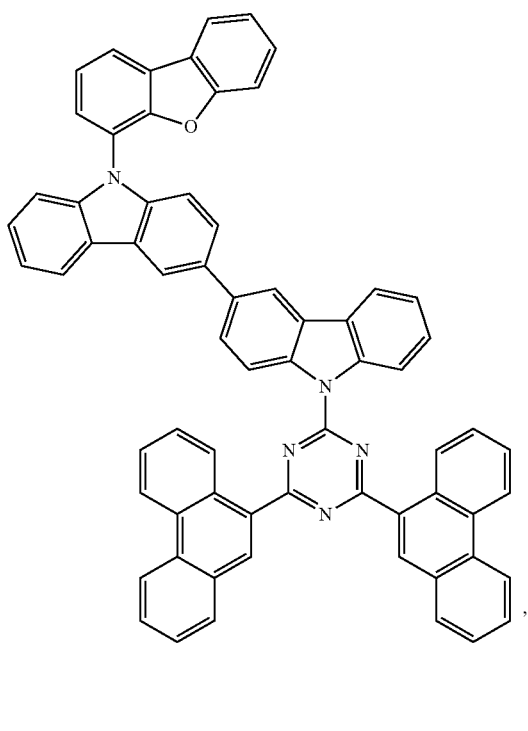
Compound 81
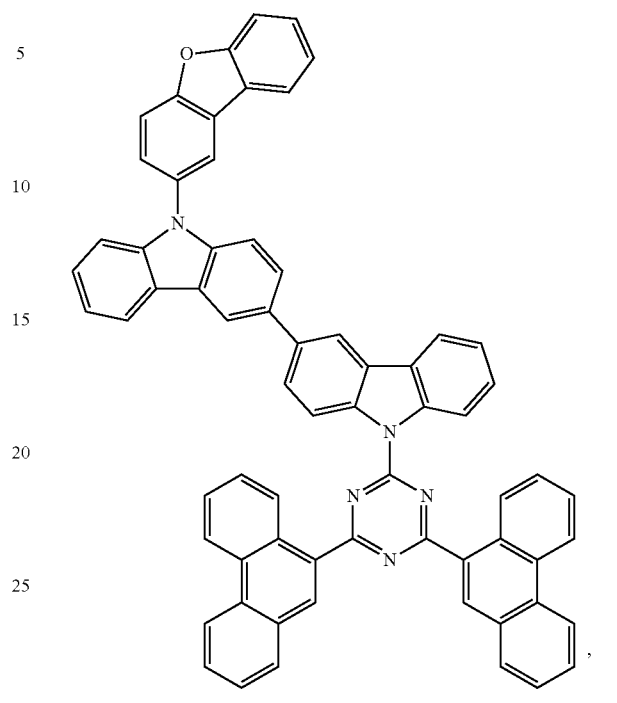
Compound 80
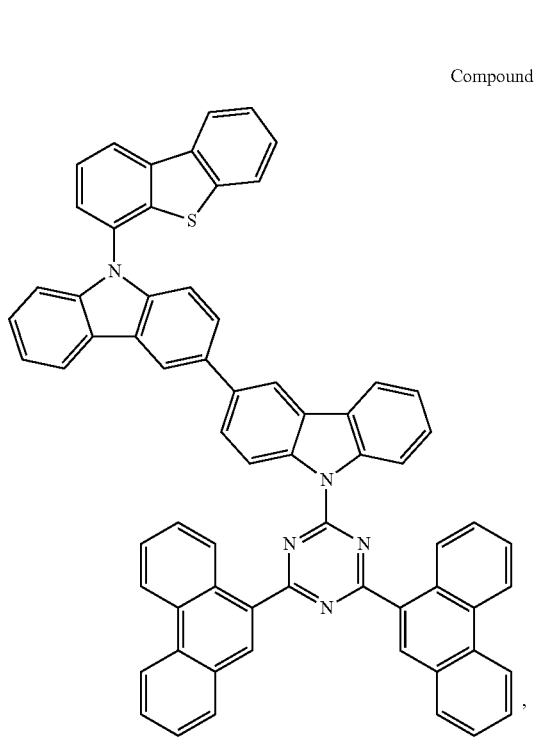
Compound 82
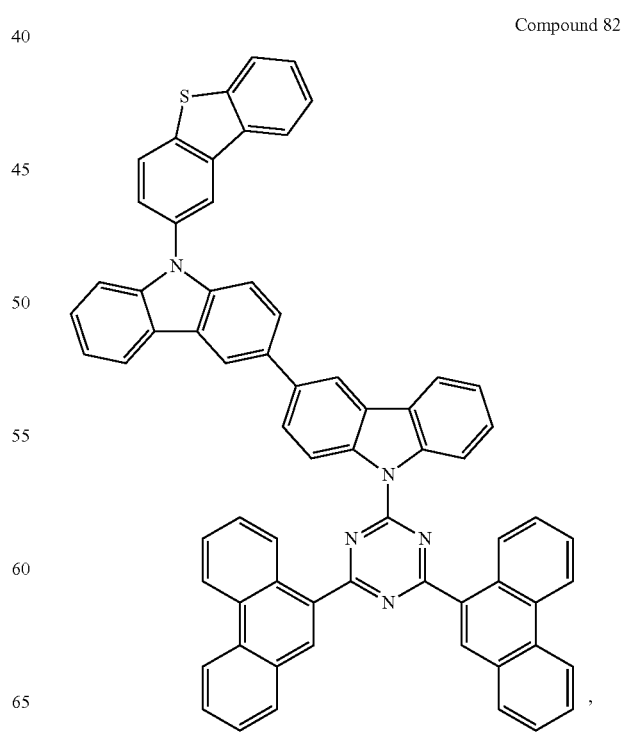

Compound 83
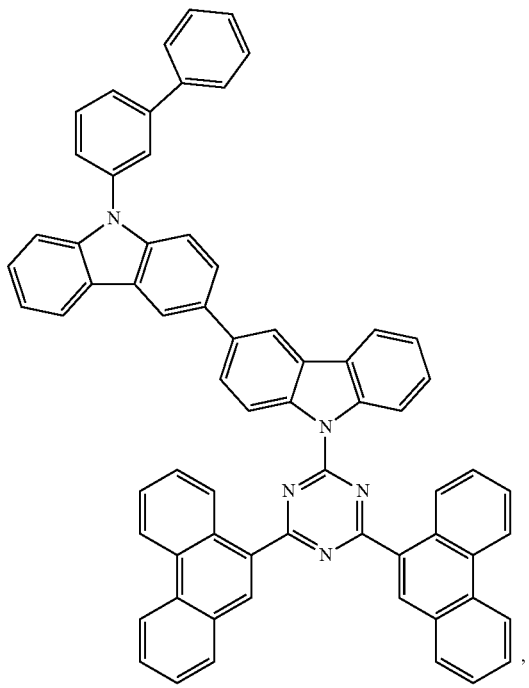
Compound 84
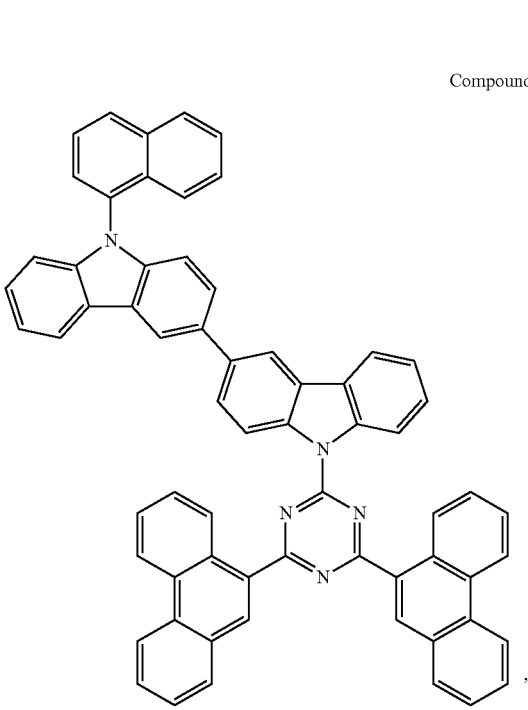
Compound 85
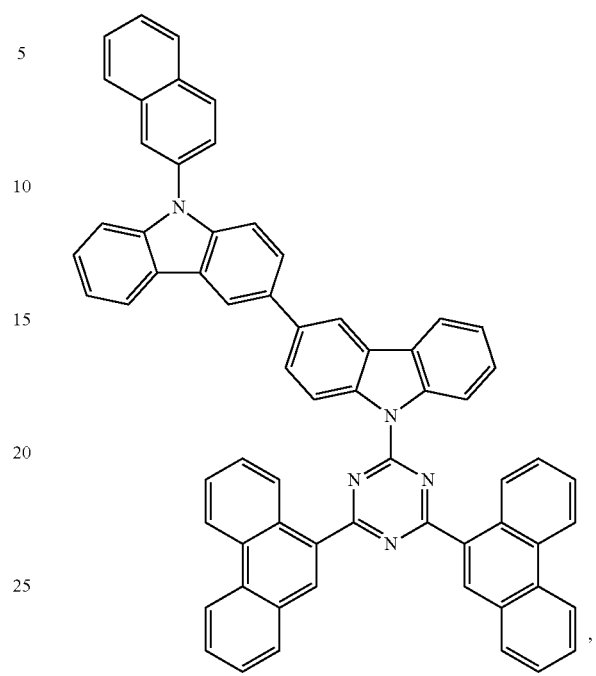
Compound 86
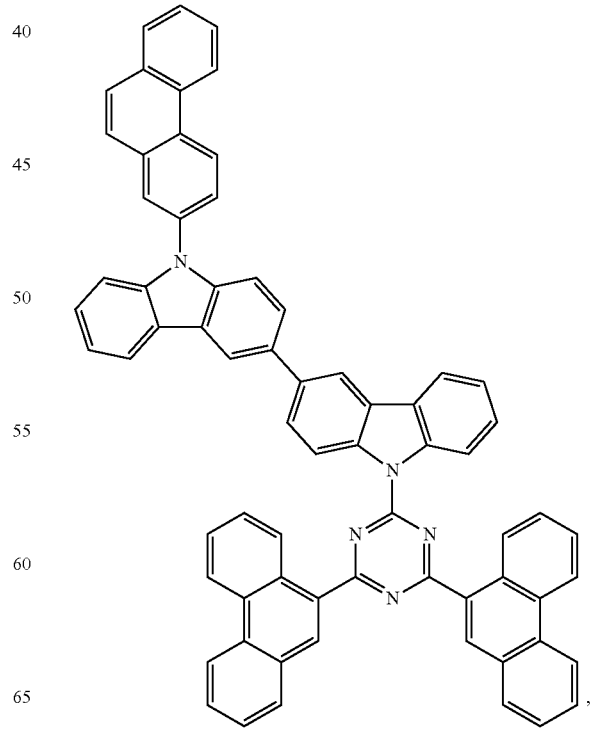

Compound 87
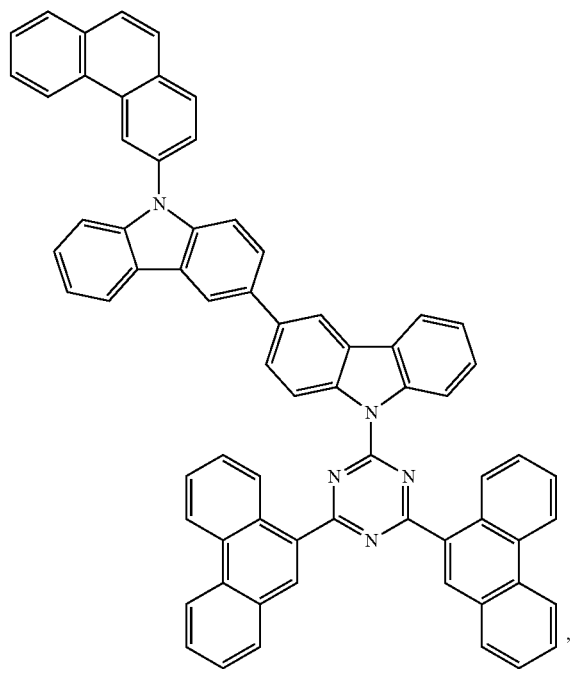
Compound 88
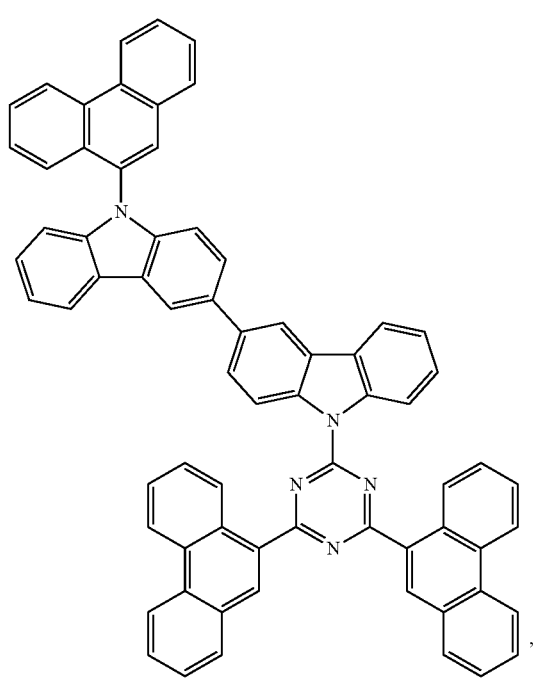
Compound 89
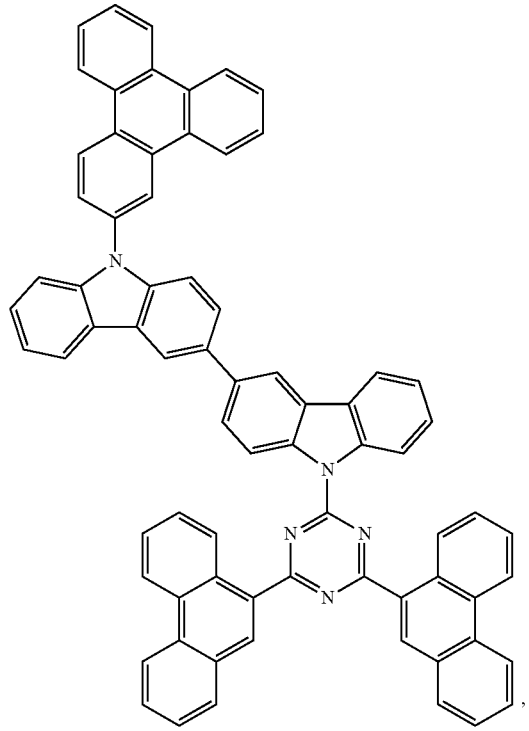
Compound 90
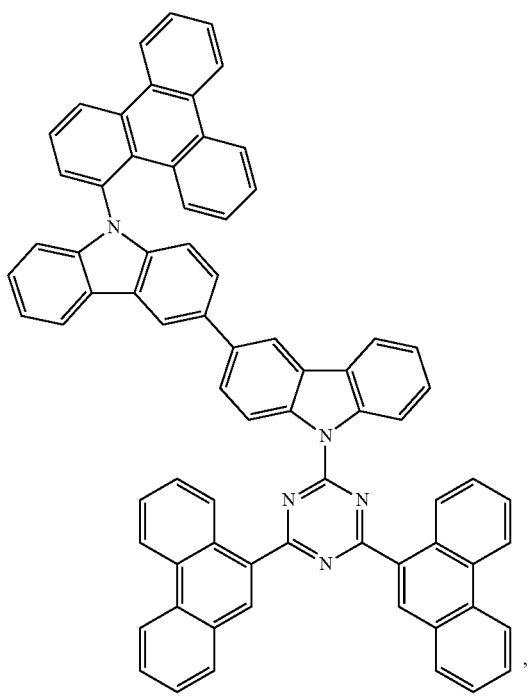

Compound 106
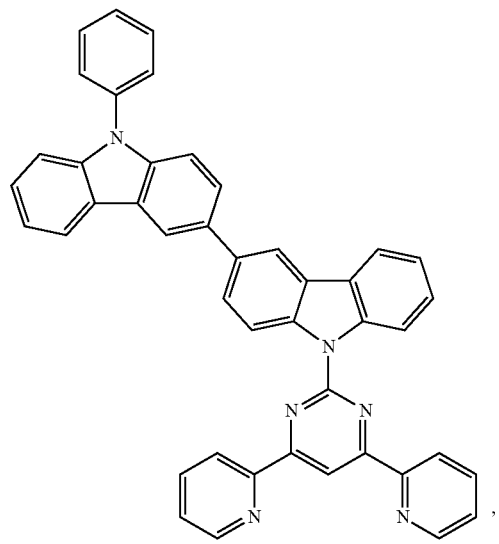
Compound 107
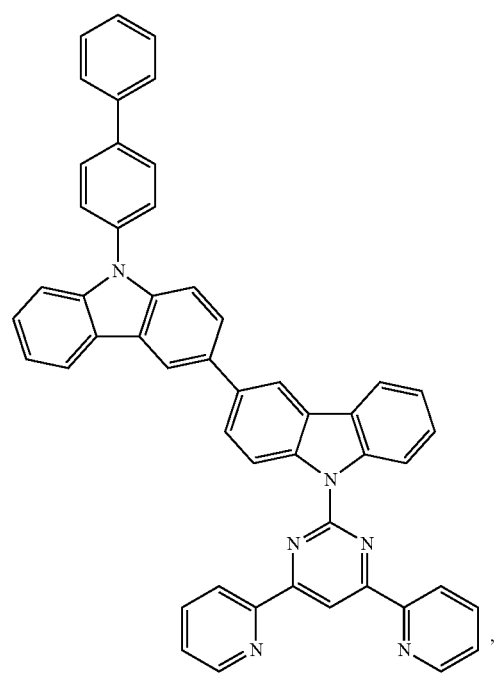
Compound 108
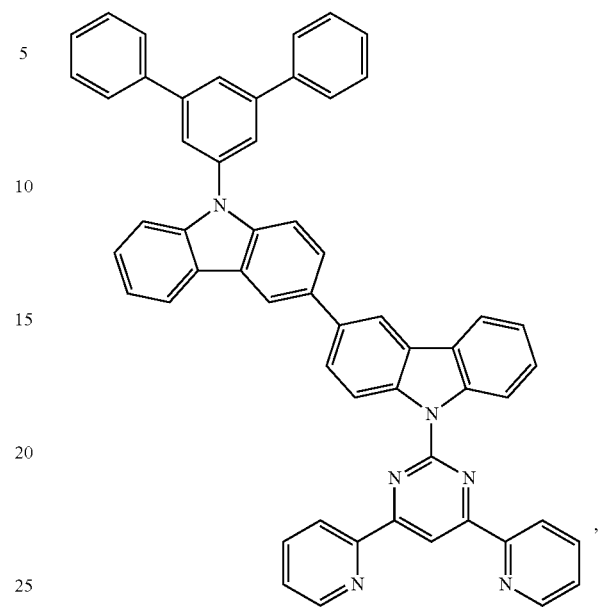
Compound 109
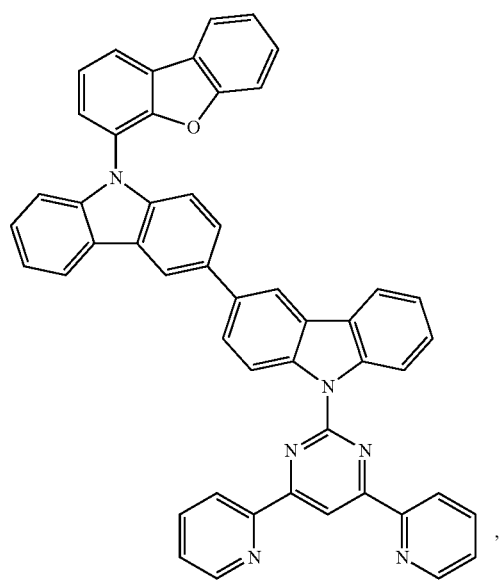

Compound 110
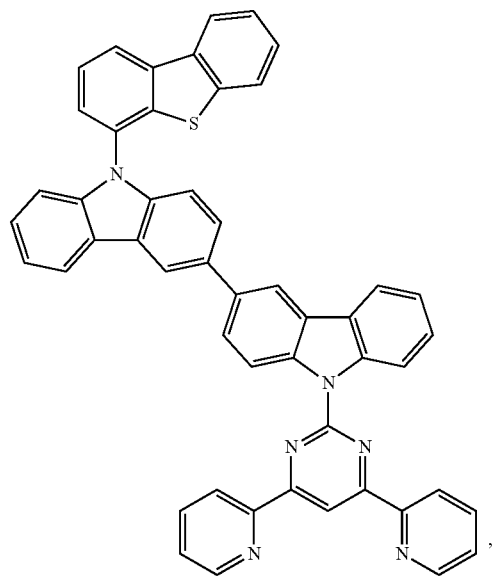
Compound 111
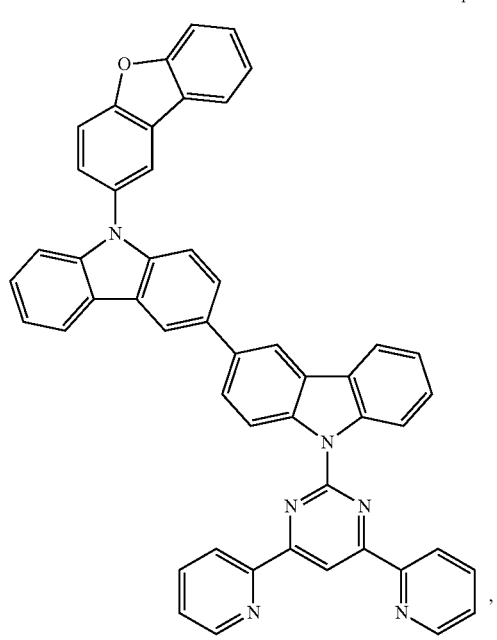
Compound 112
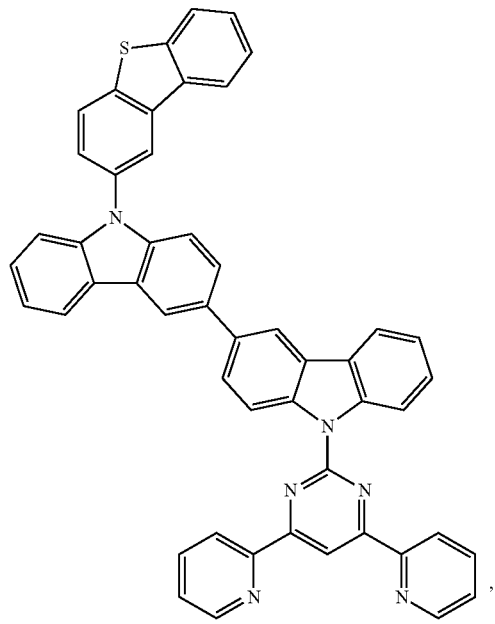
Compound 113
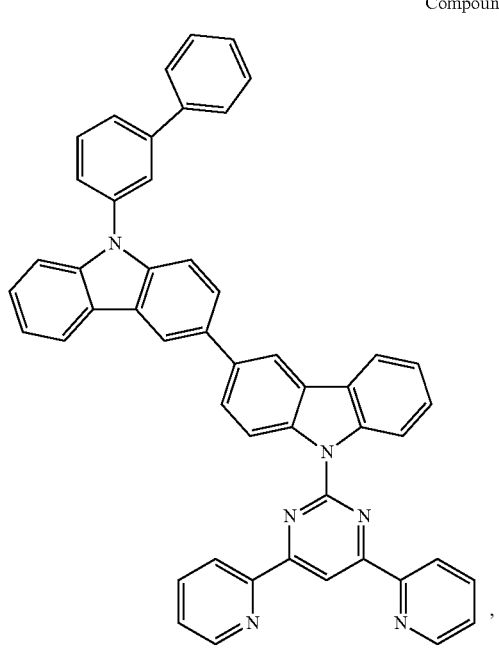

Compound 114
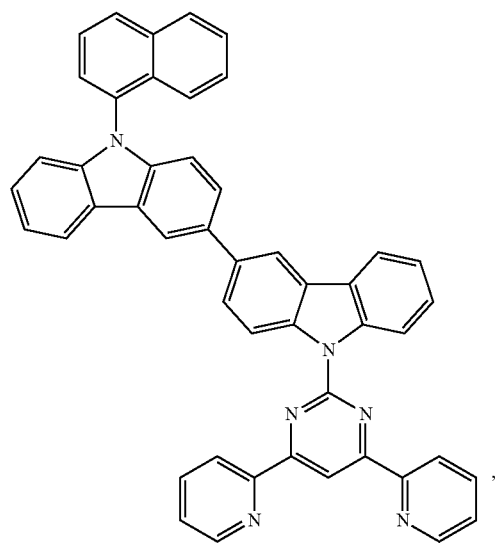
Compound 115
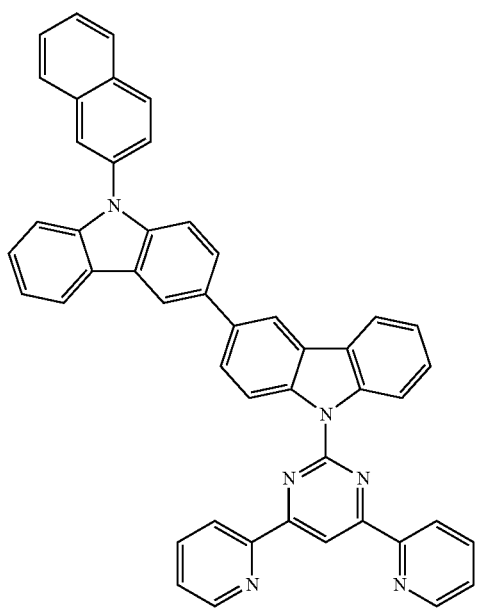
Compound 116
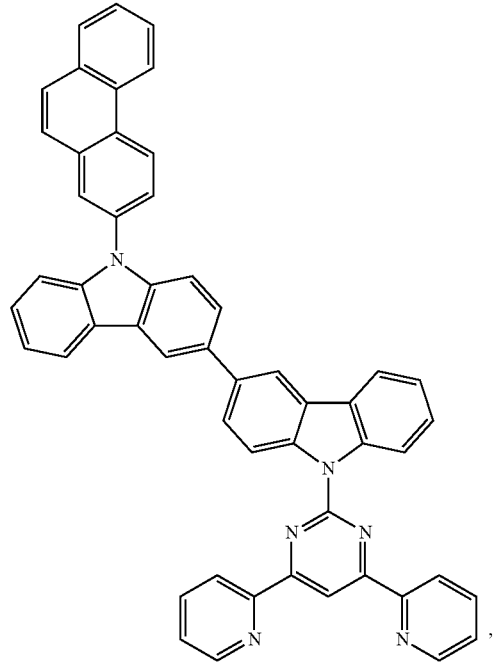
Compound 117
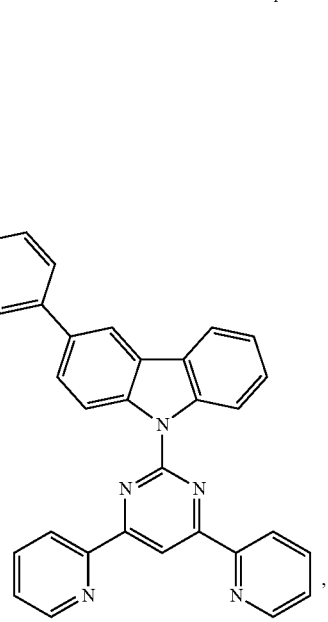

Compound 118
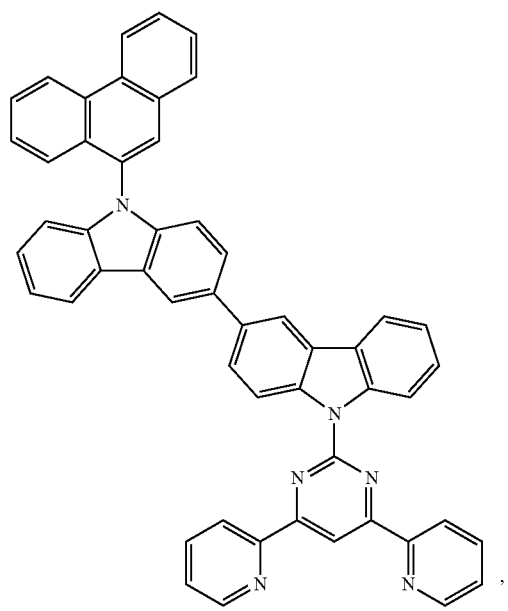
Compound 119
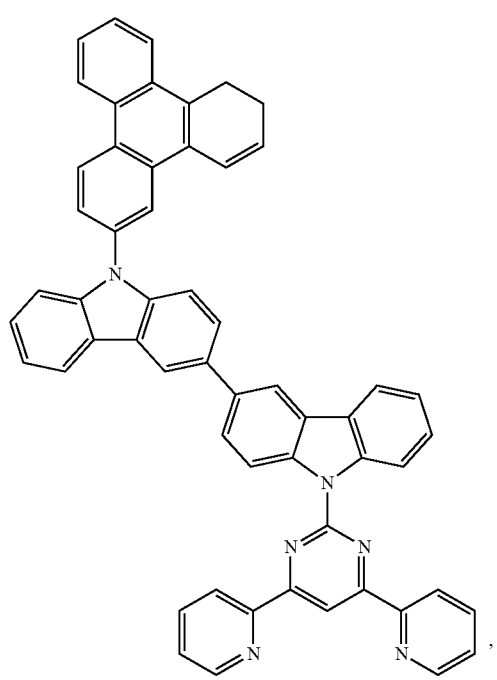
Compound 120
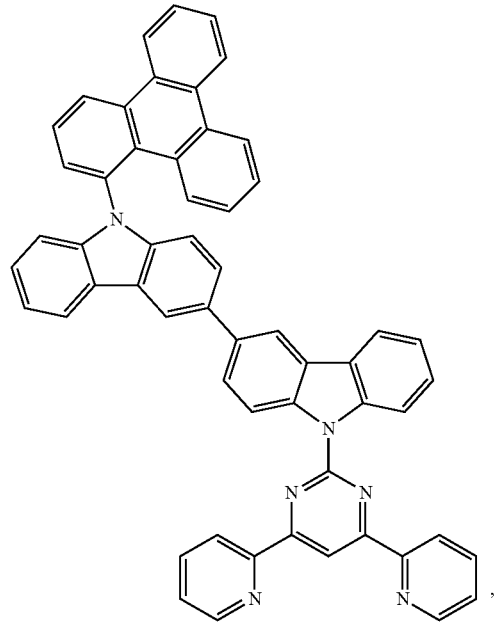
Compound 121
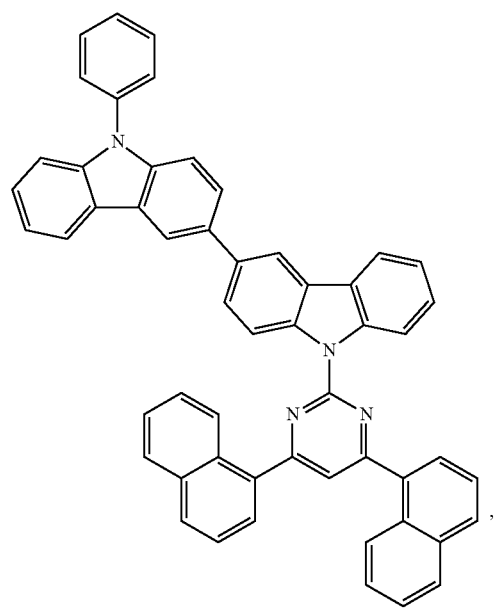

Compound 122
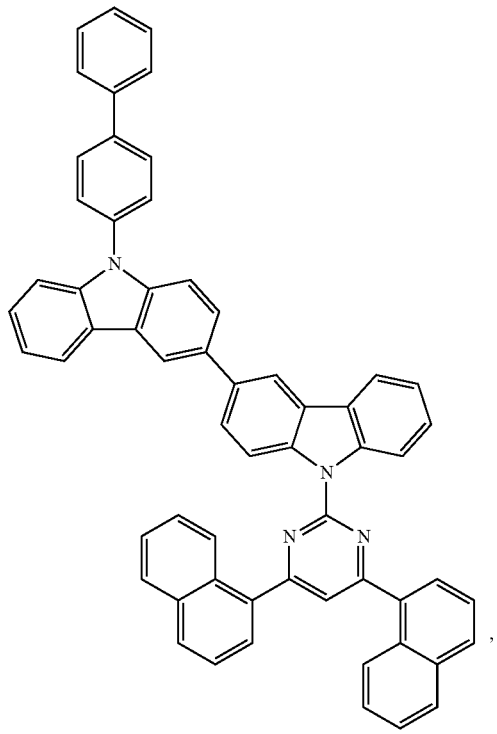
Compound 123
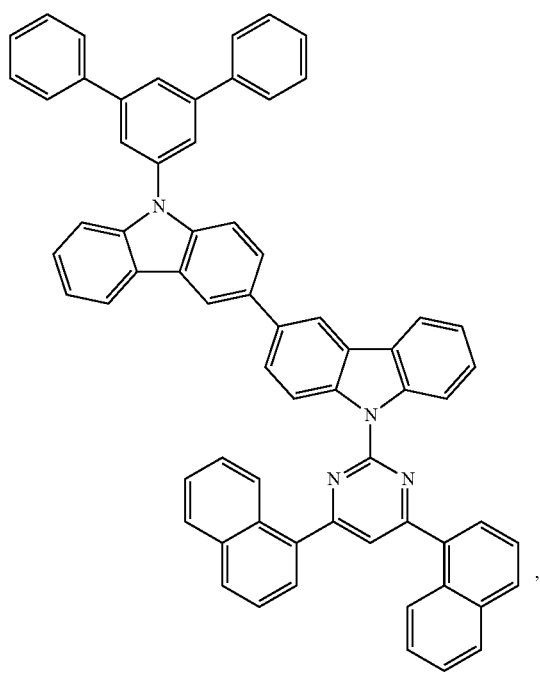
Compound 124
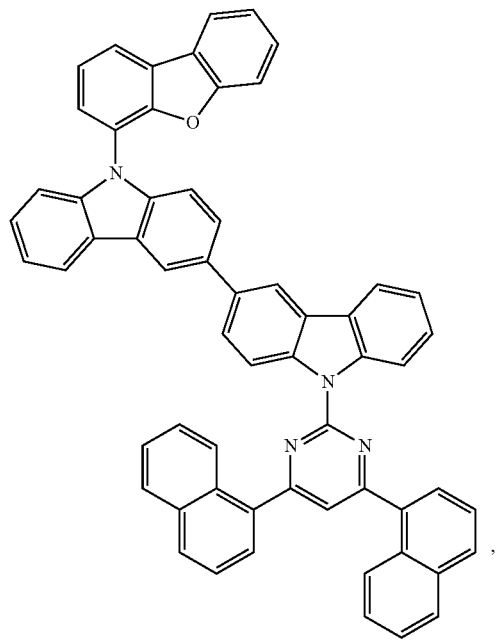
Compound 125

-continued
Compound 126
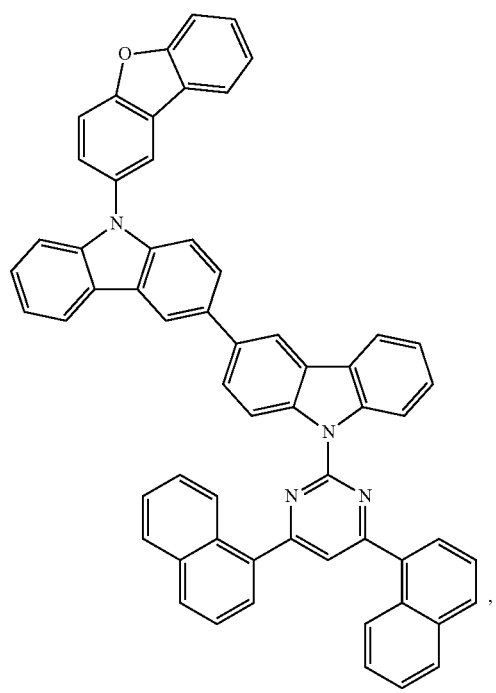
Compound 127
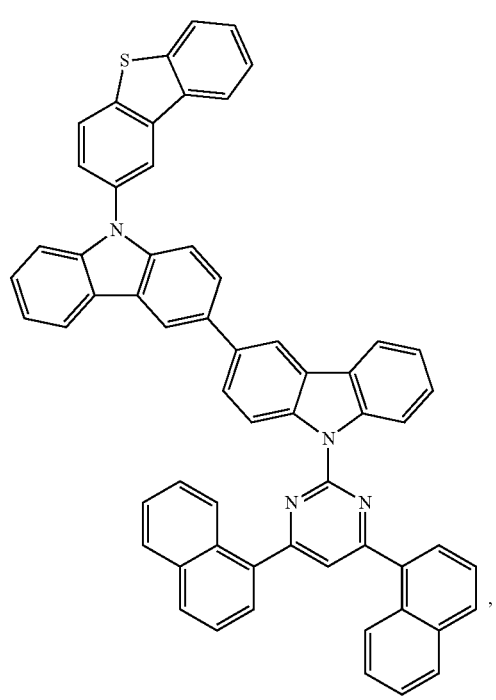
-continued
Compound 128
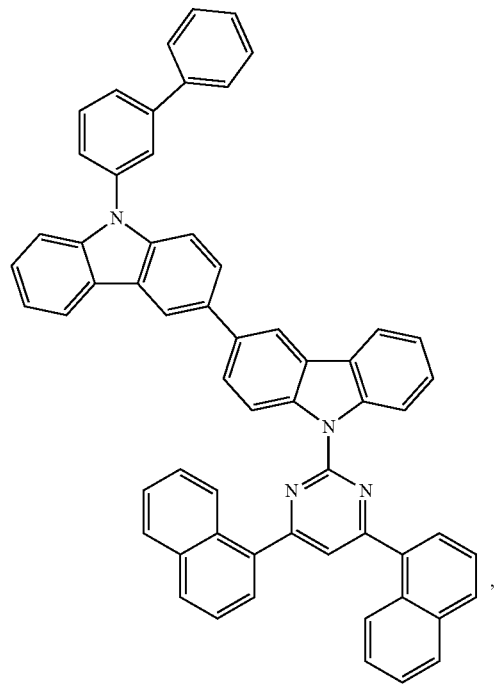
Compound 129
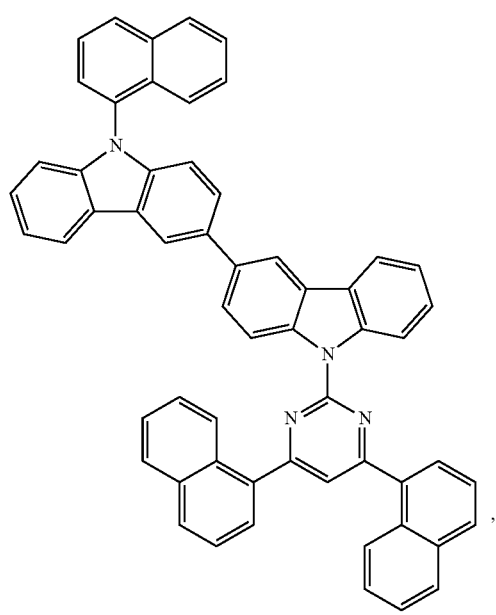

-continued
Compound 130
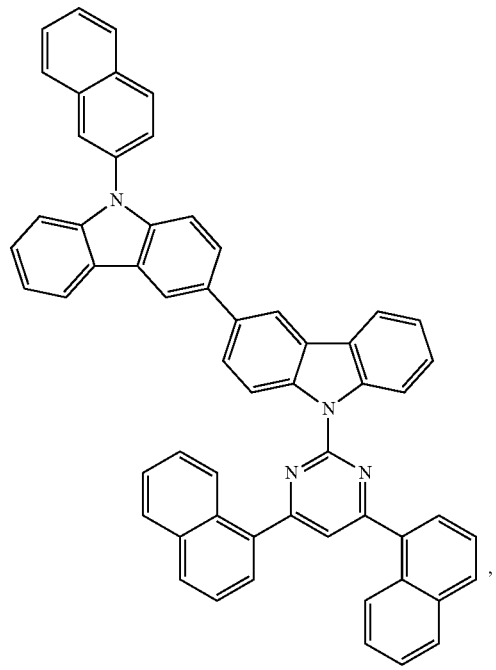
Compound 131
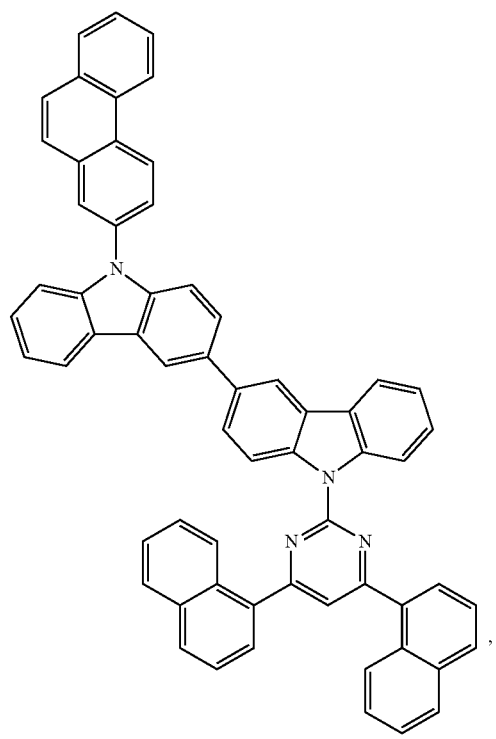
Compound 132
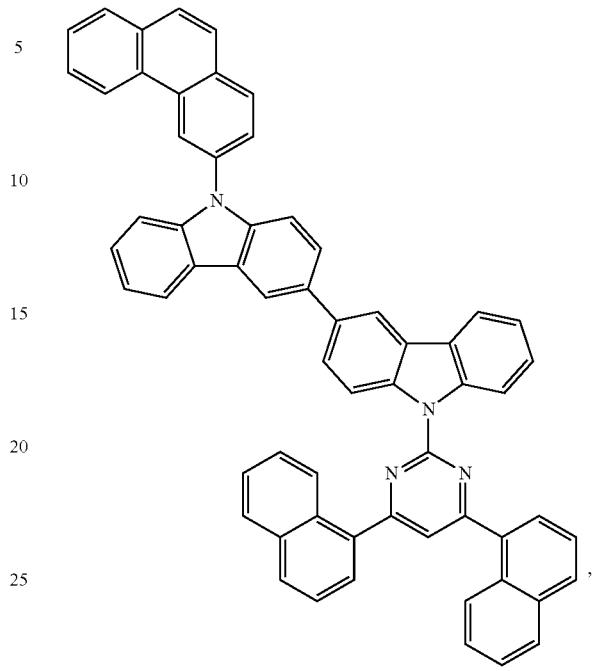
Compound 133
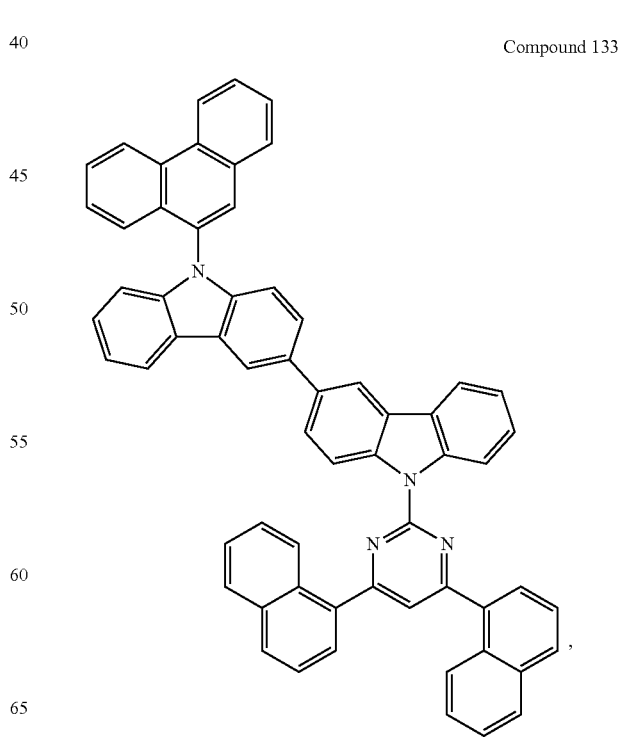

Compound 134
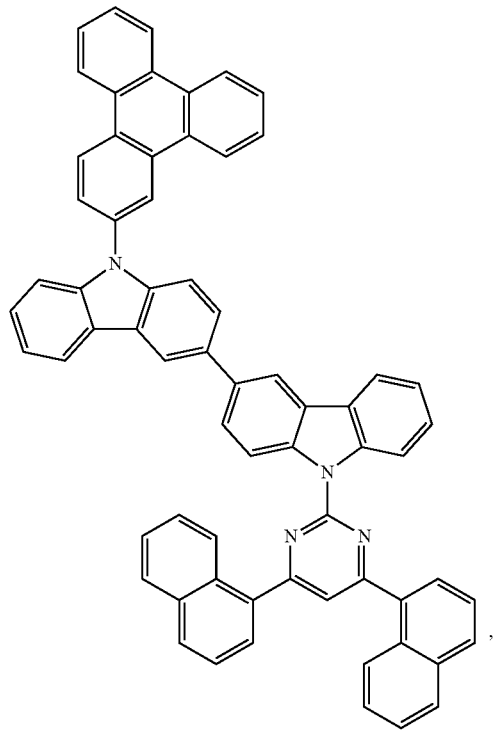
Compound 135
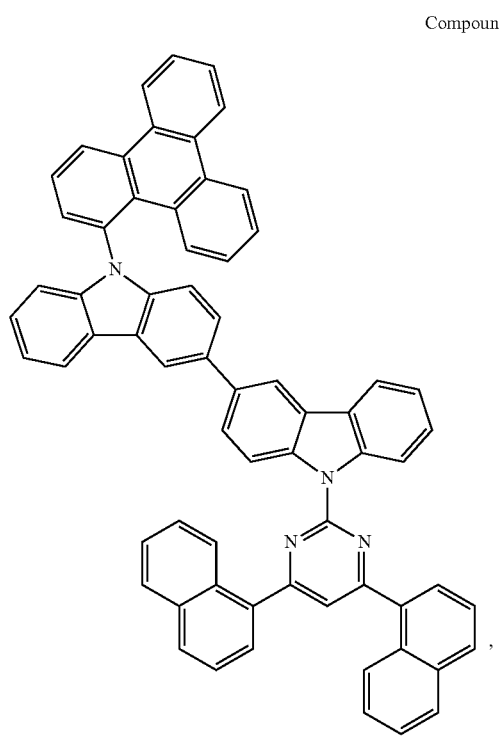
Compound 136
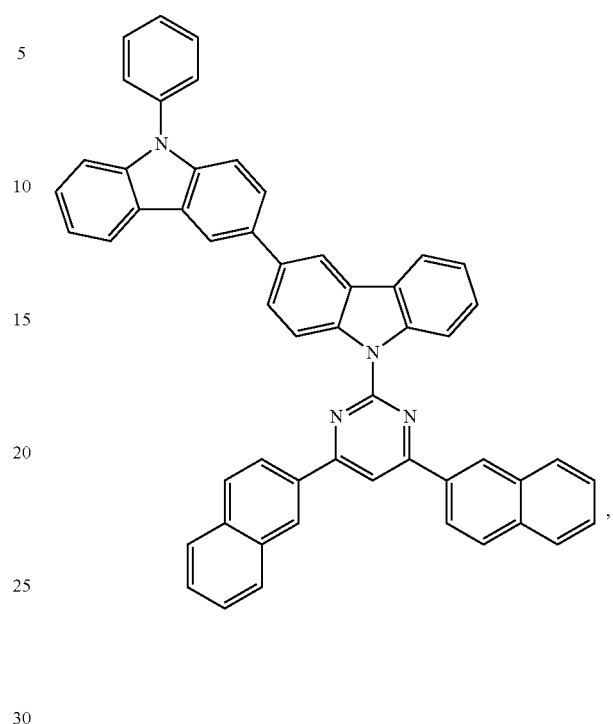
Compound 137
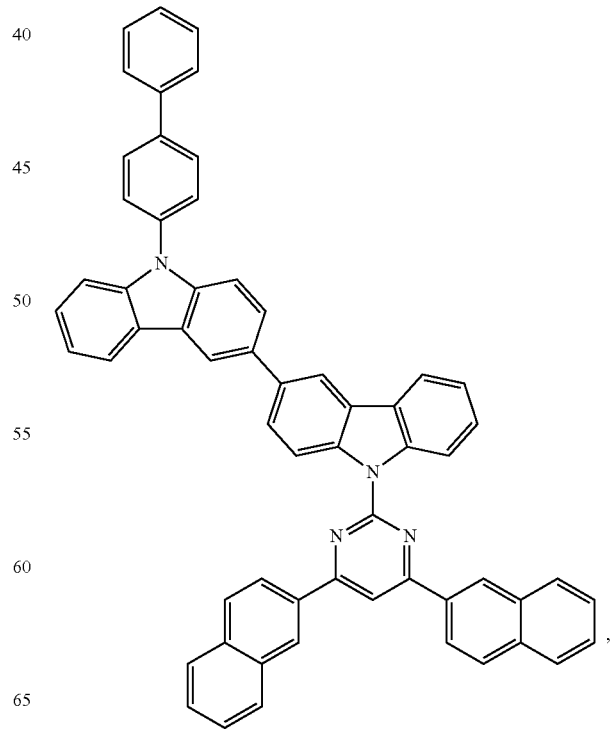

Compound 138
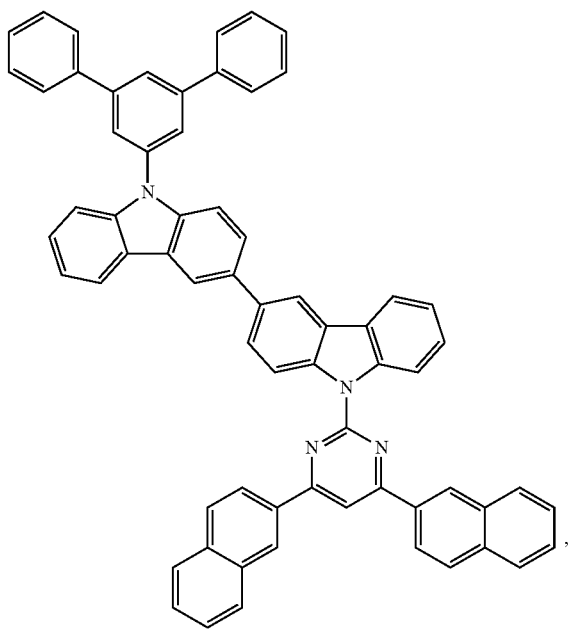
Compound 140
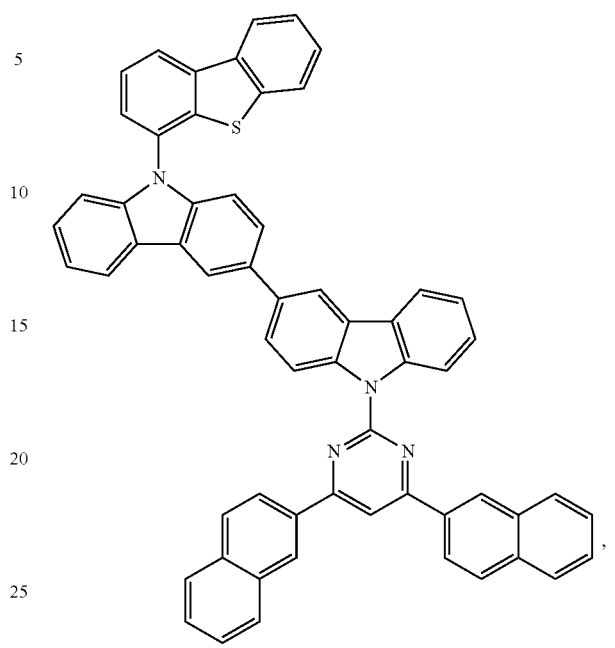
Compound 139
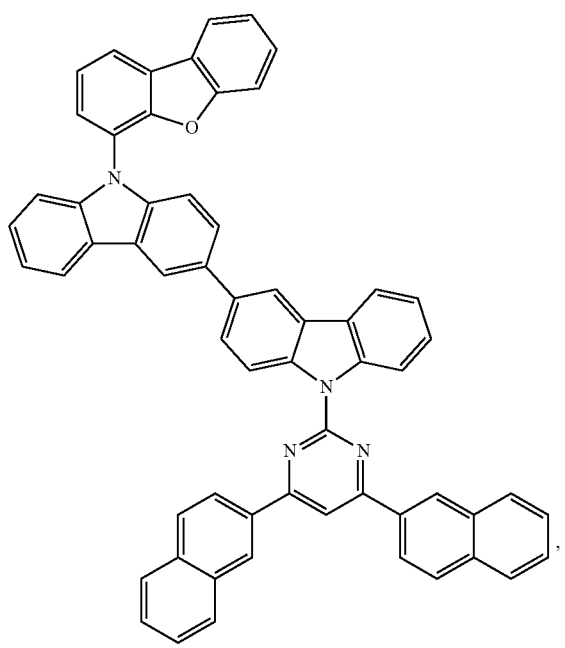
Compound 141
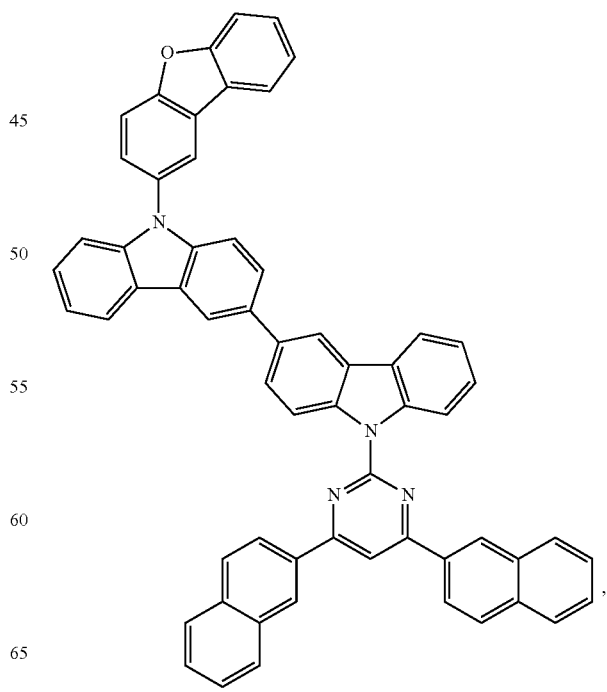

Compound 142
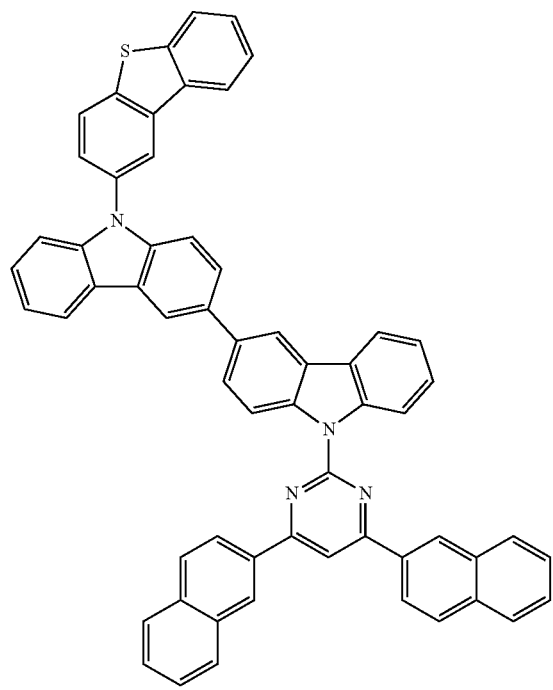
Compound 143
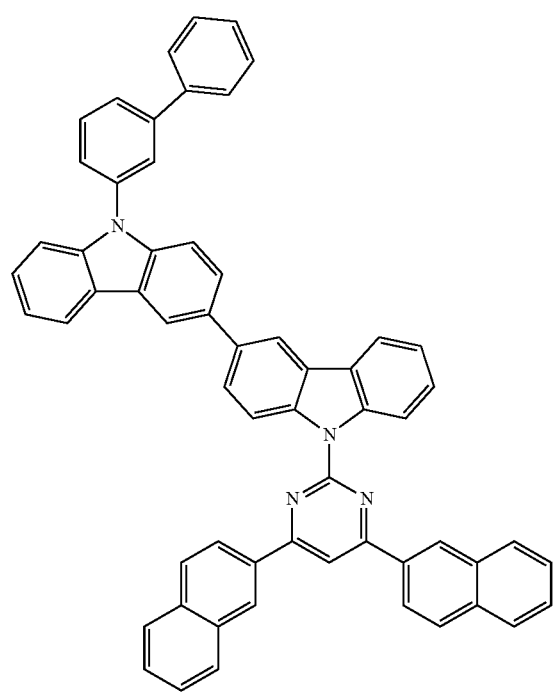
Compound 144
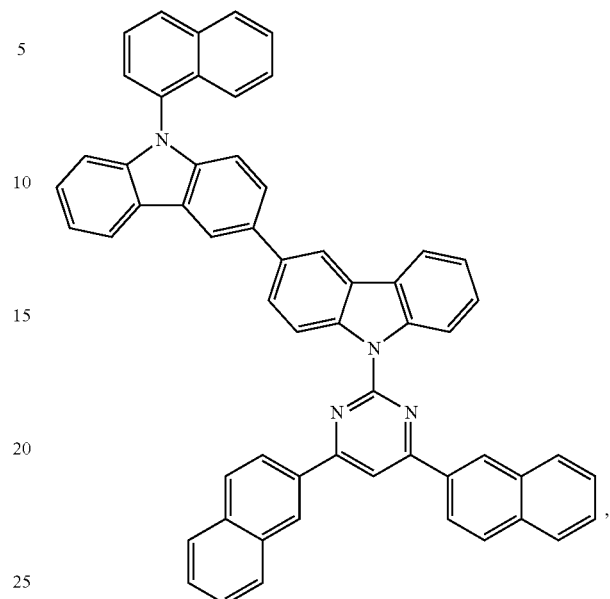
Compound 145
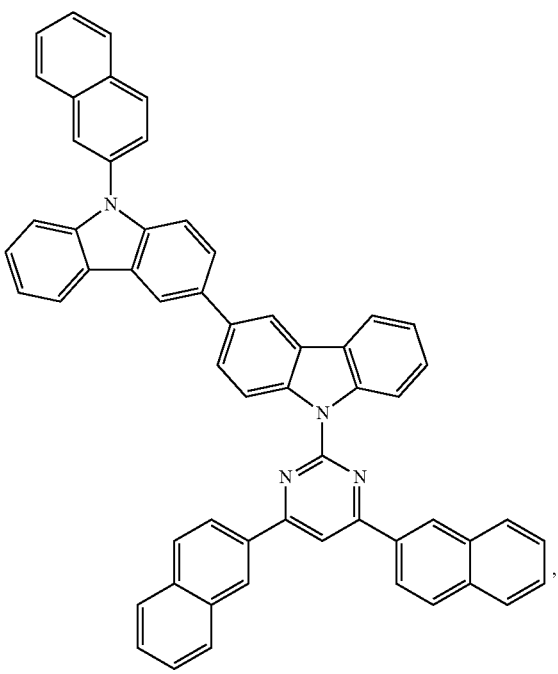

Compound 146
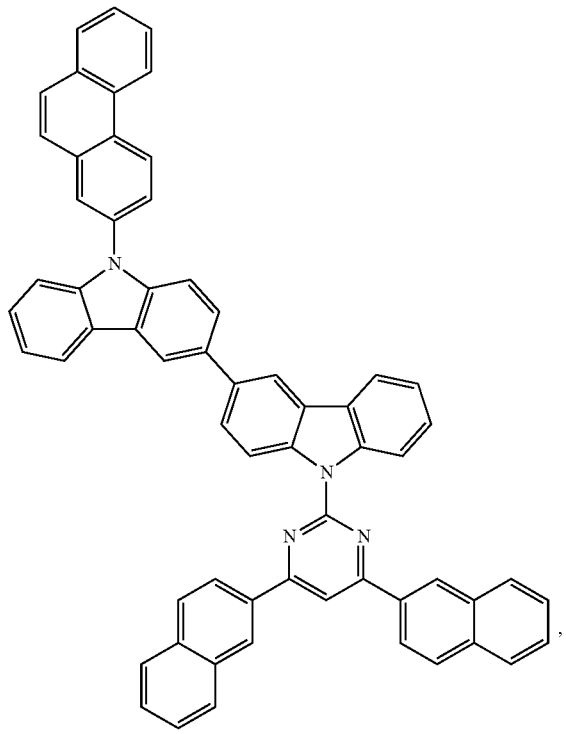
Compound 147
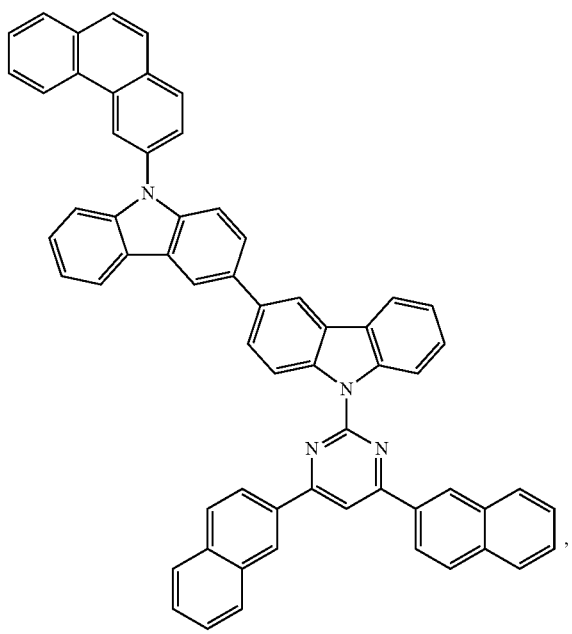
Compound 148
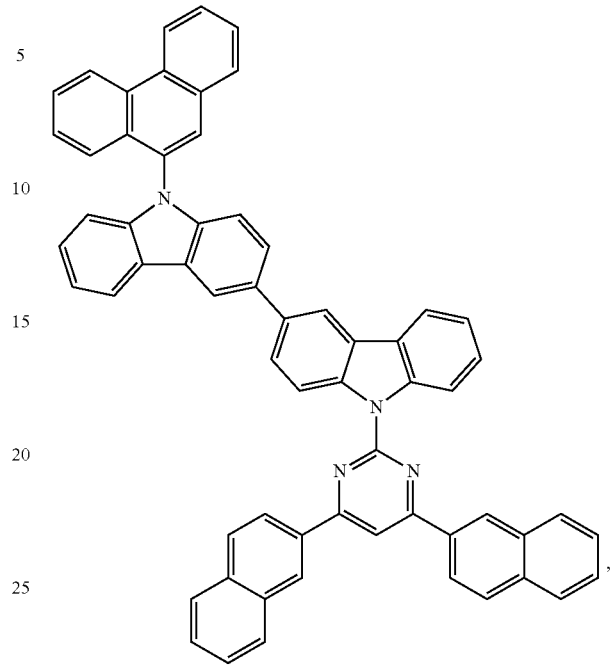
Compound 149
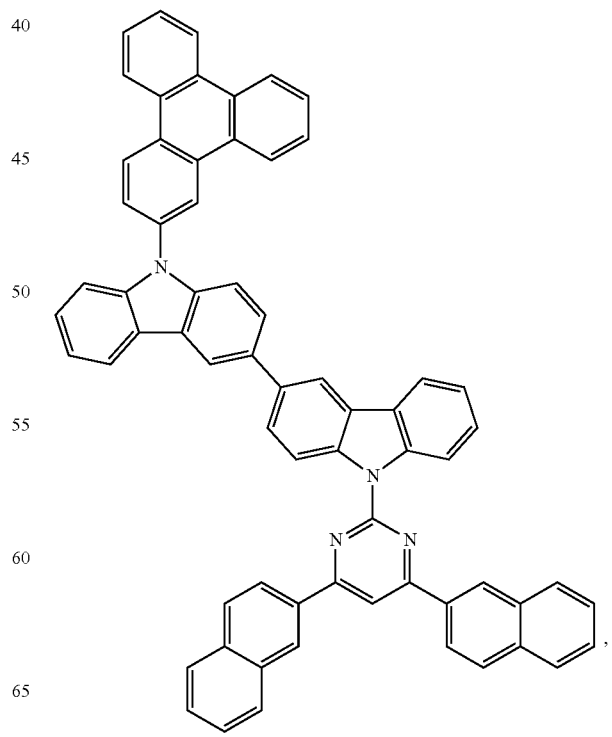

Compound 150
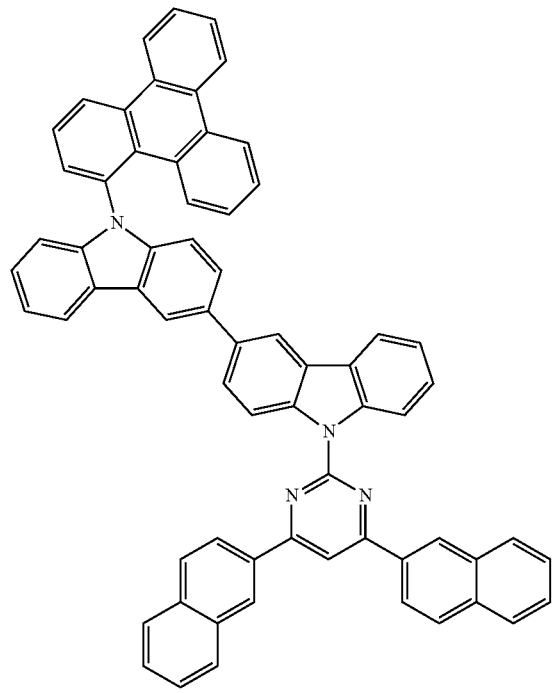
Compound 151
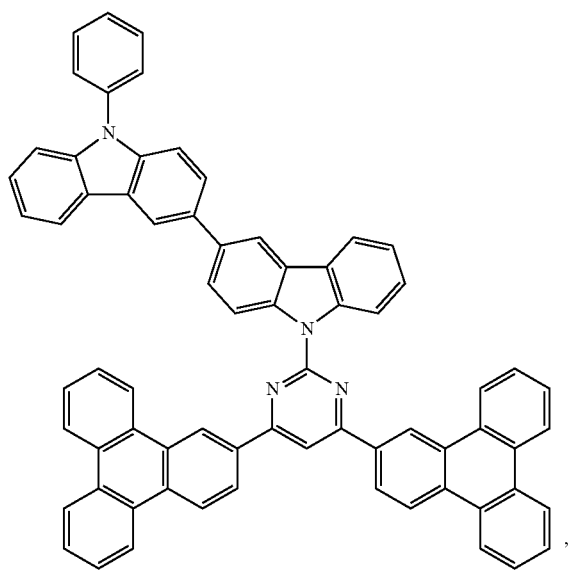
Compound 152
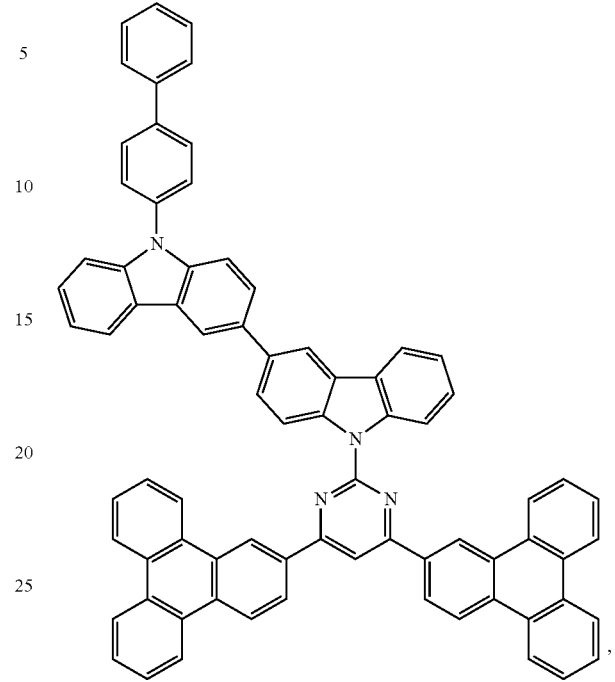
Compound 153
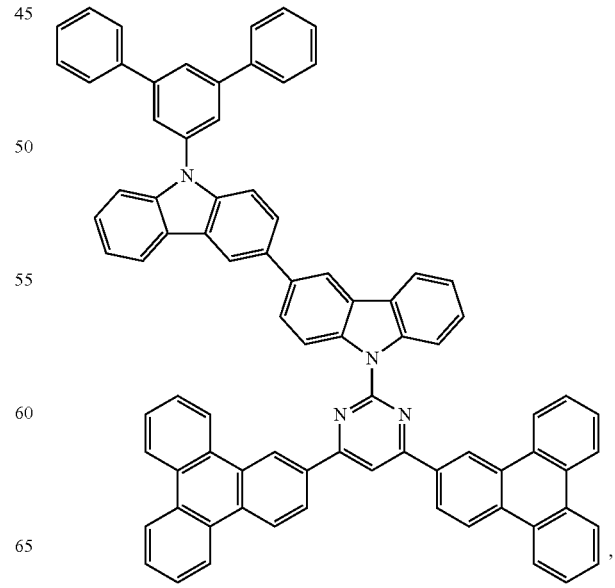

-continued
Compound 154
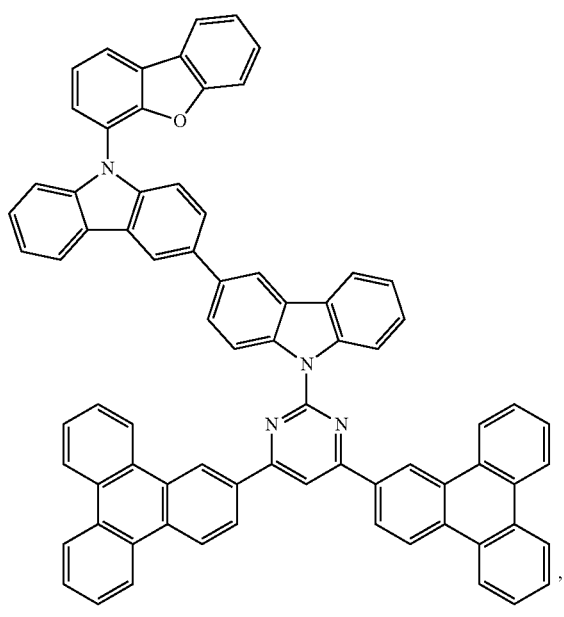
Compound 155
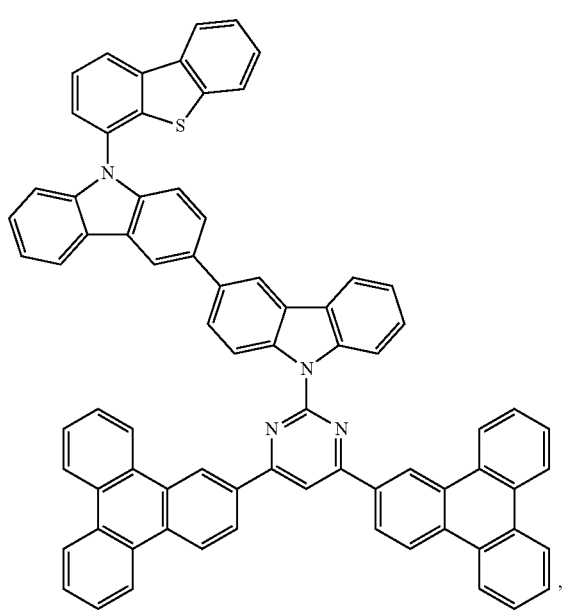
Compound 156
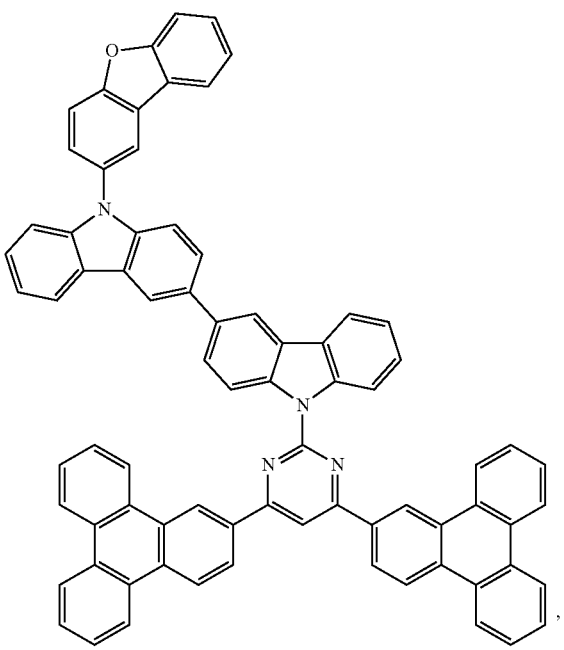
Compound 157

Compound 158
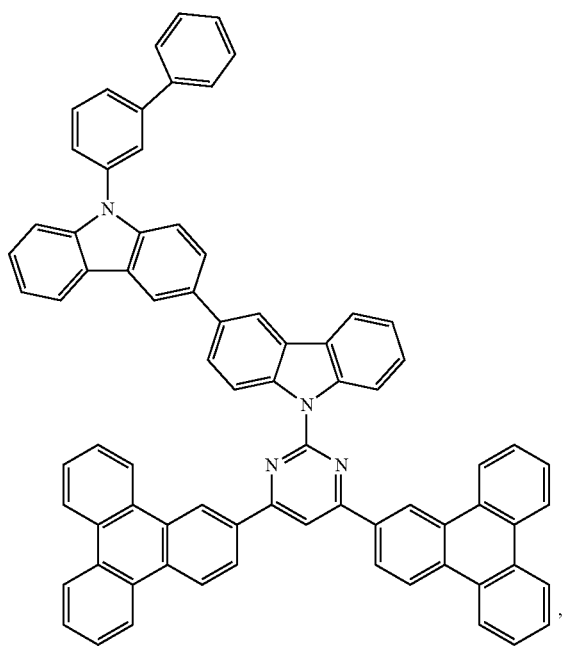
Compound 159
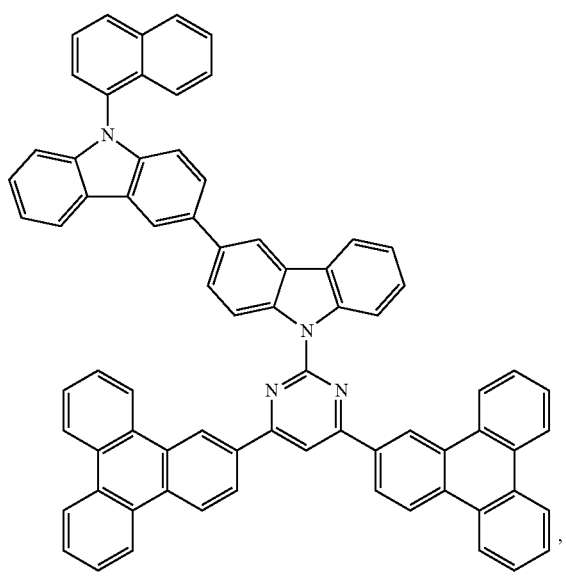
Compound 160
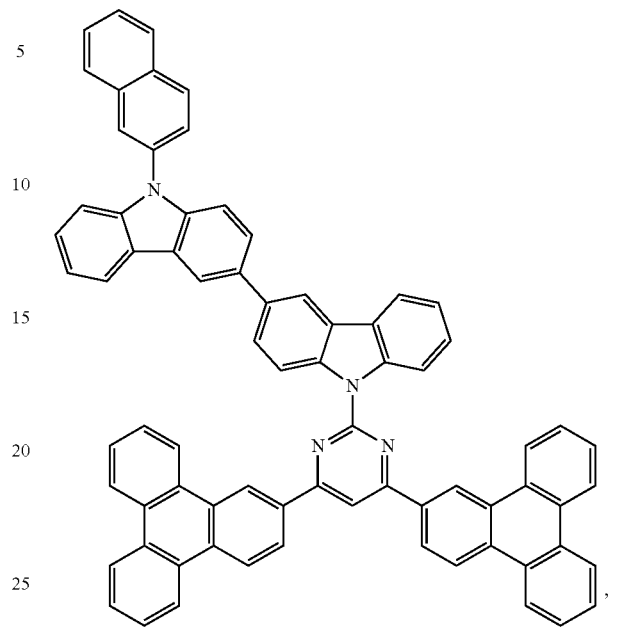
Compound 161

Compound 162
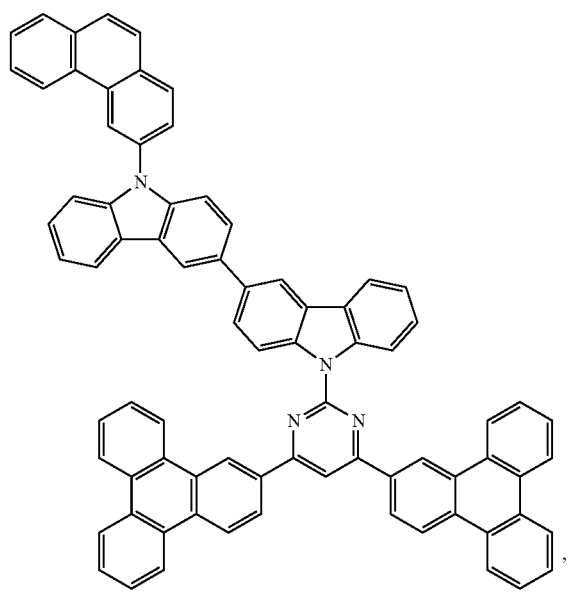
Compound 164
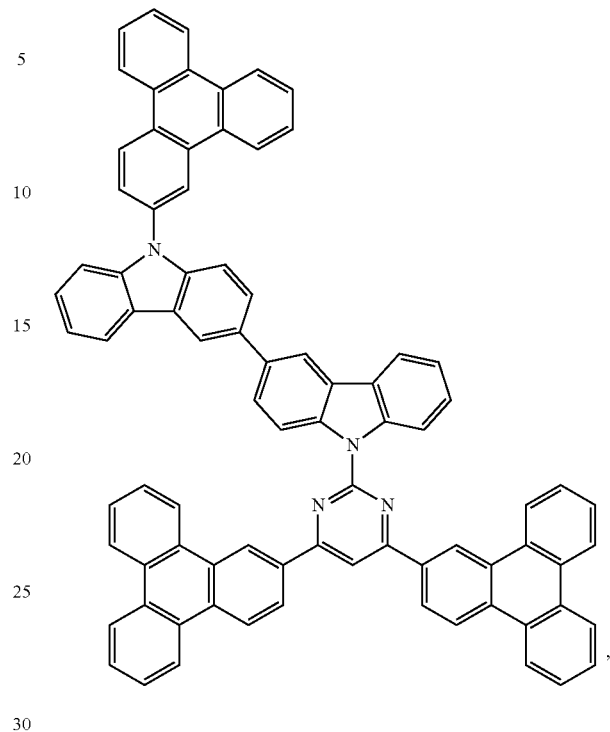
Compound 163
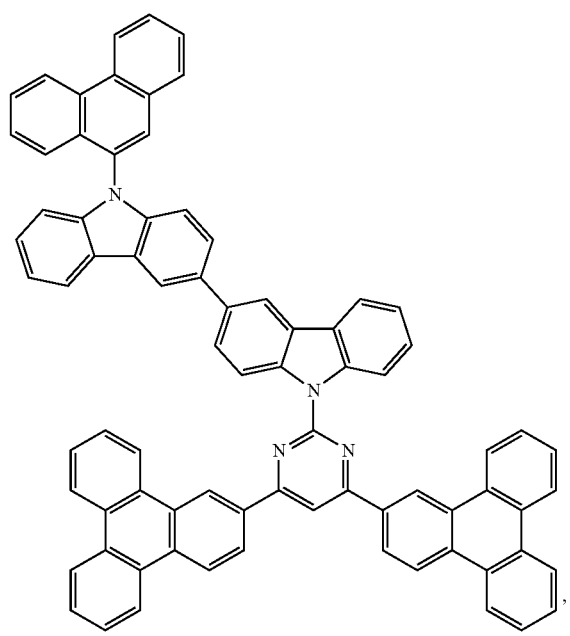
Compound 165
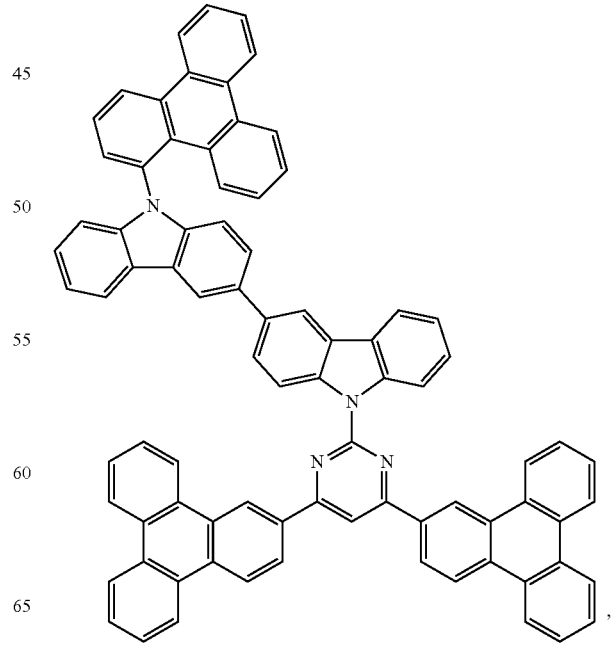

Compound 166
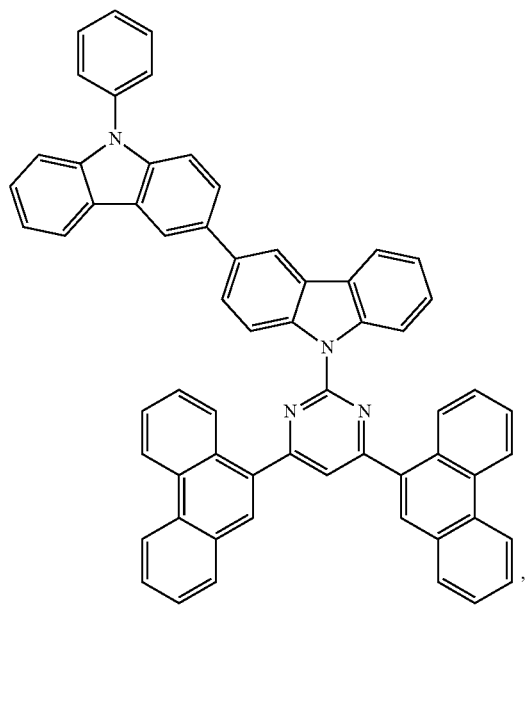
Compound 168
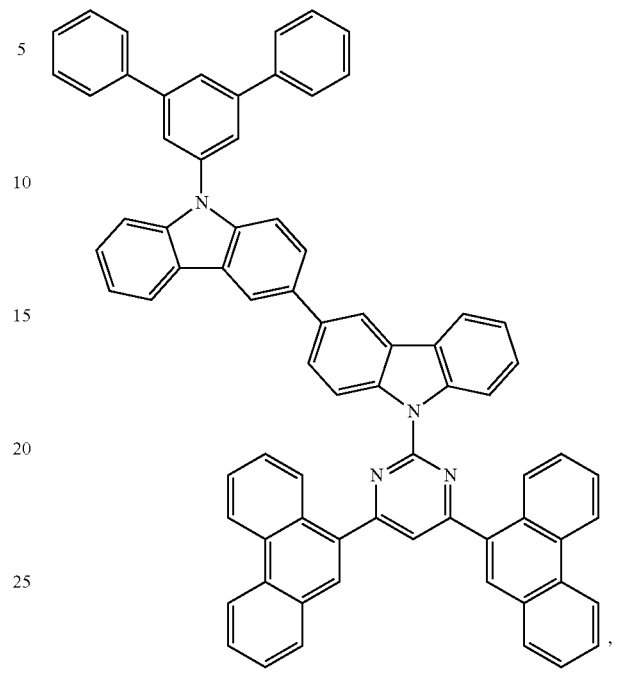
Compound 167
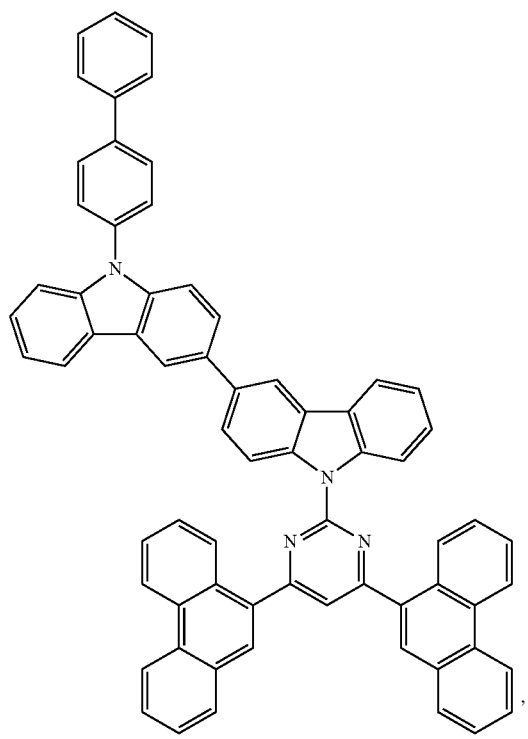
Compound 169
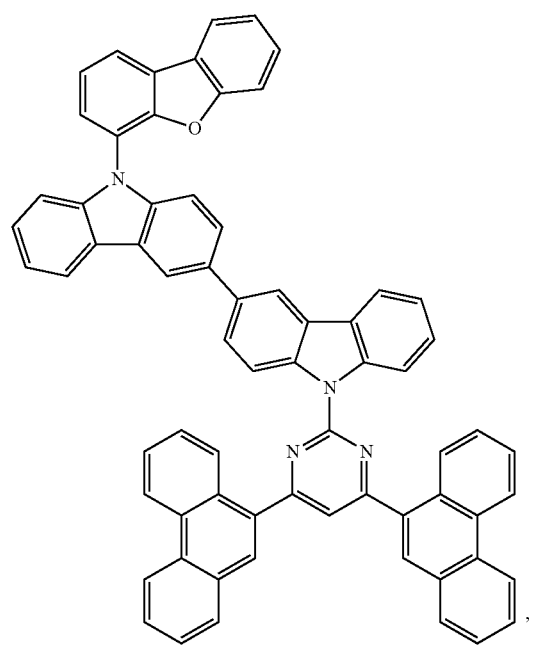

Compound 170
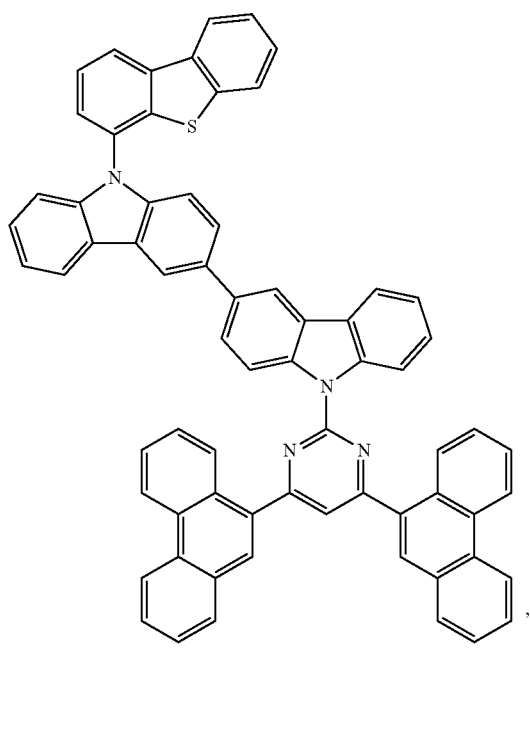
Compound 172
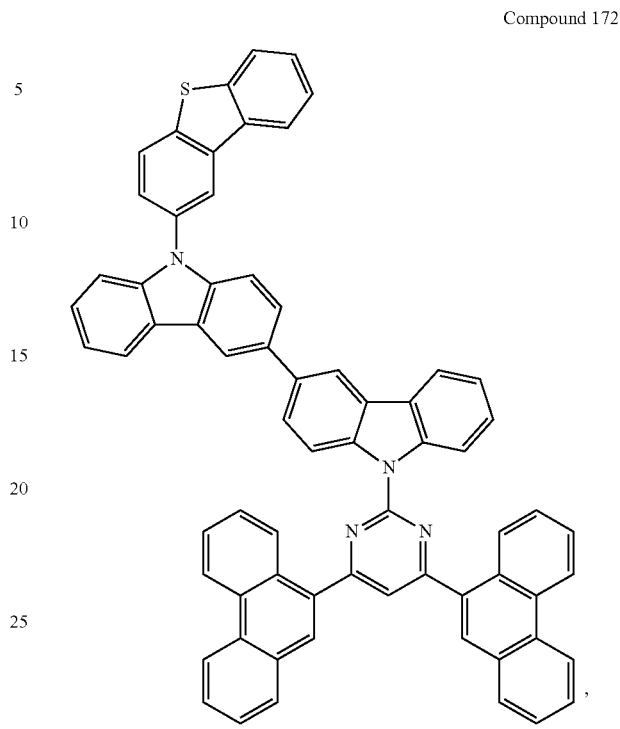
Compound 171
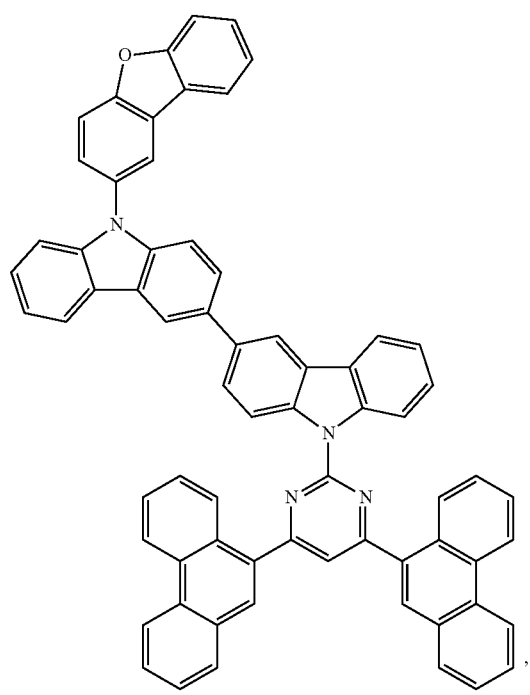
Compound 173
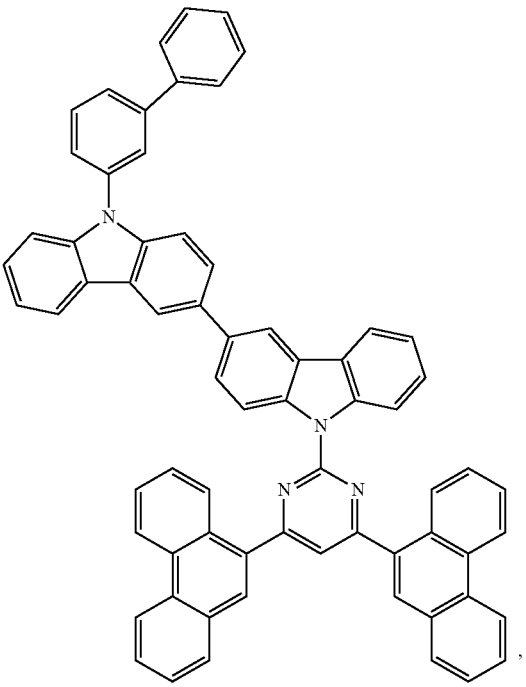

Compound 174
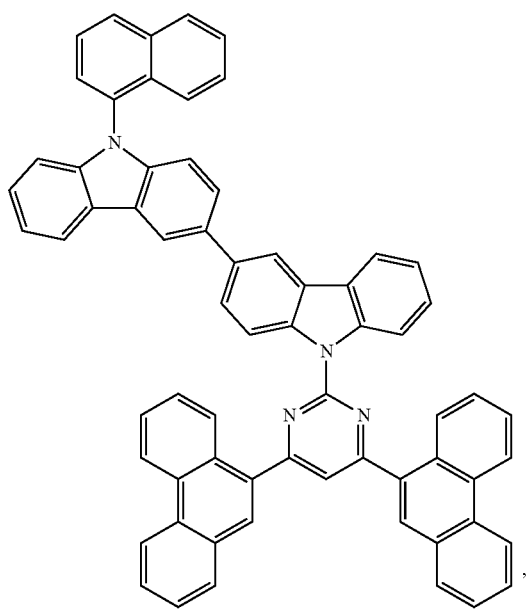
Compound 176
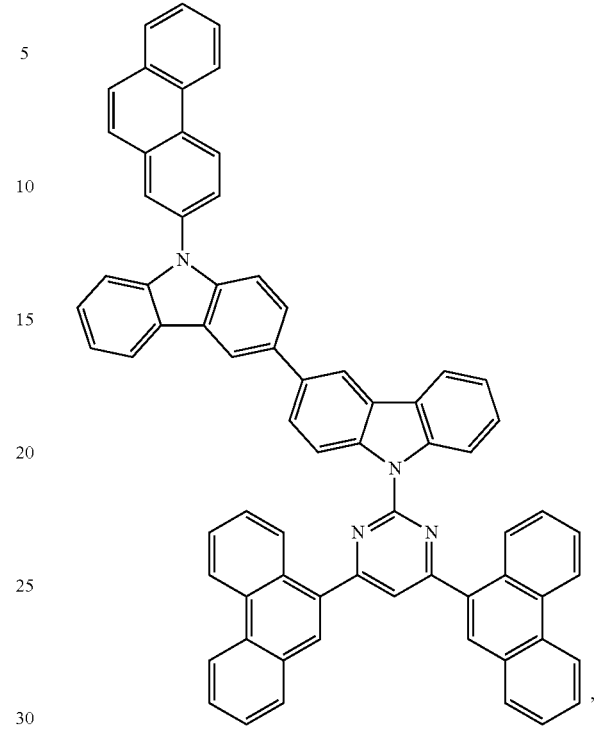
Compound 175
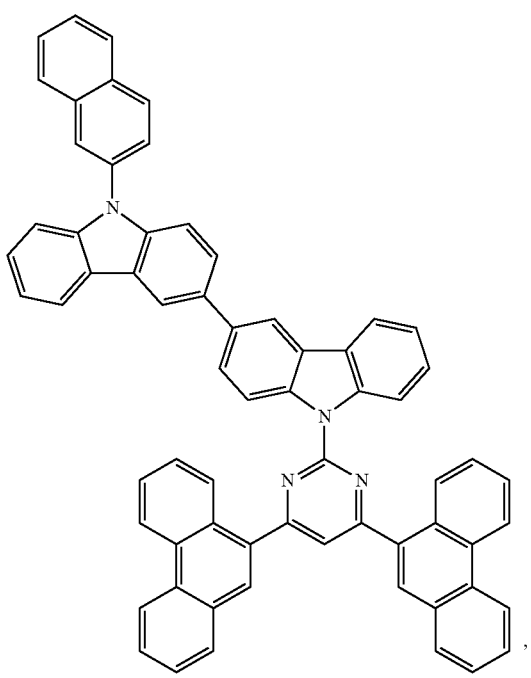
Compound 177
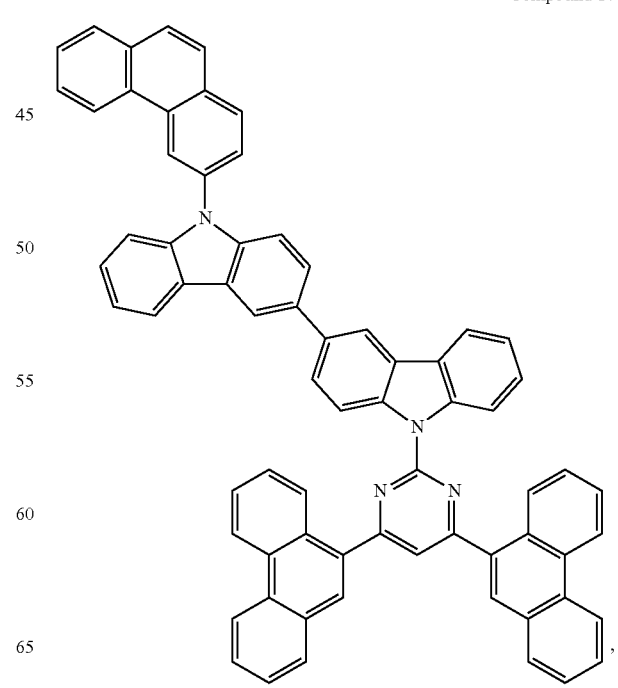

Compound 178

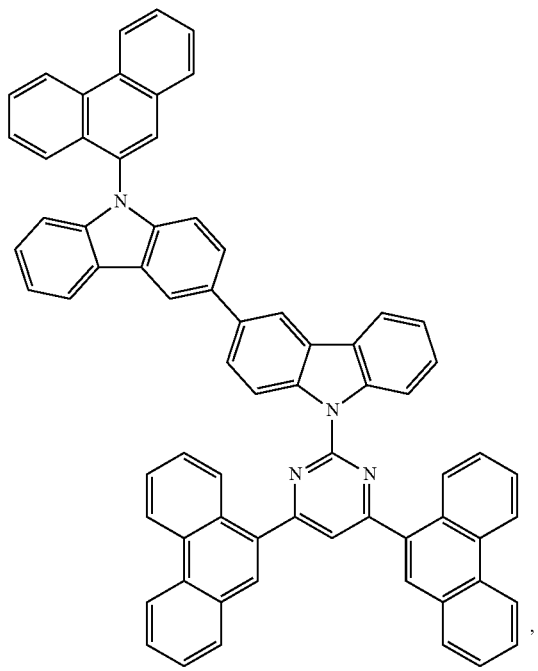

,

Compound 179

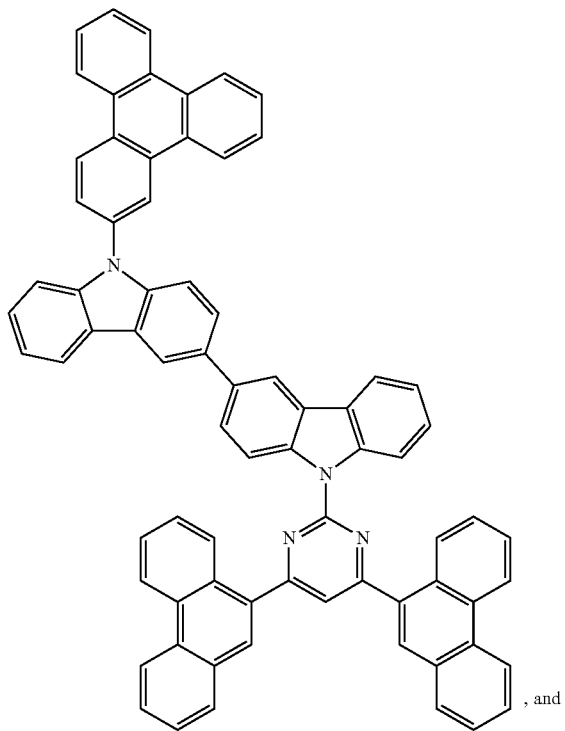

, and

Compound 180

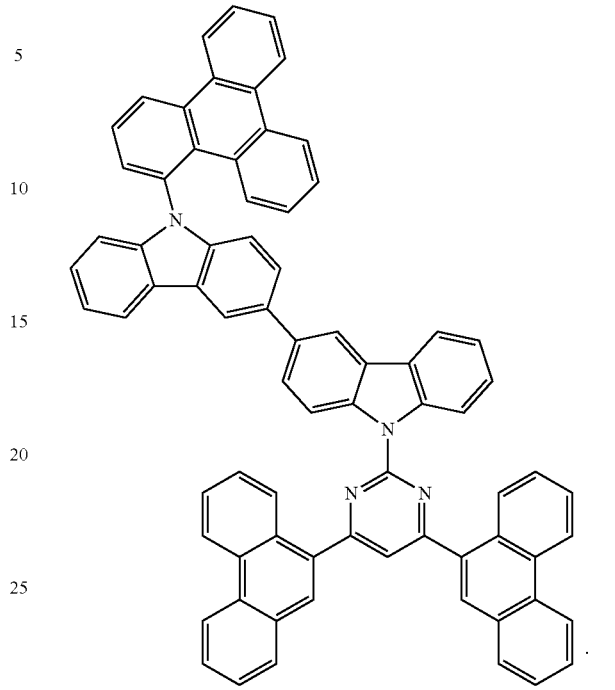

.

18. A consumer product comprising an organic light emitting device, the organic light emitting device comprising:
- an anode;
- a cathode; and
- an organic layer, disposed between the anode and the cathode, wherein the organic layer comprises a compound having the formula:

Formula I

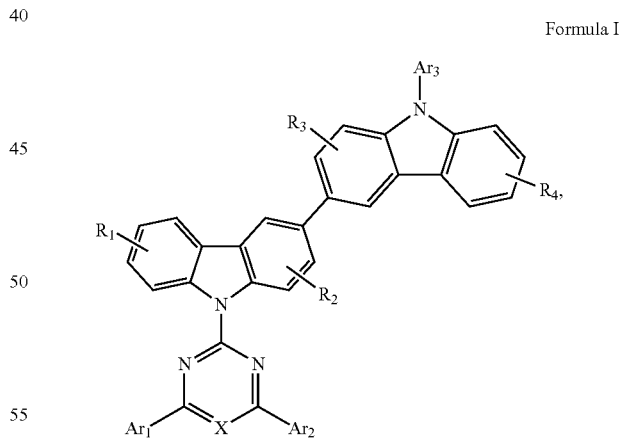

wherein $R_1$, $R_2$, $R_3$, and $R_4$ may represent mono up to the maximum available substitutions, or no substitutions;

wherein $R_1$, $R_2$, $R_3$, and $R_4$ are independently selected from the group consisting of hydrogen, alkyl, alkoxy, amino, alkenyl, alkynyl, aryl and heteroaryl;

wherein $Ar_2$ and $Ar_3$ are independently selected from aryl or heteroaryl;

wherein $Ar_1$ is selected from the group consisting of pyridine, naphthalene, fluorene, phenanthrene, and triphenylene;

wherein Ar$_2$ and Ar$_3$ are independently optionally substituted; and wherein X is C or N.

19. The consumer product of claim 18, wherein the consumer product is selected from the group consisting of flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, walls, theater or stadium screens, and signs.

* * * * *